(12) United States Patent
Chen et al.

(10) Patent No.: US 9,951,019 B2
(45) Date of Patent: Apr. 24, 2018

(54) THERAPEUTIC COMPOUNDS

(71) Applicant: REGENTS OF THE UNIVERSITY OF MINNESOTA, Minneapolis, MN (US)

(72) Inventors: Liqiang Chen, Minneapolis, MN (US); Teng Ai, Minneapolis, MN (US); Swati More, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/192,728

(22) Filed: Jun. 24, 2016

(65) Prior Publication Data

US 2016/0376238 A1    Dec. 29, 2016

Related U.S. Application Data

(60) Provisional application No. 62/185,417, filed on Jun. 26, 2015.

(51) Int. Cl.
| | | |
|---|---|---|
| *C07C 57/34* | (2006.01) | |
| *C07D 213/82* | (2006.01) | |
| *C07D 409/12* | (2006.01) | |
| *C07D 405/12* | (2006.01) | |
| *C07D 401/12* | (2006.01) | |
| *C07D 417/12* | (2006.01) | |
| *C07D 409/14* | (2006.01) | |
| *C07D 405/14* | (2006.01) | |
| *C07D 401/14* | (2006.01) | |
| *C07D 413/12* | (2006.01) | |
| *C07B 59/00* | (2006.01) | |

(52) U.S. Cl.
CPC .......... *C07D 213/82* (2013.01); *C07B 59/002* (2013.01); *C07D 401/12* (2013.01); *C07D 401/14* (2013.01); *C07D 405/12* (2013.01); *C07D 405/14* (2013.01); *C07D 409/12* (2013.01); *C07D 409/14* (2013.01); *C07D 413/12* (2013.01); *C07D 417/12* (2013.01)

(58) Field of Classification Search
CPC .. C07D 213/82; C07D 409/14; C07D 405/12; C07D 401/12; C07D 417/12; C07D 409/12; C07D 405/14; C07D 401/14; C07D 413/12; C07B 59/002; C07B 2200/05
See application file for complete search history.

(56) References Cited

U.S. PATENT DOCUMENTS

2008/0221195 A1* 9/2008 Wortmann ........... C07D 209/16
514/415

FOREIGN PATENT DOCUMENTS

WO    WO 0153274 A1 * 7/2001 ........... C07D 213/30

OTHER PUBLICATIONS

Ai, et al., "5-((3-Amidobenzyl)oxy)nicotinamides as Sirtuin 2 Inhibitors", J Med Chem 59(7), 2928-2941 (2016).
Arteaga, et al., "Inhibition of SIRT2 suppresses hepatic fibrosis", Am J Physiol Gastrointest Liver Physiol 310, G1155-68 (2016).
Chen, "Medicinal chemistry of sirtuin inhibitors", Curr Med Chem 18, 1936-1946 (2011).
Chen, "SIRT2 Inhibitors as Potential Parkinson's Disease Therapeutics", Department of Neurology Grand Rounds, Presentation, 54 pages (May 22, 2015).
Chen, et al., "The sirtuin-2 inhibitor AK7 is neuroprotective in models of Parkinson's disease but not amyotrophic lateral sclerosis and cerebral ischemia", PLoS One 10, e0116919 (2015).
Cui, et al., "Discovery of Potent and Selective Sirtuin 2 (SIRT2) Inhibitors Using a Fragment-Based Approach", Journal of Medicinal Chemistry 57, 8340-8357 (2014).
Deng, et al., "SIRT2 is an unfavorable prognostic biomarker in patients with acute myeloid leukemia", Sci Rep 6:27694 (2016).
Eskandarian, et al., "A role for SIRT2-dependent histone H3K18 deacetylation in bacterial infection", Science 341 (6145), 1238858 (2013).
Godena, et al., "Increasing microtubule acetylation rescues axonal transport and locomotor deficits caused by LRRK2 Roc-COR domain mutations", Nat Commun 5, 5245 (2014).
Green, et al., "Nicotinamide restores cognition in Alzheimer's disease transgenic mice via a mechanism involving sirtuin inhibition and selective reduction of Thr231-phosphotau", J Neurosci 28, 11500-11510 (2008).
Harting, et al., "SIRT2-mediated protein deacetylation: An emerging key regulator in brain physiology and pathology", Eur J Cell Biol 89, 262-269 (2010).
Hasegawa, et al., "Role of TPPP/p25 on α-synuclein-mediated oligodendroglial degeneration and the protective effect of SIRT2 inhibition in a cellular model of multiple system atrophy", Neurochem Int 57, 857-866 (2010).
Houtkooper, et al., "Sirtuins as regulators of metabolism and healthspan", Nat Rev Mol Cell Biol 13, 225-238 (2012).
Hu, et al., "Sirtuin inhibitors as anticancer agents", Future Med Chem 6, 945-966 (2014).

(Continued)

*Primary Examiner* — Sudhakar Katakam
(74) *Attorney, Agent, or Firm* — Viksnins Harris Padys Malen LLP

(57) ABSTRACT

The invention provides compounds of formula (I):

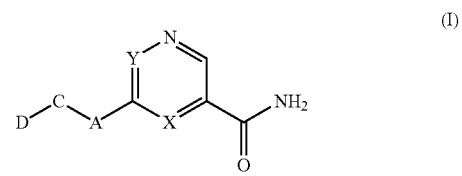

wherein, A, C, D, X, and Y have any of the values defined in the specification, and salts thereof. The compounds are SIRT2 inhibitors and are useful for treating SIRT2 associated conditions.

12 Claims, No Drawings

(56) References Cited

OTHER PUBLICATIONS

Jing, et al, "A SIRT2-Selective Inhibitor Promotes c-Myc Oncoprotein Degradation and Exhibits Broad Anticancer Activity", Cancer Cell 29, 297 (2016).

Jing, et al., "Lessons learned from a SIRT2-selective inhibitor", Oncotarget 7(17), 22971-22972 (2016).

Jung, et al., "SIRT2 Regulates LPS-Induced Renal Tubular CXCL2 and CCL2 Expression", J Am Soc Nephrol 26, 1549-1560 (2015).

Liu, et al., "SIRT2 enhances 1-methyl-4-phenyl-1,2,3,6-tetrahydropyridine (MPTP)-induced nigrostriatal damage via apoptotic pathway", Front Aging Neurosci 6, 184 (2014).

Luthi-Carter, et al., "SIRT2 inhibition achieves neuroprotection by decreasing sterol biosynthesis", Proc Natl Acad Sci 107, 7927-7932 (2010).

Moscardo, et al., "The histone deacetylase sirtuin 2 is a new player in the regulation of platelet function", J Thromb Haemost 13, 1335-44 (2015).

North, et al., "The human Sir2 ortholog, SIRT2, is an NAD+-dependent tubulin deacetylase", Mol Cell 11, 437-444 (2003).

Outeiro, et al., "Sirtuin 2 inhibitors rescue alpha-synuclein-mediated toxicity in models of Parkinson's disease", Science 317, 516-519 (2007).

Pandithage, et al., "The regulation of SIRT2 function by cyclin-dependent kinases affects cell motility", J Cell Biol 180, 915-929 (2008).

Pfister, et al., "Opposing effects of sirtuins on neuronal survival: SIRT1-mediated neuroprotection is independent of its deacetylase activity", PLoS One 3(12), e4090 (2008).

Ponnusamy, et al., "Blocking sirtuin 1 and 2 inhibits renal interstitial fibroblast activation and attenuates renal interstitial fibrosis in obstructive nephropathy", J Pharmacol Exp Ther 350, 243-256 (2014).

Silva, et al., "Mitochondrial Metabolism Power SIRT2-Dependent Deficient Traffic Causing Alzheimer's-Disease Related Pathology", Mol Neurobiol PMID: 27311773 (2016).

Soung, et al., "Epigenetic silencing of ARRDC3 expression in basal-like breast cancer cells", Sci Rep 4, 3846 (2014).

Spires-Jones, et al., "Inhibition of Sirtuin 2 with Sulfobenzoic Acid Derivative AK1 is Non-Toxic and Potentially Neuroprotective in a Mouse Model of Frontotemporal Dementia", Front Pharmacol 3, 42 (2012).

Suzuki, et al., "Mammalian Sir2-related protein (SIRT) 2-mediated modulation of resistance to axonal degeneration in slow Wallerian degeneration mice: a crucial role of tubulin deacetylation", Neuroscience 147, 599-612 (2007).

Theendakara, et al., "Neuroprotective Sirtuin ratio reversed by ApoE4", Proc Natl Acad Sci 110, 18303-18308 (2013).

Zhao, et al., "Selective Inhibition of SIRT2 Improves Outcomes in a Lethal Septic Model", Curr Mol Med 15, 634-641 (2015).

Zhou, et al., "SIRT2 regulates ciliogenesis and contributes to abnormal centrosome amplification caused by loss of polycystin-1", Hum Mol Genet 23, 1644-1655 (2014).

* cited by examiner

THERAPEUTIC COMPOUNDS

PRIORITY

This application claims priority to U.S. Provisional Patent Application No. 62/185,417, filed 26 Jun. 2015. The entire content of this provisional application is hereby incorporated by reference herein.

BACKGROUND

Sirtuin 2 (SIRT2) is a member of the mammalian sirtuin (NAD$^+$-dependent histone deacetylase) family that comprises SIRT1-7 (Houtkooper, R. H., et al., *Nat. Rev. Mol. Cell Biol.* 2012, 13, 225-238). SIRT2 is the only sirtuin that predominantly resides in the cytosol even though it is localized in the nucleus during mitosis. Interestingly, an alternatively spliced isoform has been reported to permanently reside in the nucleus. As the most abundant sirtuin homolog in the brain (Pandithage, R., et al., *J. Cell Biol.* 2008, 180, 915-929), SIRT2 has emerged as an important regulator in brain physiology and pathology (Harting, K., et al., *Eur. J. Cell Biol.* 2010, 89, 262-269). Several studies have suggested that selective pharmacological inhibition of SIRT2 is a promising therapeutic approach for Parkinson's disease (PD). First, overexpression of SIRT2 induced neuronal apoptosis (Pfister, J. A., et al., *PLoS One* 2008, 3, e4090). Second, blocking SIRT2 protected cells from the neurotoxicity induced by α-synuclein, a risk factor associated with the familial PD, in the cellular and fruit fly models of PD (Outeiro, T. F., et al., *Science* 2007, 317, 516-519). Third, SIRT2 exacerbated the nigrostriatal neurotoxicity induced by neurotoxin 1-methyl-4-phenyl-1,2,3,6-tetrahydropyridine (MPTP) while genetic deletion (Liu, L., et al., *Front. Aging Neurosci.* 2014, 6, 184) or pharmacological inhibition (Chen, X., et al., *PLoS One* 2015, 10, e0116919) of SIRT2 prevented MPTP-induced neurodegeneration in mice. Furthermore, as a major deacetylase of α-tubulin (North, B. J., et al., *Mol. Cell* 2003, 11, 437-444.), SIRT2 decreased the acetylation level of microtubules, enhancing their association with pathologically mutated leucine-rich kinase 2 (LRRK2) in the Roc-COR domain (R1441C and Y1699C). While this strengthened association impaired axonal transport, genetic knockdown of SIRT2 restored both axonal transport and locomotion in fruit flies (Godena, V. K., et. al., *Nat. Commun.* 2014, 5, 5245).

Besides PD, blocking SIRT2 may also provide protection in other neurodegenerative diseases. First, inhibition of SIRT2 had a protective effect in a cellular model of multiple system atrophy (Hasegawa, T., et al., *Neurochem. Int.* 2010, 57, 857-866), which is one form of synucleinopathy like PD. Second, in the granule cells obtained from slow Wallerian degeneration (Wld(s)) mice, genetic knockdown of SIRT2 enhanced resistance to axonal degeneration while overexpression of SIRT2 abrogated the resistance (Suzuki, K., et al., *Neuroscience* 2007, 147, 599-612). Third, inhibiting SIRT2 offered neuroprotection in the fly, worm, and primary striatal neuron models of Huntington's disease, likely by reducing sterol biosynthesis ((a) Luthi-Carter, R., et al., *Proc. Natl. Acad. Sci. U.S.A.* 2010, 107, 7927-7932; (b) Taylor, D. M., et al., *ACS Chem. Biol.* 2011, 6, 540-546), even though the therapeutic potential still remains to be unequivocally defined. Four, SIRT2 inhibitors have been explored for their potential therapeutic applications in the mouse models of tauopathies, such as Alzheimer's disease (AD) (Green, K. N., et al., *J. Neurosci.* 2008, 28, 11500-11510) and frontotemporal dementia (Spires-Jones, T. L., et al., *Front. Pharmacol.* 2012, 3, 42). Lastly, a neurotoxic role of SIRT2 in AD has been recently proposed ((a) Theendakara, V., et al., *Proc. Natl. Acad. Sci. U.S.A.* 2013, 110, 18303-18308; (b) Silva, D. F., et al., *Mol. Neurobiol.* 2016, PMID: 27311773). Taken together, these studies suggest that optimized SIRT2 inhibitors will have a broad impact on the treatment of neurodegenerative diseases.

Recently, SIRT2 has been shown as a key player in the transcription regulation signalling initiated by bacterial infection, suggesting that blocking host SIRT2 may be a viable approach to fight bacterial infection (Eskandarian, H. A., et al., *Science* 2013, 341, 1238858). Furthermore, there are studies that suggest that SIRT2 inhibitors can be therapeutically useful in the treatment of cancer ((a) Hu, J.; Jing, H.; Lin, H., *Future Med. Chem.* 2014, 6, 945-966; (b) Soung, Y. H., et al., *Sci. Rep.* 2014, 4, 3846; (c) Jing, H., et al., *Cancer Cell* 2016, 29, 297; (d) Deng, A., et al., *Sci. Rep.* 2016, doi: 10.1038/srep27694; (e) Jing, H.; Lin, H., *Oncotarget* 2016, doi: 10.18632/oncotarget.8502.) and kidney diseases ((a) Zhou, X., et al., *Hum. Mol. Genet.* 2014, 23, 1644-1655; (b) Ponnusamy, M., et al., *J. Pharmacol. Exp. Ther.* 2014, 350, 243; (c) Jung, Y. J., et al., *J. Am. Soc. Nephroi.* 2015, 26, 1549). SIRT2 inhibitors can also be useful for the treatment of sepsis (Zhao, T., et al., *Curr. Mol. Med.* 2015, 15, 634.) and hepatic fibrosis (Arteaga, M., et al., *Am. J. Physiol. Gastrointest. Liver Physiol.* 2016, 310, G1155), and for the control of platelet function (Moscardo, A., et al., *J. Thromb. Haemost.* 2015, 13, 1335).

Currently there is a need for agents that are useful for inhibiting SIRT2. Such agents may be useful to treat pathologies associated with SIRT2, such as, for example, Parkinson's disease.

SUMMARY

The invention provides compounds that are inhibitors of SIRT2. Accordingly in one embodiment the invention provides a compound of formula (I):

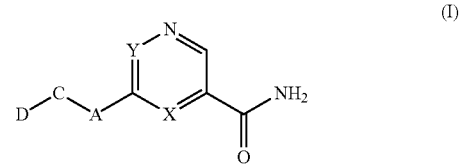

wherein:
X is CH or N;
Y is CH or N;
A is selected from the group consisting of: -A'-B'—,

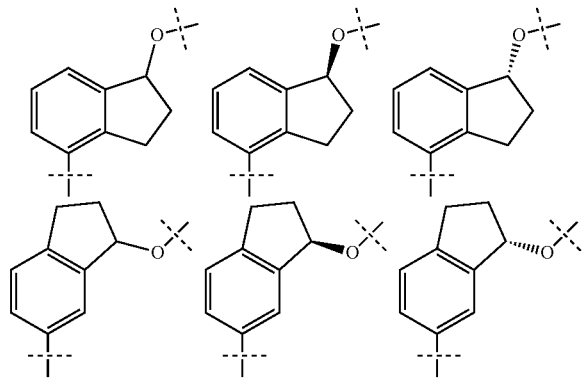

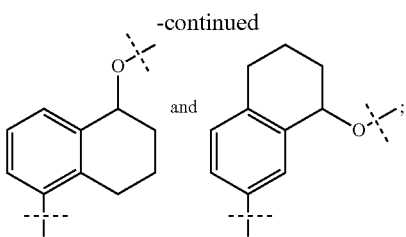

A' is selected from the group consisting of:

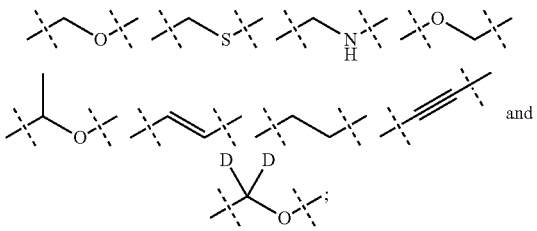

B' is phenyl, a 5-membered heteroaryl, or a 6-membered heteroaryl, wherein A' and C are attached to B' in a meta-orientation, and the phenyl, 5-membered heteroaryl, and 6-membered heteroaryl are optionally substituted with one or more groups independently selected from F, Cl, deuterium, methyl, trifluoromethyl, methoxy, and trifluoromethoxy;

C is selected from the group consisting of:

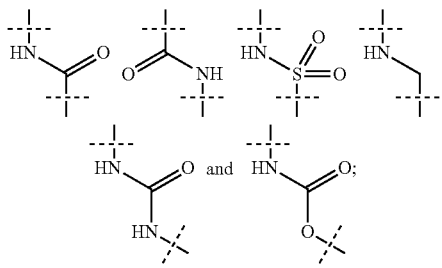

D is selected from the group consisting of $(C_1-C_6)$alkyl, $(C_2-C_6)$alkenyl, $(C_3-C_{15})$carbocycle, aryl, and heteroaryl, wherein the $(C_1-C_6)$alkyl, $(C_2-C_6)$alkenyl, $(C_3-C_{15})$carbocycle, aryl, and heteroaryl, are optionally substituted with one or more groups $R^z$ independently selected from halo, deuterium, nitro, hydroxy, cyano, carboxy, $-NR^aR^b$, $-C(=O)NR^aR^b$, $-N-S(O)_2R^a$, $-NR^aC(=O)NR^aR^b$, $(C_1-C_4)$alkyl, $(C_2-C_4)$alkenyl, $(C_2-C_4)$alkynyl, $(C_1-C_4)$alkoxy, $(C_1-C_4)$alkanoyl, $(C_1-C_4)$alkoxycarbonyl, $(C_1-C_4)$alkanoyloxy, $(C_3-C_{15})$carbocycle, aryl, aryloxy, and heteroaryl, wherein any $(C_1-C_4)$alkyl, $(C_2-C_4)$alkenyl, $(C_2-C_4)$alkynyl, $(C_1-C_4)$alkoxy, $(C_1-C_4)$alkanoyl, $(C_1-C_4)$alkoxycarbonyl, $(C_3-C_{15})$carbocycle, and $(C_1-C_4)$alkanoyloxy of $R^z$ is optionally substituted with one or more groups independently selected from the group consisting of halo, hydroxy, deuterium, $-NR^aR^b$, $(C_1-C_4)$alkoxy, $(C_1-C_4)$alkoxycarbonyl, $(C_1-C_4)$alkanoyloxy, aryl, aryloxy, and heteroaryl, wherein any aryl, aryloxy, and heteroaryl, of $R^z$ is optionally substituted with one or more groups independently selected from the group consisting of deuterium, halo, nitro, cyano, hydroxy, $-NR^aR^b$, $(C_1-C_4)$alkyl, $(C_2-C_4)$alkenyl, $(C_2-C_4)$alkynyl, $(C_1-C_4)$alkoxy, $(C_1-C_4)$alkoxycarbonyl, $(C_1-C_4)$alkanoyloxy, $(C_1-C_4)$haloalkyl, $R^x$, and $(C_1-C_4)$haloalkoxy;

each $R^a$ and $R^b$ is independently selected from the group consisting of H, $(C_1-C_4)$alkyl, $(C_3-C_8)$cycloalkyl, $(C_2-C_4)$alkenyl, $(C_2-C_4)$alkynyl, $(C_1-C_4)$alkoxy, $(C_1-C_4)$alkanoyl, $(C_1-C_4)$alkoxycarbonyl, $(C_1-C_4)$alkanoyloxy, aryl, and heteroaryl, wherein any $(C_1-C_4)$alkyl, $(C_3-C_8)$cycloalkyl, $(C_2-C_4)$alkenyl, $(C_2-C_4)$alkynyl, $(C_1-C_4)$alkoxy, $(C_1-C_4)$alkanoyl, $(C_1-C_4)$alkoxycarbonyl, and $(C_1-C_4)$alkanoyloxy is optionally substituted with one or more groups independently selected from the group consisting of halo, deuterium, hydroxy, $(C_3-C_{15})$carbocycle, $(C_1-C_4)$alkoxy, $(C_1-C_4)$alkoxycarbonyl, $(C_1-C_4)$alkanoyloxy, oxo (=O), aryl, and heteroaryl, and wherein any aryl and heteroaryl is optionally substituted with one or more groups independently selected from the group consisting of halo, deuterium, nitro, cyano, carboxy, $(C_1-C_4)$alkyl, $(C_2-C_4)$alkenyl, $(C_2-C_4)$alkynyl, $(C_3-C_{15})$carbocycle, $-NR^cR^d$, $-C(=O)NR^cR^d$, $(C_1-C_4)$alkoxycarbonyl, $(C_1-C_4)$haloalkyl, aryl, heteroaryl, and $R^eO-$; or $R^a$ and $R^b$ together with the nitrogen to which they are attached form an azetidinyl, morpholino, piperazino, pyrrolidino or piperidino, wherein any a azetidinyl, morpholino, piperazino, pyrrolidino, 1,1-(dioxido)thiomorpholino and piperidino is optionally substituted with one or more groups independently selected from halo, oxo, and $(C_1-C_4)$alkyl;

each $R^c$ and $R^d$ is independently selected from the group consisting of H, $(C_1-C_4)$alkyl, $(C_3-C_8)$cycloalkyl, $(C_2-C_4)$alkenyl, $(C_2-C_4)$alkynyl, and $(C_1-C_4)$alkoxy, wherein any $(C_1-C_4)$alkyl, $(C_3-C_8)$cycloalkyl, $(C_2-C_4)$alkenyl, $(C_2-C_4)$alkynyl, $(C_1-C_4)$alkoxy, $(C_1-C_4)$alkanoyl, $(C_1-C_4)$alkoxycarbonyl, and $(C_1-C_4)$alkanoyloxy is optionally substituted with one or more groups independently selected from the group consisting of halo, hydroxy, deuterium, $(C_3-C_{15})$carbocycle, $(C_1-C_4)$alkoxy, $(C_1-C_4)$alkoxycarbonyl, $(C_1-C_4)$alkanoyloxy, and oxo (=O); or $R^c$ and $R^d$ together with the nitrogen to which they are attached form a morpholino, piperazino, pyrrolidino or piperidino;

$R^e$ is selected from the group consisting of H, $(C_1-C_4)$alkyl, $(C_3-C_8)$cycloalkyl, $(C_2-C_4)$alkenyl, $(C_2-C_4)$alkynyl, aryl, and $(C_1-C_4)$alkanoyl, wherein any $(C_1-C_4)$alkyl, $(C_3-C_8)$cycloalkyl, $(C_2-C_4)$alkenyl, $(C_2-C_4)$alkynyl, and $(C_1-C_4)$alkanoyl is optionally substituted with one or more groups independently selected from halo and aryl, and wherein any aryl is optionally substituted with one or more groups independently selected from halo deuterium, nitro, cyano, hydroxy, carboxy, $(C_1-C_4)$alkyl, $(C_1-C_4)$alkoxy, $(C_1-C_4)$alkoxycarbonyl, and $(C_1-C_4)$alkanoyloxy; and $R^x$ is $(C_1-C_4)$alkyl that is substituted with one or more (e.g. 1, 2, 3, or 4) groups independently selected from oxo, carboxy, $(C_1-C_4)$alkoxycarbonyl, and amino;

or a salt thereof.

The invention also provides a pharmaceutical composition comprising a compound of formula (I) or a pharmaceutically acceptable salt thereof, and a pharmaceutically acceptable diluent or carrier.

The invention also provides a method for inhibiting the activity of SIRT2 in vitro or in vivo comprising contacting the SIRT2 with a compound of formula (I) or a salt thereof.

The invention also provides a method for inhibiting the activity of SIRT2 in an animal comprising administering to the animal a compound of formula (I) or a pharmaceutically acceptable salt thereof.

The invention also provides a method for treating Parkinson's disease in an animal comprising administering to the animal a compound of formula (I) or a pharmaceutically acceptable salt thereof.

The invention also provides a method for treating neurodegeneration in an animal comprising administering to the animal a compound of formula (I) or a pharmaceutically acceptable salt thereof.

The invention also provides a method for treating a neurodegenerative disease in an animal comprising administering to the animal a compound of formula (I) or a pharmaceutically acceptable salt thereof.

The invention also provides a method for promoting neuroprotection in an animal comprising administering to the animal a compound of formula (I) or a pharmaceutically acceptable salt thereof.

The invention also provides a method for treating Alzheimer's disease (AD) or frontotemporal dementia in an animal comprising administering to the animal a compound of formula (I) or a pharmaceutically acceptable salt thereof.

The invention also provides a method for treating a bacterial infection in an animal comprising administering to the animal a compound of formula (I) or a pharmaceutically acceptable salt thereof.

The invention also provides a method for treating cancer in an animal comprising administering to the animal a compound of formula (I) or a pharmaceutically acceptable salt thereof.

The invention also provides a method for treating kidney disease in an animal comprising administering to the animal a compound of formula (I) or a pharmaceutically acceptable salt thereof.

The invention also provides a compound of formula (I) or a pharmaceutically acceptable salt thereof for use in medical therapy.

The invention also provides a compound of formula (I) or a pharmaceutically acceptable salt thereof for the prophylactic or therapeutic treatment of a SIRT2 associated disorder.

The invention also provides a compound of formula (I) or a pharmaceutically acceptable salt thereof for the prophylactic or therapeutic treatment of Parkinson's.

The invention also provides a compound of formula (I) or a pharmaceutically acceptable salt thereof for the prophylactic or therapeutic treatment of neurodegeneration.

The invention also provides a compound of formula (I) or a pharmaceutically acceptable salt thereof for the prophylactic or therapeutic treatment of a neurodegenerative disease.

The invention also provides a compound of formula (I) or a pharmaceutically acceptable salt thereof for promoting neuroprotection.

The invention also provides a compound of formula (I) or a pharmaceutically acceptable salt thereof for the prophylactic or therapeutic treatment of Alzheimer's disease (AD) or frontotemporal dementia.

The invention also provides a compound of formula (I) or a pharmaceutically acceptable salt thereof for the prophylactic or therapeutic treatment of a bacterial infection.

The invention also provides a compound of formula (I) or a pharmaceutically acceptable salt thereof for the prophylactic or therapeutic treatment of kidney disease.

The invention also provides a compound of formula (I) or a pharmaceutically acceptable salt thereof for the prophylactic or therapeutic treatment of cancer.

The invention also provides the use of a compound of formula (I) or a pharmaceutically acceptable salt thereof to prepare a medicament for inhibiting the activity of SIRT2 in an animal.

The invention also provides the use of a compound of formula (I) or a pharmaceutically acceptable salt thereof as described in any one of claims 1-13 to prepare a medicament for treating Parkinson's disease in an animal.

The invention also provides the use of a compound of formula (I) or a pharmaceutically acceptable salt thereof to prepare a medicament for treating neurodegeneration in an animal.

The invention also provides the use of a compound of formula (I) or a pharmaceutically acceptable salt thereof to prepare a medicament for treating a neurodegenerative disease in an animal.

The invention also provides the use of a compound of formula (I) or a pharmaceutically acceptable salt thereof to prepare a medicament for promoting neuroprotection in an animal.

The invention also provides the use of a compound of formula (I) or a pharmaceutically acceptable salt thereof to prepare a medicament for treating Alzheimer's disease (AD) or frontotemporal dementia in an animal.

The invention also provides the use of a compound of formula (I) or a pharmaceutically acceptable salt thereof to prepare a medicament for treating a bacterial infection in an animal.

The invention also provides the use of a compound of formula (I) or a pharmaceutically acceptable salt thereof to prepare a medicament for treating cancer in an animal.

The invention also provides the use of a compound of formula (I) or a pharmaceutically acceptable salt thereof to prepare a medicament for treating kidney disease in an animal.

The invention also provides processes and intermediates disclosed herein that are useful for preparing a compound of formula I or a salt thereof.

DETAILED DESCRIPTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic ring of about eight to ten ring atoms comprising one to four heteroatoms each selected from the group consisting of non-peroxide oxygen, sulfur, and N(X).

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e., ($C_3$-$C_7$)carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). In one embodiment the term carbocycle includes a 3-15 membered carbocycle. In one embodiment the term carbocycle includes a 3-8 membered carbocycle. In one embodiment the term carbocycle includes a 3-6 membered carbocycle. In one embodiment the term carbocycle includes a 3-5 membered carbocycle.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_3-C_8)$cycloalkyl can be cyclopropyl, cyclobutyl, cyclopentyl, cyclohexyl, cycloheptyl, or cyclooctyl; $(C_3-C_8)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The invention also provides a compound of formula (Ia):

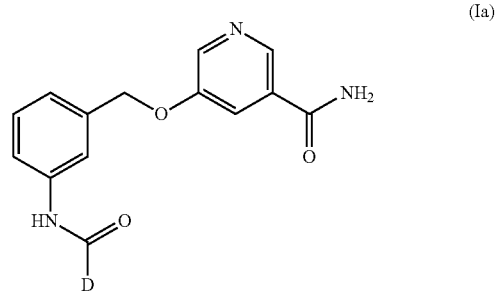 [SMILES: [2H]C(=O)Nc1cccc(COc2cncc(C(N)=O)c2)c1]

or a salt thereof.

The invention also provides a compound of formula (Ib):

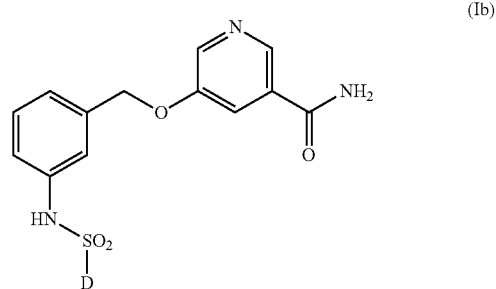

or a salt thereof.

The invention also provides a compound of formula (Ic):

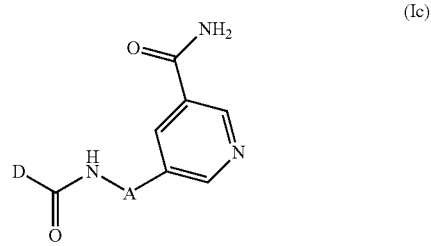

or a salt thereof.

The invention also provides a compound of formula (Id):

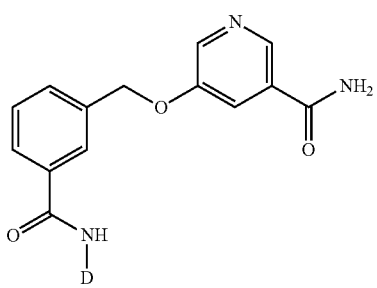

(Id)

or a salt thereof.

The invention also provides a compound of formula (Ie):

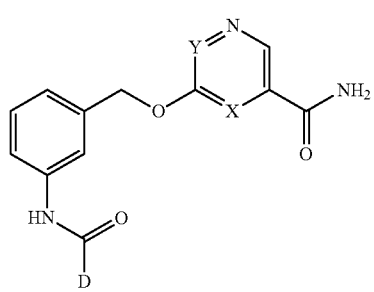

(Ie)

wherein: X is CH and Y is N; or X is N and Y is CH; or X is N and Y is N; or a salt thereof.

The invention also provides a compound of formula (I), wherein:
A is -A'-B'—;
A' is selected from the group consisting of:

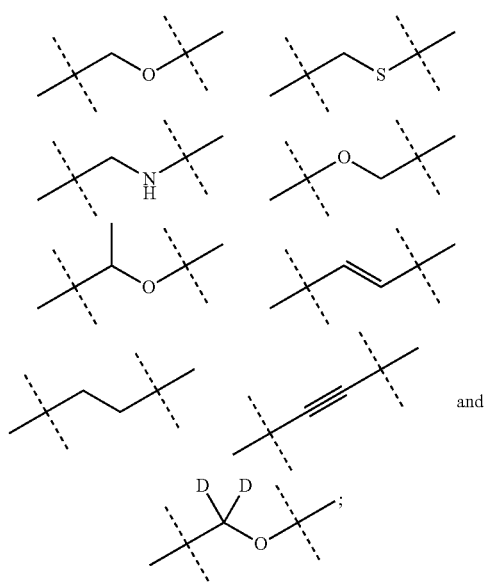

and

B' is phenyl wherein A' and C are attached to B' in a meta-orientation, and the phenyl is substituted with one or more groups independently selected from F, Cl, deuterium, methyl, trifluoromethyl, methoxy, and trifluoromethoxy; or a salt thereof.

The invention also provides a compound of formula (If):

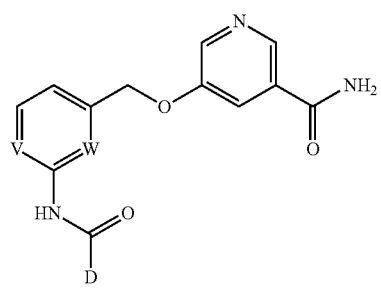

(If)

wherein: V is CH and W is N; or V is N and W is CH; or V is N and W is N; or a salt thereof.

The invention also provides a compound of formula (Ig):

(Ig)

wherein: R is selected from F, Cl, deuterium, methyl, trifluoromethyl, methoxy, and trifluoromethoxy; or a salt thereof.

The invention also provides a compound of formula (Ih):

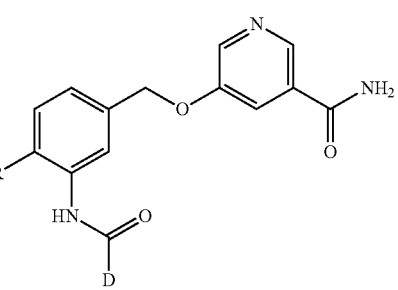

(Ih)

wherein: R is selected from F, Cl, deuterium, methyl, trifluoromethyl, methoxy, and trifluoromethoxy; or a salt thereof.

The invention also provides a compound of formula (Ii):

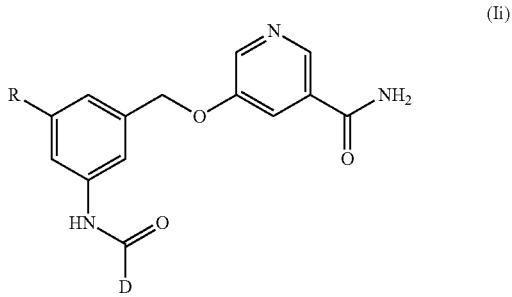

wherein: R is selected from F, Cl, deuterium, methyl, trifluoromethyl, methoxy, and trifluoromethoxy; or a salt thereof.

The invention also provides a compound of formula (I), wherein D is selected from the group consisting of methyl, ethyl, vinyl, naphthyl, cyclohexyl, adamantly, cyclohex-1-enyl, thienyl, benzothienyl, benzofuranyl, indolyl, benzothiazolyl, indazolyl, phenyl, pyridyl, pyrimidinyl, pyridazinyl, and pirazinyl, wherein D is optionally substituted with one or more groups $R^z$ independently selected from halo, deuterium, nitro, hydroxy, cyano, —$NR^aR^b$, —N—$S(O)_2R^a$, —$NR^aC(=O)NR^aR^b$, $(C_1-C_4)$alkyl, $(C_2-C_4)$alkenyl, $(C_2-C_4)$alkynyl, $(C_1-C_4)$alkoxy, $(C_1-C_4)$alkanoyl, $(C_1-C_4)$alkoxycarbonyl, $(C_1-C_4)$alkanoyloxy, aryl, aryloxy, and heteroaryl, wherein any $(C_1-C_4)$alkyl, $(C_2-C_4)$alkenyl, $(C_2-C_4)$alkynyl, $(C_1-C_4)$alkoxy, $(C_1-C_4)$alkanoyl, $(C_1-C_4)$alkoxycarbonyl, and $(C_1-C_4)$alkanoyloxy of $R^z$ is optionally substituted with one or more groups independently selected from the group consisting of halo, hydroxy, deuterium, —$NR^aR^b$, $(C_1-C_4)$alkoxy, $(C_1-C_4)$alkoxycarbonyl, $(C_1-C_4)$alkanoyloxy, aryl, and heteroaryl, wherein any aryl, and heteroaryl, of $R^z$ is optionally substituted with one or more groups independently selected from the group consisting of halo, deuterium, halo, nitro, cyano, hydroxy, —$NR^aR^b$, $(C_1-C_4)$alkyl, $(C_2-C_4)$alkenyl, $(C_2-C_4)$alkynyl, $(C_1-C_4)$alkoxy, $(C_1-C_4)$alkoxycarbonyl, $(C_1-C_4)$alkanoyloxy, $(C_1-C_4)$haloalkyl, and $(C_1-C_4)$haloalkoxy; or a salt thereof.

The invention also provides a compound of formula (I), wherein D is selected from the group consisting of naphthyl, cyclohexyl, adamantly, cyclohex-1-enyl, thienyl, benzothienyl, benzofuranyl, indolyl, benzothiazolyl, indazolyl, phenyl, pyridyl, pyrimidinyl, pyridazinyl, and pirazinyl, wherein D is optionally substituted with one or more groups $R^z$ independently selected from halo, deuterium, nitro, hydroxy, cyano, —$NR^aR^b$, —N—$S(O)_2R^a$, —$NR^aC(=O)NR^aR^b$, $(C_1-C_4)$alkyl, $(C_2-C_4)$alkenyl, $(C_2-C_4)$alkynyl, $(C_1-C_4)$alkoxy, $(C_1-C_4)$alkanoyl, $(C_1-C_4)$alkoxycarbonyl, $(C_1-C_4)$alkanoyloxy, aryl, aryloxy, and heteroaryl, wherein any $(C_1-C_4)$alkyl, $(C_2-C_4)$alkenyl, $(C_2-C_4)$alkynyl, $(C_1-C_4)$alkoxy, $(C_1-C_4)$alkanoyl, $(C_1-C_4)$alkoxycarbonyl, and $(C_1-C_4)$alkanoyloxy of $R^z$ is optionally substituted with one or more groups independently selected from the group consisting of halo, hydroxy, deuterium, —$NR^aR^b$, $(C_1-C_4)$alkoxy, $(C_1-C_4)$alkoxycarbonyl, $(C_1-C_4)$alkanoyloxy, aryl, and heteroaryl, wherein any aryl, and heteroaryl, of $R^z$ is optionally substituted with one or more groups independently selected from the group consisting of halo, deuterium, halo, nitro, cyano, hydroxy, —$NR^aR^b$, $(C_1-C_4)$alkyl, $(C_2-C_4)$alkenyl, $(C_2-C_4)$alkynyl, $(C_1-C_4)$alkoxy, $(C_1-C_4)$alkoxycarbonyl, $(C_1-C_4)$alkanoyloxy, $(C_1-C_4)$haloalkyl, and $(C_1-C_4)$haloalkoxy; or a salt thereof.

The invention also provides a compound of formula (I), wherein D is substituted with —$NR^aR^b$; or a salt thereof.

The invention also provides a compound of formula (I), wherein $R^a$ is $(C_1-C_4)$alkanoyl, that is optionally substituted with one or more groups independently selected from the group consisting of halo, deuterium, $(C_3-C_{15})$carbocycle, $(C_1-C_4)$alkoxy, $(C_1-C_4)$alkoxycarbonyl, $(C_1-C_4)$alkanoyloxy, oxo (=O), aryl, and heteroaryl, and wherein any aryl and heteroaryl is optionally substituted with one or more groups independently selected from the group consisting of halo, deuterium, nitro, cyano, carboxy, $(C_1-C_4)$alkyl, $(C_2-C_4)$alkenyl, $(C_2-C_4)$alkynyl, $(C_3-C_{15})$carbocycle, —C(=O)$NR^cR^d$, $(C_1-C_4)$alkoxycarbonyl, $(C_1-C_4)$haloalkyl, aryl, heteroaryl, and $R^eO$—; or a salt thereof.

The invention also provides a compound of formula (I), wherein $R^a$ and $R^b$ together with the nitrogen to which they are attached form an azetidinyl, morpholino, piperazino, pyrrolidino or piperidino, wherein any a azetidinyl, morpholino, piperazino, pyrrolidino and piperidino is optionally substituted with one or more groups independently selected from halo and $(C_1-C_4)$alkyl; or a salt thereof.

The invention also provides a compound of formula (I):

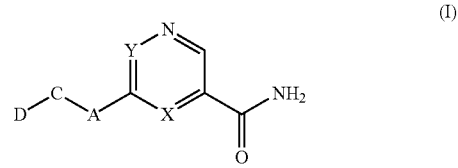

wherein:
X is CH or N;
Y is CH or N;
A is selected from the group consisting of: -A'-B'—,

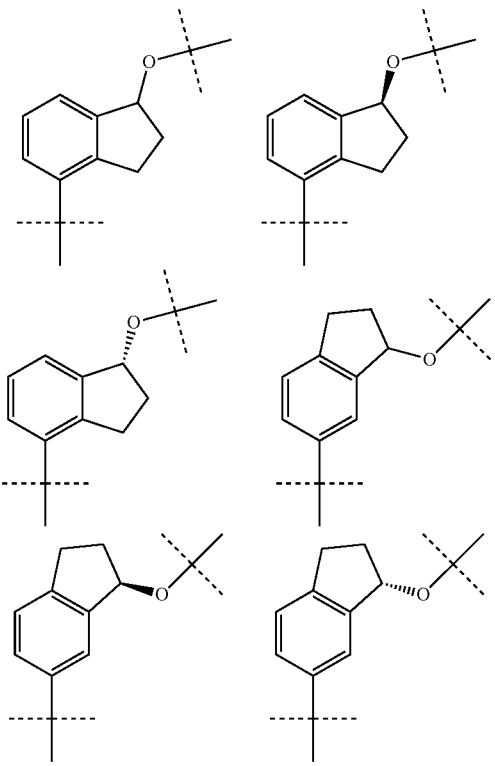

-continued

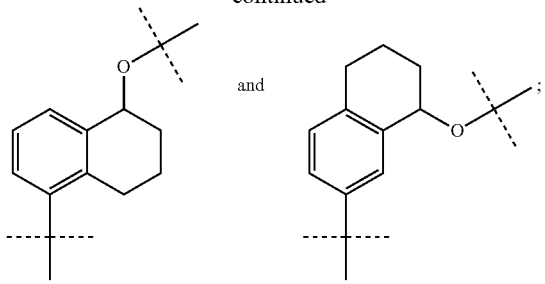

and

A' is selected from the group consisting of:

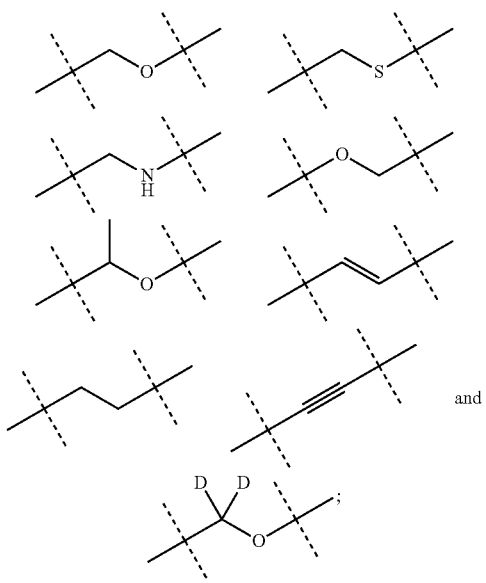

and

B' is phenyl, a 5-membered heteroaryl, or a 6-membered heteroaryl, wherein A' and C are attached to B' in a meta-orientation, and the phenyl, 5-membered heteroaryl, and 6-membered heteroaryl are optionally substituted with one or more groups independently selected from F, Cl, deuterium, methyl, trifluoromethyl, methoxy, and trifluoromethoxy;

C is selected from the group consisting of:

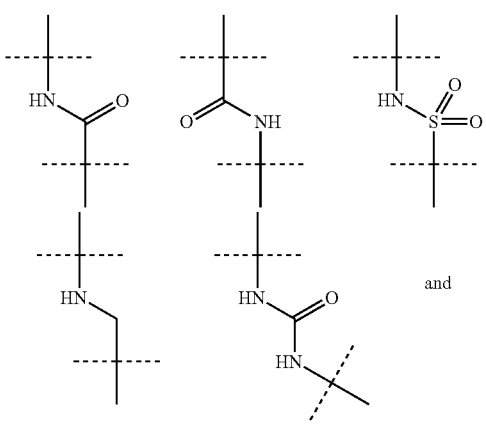

and

-continued

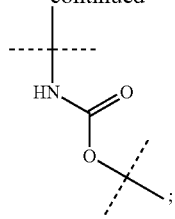

D is selected from the group consisting of $(C_1\text{-}C_6)$alkyl, $(C_2\text{-}C_6)$alkenyl, $(C_3\text{-}C_{15})$carbocycle, aryl, and heteroaryl, wherein the $(C_1\text{-}C_6)$alkyl, $(C_2\text{-}C_6)$alkenyl, $(C_3\text{-}C_{15})$carbocycle, aryl, and heteroaryl, are optionally substituted with one or more groups $R^z$ independently selected from halo, deuterium, nitro, hydroxy, cyano, carboxy, —$NR^aR^b$, —$C(=O)NR^aR^b$, —N—$S(O)_2R^a$, —$NR^aC(=O)NR^aR^b$, $(C_1\text{-}C_4)$alkyl, $(C_2\text{-}C_4)$alkenyl, $(C_2\text{-}C_4)$alkynyl, $(C_1\text{-}C_4)$alkoxy, $(C_1\text{-}C_4)$alkanoyl, $(C_1\text{-}C_4)$alkoxycarbonyl, $(C_1\text{-}C_4)$alkanoyloxy, $(C_3\text{-}C_{15})$carbocycle, aryl, aryloxy, and heteroaryl, wherein any $(C_1\text{-}C_4)$alkyl, $(C_2\text{-}C_4)$alkenyl, $(C_2\text{-}C_4)$alkynyl, $(C_1\text{-}C_4)$alkoxy, $(C_1\text{-}C_4)$alkanoyl, $(C_1\text{-}C_4)$alkoxycarbonyl, $(C_3\text{-}C_{15})$carbocycle, and $(C_1\text{-}C_4)$alkanoyloxy of $R^z$ is optionally substituted with one or more groups independently selected from the group consisting of halo, hydroxy, deuterium, —$NR^aR^b$, $(C_1\text{-}C_4)$alkoxy, $(C_1\text{-}C_4)$alkoxycarbonyl, $(C_1\text{-}C_4)$alkanoyloxy, aryl, and heteroaryl, wherein any aryl, and heteroaryl, of $R^z$ is optionally substituted with one or more groups independently selected from the group consisting of halo, deuterium, halo, nitro, cyano, hydroxy, —$NR^aR^b$, $(C_1\text{-}C_4)$alkyl, $(C_2\text{-}C_4)$alkenyl, $(C_2\text{-}C_4)$alkynyl, $(C_1\text{-}C_4)$alkoxy, $(C_1\text{-}C_4)$alkoxycarbonyl, $(C_1\text{-}C_4)$alkanoyloxy, $(C_1\text{-}C_4)$haloalkyl, and $(C_1\text{-}C_4)$haloalkoxy;

each $R^a$ and $R^b$ is independently selected from the group consisting of H, $(C_1\text{-}C_4)$alkyl, $(C_3\text{-}C_8)$cycloalkyl, $(C_2\text{-}C_4)$alkenyl, $(C_2\text{-}C_4)$alkynyl, $(C_1\text{-}C_4)$alkoxy, $(C_1\text{-}C_4)$alkanoyl, $(C_1\text{-}C_4)$alkoxycarbonyl, $(C_1\text{-}C_4)$alkanoyloxy, aryl, and heteroaryl, wherein any $(C_1\text{-}C_4)$alkyl, $(C_3\text{-}C_8)$cycloalkyl, $(C_2\text{-}C_4)$alkenyl, $(C_2\text{-}C_4)$alkynyl, $(C_1\text{-}C_4)$alkoxy, $(C_1\text{-}C_4)$alkanoyl, $(C_1\text{-}C_4)$alkoxycarbonyl, and $(C_1\text{-}C_4)$alkanoyloxy is optionally substituted with one or more groups independently selected from the group consisting of halo, deuterium, hydroxy, $(C_3\text{-}C_{15})$carbocycle, $(C_1\text{-}C_4)$alkoxy, $(C_1\text{-}C_4)$alkoxycarbonyl, $(C_1\text{-}C_4)$alkanoyloxy, oxo (=O), aryl, and heteroaryl, and wherein any aryl and heteroaryl is optionally substituted with one or more groups independently selected from the group consisting of halo, deuterium, nitro, cyano, carboxy, $(C_1\text{-}C_4)$alkyl, $(C_2\text{-}C_4)$alkenyl, $(C_2\text{-}C_4)$alkynyl, $(C_3\text{-}C_{15})$carbocycle, —$NR^cR^d$, —$C(=O)NR^cR^d$, $(C_1\text{-}C_4)$alkoxycarbonyl, $(C_1\text{-}C_4)$haloalkyl, aryl, heteroaryl, and $R^eO$—; or $R^a$ and $R^b$ together with the nitrogen to which they are attached form an azetidinyl, morpholino, piperazino, pyrrolidino or piperidino, wherein any a azetidinyl, morpholino, piperazino, pyrrolidino and piperidino is optionally substituted with one or more groups independently selected from halo and $(C_1\text{-}C_4)$alkyl;

each $R^c$ and $R^d$ is independently selected from the group consisting of H, $(C_1\text{-}C_4)$alkyl, $(C_3\text{-}C_8)$cycloalkyl, $(C_2\text{-}C_4)$alkenyl, $(C_2\text{-}C_4)$alkynyl, and $(C_1\text{-}C_4)$alkoxy, wherein any $(C_1\text{-}C_4)$alkyl, $(C_3\text{-}C_8)$cycloalkyl, $(C_2\text{-}C_4)$alkenyl, $(C_2\text{-}C_4)$alkynyl, $(C_1\text{-}C_4)$alkoxy, $(C_1\text{-}C_4)$alkanoyl, $(C_1\text{-}C_4)$alkoxycarbonyl, and $(C_1\text{-}C_4)$alkanoyloxy is optionally substituted with one or more groups independently selected from the group consisting of halo, hydroxy, deuterium, $(C_3\text{-}C_{15})$carbocycle, $(C_1\text{-}C_4)$ alkoxy, $(C_1-C_4)$alkoxycarbonyl, $(C_1-C_4)$alkanoyloxy, and oxo (=O); or W and $R^d$ together with the nitrogen to which they are attached form a morpholino, piperazino, pyrrolidino or piperidino; and $R^e$ is selected from the group consisting of H, $(C_1-C_4)$ alkyl, $(C_3-C_8)$cycloalkyl, $(C_2-C_4)$alkenyl, $(C_2-C_4)$alkynyl, aryl, and $(C_1-C_4)$alkanoyl, wherein any $(C_1-C_4)$alkyl, $(C_3-C_8)$cycloalkyl, $(C_2-C_4)$alkenyl, $(C_2-C_4)$alkynyl, and $(C_1-C_4)$ alkanoyl is optionally substituted with one or more groups independently selected from halo and aryl, and wherein any aryl is optionally substituted with one or more groups independently selected from halo deuterium, nitro, cyano, hydroxy, carboxy, $(C_1-C_4)$alkyl, $(C_1-C_4)$alkoxy, $(C_1-C_4)$ alkoxycarbonyl, and $(C_1-C_4)$alkanoyloxy;

or a salt thereof.

Processes for preparing compounds of formula I are provided as further embodiments of the invention and are illustrated by the procedures illustrated in the Examples below.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Example 1

Representative compounds of formula (I) can be prepared as described below.

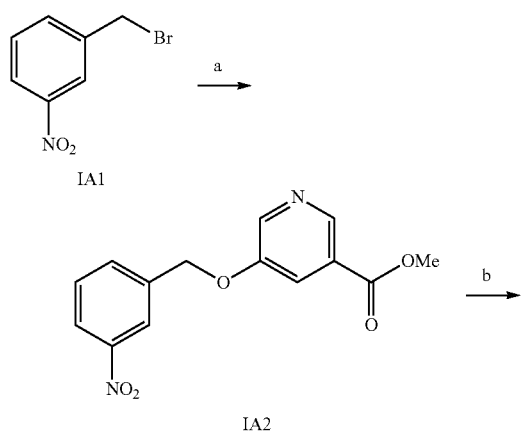

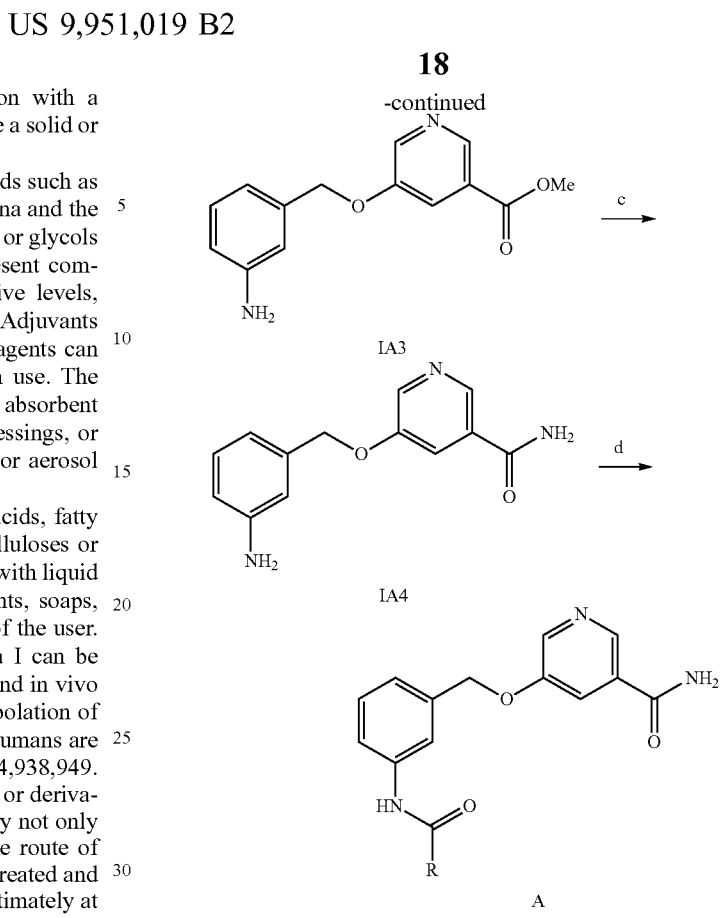

Methyl 5-((3-Nitrobenzyl)oxy)nicotinate (IA2)

To a solution of 3-nitrobenzyl bromide (IA1, 9.50 g, 44 mmol) in DMF (80 mL) were added methyl 5-hydroxynicotinate (6.12 g, 40 mmol) and $Cs_2CO_3$ (26.1 g, 80 mmol) and the mixture was allowed to stir at rt for 12 h. After water (200 ml) was added, the precipitate was filtered, washed with hexanes, and dried in vacuo to yield compound IA2 as a light yellow solid (8.64 g, 75%). $^1$H NMR (CDCl$_3$, 600 MHz) δ 8.89 (d, J=1.2 Hz, 1H), 8.58 (d, J=3.0 Hz, 1H), 8.35 (s, 1H), 8.24 (d, J=8.4 Hz, 1H), 7.87 (dd, J=3.0, 1.8, Hz, 1H), 7.79 (d, J=7.2 Hz, 1H), 6.61 (dd, J=7.8, 7.8 Hz, 1H), 5.25 (s, 2H), 3.97 (s, 3H). HRMS (ESI$^+$) calcd for $C_{14}H_{13}N_2O_5$ (M+H)$^+$ 289.0824, found 289.0820.

Methyl 5-((3-Aminobenzyl)oxy)nicotinate (IA3)

To a solution of compound IA2 (8.64 g, 30 mmol) and NiCl$_2$·6H$_2$O (14.3 g, 44 mmol) in MeOH (100 mL) was slowly added NaBH$_4$ (4.8 g, 120 mmol) and the mixture was allowed to stir at rt for 3 h. The reaction was quenched with saturated NH$_4$Cl (50 mL) and the mixture was extracted with EtOAc. The organic phase was washed with water and brine, dried over anhydrous K$_2$CO$_3$, and concentrated in vacuo. The residue was purified by flash column chromatography (EtOAc/hexanes) to afford compound IA3 as a light yellow solid (6.19 g, 80%). $^1$H NMR (CDCl$_3$, 600 MHz) δ 8.83 (d, J=1.8 Hz, 1H), 8.53 (d, J=3.0 Hz, 1H), 8.83 (dd, J=2.4, 1.8, Hz, 1H), 7.18 (d, J=7.8 Hz, 1H), 6.80 (d, J=7.8 Hz, 1H), 6.76 (s, 1H), 6.66 (dd, J=7.8, 1.8 Hz, 1H), 5.30 (s, 2H), 5.06 (s, 2H), 3.95 (s, 3H). HRMS (ESI$^+$) calcd for $C_{14}H_{15}N_2O_3$ (M+H)$^+$ 259.1083, found 259.1080.

5-((3-Aminobenzyl)oxy)nicotinamide (IA4)

A solution of methyl ester IA3 (6.19 g, 24 mmol) and CaCl$_2$ (2.66 g, 24 mmol) in NH$_3$/MeOH (ca. 7 N, 20 mL) in a seal tube was heated at 70° C. for 24 h. After the solvent was evaporated in vacuo, the residue was dissolved in EtOAc (150 mL) and the resulting solution was washed with H$_2$O (150 mL) and brine (100 mL). After the organic layer was dried over Na$_2$SO$_4$ and filtered, the filtrate was concentrated and the residue was purified by flash column chromatography (5% MeOH/CH$_2$Cl$_2$) to afford compound IA4 as a light yellow solid (5.25 g, 90%). $^1$H NMR (DMSO-d$_6$, 600 MHz) δ 8.63 (s, 1H), 8.44 (d, J=3.0 Hz, 1H), 8.12 (s, 1H), 7.81 (s, 1H), 7.60 (s, 1H), 7.02 (dd, J=7.5, 7.5 Hz, 1H), 6.63 (s, 1H), 6.57 (d, J=7.8 Hz, 1H), 6.52 (d, J=7.8 Hz, 1H), 5.13 (s, 2H), 5.07 (s, 2H). HRMS (ESI$^+$) calcd for C$_{13}$H$_{14}$N$_3$O$_2$ (M+H)$^+$ 244.1081, found 244.1082.

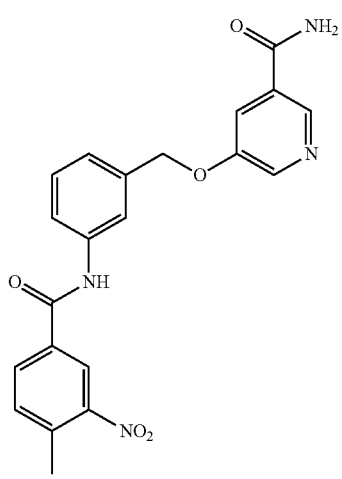 [SMILES: Cc1ccc(C(=O)Nc2cccc(COc3cncc(C(N)=O)c3)c2)cc1[N+](=O)[O-]]

5-((3-(4-Methyl-3-nitrobenzamido)benzyl)oxy)nicotinamide (A-1)

To a solution of amine IA4 (52 mg, 0.21 mmol) and DIPEA (80 µL, 0.46 mmol) in anhydrous CH$_2$Cl$_2$ (5 mL) and DMF (1 mL) was added 4-methyl-3-nitrobenzoyl chloride (50 µL, 0.34 mmol) and the mixture was allowed to stir at rt for 24 h. After the solvents were removed, the residue was diluted with EtOAc (30 mL), H$_2$O (10 mL) and saturated NaHCO$_3$ (10 mL). After separation, the organic layer was washed with brine (20 mL) and concentrated. The residue was purified by flash column chromatography to give compound A-1 as a white solid (51 mg, 59%). $^1$H NMR (DMSO-d$_6$, 600 MHz) δ 10.54 (s, 1H), 8.65 (s, 1H), 8.58 (s, 1H), 8.50 (d, J=3.0 Hz, 1H), 8.22 (d, J=7.8 Hz, 1H), 8.14 (s, 1H), 7.91 (s, 1H), 7.86 (s, 1H), 7.77 (d, J=7.8 Hz, 1H), 7.68 (d, J=7.8 Hz, 1H), 7.62 (s, 1H), 7.41 (dd, J=7.8, 7.8 Hz, 1H), 7.24 (d, J=7.2 Hz, 1H), 5.26 (s, 2H), 2.60 (s, 3H). HRMS (ESI$^+$) calcd for C$_{21}$H$_{19}$N$_4$O$_5$ (M+H)$^+$ 407.1350, found 407.1353.

The following compounds were prepared through an amide formation reaction in a manner similar to that described for compound A-1.

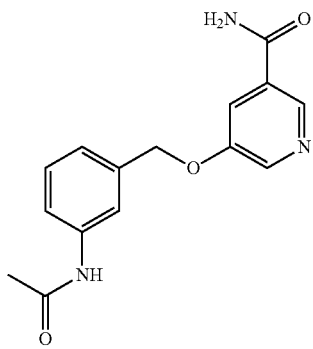 [SMILES: CC(=O)Nc1cccc(COc2cncc(C(N)=O)c2)c1]

5-((3-Acetamidobenzyl)oxy)nicotinamide (A-2)

White solid (60 mg, 88%). $^1$H NMR (DMSO-d$_6$, 600 MHz) δ 9.99 (s, 1H), 8.64 (s, 1H), 8.47 (d, J=3.0 Hz, 1H), 8.13 (s, 1H), 7.84-7.82 (m, 1H), 7.70 (s, 1H), 7.61 (s, 1H), 7.54 (d, J=8.1 Hz, 1H), 7.31 (dd, J=7.8, 7.8 Hz, 1H), 7.13 (d, J=7.6 Hz, 1H), 5.20 (s, 2H), 2.03 (s, 3H). HRMS (ESI$^+$) calcd for C$_{15}$H$_{16}$N$_3$O$_3$ (M+H)$^+$ 286.1186, found 286.1191.

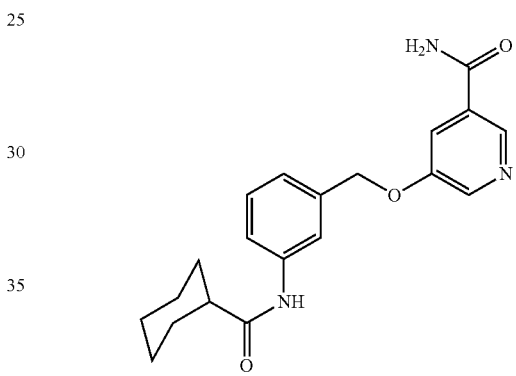

5-((3-(Cyclohexanecarboxamido)benzyl)oxy)nicotinamide (A-3)

White solid (52 mg, 62%). $^1$H NMR (DMSO-d$_6$, 600 MHz) δ 9.85 (s, 1H), 8.64 (d, J=1.2 Hz, 1H), 8.47 (d, J=2.4 Hz, 1H), 8.13 (s, 1H), 7.84-7.83 (m, 1H), 7.75 (s, 1H), 7.61 (s, 1H), 7.55 (d, J=8.2 Hz, 1H), 7.30 (dd, J=7.8, 7.8 Hz, 1H), 7.11 (d, J=7.5 Hz, 1H), 5.20 (s, 2H), 2.34-2.29 (m, 1H), 1.80-1.73 (m, 4H), 1.64 (d, J=12.3 Hz, 1H), 1.43-1.37 (m, 2H), 1.29-1.16 (m, 3H). HRMS (ESI$^+$) calcd for C$_{20}$H$_{24}$N$_3$O$_3$ (M+H)$^+$ 354.1812, found 354.1818.

5-((3-((3R,5R,7R)-Adamantane-1-carboxamido)benzyl)oxy)nicotinamide (A-4)

White solid (40 mg, 41%). $^1$H NMR (DMSO-d$_6$, 600 MHz) δ 9.18 (s, 1H), 8.64 (s, 1H), 8.48 (d, J=3.0 Hz, 1H), 8.13 (s, 1H), 7.83 (s, 1H), 7.80 (s, 1H), 7.64-7.60 (m, 2H), 7.30 (dd, J=7.9, 7.9 Hz, 1H), 7.13 (d, J=7.5 Hz, 1H), 5.19 (s, 2H), 2.03-1.99 (m, 3H), 1.92-1.88 (m, 6H), 1.72-1.68 (m, 6H). HRMS (ESI$^+$) calcd for C$_{24}$H$_{28}$N$_3$O$_3$ (M+H)$^+$ 406.2125, found 406.2132.

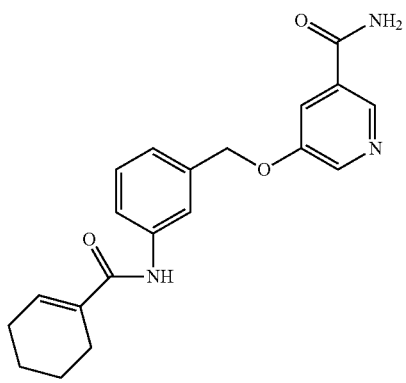 [SMILES: NC(=O)c1cncc(OCc2cccc(NC(=O)C3=CCCCC3)c2)c1]

5-((3-(Cyclohex-1-enecarboxamido)benzyl)oxy)nicotinamide (A-5)

White solid (120 mg, 84%). $^1$H NMR (DMSO-d$_6$, 600 MHz) δ 9.65 (s, 1H), 8.64 (s, 1H), 8.47 (d, J=3.0 Hz, 1H), 8.14 (s, 1H), 7.85-7.82 (m, 1H), 7.81 (s, 1H), 7.65-7.57 (m, 2H), 7.32 (dd, J=8.1, 8.1 Hz, 1H), 7.14 (dd, J=7.8, 7.8 Hz, 1H), 6.65 (s, 1H), 5.20 (s, 2H), 2.27-2.22 (m, 2H), 2.20-2.14 (m, 2H), 1.66-1.60 (m, 2H), 1.60-1.54 (m, 2H). HRMS (ESI$^+$) calcd for C$_{20}$H$_{22}$N$_3$O$_3$ (M+H)$^+$ 352.1656, found 352.1669.

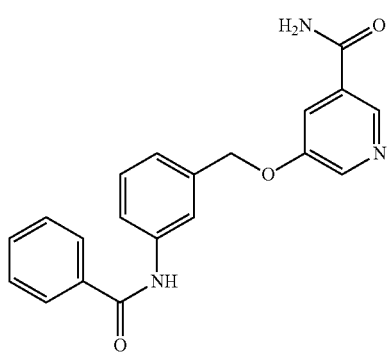 [SMILES: NC(=O)c1cncc(OCc2cccc(NC(=O)c3ccccc3)c2)c1]

5-((3-Benzamidobenzyl)oxy)nicotinamide (A-6)

White solid (22 mg, 30%). $^1$H NMR (DMSO-d$_6$, 600 MHz) δ 10.32 (s, 1H), 8.65 (d, J=1.8 Hz, 1H), 8.49 (d, J=3.0 Hz, 1H), 8.15 (s, 1H), 7.96 (d, J=7.3 Hz, 2H), 7.93 (s, 1H), 7.88-7.86 (m, 1H), 7.76 (d, J=8.4 Hz, 1H), 7.63-7.58 (m, 2H), 7.52 (dd, J=7.8, 7.8 Hz, 2H), 7.39 (dd, J=7.9, 7.9 Hz, 1H), 7.21 (d, J=7.3 Hz, 2H), 5.25 (s, 2H). HRMS (ESI$^+$) calcd for C$_{20}$H$_{18}$N$_3$O$_3$ (M+H)$^+$ 348.1343, found 348.1350.

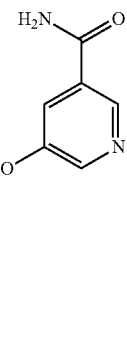

5-((3-(Thiophene-2-carboxamido)benzyl)oxy)nicotinamide (A-7)

White solid (40 mg, 54%). $^1$H NMR (DMSO-d$_6$, 600 MHz) δ 10.29 (s, 1H), 8.65 (s, 1H), 8.49 (d, J=2.4 Hz, 1H), 8.14 (s, 1H), 8.04 (d, J=3.7 Hz, 1H), 7.88-7.84 (m, 3H), 7.72 (d, J=8.1 Hz, 1H), 7.61 (s, 1H), 7.39 (dd, J=7.9, 7.9 Hz, 1H), 7.24-7.20 (m, 2H), 5.25 (s, 2H). HRMS (ESI$^+$) calcd for C$_{18}$H$_{16}$N$_3$O$_3$S (M+H)$^+$ 354.0907, found 354.0913.

5-((3-(2-Phenylacetamido)benzyl)oxy)nicotinamide (A-8)

Yellow solid (41 mg, 54%). $^1$H NMR (DMSO-d$_6$, 600 MHz) δ 10.26 (s, 1H), 8.64 (s, 1H), 8.47 (d, J=2.8 Hz, 1H), 8.13 (s, 1H), 7.84-7.82 (m, 1H), 7.73 (s, 1H), 7.60 (s, 1H), 7.57 (d, J=7.8 Hz, 1H), 7.35-7.30 (m, 5H), 7.26-7.22 (m, 1H), 7.14 (d, J=7.6 Hz, 1H), 5.20 (s, 2H), 3.63 (s, 2H). HRMS (ESI$^+$) calcd for C$_{21}$H$_{20}$N$_3$O$_3$ (M+H)$^+$ 362.1499, found 362.1510.

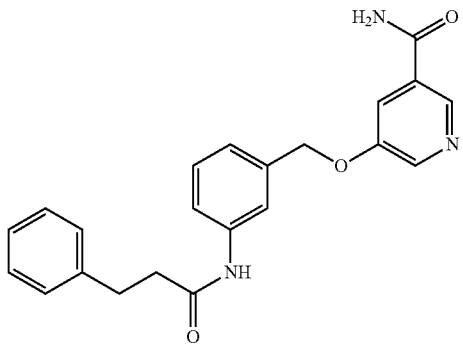 [SMILES: NC(=O)c1cncc(OCc2cccc(NC(=O)CCc3ccccc3)c2)c1]

5-((3-(3-Phenylpropanamido)benzyl)oxy)nicotinamide (A-9)

Yellow solid (47 mg, 60%). $^1$H NMR (DMSO-d$_6$, 600 MHz) δ 9.97 (s, 1H), 8.65 (d, J=1.6 Hz, 1H), 8.47 (d, J=2.8 Hz, 1H), 8.13 (s, 1H), 7.84 (dd, J=2.6, 1.8 Hz, 1H), 7.71 (s, 1H), 7.61 (s, 1H), 7.54 (d, J=8.2 Hz, 1H), 7.33-7.21 (m, 5H), 7.18 (dd, J=7.2, 7.2 Hz, 1H), 7.13 (d, J=7.6 Hz, 1H), 5.21 (s, 2H), 3.91 (t, J=7.5 Hz, 2H), 2.62 (t, J=8.1 Hz, 2H). HRMS (ESI$^+$) calcd for C$_{22}$H$_{22}$N$_3$O$_3$ (M+H)$^+$ 376.1656, found 376.1661.

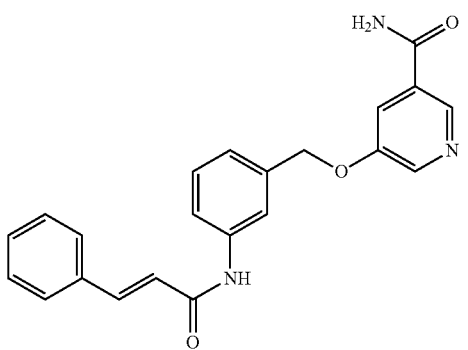 [SMILES: NC(=O)c1cncc(OCc2cccc(NC(=O)/C=C/c3ccccc3)c2)c1]

(E)-5-((3-Cinnamamidobenzyl)oxy)nicotinamide (A-10)

White solid (35 mg, 45%). $^1$H NMR (DMSO-d$_6$, 600 MHz) δ 10.35 (s, 1H), 8.66 (d, J=1.0 Hz, 1H), 8.49 (d, J=2.8 Hz, 1H), 8.16 (s, 1H), 7.87 (s, 1H), 7.84 (s, 1H), 7.69 (d, J=8.8 Hz, 1H), 7.63-7.58 (m, 4H), 7.47-7.36 (m, 4H), 7.18 (d, J=7.6 Hz, 1H), 6.87 (d, J=15.7 Hz, 1H), 5.25 (s, 2H). HRMS (ESI$^+$) calcd for C$_{22}$H$_{20}$N$_3$O$_3$ (M+H)$^+$ 374.1499, found 374.1515.

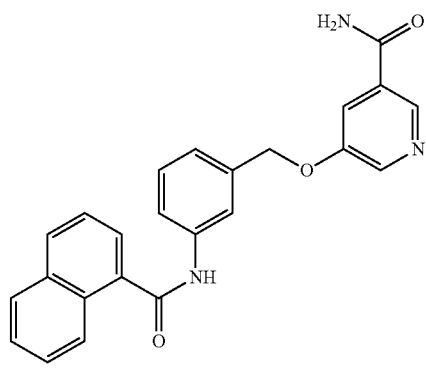 [SMILES: NC(=O)c1cncc(OCc2cccc(NC(=O)c3cccc4ccccc34)c2)c1]

5-((3-(1-Naphthamido)benzyl)oxy)nicotinamide (A-11)

White solid (16 mg, 17%). $^1$H NMR (DMSO-d$_6$, 600 MHz) δ 10.65 (s, 1H), 8.66 (s, 1H), 8.51 (s, 1H), 8.19 (d, J=7.8 Hz 1H), 8.15 (s, 1H), 8.08 (d, J=8.2 Hz, 1H), 8.03-8.00 (m, 2H), 7.88 (d, J=1.5 Hz, 1H), 7.76 (d, J=6.8 Hz, 2H), 7.63-7.58 (m, 4H), 7.42 (dd, J=7.8, 7.8 Hz, 1H), 7.24 (d, J=7.5 Hz, 1H), 5.27 (s, 2H). HRMS (ESI$^+$) calcd for C$_{24}$H$_{20}$N$_3$O$_3$ (M+H)$^+$ 398.1499, found 398.1503.

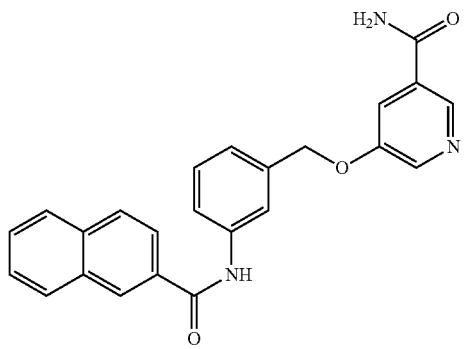 [SMILES: NC(=O)c1cncc(OCc2cccc(NC(=O)c3ccc4ccccc4c3)c2)c1]

5-((3-(2-Naphthamido)benzyl)oxy)nicotinamide (A-12)

White solid (60 mg, 63%). $^1$H NMR (DMSO-d$_6$, 600 MHz) δ 10.50 (s, 1H), 8.66 (s, 1H), 8.59 (s, 1H), 8.51 (d, J=2.6 Hz, 1H), 8.14 (s, 1H), 8.09 (d, J=7.6 Hz, 1H), 8.07-8.00 (m, 3H), 7.97 (s, 1H), 7.87 (s, 1H), 7.82 (d, J=8.1 Hz, 1H), 7.66-7.61 (m, 3H), 7.41 (dd, J=7.6, 7.6 Hz, 1H), 7.24 (d, J=7.5 Hz, 1H), 5.27 (s, 2H). HRMS (ESI$^+$) calcd for C$_{24}$H$_{20}$N$_3$O$_3$ (M+H)$^+$ 398.1499, found 398.1507.

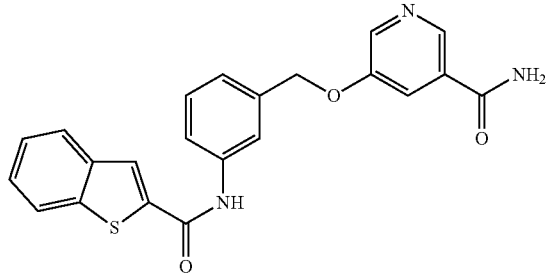

5-((3-(Benzo[b]thiophene-2-carboxamido)benzyl)oxy)nicotinamide (A-13)

Pale solid (48 mg, 57%). $^1$H NMR (DMSO-d$_6$, 600 MHz) δ 10.58 (s, 1H), 8.66 (s, 1H), 8.51 (d, J=3.0 Hz, 1H), 8.38 (s, 1H), 8.14, (s, 1H), 8.06 (d, J=8.4 Hz, 1H), 8.01 (d, J=7.2 Hz, 1H), 7.91 (s, 1H), 7.87 (s, 1H), 7.76 (d, J=9.6 Hz, 1H), 7.61 (s, 1H), 7.52-7.45 (m, 2H), 7.42 (dd, J=7.8, 7.8 Hz, 1H), 7.24 (d, J=7.2 Hz, 1H) 5.27 (s, 2H). HRMS (ESI$^+$) calcd for C$_{22}$H$_{18}$H$_3$O$_3$S (M+H)$^+$ 404.1069, found 404.1064.

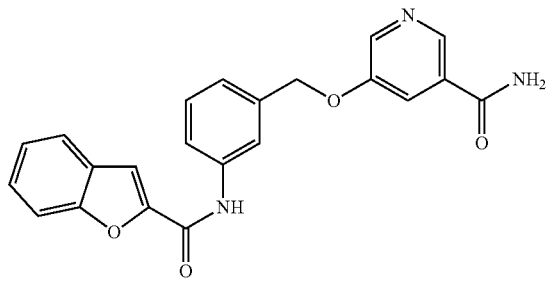 [SMILES: NC(=O)c1cncc(OCc2cccc(NC(=O)c3cc4ccccc4s3)c2)c1]

5-((3-(Benzofuran-2-carboxamido)benzyl)oxy)nicotinamide (A-14)

Yellowish solid (44 mg, 56%). $^1$H NMR (DMSO-$d_6$, 600 MHz) δ 10.59 (s, 1H), 8.67 (s, 1H), 8.51 (s, 1H), 8.15 (s, 1H), 7.96 (s, 1H), 7.87 (s, 1H), 7.83 (d, J=8.4 Hz, 1H), 7.81-7.77 (m, 2H), 7.72 (d, J=8.4 Hz, 1H), 7.62 (s, 1H), 7.51 (dd, J=7.8, 7.8 Hz, 1H), 7.42 (dd, J=7.5, 7.5 Hz, 1H), 7.37 (dd, J=7.5, 7.5 Hz, 1H), 7.24 (d, J=7.2 Hz, 1H), 5.27 (s, 2H). HRMS (ESI$^+$) calcd for $C_{22}H_{18}N_3O_4$ (M+H)$^+$ 388.1292, found 388.1295.

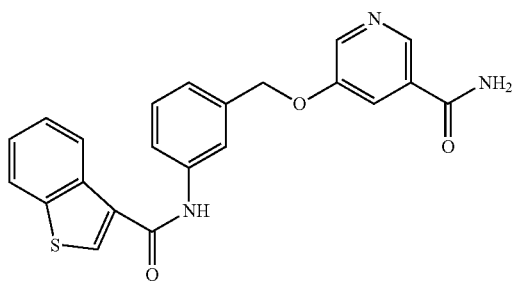

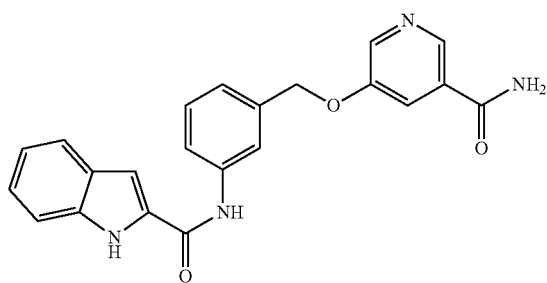 [SMILES: NC(=O)c1cncc(OCc2cccc(NC(=O)c3cc4ccccc4[nH]3)c2)c1]

N-(3-(((5-Carbamoylpyridin-3-yl)oxy)methyl)phenyl)-1H-indole-2-carboxamide (A-15)

Yellowish solid (33 mg, 42%). $^1$H NMR (DMSO-$d_6$, 600 MHz) δ 11.72 (s, 1H), 10.27 (s, 1H), 8.66 (s, 1H), 8.51 (d, J=3.0 Hz, 1H) 8.14 (s, 1H), 7.93 (s, 1H), 7.87 (s, 1H), 7.81 (d, J=9.6 Hz, 1H), 7.68 (d, J=7.8 Hz, 1H), 7.62 (s, 1H), 7.47 (d, J=7.8 Hz, 1H), 7.44-7.39 (m, 2H), 7.24-7.21 (m, 2H), 7.07 (dd, J=7.2, 7.2 Hz, 1H), 5.27 (s, 2H). HRMS (ESI$^+$) calcd for $C_{22}H_{19}H_4O_3$ (M+H)$^+$ 387.1457, found 387.1451.

5-((3-(Benzo[b]thiophene-3-carboxamido)benzyl)oxy)nicotinamide (A-17)

Yellowish solid (19 mg, 23%). $^1$H NMR (DMSO-$d_6$, 600 MHz) δ 10.41 (s, 1H), 8.66 (s, 1H), 8.57 (s, 1H), 8.51 (s, 1H), 8.42 (d, J=8.4 Hz, 1H), 8.14, (s, 1H), 8.08 (d, J=7.8 Hz, 1H), 7.93 (s, 1H), 7.87 (s, 1H), 7.76 (d, J=9.0 Hz, 1H), 7.61 (s, 1H), 7.50-7.43 (m, 2H), 7.41 (dd, J=7.5, 7.5 Hz, 1H), 7.22 (d, J=7.2 Hz, 1H) 5.27 (s, 2H). HRMS (ESI$^+$) calcd for $C_{22}H_{18}H_3O_3S$ (M+H)$^+$ 404.1069, found 404.1065.

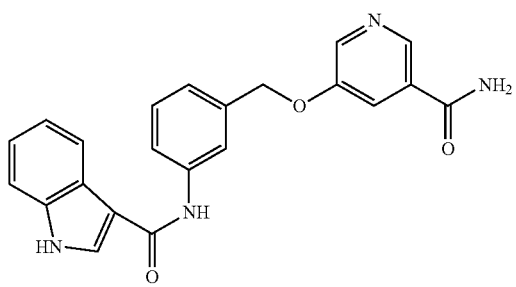

N-(3-(((5-Carbamoylpyridin-3-yl)oxy)methyl)phenyl)-1H-indole-3-carboxamide (A-18)

Brownish solid (4 mg, 5%) $^1$H NMR (CD$_3$OD, 600 MHz) δ 8.63 (s, 1H), 8.48 (s, 1H), 8.18 (d, J=7.8 Hz, 1H), 8.10 (s, 1H), 7.94 (s, 1H), 7.88-7.85 (m, 2H), 7.74 (d, J=8.4 Hz, 1H), 7.66 (d, J=8.4 Hz, 1H), 7.54 (dd, J=7.8, 7.8 Hz, 1H), 7.49-7.43 (m, 2H), 7.39 (dd, J=7.8, 7.8 Hz, 1H), 7.23-7.15 (m, 3H), 5.26 (s, 2H). HRMS (ESI$^+$) calcd for $C_{22}H_{19}N_4O_3$ (M+H)$^+$ 387.1452, found 387.1459.

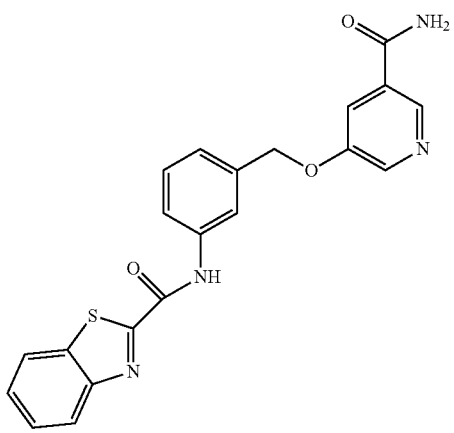 [SMILES: NC(=O)c1cncc(OCc2cccc(NC(=O)c3nc4ccccc4s3)c2)c1]

N-(3-(((5-Carbamoylpyridin-3-yl)oxy)methyl)phenyl)benzo[d]thiazole-2-carboxamide (A-16)

Pale solid (10 mg, 12%). $^1$H NMR (DMSO-$d_6$, 600 MHz) δ 11.18 (s, 1H), 8.67 (s, 1H), 8.51 (d, J=2.4 Hz, 1H), 8.28 (d, J=8.4 Hz, 1H), 8.23 (d, J=8.4 Hz, 1H), 8.14 (s, 1H), 8.09 (s, 1H), 7.87 (s, 2H), 7.67 (dd, J=7.8, 7.8 Hz, 1H), 7.64-7.58 (m, 2H), 7.43 (dd, J=7.8, 7.8 Hz, 1H), 7.28 (d, J=7.2 Hz, 1H), 5.27 (s, 2H). HRMS (ESI$^+$) calcd for $C_{21}H_{17}H_4O_3S$ (M+H)$^+$ 405.1016, found 405.1016.

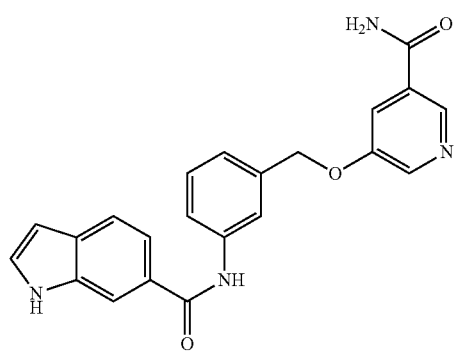 [SMILES: NC(=O)c1cncc(OCc2cccc(NC(=O)c3ccc4cc[nH]c4c3)c2)c1]

N-(3-(((5-Carbamoylpyridin-3-yl)oxy)methyl)phenyl)-1H-indole-6-carboxamide (A-19)

White solid (60 mg, 65%). $^1$H NMR (DMSO-d$_6$, 600 MHz) δ 11.45 (s, 1H), 10.22 (s, 1H), 8.65 (s, 1H), 8.51 (d, J=2.8 Hz, 1H), 8.13 (s, 1H), 8.06 (s, 1H), 7.96 (s, 1H), 7.86 (s, 1H), 7.78 (d, J=8.2 Hz, 1H), 7.64 (s, 2H), 7.60 (s, 1H), 7.54 (dd, J=2.6, 2.6 Hz, 1H), 7.37 (dd, J=7.8, 7.8 Hz, 1H), 7.19 (d, J=7.5 Hz, 1H), 6.51 (s, 1H), 5.24 (s, 2H). HRMS (ESI$^+$) calcd for C$_{22}$H$_{19}$N$_4$O$_3$ (M+H)$^+$ 387.1452, found 387.1457.

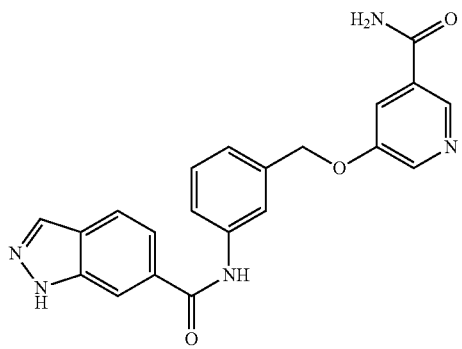 [SMILES: NC(=O)c1cncc(OCc2cccc(NC(=O)c3ccc4cn[nH]c4c3)c2)c1]

N-(3-(((5-Carbamoylpyridin-3-yl)oxy)methyl)phenyl)-1H-indazole-6-carboxamide (A-20)

White solid (20 mg, 21%). $^1$H NMR (DMSO-d$_6$, 600 MHz) δ 13.44 (s, 1H), 10.42 (s, 1H), 8.84 (s, 1H), 8.63 (d, J=2.2 Hz, 1H), 8.17 (d, J=6.0 Hz, 2H), 8.14 (s, 1H), 7.96 (s, 1H), 7.90-7.86 (m, 2H), 7.77 (d, J=7.8 Hz, 1H), 7.68 (d, J=8.4 Hz, 1H), 7.61 (s, 1H), 7.40 (dd, J=8.1, 8.1 Hz, 1H), 7.21 (d, J=7.8 Hz, 1H), 5.26 (s, 2H). HRMS (ESI$^+$) calcd for C$_{21}$H$_{18}$N$_5$O$_3$ (M+H)$^+$ 388.1404, found 388.1401.

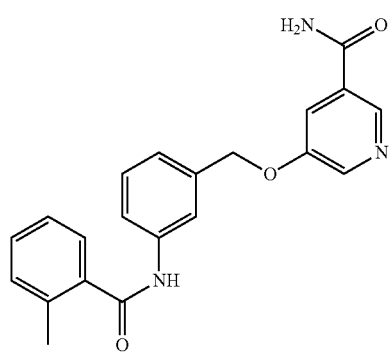 [SMILES: Cc1ccccc1C(=O)Nc1cccc(COc2cncc(C(N)=O)c2)c1]

5-((3-(2-Methylbenzamido)benzyl)oxy)nicotinamide (A-21)

White solid (43 mg, 57%). $^1$H NMR (DMSO-d$_6$, 600 MHz) δ 10.36 (s, 1H), 8.65 (d, J=1.2 Hz, 1H), 8.49 (d, J=2.6 Hz, 1H), 8.13 (s, 1H), 7.92 (s, 1H), 7.86 (s, 1H), 7.69 (d, J=7.0 Hz, 1H), 7.60 (s, 1H), 7.45 (d, J=7.3 Hz, 1H), 7.41-7.35 (m, 2H), 7.31-7.28 (m, 2H), 7.20 (d, J=7.5 Hz, 1H), 5.24 (s, 2H), 2.38 (s, 3H). HRMS (ESI$^+$) calcd for C$_{21}$H$_{20}$N$_3$O$_3$ (M+H)$^+$ 362.1499, found 362.1506.

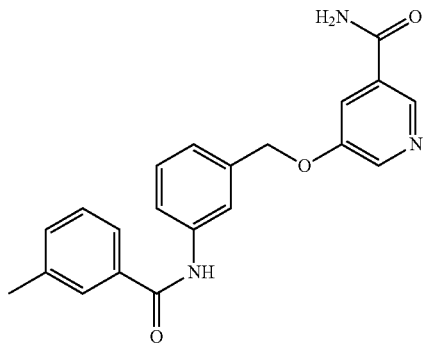 [SMILES: Cc1cccc(C(=O)Nc2cccc(COc3cncc(C(N)=O)c3)c2)c1]

5-((3-(3-Methylbenzamido)benzyl)oxy)nicotinamide (A-22)

White solid (69 mg, 93%). $^1$H NMR (DMSO-d$_6$, 600 MHz) δ 10.27 (s, 1H), 8.65 (s, 1H), 8.50 (d, J=2.5 Hz, 1H), 8.14 (s, 1H), 7.92 (s, 1H), 7.86 (s, 1H), 7.78-7.72 (m, 3H), 7.61 (s, 1H), 7.43-7.37 (m, 3H), 7.21 (d, J=7.5 Hz, 1H), 5.25 (s, 2H), 2.40 (s, 3H). HRMS (ESI$^+$) calcd for C$_{21}$H$_{20}$N$_3$O$_3$ (M+H)$^+$ 362.1499, found 362.1504.

5-((3-(4-Methylbenzamido)benzyl)oxy)nicotinamide (A-23)

White solid (38 mg, 51%). $^1$H NMR (DMSO-d$_6$, 600 MHz) δ 10.21 (s, 1H), 8.64 (s, 1H), 8.48 (d, J=2.2 Hz, 1H), 8.12 (s, 1H), 7.91 (s, 1H), 7.87-7.84 (m, 3H), 7.73 (d, J=8.1 Hz, 1H), 7.60 (s, 1H), 7.37 (dd, J=7.8, 7.8 Hz, 1H), 7.32 (d, J=7.9 Hz, 2H), 7.18 (d, J=7.5 Hz, 1H), 5.23 (s, 2H), 2.37 (s, 3H). HRMS (ESI$^+$) calcd for C$_{21}$H$_{20}$N$_3$O$_3$ (M+H)$^+$ 362.1499, found 362.1506.

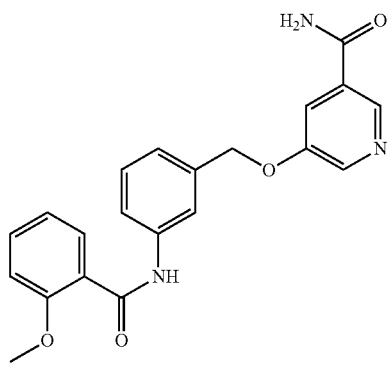 [SMILES: COc1ccccc1C(=O)Nc1cccc(COc2cncc(C(N)=O)c2)c1]

5-((3-(2-Methoxybenzamido)benzyl)oxy)nicotinamide (A-24)

White solid (53 mg, 54%). $^1$H NMR (DMSO-d$_6$, 600 MHz) δ 10.18 (s, 1H), 8.65 (d, J=1.6 Hz, 1H), 8.49 (d, J=2.8 Hz, 1H), 8.14 (s, 1H), 7.91 (s, 1H), 7.86 (dd, J=2.6, 1.8 Hz, 1H), 7.68 (d, J=8.4 Hz, 1H), 7.62 (dd, J=7.6, 1.6 Hz, 1H), 7.61 (s, 1H), 7.52-7.48 (m, 1H), 7.37 (dd, J=7.8, 7.8 Hz, 1H), 7.21-7.16 (m, 2H), 7.06 (dd, J=7.5, 7.5 Hz, 1H), 5.24 (s, 2H), 3.89 (s, 3H). HRMS (ESI$^+$) calcd for C$_{21}$H$_{20}$N$_3$O$_4$ (M+H)$^+$ 378.1448, found 378.1453.

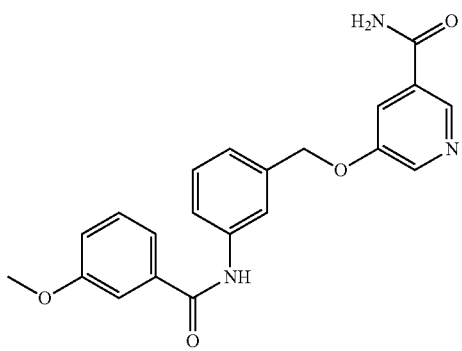 [SMILES: COc1cccc(C(=O)Nc2cccc(COc3cncc(C(N)=O)c3)c2)c1]

5-((3-(3-Methoxybenzamido)benzyl)oxy)nicotinamide (A-25)

White solid (51 mg, 64%). $^1$H NMR (DMSO-d$_6$, 600 MHz) δ 10.28 (s, 1H), 8.65 (s, 1H), 8.49 (d, J=2.8 Hz, 1H), 8.14 (s, 1H), 7.92 (s, 1H), 7.88-7.85 (m, 1H), 7.75 (d, J=7.9 Hz, 1H), 7.61 (s, 1H), 7.54 (d, J=7.6 Hz, 1H), 7.49 (s, 1H), 7.44 (dd, J=7.9, 7.9 Hz, 1H), 7.39 (dd, J=7.8, 7.8 Hz, 1H), 7.21 (d, J=7.6 Hz, 1H), 7.15 (dd, J=8.2, 2.0 Hz, 1H), 5.25 (s, 2H), 3.84 (s, 3H). HRMS (ESI$^+$) calcd for C$_{21}$H$_{20}$N$_3$O$_4$ (M+H)$^+$ 378.1448, found 378.1450.

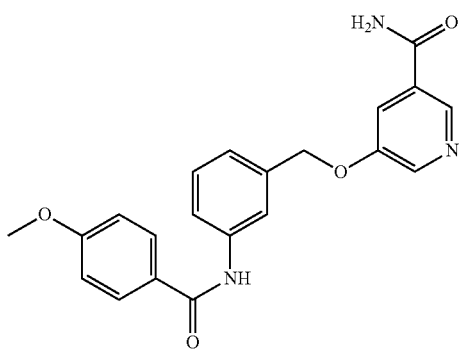 [SMILES: COc1ccc(C(=O)Nc2cccc(COc3cncc(C(N)=O)c3)c2)cc1]

5-((3-(4-Methoxybenzamido)benzyl)oxy)nicotinamide (A-26)

White solid (40 mg, 51%). $^1$H NMR (DMSO-d$_6$, 600 MHz) δ 10.15 (s, 1H), 8.65 (s, 1H), 8.49 (d, J=2.6 Hz, 1H), 8.14 (s, 1H), 7.97 (d, J=8.8 Hz, 2H), 7.91 (s, 1H), 7.85 (s, 1H), 7.75 (d, J=8.2 Hz, 1H), 7.62 (s, 1H), 7.37 (dd, J=7.9, 7.9 Hz, 1H), 7.19 (d, J=7.6 Hz, 1H), 7.06 (d, J=8.7 Hz, 2H), 5.24 (s, 2H), 3.84 (s, 3H). HRMS (ESI$^+$) calcd for C$_{21}$H$_{20}$N$_3$O$_4$ (M+H)$^+$ 378.1448, found 378.1455.

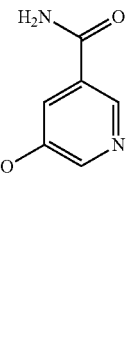

5-((3-(2-Chlorobenzamido)benzyl)oxy)nicotinamide (A-27)

White solid (35 mg, 43%). $^1$H NMR (DMSO-d$_6$, 600 MHz) δ 10.57 (s, 1H), 8.65 (s, 1H), 8.49 (d, J=2.5 Hz, 1H), 8.14 (s, 1H), 7.89 (s, 1H), 7.86 (s, 1H), 7.66 (d, J=7.9 Hz, 1H), 7.64-7.55 (m, 3H), 7.50 (dd, J=7.6, 7.6 Hz, 1H), 7.45 (dd, J=7.5, 7.5 Hz, 1H), 7.38 (dd, J=7.9, 7.9 Hz, 1H), 7.22 (d, J=7.5 Hz, 1H), 5.25 (s, 2H). HRMS (ESI$^+$) calcd for C$_{20}$H$_{17}$ClN$_3$O$_3$ (M+H)$^+$ 382.0953, found 382.0962.

5-((3-(3-Chlorobenzamido)benzyl)oxy)nicotinamide (A-28)

White solid (45 mg, 56%). $^1$H NMR (DMSO-d$_6$, 600 MHz) δ 10.42 (s, 1H), 8.66 (d, J=1.5 Hz, 1H), 8.50 (d, J=2.8 Hz, 1H), 8.15 (s, 1H), 8.01 (s, 1H), 7.94-7.90 (m, 2H), 7.87 (dd, J=2.2, 2.2 Hz, 1H), 7.76 (d, J=8.4 Hz, 1H), 7.66 (d, J=7.8 Hz, 1H), 7.61 (s, 1H), 7.57 (dd, J=7.8, 7.8 Hz, 1H), 7.40 (dd, J=7.8, 7.8 Hz, 1H), 7.23 (d, J=7.6 Hz, 1H), 5.30 (s, 2H). HRMS (ESI$^+$) calcd for C$_{20}$H$_{17}$ClN$_3$O$_3$ (M+H)$^+$ 382.0953, found 382.0960.

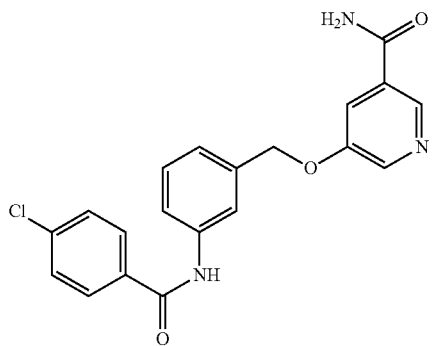

5-((3-(4-Chlorobenzamido)benzyl)oxy)nicotinamide (A-29)

White solid (53 mg, 66%). $^1$H NMR (DMSO-d$_6$, 600 MHz) δ 10.43 (s, 1H), 8.66 (d, J=1.5 Hz, 1H), 8.49 (d, J=2.8 Hz, 1H), 8.17 (s, 1H), 8.00 (d, J=8.5 Hz, 2H), 7.93 (s, 1H), 7.88 (dd, J=1.9, 1.9 Hz, 1H), 7.76 (d, J=8.2 Hz, 1H), 7.63-7.58 (m, 3H), 7.39 (dd, J=7.8, 7.8 Hz, 1H), 7.22 (d, J=7.5 Hz, 1H), 5.25 (s, 2H). HRMS (ESI$^+$) calcd for C$_{20}$H$_{17}$ClN$_3$O$_3$ (M+H)$^+$ 382.0953, found 382.0962.

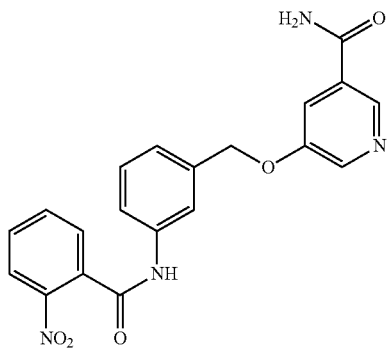 [SMILES: NC(=O)c1cncc(OCc2cccc(NC(=O)c3ccccc3[N+](=O)[O-])c2)c1]

5-((3-(2-Nitrobenzamido)benzyl)oxy)nicotinamide (A-30)

White solid (42 mg, 51%). $^1$H NMR (DMSO-d$_6$, 600 MHz) δ 10.74 (s, 1H), 8.65 (s, 1H), 8.49 (d, J=2.8 Hz, 1H), 8.15 (d, J=8.2 Hz, 1H), 8.13 (s, 1H), 7.89-7.86 (m, 2H), 7.82 (s, 1H), 7.79-7.75 (m, 2H), 7.63 (d, J=8.2 Hz, 1H), 7.61 (s, 1H), 7.40 (dd, J=7.8, 7.8 Hz, 1H), 7.24 (d, J=7.6 Hz, 1H), 5.26 (s, 2H). HRMS (ESI$^+$) calcd for C$_{20}$H$_{17}$N$_4$O$_5$ (M+H)$^+$ 393.1193 found 393.1199.

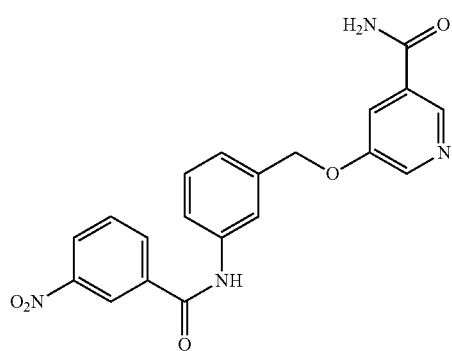 [SMILES: NC(=O)c1cncc(OCc2cccc(NC(=O)c3cccc([N+](=O)[O-])c3)c2)c1]

5-((3-(3-Nitrobenzamido)benzyl)oxy)nicotinamide (A-31)

White solid (67 mg, 82%). $^1$H NMR (DMSO-d$_6$, 600 MHz) δ 10.65 (s, 1H), 8.80 (s, 1H), 8.65 (s, 1H) 8.50 (d, J=2.2 Hz, 1H), 8.44 (d, J=8.4 Hz, 1H), 8.41 (d, J=7.8 Hz, 1H), 8.14 (s, 1H), 7.92 (s, 1H), 7.88-7.83 (m, 2H), 7.78 (d, J=8.2 Hz, 1H), 7.61 (s, 1H), 7.42 (dd, J=7.9, 7.9 Hz, 1H), 7.26 (d, J=7.6 Hz, 1H), 5.27 (s, 2H). HRMS (ESI$^+$) calcd for C$_{20}$H$_{17}$N$_4$O$_5$ (M+H)$^+$ 393.1193, found 393.1196.

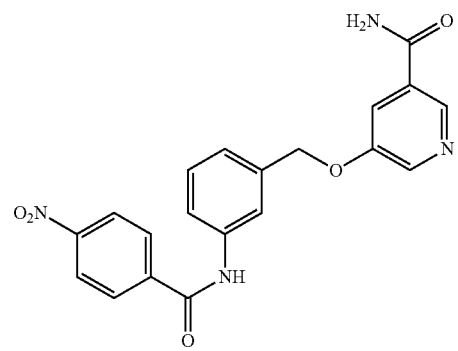 [SMILES: NC(=O)c1cncc(OCc2cccc(NC(=O)c3ccc([N+](=O)[O-])cc3)c2)c1]

5-((3-(4-Nitrobenzamido)benzyl)oxy)nicotinamide (A-32)

White solid (41 mg, 50%). $^1$H NMR (DMSO-d$_6$, 600 MHz) δ 10.64 (s, 1H), 8.65 (s, 1H), 8.50 (d, J=2.6 Hz, 1H), 8.37 (d, J=8.8 Hz, 2H), 8.19 (d, J=8.7 Hz, 2H), 8.15 (s, 1H), 7.92 (s, 1H), 7.86 (s, 1H), 7.77 (d, J=8.1 Hz, 1H), 7.61 (s, 1H), 7.42 (dd, J=7.9, 7.9 Hz, 1H), 7.25 (d, J=7.6 Hz, 1H), 5.26 (s, 2H). HRMS (ESI$^+$) calcd for C$_{20}$H$_{17}$N$_4$O$_5$ (M+H)$^+$ 393.1193 found 393.1200.

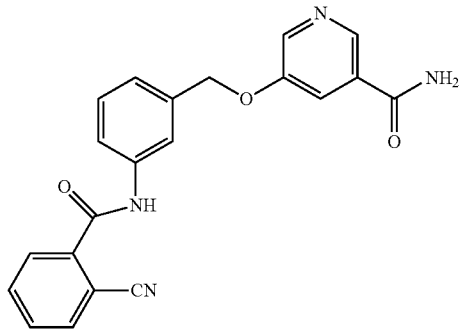 [SMILES: N#Cc1ccccc1C(=O)Nc1cccc(COc2cncc(C(N)=O)c2)c1]

683_ 5-((3-(2-Cyanobenzamido)benzyl)oxy)nicotinamide (A-33)

Pale solid (10 mg, 13%). $^1$H NMR (DMSO-d$_6$, 600 MHz) δ 10.29 (s, 1H), 8.66 (s, 1H), 8.51 (d, J=2.4 Hz, 1H), 8.27 (d, J=7.2 Hz, 1H), 8.14 (s, 1H), 7.92-7.85 (m, 3H), 7.82-7.78 (m, 1H), 7.64-7.52 (m, 4H), 7.45 (d, J=7.8 Hz, 1H), 5.30 (s, 2H). HRMS (ESI$^+$) calcd for C$_{21}$H$_{17}$N$_4$O$_3$ (M+H)$^+$ 373.1301, found 373.1302.

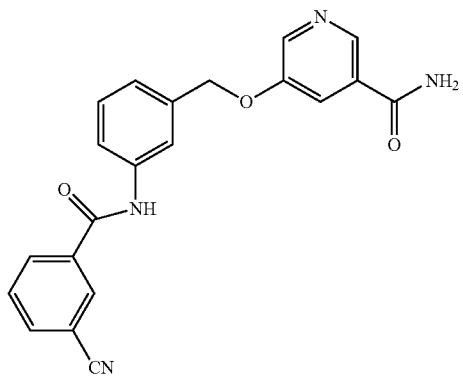 [SMILES: N#Cc1cccc(C(=O)Nc2cccc(COc3cncc(C(N)=O)c3)c2)c1]

5-((3-(3-Cyanobenzamido)benzyl)oxy)nicotinamide (A-34)

White solid (30 mg, 39%). $^1$H NMR (DMSO-d$_6$, 600 MHz) δ 10.38 (s, 1H), 8.65 (s, 1H), 8.50 (d, J=2.4 Hz, 1H), 8.41 (s, 1H), 8.25 (d, J=8.4 Hz, 1H), 8.14 (s, 1H), 8.07 (d, J=7.8 Hz, 1H), 7.91 (s, 1H), 7.86 (s, 1H), 7.78-7.73 (m, 2H), 7.62 (s, 1H), 7.42 (dd, J=8.1, 8.1 Hz, 1H), 7.24 (d, J=7.8 Hz, 1H), 5.27 (s, 2H). HRMS (ESI$^+$) calcd for C$_{21}$H$_{17}$N$_4$O$_3$ (M+H)$^+$ 373.1301, found 373.1300.

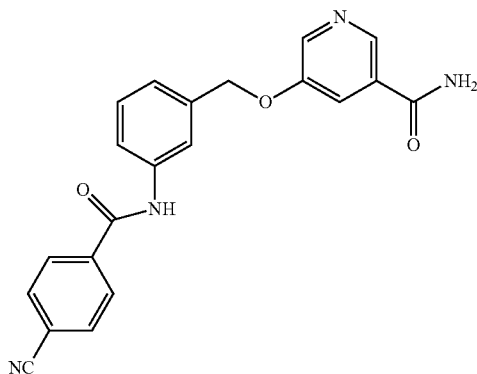 [SMILES: N#Cc1ccc(C(=O)Nc2cccc(COc3cncc(C(N)=O)c3)c2)cc1]

5-((3-(4-Cyanobenzamido)benzyl)oxy)nicotinamide (A-35)

Pale solid (28 mg, 37%). $^1$H NMR (DMSO-d$_6$, 600 MHz) δ 10.55 (s, 1H), 8.65 (s, 1H), 8.49 (d, J=3.0 Hz, 1H), 8.14 (s, 1H), 8.11 (d, J=9.0 Hz, 2H), 8.03 (d, J=7.8 Hz, 2H), 7.92 (s, 1H), 7.88-7.84 (m, 1H), 7.75 (d, J=7.8 Hz, 1H), 7.62 (s, 1H), 7.41 (dd, J=8.1, 8.1 Hz, 1H), 7.24 (d, J=7.8 Hz, 1H), 5.28 (s, 2H). HRMS (ESI$^+$) calcd for C$_{21}$H$_{17}$N$_4$O$_3$ (M+H)$^+$ 373.1301, found 373.1303.

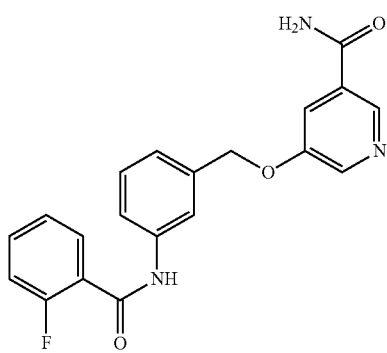

5-((3-(2-Fluorobenzamido)benzyl)oxy)nicotinamide (A-36)

White solid (80 mg, 91%). $^1$H NMR (DMSO-d$_6$, 600 MHz) δ 10.48 (s, 1H), 8.65 (s, 1H), 8.49 (d, J=2.0 Hz, 1H), 8.13 (s, 1H), 7.87 (d, J=14.5 Hz, 2H), 7.68-7.65 (m, 2H), 7.61-7.55 (m, 2H), 7.40-7.31 (m, 3H), 7.22 (d, J=7.5 Hz, 1H), 5.24 (s, 2H). HRMS (ESI$^+$) calcd for C$_{20}$H$_{17}$FN$_3$O$_3$ (M+H)$^+$ 366.1248, found 366.1253.

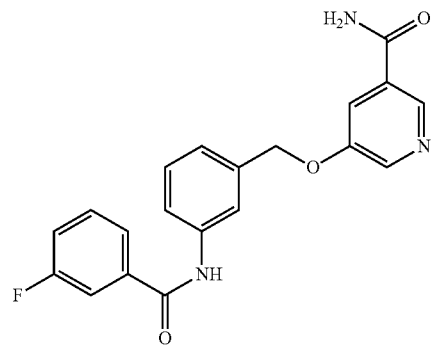 [SMILES: NC(=O)c1cncc(OCc2cccc(NC(=O)c3cccc(F)c3)c2)c1]

5-((3-(3-Fluorobenzamido)benzyl)oxy)nicotinamide (A-37)

White solid (50 mg, 57%). $^1$H NMR (DMSO-d$_6$, 600 MHz) δ 10.37 (s, 1H), 8.65 (s, 1H), 8.49 (s, 1H), 8.13 (s, 1H), 7.91 (s, 1H), 7.86 (s, 1H), 7.82 (d, J=7.8 Hz, 1H), 7.76 (dd, J=15.0, 11.7 Hz, 2H), 7.61-7.57 (m, 2H), 7.48-7.38 (m, 2H), 7.23 (d, J=7.3 Hz, 1H), 5.25 (s, 2H). HRMS (ESI$^+$) calcd for C$_{20}$H$_{17}$FN$_3$O$_3$ (M+H)$^+$ 366.1248, found 366.1250.

5-((3-(4-Fluorobenzamido)benzyl)oxy)nicotinamide (A-38)

White solid (40 mg, 46%). $^1$H NMR (DMSO-d$_6$, 600 MHz) δ 10.34 (s, 1H), 8.66 (s, 1H), 8.49 (d, J=2.6 Hz, 1H), 8.15 (s, 1H), 8.04 (dd, J=8.4, 5.6 Hz, 2H), 7.91 (s, 1H), 7.87 (s, 1H), 7.74 (d, J=8.1 Hz, 1H), 7.61 (s, 1H), 7.42-7.35 (m, 2H), 7.25 (dd, J=8.4, 8.4 Hz, 1H), 7.22 (d, J=7.6 Hz, 1H), 5.25 (s, 2H). HRMS (ESI$^+$) calcd for C$_{20}$H$_{17}$FN$_3$O$_3$ (M+H)$^+$ 366.1248, found 366.1250.

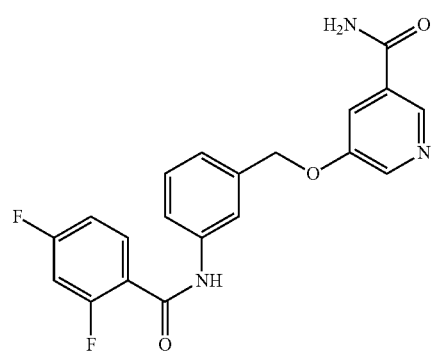 [SMILES: NC(=O)c1cncc(OCc2cccc(NC(=O)c3ccc(F)cc3F)c2)c1]

5-((3-(2,4-Difluorobenzamido)benzyl)oxy)nicotinamide (A-39)

White solid (60 mg, 65%). $^1$H NMR (DMSO-d$_6$, 600 MHz) δ 10.47 (s, 1H), 8.65 (s, 1H), 8.49 (d, J=2.5 Hz, 1H), 8.13 (s, 1H), 7.84 (s, 2H), 7.75 (dd, J=15.3, 8.2 Hz, 1H), 7.67 (d, J=7.9 Hz, 1H), 7.61 (s, 1H), 7.44-7.37 (m, 2H), 7.24-7.20 (m, 2H), 5.24 (s, 2H). HRMS (ESI$^+$) calcd for C$_{20}$H$_{16}$F$_2$N$_3$O$_3$ (M+H)$^+$ 384.1154, found 384.1151.

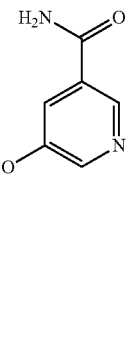

5-((3-(3,4-Difluorobenzamido)benzyl)oxy)nicotinamide (A-40)

White solid (30 mg, 33%). $^1$H NMR (DMSO-d$_6$, 600 MHz) δ 10.37 (s, 1H), 8.66 (d, J=1.6 Hz, 1H), 8.49 (d, J=2.8 Hz, 1H), 8.13 (s, 1H), 8.05-8.02 (m, 1H), 7.89 (s, 1H), 7.88-7.84 (m, 2H), 7.74 (d, J=8.1 Hz, 1H), 7.63-7.56 (m, 2H), 7.40 (dd, J=7.8, 7.8 Hz, 1H), 7.23 (d, J=7.6 Hz, 1H), 5.25 (s, 2H). HRMS (ESI$^+$) calcd for C$_{20}$H$_{16}$F$_2$N$_3$O$_3$ (M+H)$^+$ 384.1154, found 384.1161.

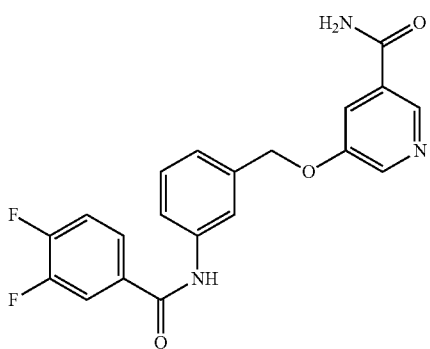 [SMILES: NC(=O)c1cncc(OCc2cccc(NC(=O)c3ccc(F)c(F)c3)c2)c1]

5-((3-(2-Fluoro-4-methylbenzamido)benzyl)oxy)nicotinamide (A-41)

White solid (18 mg, 20%). $^1$H NMR (DMSO-d$_6$, 600 MHz) δ 10.36 (s, 1H), 8.65 (s, 1H), 8.49 (d, J=2.4 Hz, 1H), 8.13 (s, 1H), 7.86 (d, J=8.4 Hz, 2H), 7.67 (d, J=7.6 Hz, 1H), 7.61 (s, 1H), 7.56 (dd, J=7.9, 7.9 Hz, 1H), 7.38 (dd, J=7.8, 7.8 Hz, 1H), 7.21 (d, J=7.9 Hz, 1H), 7.18 (d, J=11.4 Hz, 1H), 7.14 (d, J=7.6 Hz, 1H), 5.24 (s, 2H), 2.38 (s, 3H). HRMS (ESI$^+$) calcd for C$_{21}$H$_{19}$FN$_3$O$_3$ (M+H)$^+$ 380.1405, found 380.1411.

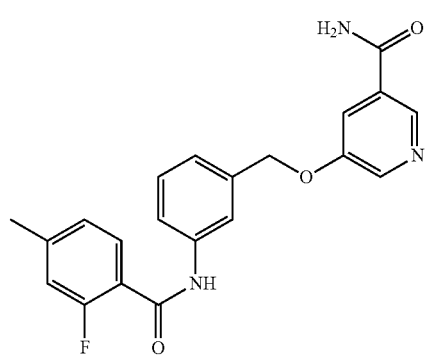 [SMILES: Cc1ccc(C(=O)Nc2cccc(COc3cncc(C(N)=O)c3)c2)c(F)c1]

5-((3-(3-Fluoro-4-methylbenzamido)benzyl)oxy)nicotinamide (A-42)

White solid (56 mg, 62%). $^1$H NMR (DMSO-d$_6$, 600 MHz) S 10.28 (s, 1H), 8.65 (d, J=1.6 Hz, 1H), 8.49 (d, J=2.9 Hz, 1H), 8.13 (s, 1H), 7.91 (s, 1H), 7.86-7.84 (m, 1H), 7.76-7.72 (m, 3H), 7.60 (s, 1H), 7.45 (dd, J=7.8, 7.8 Hz, 1H), 7.39 (dd, J=7.8, 7.8 Hz, 1H), 7.22 (d, J=7.6 Hz, 1H), 5.24 (s, 2H), 2.31 (s, 3H). HRMS (ESI$^+$) calcd for C$_{21}$H$_{19}$FN$_3$O$_3$ (M+H)$^+$ 380.1405, found 380.1406.

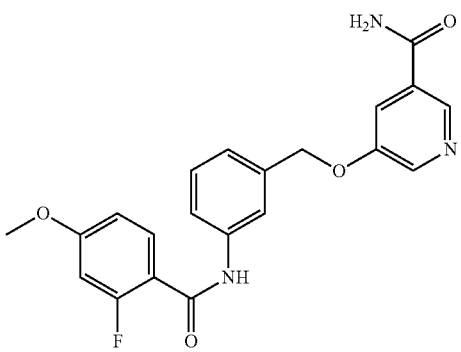 [SMILES: COc1ccc(C(=O)Nc2cccc(COc3cncc(C(N)=O)c3)c2)c(F)c1]

5-((3-(2-Fluoro-4-methoxybenzamido)benzyl)oxy)nicotinamide (A-43)

White solid (33 mg, 35%). $^1$H NMR (DMSO-d$_6$, 600 MHz) δ 10.23 (s, 1H), 8.64 (s, 1H), 8.49 (d, J=2.8 Hz, 1H), 8.12 (s, 1H), 7.86-7.83 (m, 2H), 7.68-7.58 (m, 3H), 7.36 (dd, J=7.9, 7.9 Hz, 1H), 7.20 (d, J=7.3 Hz, 1H), 6.94 (d, J=12.5 Hz, 1H), 6.88 (dd, J=8.5, 2.0 Hz, 1H), 5.23 (s, 2H), 3.83 (s, 3H). HRMS (ESI$^+$) calcd for C$_{21}$H$_{19}$FN$_3$O$_4$ (M+H)$^+$ 396.1354, found 396.1366.

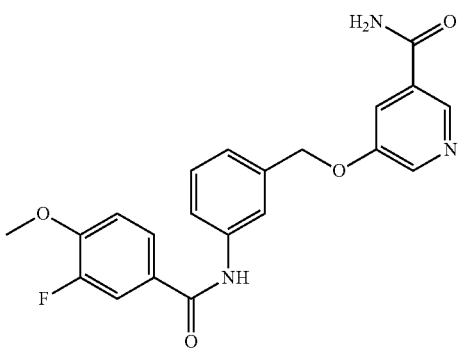 [SMILES: COc1ccc(C(=O)Nc2cccc(COc3cncc(C(N)=O)c3)c2)cc1F]

5-((3-(3-Fluoro-4-methoxybenzamido)benzyl)oxy) nicotinamide (A-44)

White solid. $^1$H NMR (DMSO-d$_6$, 600 MHz) δ 10.19 (s, 1H), 8.64 (s, 1H), 8.49 (d, J=2.5 Hz, 1H), 8.12 (s, 1H), 7.89 (s, 1H), 7.86-7.82 (m, 3H), 7.74 (d, J=7.8 Hz, 1H), 7.60 (s, 1H), 7.38 (dd, J=7.8, 7.8 Hz, 1H), 7.30 (dd, J=8.5, 8.5 Hz, 1H), 7.21 (d, J=7.5 Hz, 1H), 5.24 (s, 2H), 3.91 (s, 3H). HRMS (ESI$^+$) calcd for C$_{21}$H$_{19}$FN$_3$O$_4$ (M+H)$^+$ 396.1354, found 396.1354.

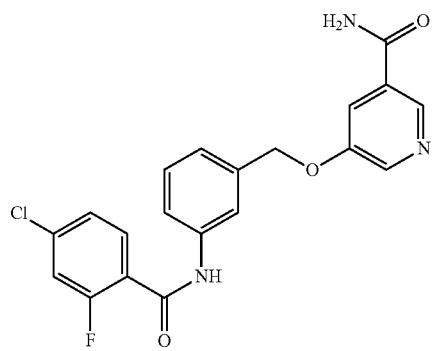 [SMILES: NC(=O)c1cncc(OCc2cccc(NC(=O)c3ccc(Cl)cc3F)c2)c1]

5-((3-(4-Chloro-2-fluorobenzamido)benzyl)oxy) nicotinamide (A-45)

White solid (70 mg, 73%). $^1$H NMR (DMSO-d$_6$, 600 MHz) δ 10.54 (s, 1H), 8.66 (s, 1H), 8.49 (d, J=2.8 Hz, 1H), 8.13 (s, 1H), 7.86 (s, 2H), 7.72 (dd, J=8.1, 8.1 Hz, 1H), 7.66 (d, J=8.1 Hz, 1H), 7.62 (d, J=10.1 Hz, 2H), 7.43 (d, J=8.4 Hz, 1H), 7.40 (dd, J=7.8, 7.8 Hz, 1H), 7.24 (d, J=7.6 Hz, 1H), 5.25 (s, 2H). HRMS (ESI$^+$) calcd for C$_{20}$H$_{16}$ClFN$_3$O$_3$ (M+H)$^+$ 400.0859, found 400.0856.

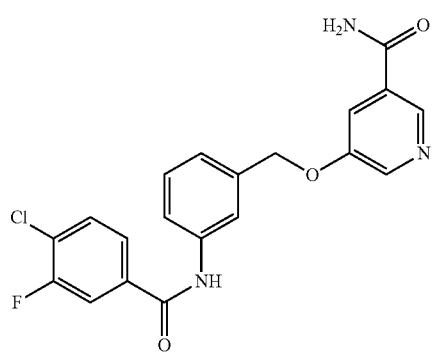 [SMILES: NC(=O)c1cncc(OCc2cccc(NC(=O)c3ccc(Cl)c(F)c3)c2)c1]

5-((3-(4-Chloro-3-fluorobenzamido)benzyl)oxy) nicotinamide (A-46)

White solid (30 mg, 31%). $^1$H NMR (DMSO-d$_6$, 600 MHz) δ 10.43 (s, 1H), 8.66 (s, 1H), 8.49 (d, J=2.8 Hz, 1H), 8.14 (s, 1H), 7.99 (dd, J=10.1, 1.8 Hz, 1H), 7.91 (s, 1H), 7.86-7.85 (m, 2H), 7.79 (dd, J=7.8, 7.8 Hz, 1H), 7.74 (dd, J=8.1, 8.1 Hz, 1H), 7.62 (d, J=7.9 Hz, 1H), 7.41 (t, J=7.9 Hz, 1H), 7.24 (d, J=7.6 Hz, 1H), 5.27 (s, 2H). HRMS (ESI$^+$) calcd for C$_{20}$H$_{16}$ClFN$_3$O$_3$ (M+H)$^+$ 400.0859, found 400.0860.

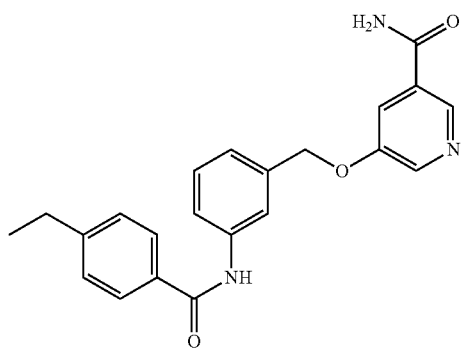

5-((3-(4-Ethylbenzamido)benzyl)oxy)nicotinamide (A-47)

White solid (55 mg, 61%). $^1$H NMR (DMSO-d$_6$, 600 MHz) δ 10.23 (s, 1H), 8.66 (s, 1H), 8.50 (d, J=2.2 Hz, 1H), 8.15 (s, 1H), 7.94 (s, 1H), 7.90 (d, J=8.1 Hz, 2H), 7.87 (s, 1H), 7.76 (d, J=8.1 Hz, 1H), 7.62 (s, 1H), 7.42-7.35 (m, 3H), 7.20 (d, J=7.6 Hz, 1H), 5.25 (s, 2H), 2.68 (q, J=7.8 Hz, 2H), 1.21 (t, J=7.5 Hz, 3H). HRMS (ESI$^+$) calcd for C$_{22}$H$_{22}$N$_3$O$_3$ (M+H)$^+$ 376.1656, found 376.1658.

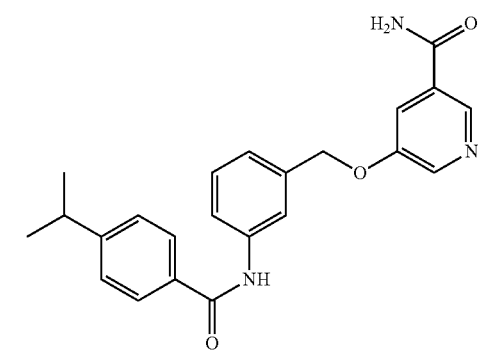 [SMILES: CC(C)c1ccc(C(=O)Nc2cccc(COc3cncc(C(N)=O)c3)c2)cc1]

5-((3-(4-Isopropylbenzamido)benzyl)oxy)nicotinamide (A-48)

Pale solid (30 mg, 32%). $^1$H NMR (DMSO-d$_6$, 600 MHz) δ 10.23 (s, 1H), 8.65 (s, 1H), 8.50 (d, J=2.6 Hz, 1H), 8.14 (s, 1H), 7.93 (s, 1H), 7.89 (d, J=8.1 Hz, 2H), 7.86 (s, 1H), 7.75 (d, J=7.9 Hz, 1H), 7.61 (s, 1H), 7.41-7.36 (m, 3H), 7.20 (d, J=7.5 Hz, 1H), 5.24 (s, 2H), 3.00-2.94 (m, 1H), 1.24 (d, J=6.9 Hz, 6H). HRMS (ESI$^+$) calcd for C$_{23}$H$_{24}$N$_3$O$_3$ (M+H)$^+$ 390.1812, found 390.1817.

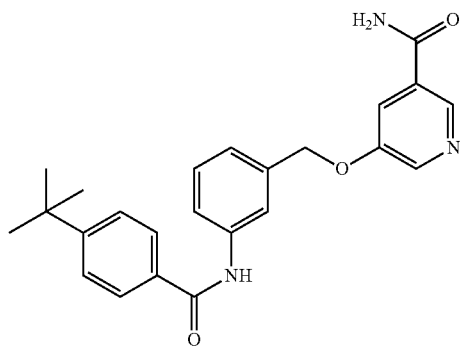 [SMILES: CC(C)(C)c1ccc(C(=O)Nc2cccc(COc3cncc(C(N)=O)c3)c2)cc1]

5-((3-(4-(tert-Butyl)benzamido)benzyl)oxy)nicotinamide (A-49)

White solid (55 mg, 57%). $^1$H NMR (DMSO-$d_6$, 600 MHz) δ 10.24 (s, 1H), 8.66 (s, 1H), 8.50 (d, J=1.8 Hz, 1H), 8.14 (s, 1H), 7.93 (s, 1H), 7.89 (d, J=8.2 Hz, 2H), 7.86 (s, 1H), 7.75 (d, J=8.1 Hz, 1H), 7.61 (s, 1H), 7.54 (d, J=8.1 Hz, 2H), 7.38 (dd, J=7.8, 7.8 Hz, 1H), 7.20 (d, J=7.3 Hz, 1H), 5.25 (s, 2H), 1.32 (s, 9H). HRMS (ESI$^+$) calcd for $C_{24}H_{26}N_3O_3$ (M+H)$^+$ 404.1969, found 404.1976.

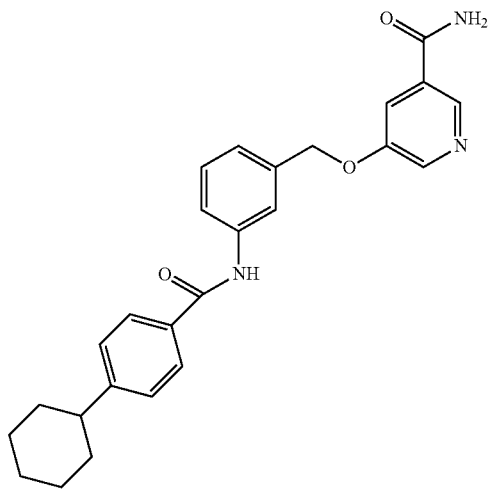 [SMILES: NC(=O)c1cncc(OCc2cccc(NC(=O)c3ccc(C4CCCCC4)cc3)c2)c1]

5-((3-(4-Cyclohexylbenzamido)benzyl)oxy)nicotinamide (A-50)

White solid (45 mg, 51%). $^1$H NMR (DMSO-$d_6$, 600 MHz) δ 10.22 (s, 1H), 8.65 (s, 1H), 8.49 (d, J=3.0 Hz, 1H), 8.14 (s, 1H), 7.93 (s, 1H), 7.90-7.84 (m, 3H), 7.74 (d, J=8.4 Hz, 1H), 7.61 (s, 1H), 7.40-7.35 (m, 3H), 7.20 (d, J=7.2 Hz, 1H), 5.24 (s, 2H), 2.59 (t, J=12.0 Hz, 1H), 1.84-1.77 (m, 4H), 1.76-1.68 (m, 1H), 1.49-1.34 (m, 4H), 1.30-1.22 (m, 1H). HRMS (ESI$^+$) calcd for $C_{26}H_{28}N_3O_3$ (M+H)$^+$ 430.2131, found 430.2124.

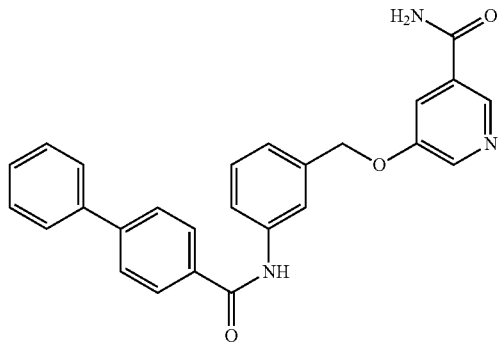 [SMILES: NC(=O)c1cncc(OCc2cccc(NC(=O)c3ccc(-c4ccccc4)cc3)c2)c1]

5-((3-(4-Phenylbenzamido)benzyl)oxy)nicotinamide (A-51)

White solid (70 mg, 69%). $^1$H NMR (DMSO-$d_6$, 600 MHz) δ 10.36 (s, 1H), 8.66 (s, 1H), 8.50 (d, J=3.0 Hz, 1H), 8.15 (s, 1H), 7.07 (d, J=8.4 Hz, 2H), 7.96 (s, 1H), 7.87 (s, 1H), 7.83 (d, J=8.4 Hz, 2H), 7.80-7.74 (m, 3H), 7.62 (s, 1H), 7.50 (dd, J=7.5, 7.5 Hz, 2H), 7.53-7.38 (m, 2H), 7.22 (d, J=7.5 Hz, 1H), 5.26 (s, 2H). HRMS (ESI$^+$) calcd for $C_{26}H_{22}N_3O_3$ (M+H)$^+$ 424.1661, found 424.1666.

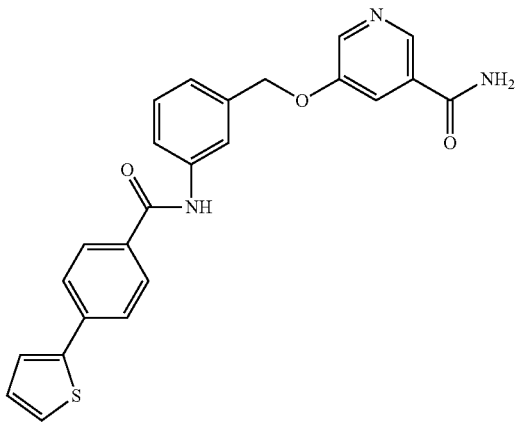 [SMILES: NC(=O)c1cncc(OCc2cccc(NC(=O)c3ccc(-c4cccs4)cc3)c2)c1]

5-((3-(4-(Thiophen-2-yl)benzamido)benzyl)oxy)nicotinamide (A-52)

White solid (9.0 mg, 10%). $^1$H NMR (DMSO-$d_6$, 600 MHz) δ 10.34 (s, 1H), 8.65 (s, 1H), 8.50 (s, 1H), 8.14 (s, 1H), 8.02 (d, J=7.8 Hz, 2H), 7.94 (s, 1H), 7.87 (s, 1H), 7.82 (d, J=7.8 Hz, 2H), 7.77 (d, J=8.4 Hz, 1H), 7.69 (s, 1H), 7.75 (d, J=5.4 Hz, 1H), 7.61 (s, 1H), 7.40 (dd, J=8.1, 8.1 Hz, 1H), 7.24-7.17 (m, 2H), 5.26 (s, 2H). HRMS (ESI$^+$) calcd for $C_{24}H_{20}N_3O_3S$ (M+H)$^+$ 430.1225, found 430.1227.

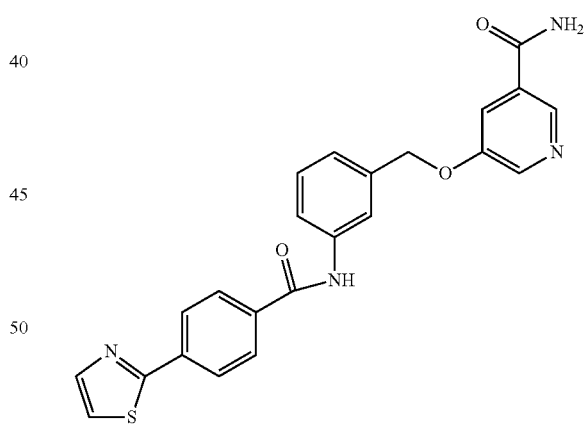

5-((3-(4-(Thiazol-2-yl)benzamido)benzyl)oxy)nicotinamide (A-53)

Pale solid (31 mg, 35%). $^1$H NMR (DMSO-$d_6$, 600 MHz) δ 10.44 (s, 1H), 8.66 (s, 1H), 8.51 (s, 1H), 8.17-8.06 (m, 5H), 8.01 (d, J=3.0 Hz, 1H), 7.95 (s, 1H), 7.89 (d, J=3.0 Hz, 1H), 7.87 (s, 1H), 7.78 (d, J=7.8 Hz, 1H), 7.62 (s, 1H), 7.41 (dd, J=7.8, 7.8 Hz, 1H), 7.23 (d, J=7.8 Hz, 1H), 5.27 (s, 2H). HRMS (ESI$^+$) calcd for $C_{23}H_{19}N_4O_3S$ (M+H)$^+$ 431.1178, found 431.1183.

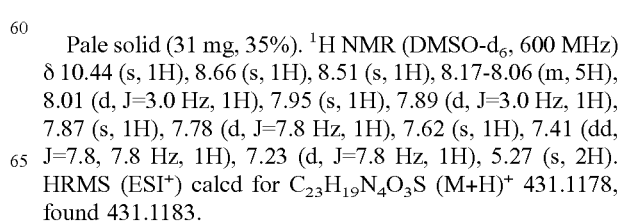

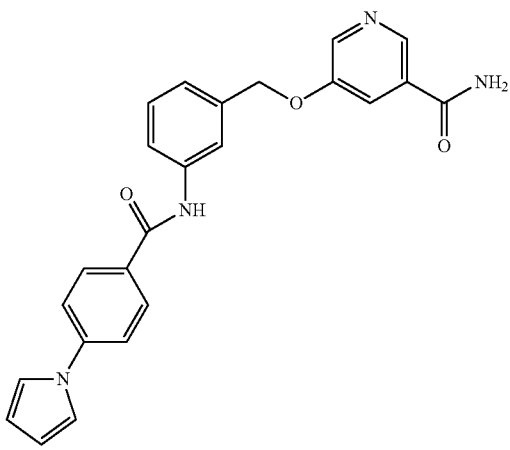 [SMILES: NC(=O)c1cncc(OCc2cccc(NC(=O)c3ccc(-n4cccc4)cc3)c2)c1]

5-((3-(4-(1H-Pyrrol-1-yl)benzamido)benzyl)oxy)
nicotinamide (A-54)

Pale solid (9.0 mg, 12%). ¹H NMR (DMSO-d₆, 600 MHz) δ 10.32 (s, 1H), 8.66 (s, 1H), 8.50 (d, J=1.2 Hz, 1H), 8.14 (s, 1H), 8.07 (d, J=7.8 Hz, 2H), 7.94 (s, 1H), 7.87 (s, 1H), 7.80-7.74 (m, 3H), 7.62 (s, 1H), 7.52 (s, 2H), 7.40 (dd, J=7.8, 7.8 Hz, 1H), 7.22 (d, J=7.8 Hz, 1H), 6.32 (s, 2H), 5.26 (s, 2H). HRMS (ESI⁺) calcd for $C_{24}H_{21}H_4O_3$ (M+H)⁺ 413.1614, found 413.1612.

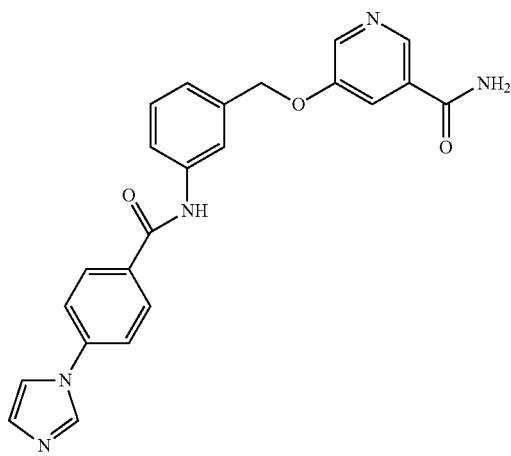

5-((3-(4-(1H-Imidazol-1-yl)benzamido)benzyl)oxy)
nicotinamide (A-56)

Brownish solid (10 mg, 8.1%). ¹H NMR (DMSO-d₆, 600 MHz) δ 10.38 (s, 1H), 8.66 (s, 1H), 8.50 (s, 1H), 8.42 (s, 1H), 8.17-8.08 (m, 3H), 7.94 (s, 1H), 7.89 (s, 1H), 7.88-7.83 (m, 3H), 7.77 (d, J=8.4 Hz, 1H), 7.62 (s, 1H), 7.41 (dd, J=8.1, 8.1 Hz, 1H), 7.23 (d, J=7.8 Hz, 1H), 7.16 (s, 1H), 5.26 (s, 2H). HRMS (ESI⁺) calcd for $C_{23}H_{20}N_5O_3$ (M+H)⁺ 414.1566, found 414.1564.

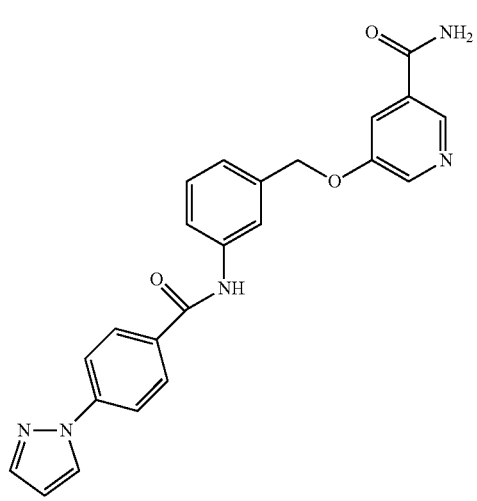 [SMILES: NC(=O)c1cncc(OCc2cccc(NC(=O)c3ccc(-n4cccn4)cc3)c2)c1]

N-(3-(((5-Carbamoylpyridin-3-yl)oxy)methyl)phenyl)-6-(1H-pyrazol-1-yl)nicotinamide (A-55)

Pale solid (16 mg, 19%). ¹H NMR (DMSO-d₆, 600 MHz) δ 10.34 (s, 1H), 8.68-8.62 (m, 2H), 8.50 (d, J=2.4 Hz, 1H), 8.17-8.08 (m, 3H), 8.02 (d, J=9.0 Hz, 2H), 7.94 (s, 1H), 7.87 (s, 1H), 7.82 (s, 1H), 7.77 (d, J=8.4 Hz, 1H), 7.62 (s, 1H), 7.40 (dd, J=8.1, 8.1 Hz, 1H), 7.22 (d, J=7.8 Hz, 1H), 6.61 (s, 1H), 5.26 (s, 2H). HRMS (ESI⁺) calcd for $C_{23}H_{20}N_5O_3$ (M+H)⁺ 414.1566, found 414.1567.

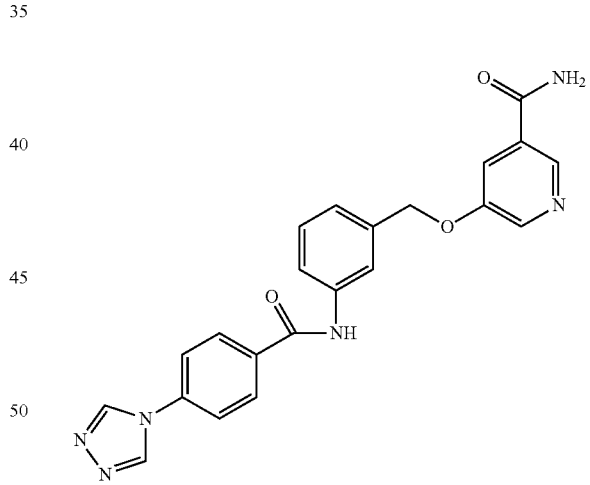

5-((3-(4-(4H-1,2,4-Triazol-4-yl)benzamido)benzyl)
oxy)nicotinamide (A-57)

Pale solid (10 mg, 12%). ¹H NMR (DMSO-d₆, 600 MHz) δ 10.42 (s, 1H), 9.26 (s, 2H), 8.66 (s, 1H), 8.50 (d, J=2.4 Hz, 1H), 8.18-8.11 (m, 3H), 7.92 (dd, J=8.7, 8.7 Hz, 3H), 7.86 (s, 1H), 7.78 (d, J=7.8 Hz, 1H), 7.62 (s, 1H), 7.41 (dd, J=7.8, 7.8 Hz, 1H), 7.24 (d, J=7.8 Hz, 1H), 5.26 (s, 2H). HRMS (ESI⁺) calcd for $C_{22}H_{19}N_6O_3$ (M+H)⁺ 415.1519, found 415.1518.

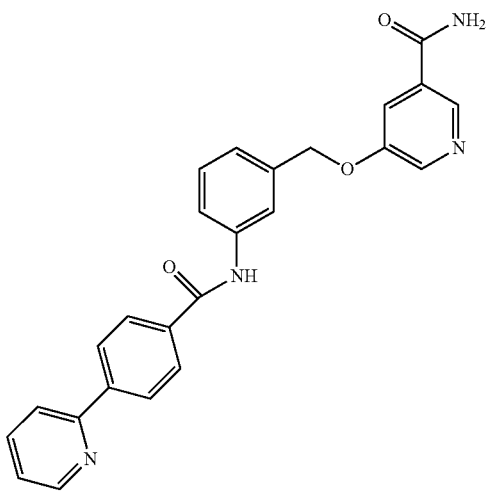 [SMILES: NC(=O)c1cncc(OCc2cccc(NC(=O)c3ccc(-c4ccccn4)cc3)c2)c1]

5-((3-(4-(Pyridin-2-yl)benzamido)benzyl)oxy)nicotinamide (A-58)

White solid (37 mg, 42%). $^1$H NMR (DMSO-$d_6$, 600 MHz) δ 10.40 (s, 1H), 8.72 (d, J=1.8 Hz, 1H), 8.66 (s, 1H), 8.52 (s, 1H), 8.28-8.22 (m, 2H), 8.15 (s, 1H), 8.12-8.05 (m, 3H), 7.98-7.92 (m, 2H), 7.87 (s, 1H), 7.79 (d, J=7.8 Hz, 1H), 7.62 (s, 1H), 7.45-7.38 (m, 2H), 7.23 (d, J=7.2 Hz, 1H), 5.27 (s, 2H). HRMS (ESI$^+$) calcd for $C_{25}H_{21}N_4O_3$ (M+H)$^+$ 425.1614, found 425.1615.

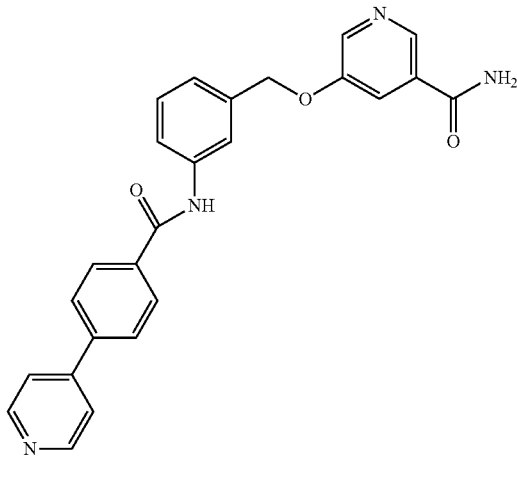

5-((3-(4-(Pyridin-4-yl)benzamido)benzyl)oxy)nicotinamide (A-60)

Pale solid (70 mg, 66%). $^1$H NMR (DMSO-$d_6$, 600 MHz) δ 10.42 (s, 1H), 8.69 (d, J=6.0 Hz, 2H), 8.66 (s, 1H), 8.50 (d, J=2.4 Hz, 1H), 8.14 (s, 1H), 8.12 (d, J=7.8 Hz, 2H), 7.98 (d, J=7.8 Hz, 2H), 7.96 (s, 1H), 7.87 (s, 1H), 7.82-7.76 (m, 3H), 7.61 (s, 1H), 7.41 (dd, J=7.8, 7.8 Hz, 1H), 7.23 (d, J=7.2 Hz, 1H), 5.27 (s, 2H). HRMS (ESI$^+$) calcd for $C_{25}H_{21}N_4O_3$ (M+H)$^+$ 425.1614, found 425.1614.

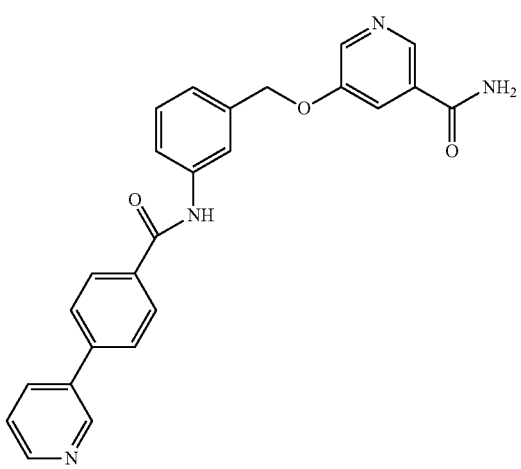 [SMILES: NC(=O)c1cncc(OCc2cccc(NC(=O)c3ccc(-c4cccnc4)cc3)c2)c1]

5-((3-(4-(Pyridin-3-yl)benzamido)benzyl)oxy)nicotinamide (A-59)

Pale solid (48 mg, 45%), $^1$H NMR (DMSO-$d_6$, 600 MHz) δ 10.40 (s, 1H), 8.99 (s, 1H), 8.66 (s, 1H), 8.63 (s, 1H), 8.51 (s, 1H), 8.18 (d, J=7.8 Hz, 1H), 8.15 (s, 1H), 8.10 (d, J=7.8 Hz, 2H), 7.96 (s, 1H), 7.92 (d, J=8.4 Hz, 2H), 7.87 (s, 1H), 7.79 (d, J=7.8 Hz, 1H), 7.62 (s, 1H), 7.54 (dd, J=6.0, 6.0 Hz, 1H), 7.41 (dd, J=8.1, 8.1 Hz, 1H), 7.23 (d, J=7.8 Hz, 1H), 5.27 (s, 2H). HRMS (ESI$^+$) calcd for $C_{25}H_{21}H_4O_3$ (M+H)$^+$ 425.1614, found 425.1617.

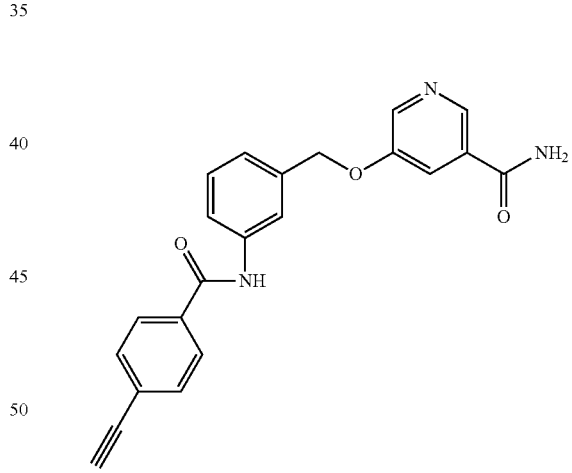

5-((3-(4-Ethynylbenzamido)benzyl)oxy)nicotinamide (A-61)

Yellowish solid (13 mg, 17%), $^1$H NMR (DMSO-$d_6$, 600 MHz) δ 10.39 (s, 1H), 8.65 (s, 1H), 8.49 (s, 1H), 8.14 (s, 1H), 7.97 (d, J=7.8 Hz, 2H), 7.92 (s, 1H), 7.86 (s, 1H), 7.75 (d, J=7.2 Hz, 1H), 7.66-7.58 (m, 3H), 7.40 (dd, J=7.8, 7.8 Hz, 1H), 7.22 (d, J=7.8 Hz, 1H), 5.25 (s, 2H), 4.41 (s, 1H). HRMS (ESI$^+$) calcd for $C_{22}H_{18}N_3O_3$ (M+H)$^+$ 372.1348, found 372.1346.

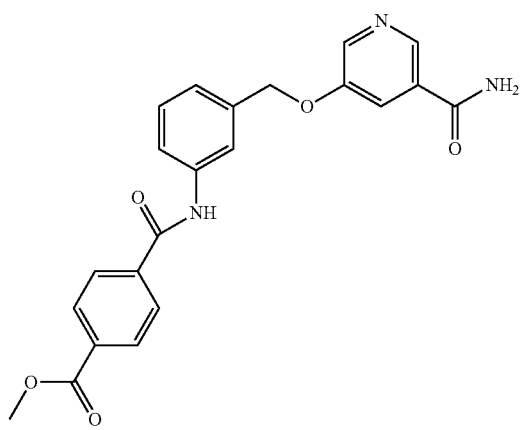 [SMILES: COC(=O)c1ccc(C(=O)Nc2cccc(COc3cncc(C(N)=O)c3)c2)cc1]

Methyl 4-((3-(((5-Carbamoylpyridin-3-yl)oxy)
methyl)phenyl)carbamoyl)benzoate (A-62)

Pale solid (250 mg, 75%). $^1$H NMR (DMSO-d$_6$, 600 MHz) δ 10.56 (s, 1H), 8.66 (s, 1H), 8.49 (d, J=1.8 Hz, 1H), 8.19 (s, 1H), 8.12-8.06 (m, 4H), 7.94 (s, 1H), 7.89 (s, 1H), 7.78 (d, J=7.8 Hz, 1H), 7.61 (s, 1H), 7.40 (dd, J=8.1, 8.1 Hz, 1H), 7.23 (d, J=7.8 Hz, 1H), 5.26 (s, 2H), 3.90 (s, 3H). HRMS (ESI$^+$) calcd for C$_{22}$H$_{20}$N$_3$O$_5$ (M+H)$^+$ 406.1403, found 406.1402.

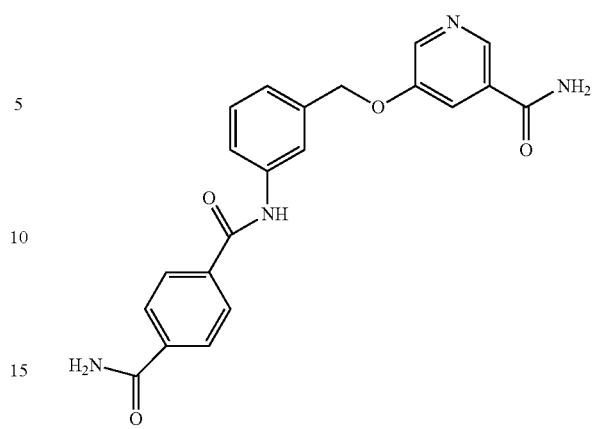

N$^1$-(3-(((5-Carbamoylpyridin-3-yl)oxy)methyl)phenyl)terephthalamide (A-64)

White solid (20 mg, 69%). $^1$H NMR (DMSO-d$_6$, 600 MHz) δ 10.41 (s, 1H), 8.65 (s, 1H), 8.50 (d, J=2.4 Hz, 1H), 8.13 (d, J=11.4 Hz, 2H), 8.04-7.97 (m, 4H), 7.94 (s, 1H), 7.86 (s, 1H), 7.76 (d, J=8.4 Hz, 1H), 7.62 (s, 1H), 7.53 (s, 1H), 7.40 (dd, J=8.1, 8.1 Hz, 1H), 7.23 (d, J=7.8 Hz, 1H), 5.26 (s, 2H). HRMS (ESI$^+$) calcd for C$_{21}$H$_{19}$N$_4$O$_4$ (M+H)$^+$ 391.1406, found 391.1401.

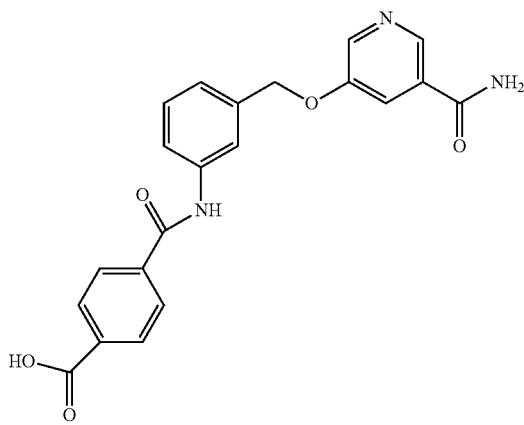 [SMILES: NC(=O)c1cncc(OCc2cccc(NC(=O)c3ccc(C(=O)O)cc3)c2)c1]

4-((3-(((5-Carbamoylpyridin-3-yl)oxy)methyl)phenyl)carbamoyl)benzoic acid (A-63)

White solid (13 mg, 45%). $^1$H NMR (DMSO-d$_6$, 600 MHz) δ 10.48 (s, 1H), 8.72-8.63 (m, 1H), 8.59 (bs, 1H), 8.50 (bs, 1H), 8.14 (s, 1H), 8.06 (dd, J=7.8, 12.0 Hz, 4H), 7.95-7.90 (m, 1H), 7.88-7.82 (m, 1H), 7.79-7.74 (m, 1H), 7.62 (s, 1H), 7.40 (dd, J=7.8, 7.8 Hz, 1H), 7.23 (d, J=7.8 Hz, 1H), 5.31-5.25 (m, 2H). HRMS (ESI$^+$) calcd for C$_{21}$H$_{18}$N$_3$O$_5$ (M+H)$^+$ 392.1246, found 392.1247.

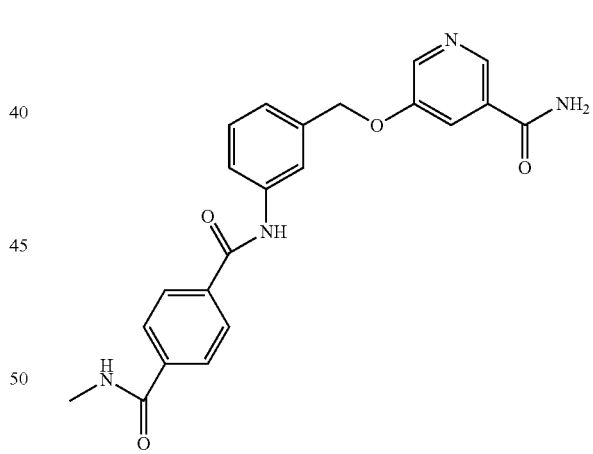

N$^1$-(3-(((5-Carbamoylpyridin-3-yl)oxy)methyl)phenyl)-M-methylterephthalamide (A-65)

White solid (22 mg, 74%). $^1$H NMR (DMSO-d$_6$, 600 MHz) δ 10.42 (s, 1H), 8.65 (s, 1H), 8.62-8.57 (m, 1H), 8.50 (d, J=3.0 Hz, 1H), 8.14 (s, 1H), 8.03 (d, J=7.8 Hz, 2H), 7.96 (d, J=8.4 Hz, 2H), 7.93 (s, 1H), 7.86 (s, 1H), 7.77 (d, J=8.4 Hz, 1H), 7.62 (s, 1H), 7.40 (dd, J=7.5, 7.5 Hz, 1H), 7.23 (d, J=7.8 Hz, 1H), 5.26 (s, 2H), 2.81 (d, J=4.2 Hz, 3H). HRMS (ESI$^+$) calcd for C$_{22}$H$_{21}$N$_4$O$_4$ (M+H)$^+$ 405.1563, found 405.1566.

47

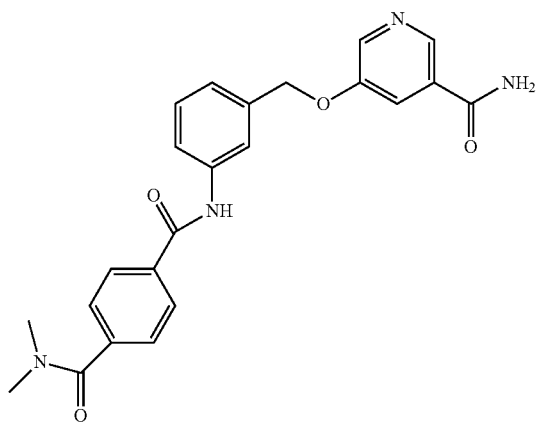 [SMILES: CN(C)C(=O)c1ccc(C(=O)Nc2cccc(COc3cncc(C(N)=O)c3)c2)cc1]

N¹-(3-(((5-Carbamoylpyridin-3-yl)oxy)methyl)phenyl)-N⁴,N⁴-dimethylterephthalamide (A-66)

White solid (0.8 mg, 4%). ¹H NMR (CD$_3$OD, 600 MHz) δ 8.63 (s, 1H), 8.47 (s, 1H), 8.02 (d, J=7.8 Hz, 2H), 7.93 (s, 1H), 7.89 (s, 1H), 7.69 (d, J=7.2 Hz, 1H), 7.56 (d, J=8.4 Hz, 2H), 7.42 (dd, J=7.8, 7.8 Hz, 1H), 7.29 (d, J=7.2 Hz, 1H), 5.27 (s, 2H), 3.13 (s, 3H), 3.01 (s, 3H). HRMS (ESI⁺) calcd for C$_{23}$H$_{23}$N$_4$O$_4$ (M+H)⁺ 419.1719, found 419.1710.

48

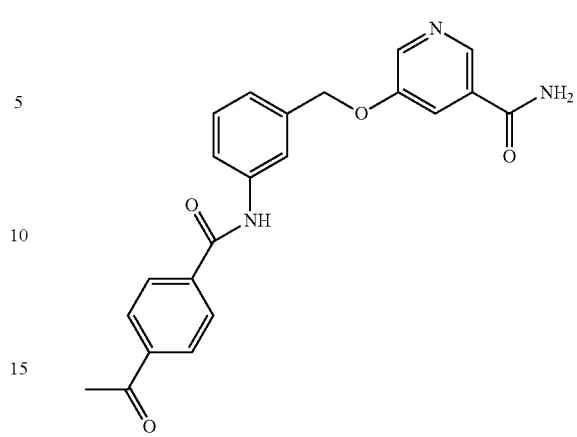

5-((3-(4-Acetylbenzamido)benzyl)oxy)nicotinamide (A-68)

Pale solid (30 mg, 37%). ¹H NMR (CD$_3$OD, 600 MHz) δ 8.62 (s, 1H), 8.45 (s, 1H), 8.46 (d, J=3.0 Hz, 1H), 8.19 (d, J=7.2 Hz, 1H), 8.17 (d, J=7.8 Hz, 1H), 7.94-7.92 (m, 1H), 7.89 (s, 1H), 7.70 (d, J=7.8 Hz, 1H), 7.66 (dd, J=8.4, 8.4 Hz, 1H), 7.42 (dd, J=7.5, 7.5 Hz, 1H), 7.28 (d, J=7.2 Hz, 1H), 5.27 (s, 2H), 2.68 (s, 3H). HRMS (ESI⁺) calcd for C$_{22}$H$_{20}$N$_3$O$_4$ (M+H)⁺ 390.1454, found 390.1459.

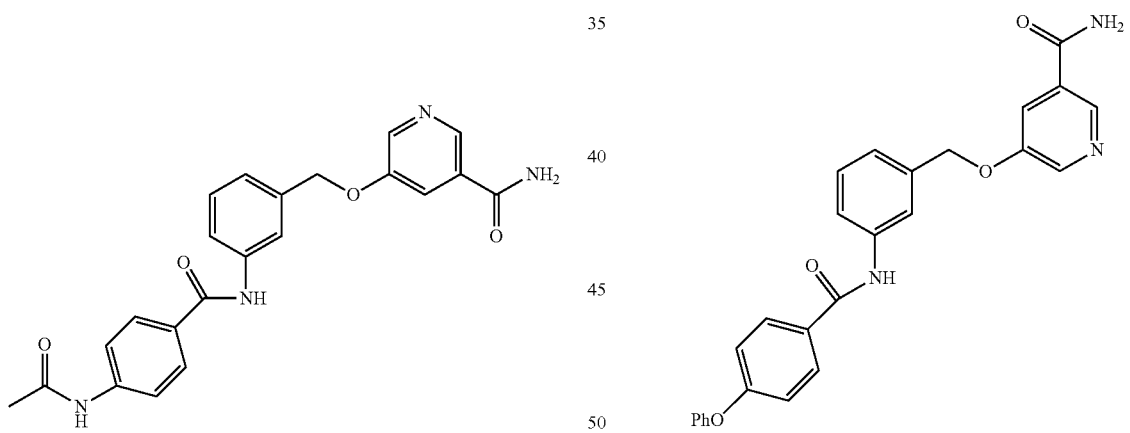

5-((3-(4-Acetamidobenzamido)benzyl)oxy)nicotinamide (A-67)

Pale solid (7.0 mg, 8%). ¹H NMR (DMSO-d$_6$, 600 MHz) δ 10.21 (s, 1H), 10.17 (s, 1H), 8.65 (s, 1H), 8.49 (d, J=2.4 Hz, 1H), 8.14 (s, 1H), 7.94-7.89 (m, 3H), 7.86 (s, 1H), 7.74 (d, J=8.4 Hz, 1H), 7.71 (d, J=8.4 Hz, 2H), 7.61 (s, 1H), 7.38 (dd, J=7.8, 7.8 Hz, 1H), 7.19 (d, J=7.8 Hz, 1H), 5.24 (s, 2H), 2.08 (s, 3H). HRMS (ESI⁺) calcd for C$_{22}$H$_{21}$N$_4$O$_4$ (M+H)⁺ 405.1563, found 405.1560.

5-((3-(4-Phenoxybenzamido)benzyl)oxy)nicotinamide (A-69)

White solid (32 mg, 35%). ¹H NMR (DMSO-d$_6$, 600 MHz) δ 10.26 (s, 1H), 8.65 (s, 1H), 8.49 (d, J=1.8 Hz, 1H), 8.14 (s, 1H), 8.00 (d, J=8.4 Hz, 2H), 7.92 (s, 1H), 7.86 (s, 1H), 7.74 (d, J=8.4 Hz, 1H), 7.61 (s, 1H), 7.46 (dd, J=7.8, 7.8 Hz, 2H), 7.39 (dd, J=7.5, 7.5 Hz, 1H), 7.25-7.19 (m, 2H), 7.14-7.07 (m, 4H), 5.25 (s, 2H). HRMS (ESI⁺) calcd for C$_{26}$H$_{22}$N$_3$O$_4$ (M+H)⁺ 440.1610, found 440.1608.

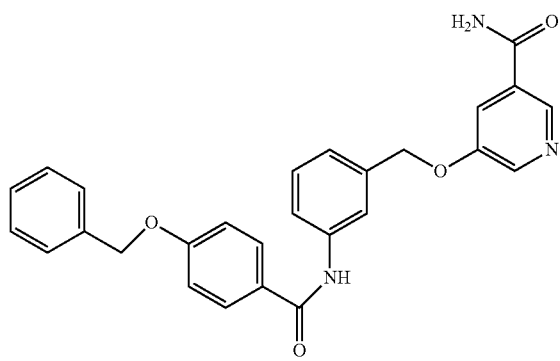 [SMILES: NC(=O)c1cncc(OCc2cccc(NC(=O)c3ccc(OCc4ccccc4)cc3)c2)c1]

5-((3-(4-(Benzyloxy)benzamido)benzyl)oxy)nicotinamide (A-70)

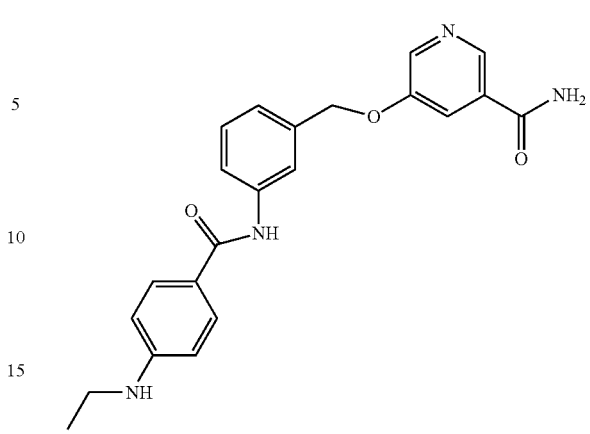

5-((3-(4-(Ethylamino)benzamido)benzyl)oxy)nicotinamide (A-72)

White solid (18 mg, 16%). ¹H NMR (DMSO-d$_6$, 600 MHz) δ 10.14 (s, 1H), 8.65 (d, J=1.6 Hz, 1H), 8.49 (d, J=2.8 Hz, 1H), 8.13 (s, 1H), 7.96-7.94 (m, 2H), 7.91 (s, 1H), 7.86 (dd, J=2.6, 1.8 Hz, 1H), 7.74 (d, J=8.1 Hz, 1H), 7.60 (s, 1H), 7.48 (d, J=7.3 Hz, 2H), 7.42-7.33 (m, 4H), 7.19 (d, J=7.6 Hz, 1H), 7.14 (d, J=8.8 Hz, 2H), 5.24 (s, 2H), 5.20 (s, 2H). HRMS (ESI⁺) calcd for $C_{27}H_{24}N_3O_4$ (M+H)⁺ 454.1761, found 454.1774.

Pale solid (2.0 mg, 2.5%). ¹H NMR (CD$_3$OD, 600 MHz) δ 8.62 (d, J=1.2 Hz, 1H), 8.46 (d, J=3.0 Hz, 1H), 7.92 (dd, J=2.1, 2.1 Hz, 1H), 7.83 (s, 1H), 7.78-7.75 (m, 2H), 7.63 (d, J=8.4 Hz, 1H), 7.37 (dd, J=7.8, 7.8 Hz, 1H), 7.22 (d, J=7.8 Hz, 1H), 6.64 (d, J=8.4 Hz, 2H), 5.25 (s, 2H), 3.19 (q, J=7.2 Hz, 2H), 1.26 (t, J=7.2 Hz, 3H). HRMS (ESI⁺) calcd for $C_{22}H_{23}H_4O_3$ (M+H)⁺ 391.1770, found 391.1771.

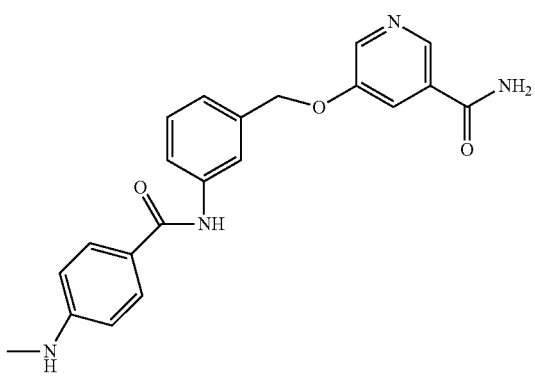 [SMILES: CNc1ccc(C(=O)Nc2cccc(COc3cncc(C(N)=O)c3)c2)cc1]

5-((3-(4-(Methylamino)benzamido)benzyl)oxy)nicotinamide (A-71)

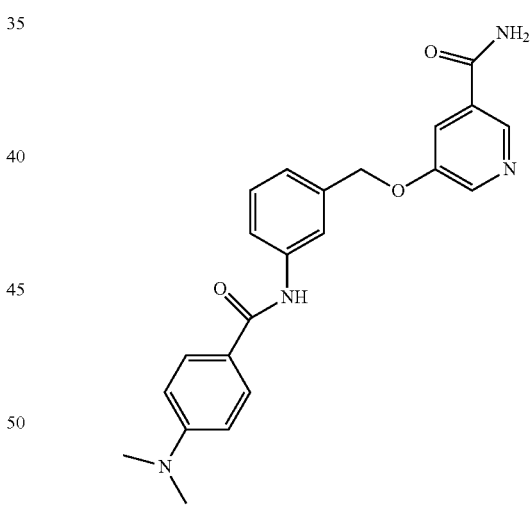

5-((3-(4-(Dimethylamino)benzamido)benzyl)oxy)nicotinamide (A-73)

Pale solid (1.0 mg, 1%). ¹H NMR (CD$_3$OD, 600 MHz) δ 8.62 (s, 1H), 8.46 (s, 1H), 7.93 (s, 1H), 7.83 (s, 1H), 7.78 (d, J=7.8 Hz, 2H), 7.63 (d, J=8.4 Hz, 1H), 7.37 (dd, J=7.5, 7.5 Hz, 1H), 7.23 (d, J=7.8 Hz, 1H), 6.63 (d, J=7.8 Hz, 2H), 5.25 (s, 2H), 2.83 (s, 3H). HRMS (ESI⁺) calcd for $C_{21}H_{21}N_4O_3$ (M+H)⁺ 377.1614, found 377.1608.

Pale solid (5.0 mg, 6%). ¹H NMR (CD$_3$OD, 600 MHz) δ 8.61 (s, 1H), 8.46 (s, 1H), 7.92 (s, 1H), 7.86-7.77 (m, 3H), 7.62 (d, J=7.8 Hz, 1H), 7.38 (dd, J=7.5, 7.5 Hz, 1H), 7.23 (d, J=6.6, 1H), 6.78 (d, J=7.2 Hz, 2H), 5.24 (s, 2H), 3.04 (s, 6H). HRMS (ESI⁺) calcd for $C_{22}H_{23}N_4O_3$ (M+H)⁺ 391.1770, found 391.1762.

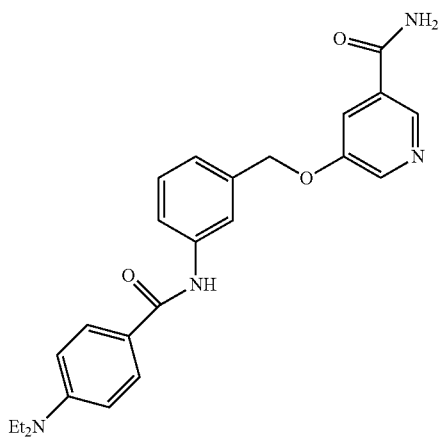

5-((3-(4-(Diethylamino)benzamido)benzyl)oxy)nicotinamide (A-74)

Pale solid (4.0 mg, 5%). ¹H NMR (CD₃OD, 600 MHz) δ 8.61 (s, 1H), 8.46 (s, 1H), 7.92 (s, 1H), 7.84-7.79 (m, 3H), 7.62 (d, J=7.8 Hz, 1H), 7.38 (dd, J=7.8, 7.8 Hz, 1H), 7.23 (d, J=6.6, 1H), 6.73 (d, J=9.0 Hz, 2H), 5.25 (s, 2H), 3.46 (q, J=6.9 Hz, 4H), 1.19 (t, J=7.2 Hz, 6H). HRMS (ESI⁺) calcd for C₂₄H₂₇N₄O₃ (M+H)⁺ 419.2083, found 419.2077.

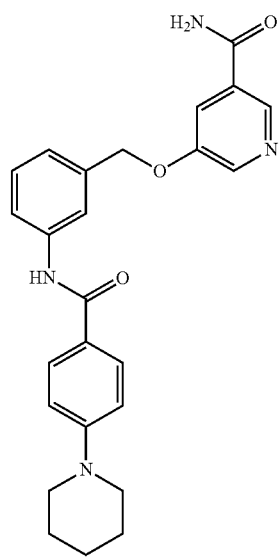

5-((3-(4-(Piperidin-1-yl)benzamido)benzyl)oxy) nicotinamide (A-76)

White solid (26 mg, 25%). ¹H NMR (DMSO-d₆, 600 MHz) δ 9.96 (s, 1H), 8.63 (s, 1H), 8.48 (s, 1H), 8.12 (s, 1H), 7.90 (s, 1H), 7.86-7.82 (m, 3H), 7.72 (d, J=7.9 Hz, 1H), 7.60 (s, 1H), 7.34 (dd, J=7.8, 7.8 Hz, 1H), 7.14 (d, J=7.4 Hz, 1H), 6.96 (d, J=8.5 Hz, 2H), 5.21 (s, 2H), 3.40-3.30 (m, 4H), 1.61-1.57 (m, 6H). HRMS (ESI⁺) calcd for C₂₅H₂₇N₄O₃ (M+H)⁺ 431.2078, found 431.208.

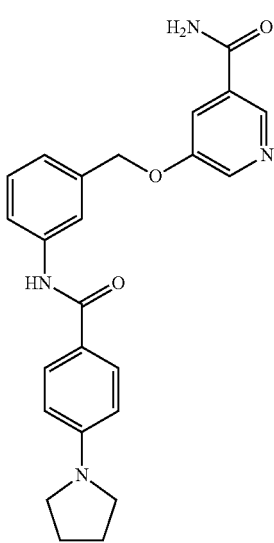 [SMILES: NC(=O)c1cncc(OCc2cccc(NC(=O)c3ccc(N4CCCC4)cc3)c2)c1]

5-((3-(4-(Pyrrolidin-1-yl)benzamido)benzyl)oxy) nicotinamide (A-75)

White solid (12 mg, 12%). ¹H NMR (DMSO-d₆, 600 MHz) δ 9.89 (s, 1H), 8.64 (s, 1H), 8.49 (s, 1H), 8.14 (s, 1H), 7.91 (s, 1H), 7.88-7.84 (m, 3H), 7.73 (d, J=8.1 Hz, 1H), 7.60 (s, 1H), 7.34 (dd, J=7.6, 7.6 Hz, 1H), 7.14 (d, J=7.6 Hz, 1H), 6.58 (d, J=8.5 Hz, 2H), 5.22 (s, 2H), 3.34-3.28 (m, 4H), 2.00-1.94 (m, 4H). HRMS (ESI⁺) calcd for C₂₄H₂₅N₄O₃ (M+H)⁺ 417.1921, found 417.1921.

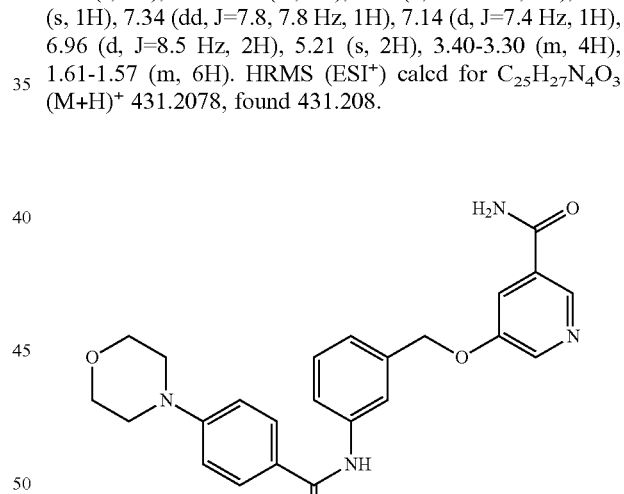

5-((3-(4-Morpholinobenzamido)benzyl)oxy)nicotinamide (A-77)

White solid (72 mg, 35%). ¹H NMR (DMSO-d₆, 600 MHz) δ 10.02 (s, 1H), 8.64 (s, 1H), 8.49 (s, 1H), 8.13 (s, 1H), 7.93-7.87 (m, 3H), 7.86 (s, 1H), 7.74 (d, J=8.1 Hz, 1H), 7.61 (s, 1H), 7.35 (dd, J=7.8, 7.8 Hz, 1H), 7.16 (d, J=7.6 Hz, 1H), 7.02 (d, J=8.7 Hz, 2H), 5.23 (s, 2H), 3.78-3.72 (m, 4H), 3.28-3.22 (m, 4H). HRMS (ESI⁺) calcd for C₂₄H₂₅N₄O₄ (M+H)⁺ 433.1870, found 433.1878.

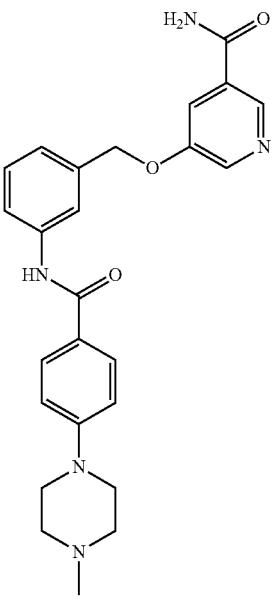 [SMILES: CN1CCN(c2ccc(C(=O)Nc3cccc(COc4cncc(C(N)=O)c4)c3)cc2)CC1]

5-((3-(4-(4-Methylpiperazin-1-yl)benzamido)benzyl)oxy)nicotinamide (A-78)

White solid (32 mg, 30%). $^1$H NMR (DMSO-d$_6$, 600 MHz) δ 10.00 (s, 1H), 8.64 (s, 1H), 8.48 (s, 1H), 8.14 (s, 1H), 7.91 (s, 1H), 7.88-7.85 (m, 3H), 7.73 (d, J=8.1 Hz, 1H), 7.60 (s, 1H), 7.35 (dd, J=7.6, 7.6 Hz, 1H), 7.16 (d, J=7.3 Hz, 1H), 7.01 (d, J=8.2 Hz, 2H), 5.23 (s, 2H), 3.40-3.30 (m, 4H), 2.50-2.45 (m, 4H), 2.24 (s, 3H). HRMS (ESI$^+$) calcd for C$_{25}$H$_{28}$N$_5$O$_3$ (M+H)$^+$ 446.2114, found 446.2194.

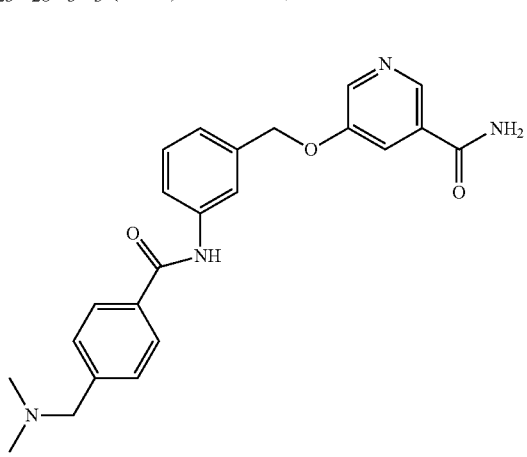

5-((3-(4-((Dimethylamino)methyl)benzamido)benzyl)oxy)nicotinamide (A-79)

Pale solid (15 mg, 71%). $^1$H NMR (CD$_3$OD, 600 MHz) δ 8.62 (s, 1H), 8.46 (d, J=2.4 Hz, 1H), 7.96-7.91 (m, 3H), 7.88 (s, 1H), 7.68 (d, J=8.4 Hz, 1H), 7.51 (d, J=7.8 Hz, 2H), 7.40 (dd, J=8.1, 8.1 Hz, 1H), 7.27 (d, J=7.8 Hz, 1H), 5.25 (s, 2H), 3.71 (s, 2H), 2.38 (s, 6H). HRMS (ESI$^+$) calcd for C$_{23}$H$_{25}$N$_4$O$_3$ (M+H)$^+$ 405.1927, found 405.1924.

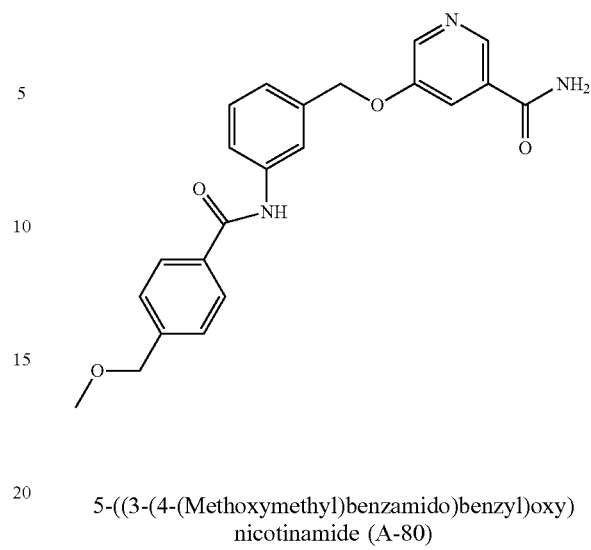

5-((3-(4-(Methoxymethyl)benzamido)benzyl)oxy)nicotinamide (A-80)

Pale solid (10 mg, 12%). $^1$H NMR (DMSO-d$_6$, 600 MHz) δ 10.30 (s, 1H), 8.65 (s, 1H), 8.50 (s, 1H), 8.14 (s, 1H), 7.93-7.91 (m, 3H), 7.86 (s, 1H), 7.75 (d, J=7.8 Hz, 1H), 7.61 (s, 1H), 7.46 (d, J=7.8 Hz, 2H), 7.39 (dd, J=7.8, 7.8 Hz, 1H), 7.21 (d, J=7.2 Hz, 1H), 5.25 (s, 2H), 4.50, (s, 2H), 3.33 (s, 3H). HRMS (ESI$^+$) calcd for C$_{22}$H$_{22}$N$_3$O$_4$ (M+H)$^+$ 392.1610, found 392.1601.

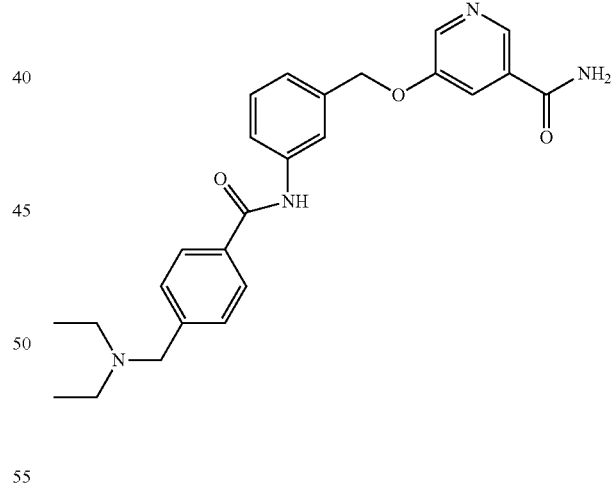

5-((3-(4-((Diethylamino)methyl)benzamido)benzyl)oxy)nicotinamide (A-81)

White solid (17 mg, 75%). $^1$H NMR (CD$_3$OD, 600 MHz) δ 8.62 (d, J=1.2 Hz, 1H), 8.45 (d, J=3.0 Hz, 1H), 7.94-7.89 (m, 3H), 7.87 (s, 1H), 7.67 (d, J=8.4 Hz, 1H), 7.50 (d, J=8.4 Hz, 2H), 7.39 (dd, J=8.1, 8.1 Hz, 1H), 7.26 (d, J=7.8 Hz, 1H), 5.24 (s, 2H), 3.72 (s, 2H), 2.61 (q, J=7.2 Hz, 4H), 1.10 (t, J=7.2 Hz, 6H). HRMS (ESI$^+$) calcd for C$_{25}$H$_{29}$H$_4$O$_3$ (M+H)$^+$ 433.2240, found 433.2236.

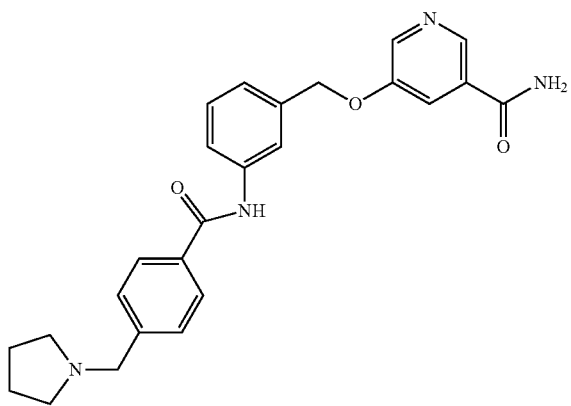 [SMILES: NC(=O)c1cncc(OCc2cccc(NC(=O)c3ccc(CN4CCCC4)cc3)c2)c1]

5-((3-(4-(Pyrrolidin-1-ylmethyl)benzamido)benzyl)oxy)nicotinamide (A-82)

Pale solid (18 mg, 82%). $^1$H NMR (CD$_3$OD, 600 MHz) δ 8.62 (s, 1H), 8.46 (d, J=2.4 Hz, 1H), 7.96-7.91 (m, 3H), 7.88 (s, 1H), 7.68 (d, J=8.4 Hz, 1H), 7.54 (d, J=7.8 Hz, 2H), 7.40 (dd, J=8.1, 8.1 Hz, 1H), 7.27 (d, J=7.8 Hz, 1H), 5.26 (s, 2H), 3.89 (s, 2H), 2.79-2.72 (m, 4H), 1.92-1.86 (m, 4H). HRMS (ESI$^+$) calcd for C$_{25}$H$_{27}$N$_4$O$_3$ (M+H)$^+$ 431.2083, found 431.2080.

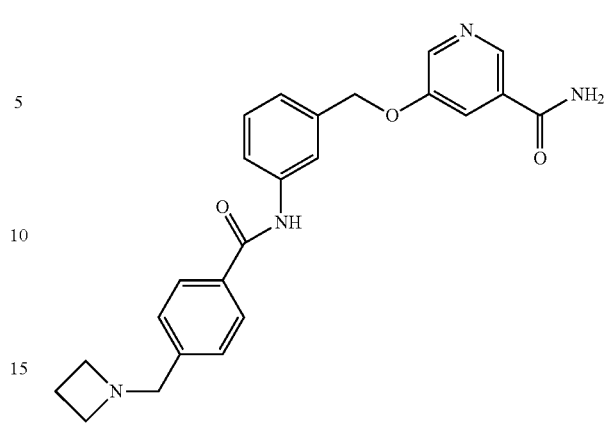

5-((3-(4-(Azetidin-1-ylmethyl)benzamido)benzyl)oxy)nicotinamide (A-84)

Pale solid (20 mg, 94%). $^1$H NMR (CD$_3$OD, 600 MHz) δ 8.62 (s, 1H), 8.45 (d, J=3.0 Hz, 1H), 7.96 (d, J=7.8 Hz, 2H), 7.94-7.91 (m, 1H), 7.88 (s, 1H), 7.68 (d, J=7.8 Hz, 1H), 7.53 (d, J=8.4 Hz, 2H), 7.39 (dd, J=8.1, 8.1 Hz, 1H), 7.26 (d, J=7.8 Hz, 1H), 5.24 (s, 2H), 4.09 (s, 2H), 3.76 (t, J=7.5 Hz, 4H), 2.33 (quin, J=7.8 Hz, 2H). HRMS (ESI$^+$) calcd for C$_{24}$H$_{25}$N$_4$O$_3$ (M+H)$^+$ 417.1927, found 417.1925.

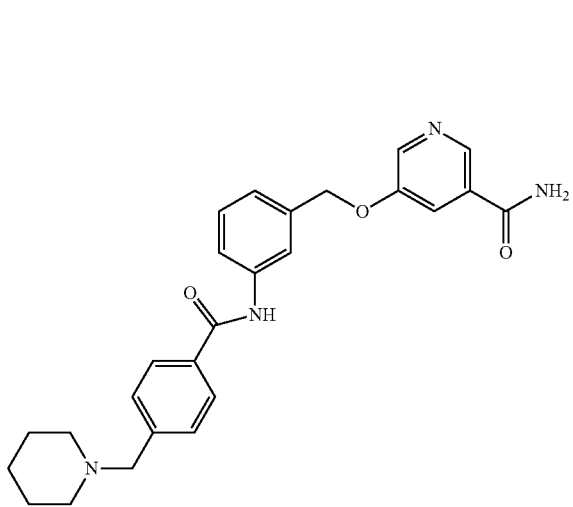 [SMILES: NC(=O)c1cncc(OCc2cccc(NC(=O)c3ccc(CN4CCCCC4)cc3)c2)c1]

5-((3-(4-(Piperidin-1-ylmethyl)benzamido)benzyl)oxy)nicotinamide (A-83)

Pale solid (19 mg, 84%). $^1$H NMR (CD$_3$OD, 600 MHz) δ 8.63 (s, 1H), 8.46 (d, J=3.0 Hz, 1H), 7.97 (d, J=7.8 Hz, 2H), 7.93 (s, 1H), 7.88 (s, 1H), 7.68 (d, J=7.8 Hz, 1H), 7.57 (d, J=7.8 Hz, 2H), 7.41 (dd, J=7.5, 7.5 Hz, 1H), 7.28 (d, J=7.2 Hz, 1H), 5.27 (s, 2H), 3.94 (s, 2H), 2.88-2.72 (m, 4H), 1.78-1.66 (m, 4H), 1.62-1.52 (m, 2H). HRMS (ESI$^+$) calcd for C$_{26}$H$_{29}$N$_4$O$_3$ (M+H)$^+$ 445.2240, found 445.2243.

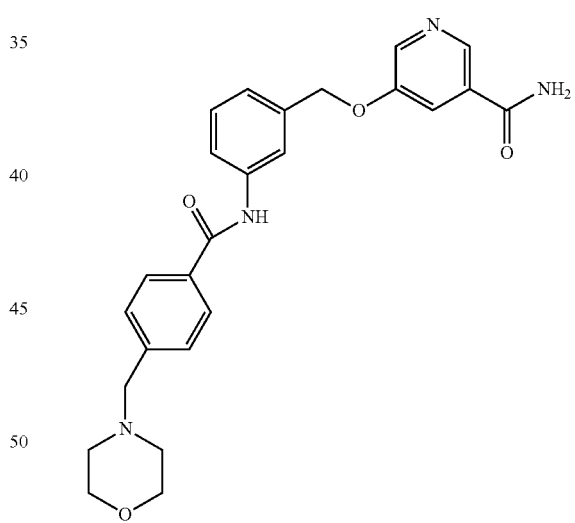

5-((3-(4-(Morpholinomethyl)benzamido)benzyl)oxy)nicotinamide (A-85)

Yellowish solid (11 mg, 12%). $^1$H NMR (CD$_3$OD, 600 MHz) δ 8.62 (s, 1H), 8.45 (d, J=2.4 Hz, 1H), 7.94-7.89 (m, 3H), 7.87 (s, 1H), 7.67 (d, J=8.4 Hz, 1H), 7.49 (d, J=7.8 Hz, 2H), 7.39 (dd, J=8.1, 8.1 Hz, 1H), 7.26 (d, J=7.8 Hz, 1H), 5.24 (s, 2H), 3.69 (t, J=4.5, 4.5 Hz, 4H), 3.59 (s, 2H), 2.50-2.44 (m, 4H). HRMS (ESI$^+$) calcd for C$_{25}$H$_{27}$H$_4$O$_4$ (M+H)$^+$ 447.2032, found 447.2029.

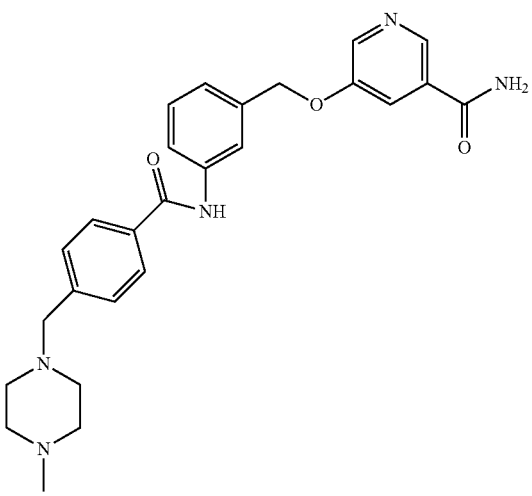 [SMILES: CN1CCN(Cc2ccc(C(=O)Nc3cccc(COc4cncc(C(N)=O)c4)c3)cc2)CC1]

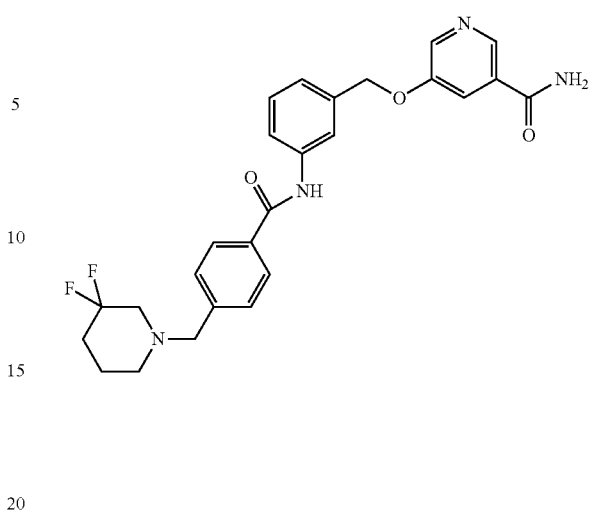

5-((3-(4-((3,3-Difluoropiperidin-1-yl)methyl)benzamido)benzyl)oxy)nicotinamide (A-88)

Pale solid (9.2 mg, 50%). $^1$H NMR (CD$_3$OD, 600 MHz) δ 8.62 (d, J=1.2 Hz, 1H), 8.45 (d, J=2.4 Hz, 1H), 7.94-7.89 (m, 3H), 7.87 (s, 1H), 7.67 (d, J=8.4 Hz, 1H), 7.49 (d, J=8.4 Hz, 2H), 7.39 (dd, J=8.1, 8.1 Hz, 1H), 7.26 (d, J=7.8 Hz, 1H), 5.24 (s, 2H), 3.67 (s, 2H), 2.62 (t, J=11.4 Hz, 2H), 2.52-2.46 (m, 2H), 1.93-1.84 (m, 2H), 1.80-1.74 (m, 2H). HRMS (ESI$^+$) calcd for C$_{26}$H$_{27}$F$_2$N$_4$O$_3$ (M+H)$^+$ 481.2051, found 481.2050.

5-((3-(4-((4-methylpiperazin-1-yl)methyl)benzamido)benzyl)oxy)nicotinamide (A-86)

Yellowish solid (3.0 mg, 3.3%). $^1$H NMR (CD$_3$OD, 600 MHz) δ 8.63 (s, 1H), 8.46 (d, J=3.0 Hz, 1H), 7.96-7.91 (m, 3H), 7.88 (s, 1H), 7.68 (d, J=8.4 Hz, 1H), 7.51 (d, J=7.8 Hz, 2H), 7.40 (dd, J=7.8, 7.8 Hz, 1H), 7.27 (d, J=7.8 Hz, 1H), 5.26 (s, 2H), 3.68 (s, 2H), 3.02-2.86 (m, 4H), 2.74-2.62 (m, 4H), 2.61 (s, 3H). HRMS (ESI$^+$) calcd for C$_{26}$H$_{30}$N$_5$O$_3$ (M+H)$^+$ 460.2349, found 460.2349.

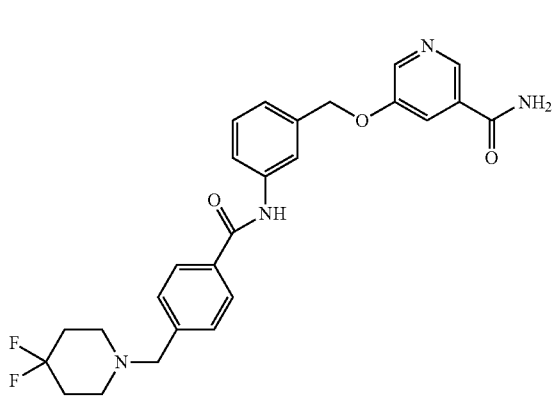 [SMILES: NC(=O)c1cncc(OCc2cccc(NC(=O)c3ccc(CN4CCC(F)(F)CC4)cc3)c2)c1]

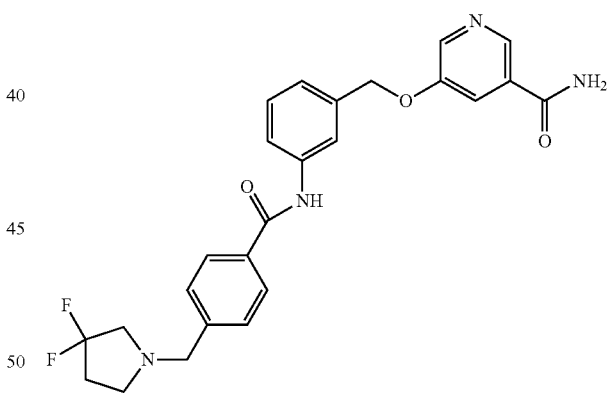

5-((3-(4-((4,4-Difluoropiperidin-1-yl)methyl)benzamido)benzyl)oxy)nicotinamide (A-87)

Pale solid (8.7 mg, 48%). $^1$H NMR (CD$_3$OD, 600 MHz) δ 8.62 (s, 1H), 8.45 (d, J=2.4 Hz, 1H), 7.94-7.89 (m, 3H), 7.87 (s, 1H), 7.67 (d, J=8.4 Hz, 1H), 7.49 (d, J=8.4 Hz, 2H), 7.39 (dd, J=8.1, 8.1 Hz, 1H), 7.26 (d, J=7.8 Hz, 1H), 5.24 (s, 2H), 3.65 (s, 2H), 2.62-2.54 (m, 4H), 2.03-1.94 (m, 4H). HRMS (ESI$^+$) calcd for C$_{26}$H$_{27}$F$_2$N$_4$O$_3$ (M+H)$^+$ 481.2051, found 481.2050.

5-((3-(4-((3,3-Difluoropyrrolidin-1-yl)methyl)benzamido)benzyl)oxy)nicotinamide (A-89)

Pale solid (12 mg, 68%). $^1$H NMR (CD$_3$OD, 600 MHz) δ 8.62 (s, 1H), 8.46 (s, 1H), 7.94-7.89 (m, 3H), 7.87 (s, 1H), 7.67 (d, J=8.4 Hz, 1H), 7.49 (d, J=7.8 Hz, 2H), 7.40 (dd, J=7.8, 7.8 Hz, 1H), 7.26 (d, J=7.2 Hz, 1H), 5.25 (s, 2H), 3.73 (s, 2H), 2.89 (t, J=13.2 Hz, 2H), 2.78 (t, J=6.9 Hz, 2H), 2.33-2.24 (m, 2H). HRMS (ESI$^+$) calcd for C$_{25}$H$_{25}$F$_2$N$_4$O$_3$ (M+H)$^+$ 467.1895, found 467.1892.

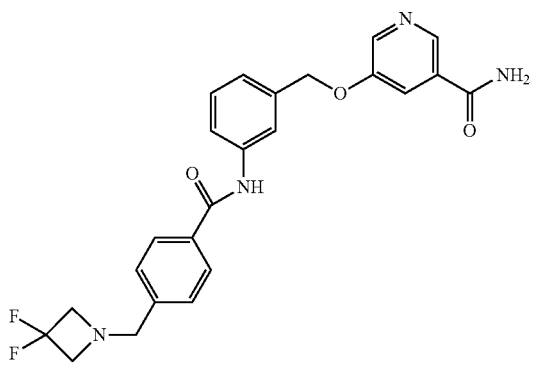 [SMILES: NC(=O)c1cncc(OCc2cccc(NC(=O)c3ccc(CN4CC(F)(F)C4)cc3)c2)c1]

5-((3-(4-((3,3-Difluoroazetidin-1-yl)methyl)benzamido)benzyl)oxy)nicotinamide (A-90)

Pale solid (5.1 mg, 30%). $^1$H NMR (CD$_3$OD, 600 MHz) δ 8.62 (s, 1H), 8.46 (d, J=2.4 Hz, 1H), 7.94-7.89 (m, 3H), 7.87 (s, 1H), 7.67 (d, J=8.4 Hz, 1H), 7.48 (d, J=8.4 Hz, 2H), 7.40 (dd, J=7.8, 7.8 Hz, 1H), 7.27 (d, J=7.8 Hz, 1H), 5.26 (s, 2H), 3.85 (s, 2H), 3.66 (t, J=12.0 Hz, 4H). HRMS (ESI$^+$) calcd for C$_{24}$H$_{23}$F$_2$N$_4$O$_3$ (M+H)$^+$ 453.1738, found 453.1740.

N-(3-(((5-Carbamoylpyridin-3-yl)oxy)methyl)phenyl)nicotinamide (A-92)

White solid (60 mg, 72%). $^1$H NMR (DMSO-d$_6$, 600 MHz) δ 10.51 (s, 1H), 9.11 (s, 1H), 8.76 (d, J=4.0 Hz, 1H), 8.65 (s, 1H), 8.50 (s, 1H), 8.29 (d, J=7.9 Hz, 1H), 8.14 (s, 1H), 7.92 (s, 1H), 7.86 (s, 1H), 7.75 (d, J=8.1 Hz, 1H), 7.62 (s, 1H), 7.57 (dd, J=6.9, 6.9 Hz, 1H), 7.41 (dd, J=7.8, 7.8 Hz, 1H), 7.24 (d, J=7.5 Hz, 1H), 5.26 (s, 2H). HRMS (ESI$^+$) calcd for C$_{19}$H$_{17}$N$_4$O$_3$ (M+H)$^+$ 349.1295, found 349.1300.

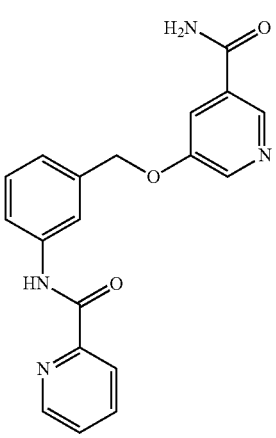 [SMILES: NC(=O)c1cncc(OCc2cccc(NC(=O)c3ccccn3)c2)c1]

N-(3-(((5-Carbamoylpyridin-3-yl)oxy)methyl)phenyl)picolinamide (A-91)

White solid (61 mg, 73%). $^1$H NMR (DMSO-d$_6$, 600 MHz) δ 10.69 (s, 1H), 8.74 (d, J=4.1 Hz, 1H), 8.65 (s, 1H), 8.50 (s, 1H), 8.17-8.12 (m, 2H), 8.10-8.05 (m, 2H), 7.88-7.84 (m, 2H), 7.68 (dd, J=5.3, 5.3 Hz, 1H), 7.61 (s, 1H), 7.40 (dd, J=7.8, 7.8 Hz, 1H), 7.23 (d, J=7.5 Hz, 1H), 5.25 (s, 2H). HRMS (ESI$^+$) calcd for C$_{19}$H$_{17}$N$_4$O$_3$ (M+H)$^+$ 349.1295, found 349.1305.

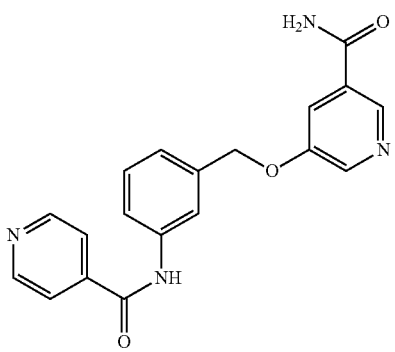 [SMILES: NC(=O)c1cncc(OCc2cccc(NC(=O)c3ccncc3)c2)c1]

5-((3-(Isonicotinamido)benzyl)oxy)nicotinamide (A-93)

White solid (30 mg, 36%). $^1$H NMR (DMSO-d$_6$, 600 MHz) δ 10.57 (s, 1H), 8.79 (d, J=5.7 Hz, 2H), 8.65 (s, 1H), 8.50 (d, J=2.5 Hz, 1H), 8.15 (s, 1H), 7.91 (s, 1H), 7.87-7.84 (m, 3H), 7.76 (d, J=8.1 Hz, 1H), 7.63 (s, 1H), 7.41 (dd, J=7.8, 7.8 Hz, 1H), 7.25 (d, J=7.5 Hz, 1H), 5.25 (s, 2H). HRMS (ESI$^+$) calcd for C$_{19}$H$_{17}$N$_4$O$_3$ (M+H)$^+$ 349.1295, found 349.1300.

61

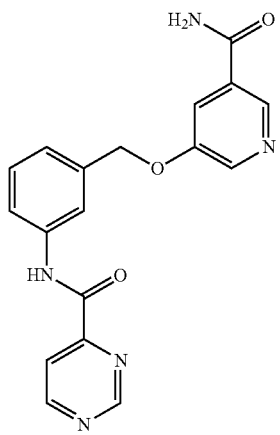 [SMILES: NC(=O)c1cncc(OCc2cccc(NC(=O)c3ccncn3)c2)c1]

N-(3-(((5-Carbamoylpyridin-3-yl)oxy)methyl)phenyl)pyrimidine-4-carboxamide (A-94)

White solid (40 mg, 48%). $^1$H NMR (DMSO-d$_6$, 600 MHz) δ 10.87 (s, 1H), 9.41 (s, 1H), 9.12 (d, J=5.1 Hz, 1H), 8.64 (s, 1H), 8.49 (d, J=2.6 Hz, 1H), 8.12 (d, J=4.7 Hz, 2H), 8.06 (s, 1H), 7.87-7.84 (m, 2H), 7.60 (s, 1H), 7.41 (dd, J=7.6, 7.6 Hz, 1H), 7.25 (d, J=8.4 Hz, 1H), 5.25 (s, 2H). HRMS (ESI$^+$) calcd for C$_{18}$H$_{16}$N$_5$O$_3$ (M+H)$^+$ 350.1248, found 350.1247.

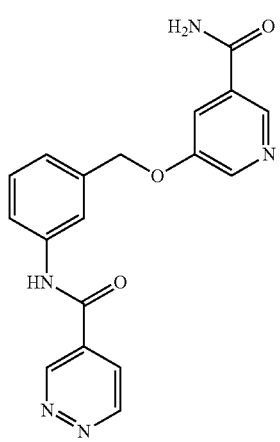 [SMILES: NC(=O)c1cncc(OCc2cccc(NC(=O)c3ccnnc3)c2)c1]

N-(3-(((5-Carbamoylpyridin-3-yl)oxy)methyl)phenyl)pyridazine-4-carboxamide (A-95)

White solid (40 mg, 48%). $^1$H NMR (DMSO-d$_6$, 600 MHz) δ 10.76 (s, 1H), 9.63 (s, 1H), 9.48 (d, J=5.4 Hz, 1H), 8.64 (s, 1H), 8.48 (d, J=2.6 Hz, 1H), 8.12 (s, 1H), 8.11-8.09 (m, 1H), 7.89 (s, 1H), 7.86 (s, 1H), 7.74 (d, J=8.7 Hz, 1H), 7.60 (s, 1H), 7.43 (dd, J=7.9, 7.9 Hz, 1H), 7.27 (d, J=7.2 Hz, 1H) 5.26 (s, 2H). HRMS (ESI$^+$) calcd for C$_{18}$H$_{16}$N$_5$O$_3$ (M+H)$^+$ 350.1248, found 350.1251.

62

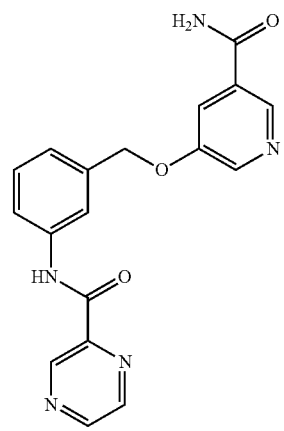 [SMILES: NC(=O)c1cncc(OCc2cccc(NC(=O)c3cnccn3)c2)c1]

N-(3-(((5-Carbamoylpyridin-3-yl)oxy)methyl)phenyl)pyrazine-2-carboxamide (A-96)

White solid (35 mg, 42%). $^1$H NMR (DMSO-d$_6$, 600 MHz) δ 10.78 (s, 1H), 9.29 (s, 1H), 8.92 (s, 1H), 8.80 (s, 1H), 8.64 (s, 1H), 8.50 (s, 1H), 8.14 (s, 1H), 8.06 (s, 1H), 7.87 (s, 1H), 7.84 (d, J=8.1 Hz, 1H), 7.61 (s, 1H), 7.41 (dd, J=7.6, 7.6 Hz, 1H), 7.25 (d, J=7.3 Hz, 1H), 5.26 (s, 2H). HRMS (ESI$^+$) calcd for C$_{18}$H$_{15}$N$_5$O$_3$ (M+H)$^+$ 350.1248, found 350.1250.

N-(3-(((5-Carbamoylpyridin-3-yl)oxy)methyl)phenyl)pyridazine-3-carboxamide (A-97)

White solid (25 mg, 30%). $^1$H NMR (DMSO-d$_6$, 600 MHz) δ 11.12 (s, 1H), 9.46 (dd, J=5.0, 1.8 Hz, 1H), 8.71 (s, 1H), 8.62 (s, 1H), 8.31 (dd, J=8.5, 1.8 Hz, 1H), 8.22 (s, 1H), 8.12 (s, 1H), 8.07 (s, 1H), 7.97 (dd, J=8.4, 5.0 Hz, 1H), 7.88 (d, J=7.8 Hz, 1H), 7.73 (s, 1H), 7.42 (dd, J=7.8, 7.8 Hz, 1H), 7.26 (d, J=7.5 Hz, 1H), 5.30 (s, 2H). HRMS (ESI$^+$) calcd for C$_{18}$H$_{16}$N$_5$O$_3$ (M+H)$^+$ 350.1248, found 350.1257.

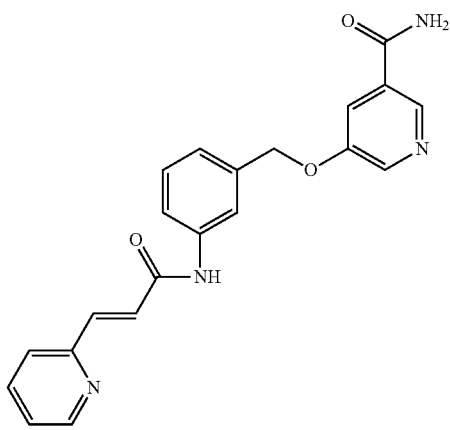 [SMILES: NC(=O)c1cncc(OCc2cccc(NC(=O)/C=C/c3ccccn3)c2)c1]

(E)-5-((3-(3-(Pyridin-2-yl)acrylamido)benzyl)oxy)
nicotinamide (A-98)

Pale solid (41 mg, 53%). $^1$H NMR (DMSO-$d_6$, 600 MHz) δ 10.43 (s, 1H), 8.67-8.62 (m, 2H), 8.49 (d, J=3.0 Hz, 1H), 8.14 (s, 1H), 7.88-7.83 (m, 3H), 7.68 (d, J=8.4 Hz, 1H), 7.65-7.58 (m, 3H), 7.42-7.35 (m, 2H), 7.32 (d, J=15.6 Hz, 1H), 7.19 (d, J=7.8 Hz, 1H), 5.25 (s, 2H). HRMS (ESI$^+$) calcd for $C_{21}H_{19}N_4O_3$ (M+H)$^+$ 375.1457, found 375.1456.

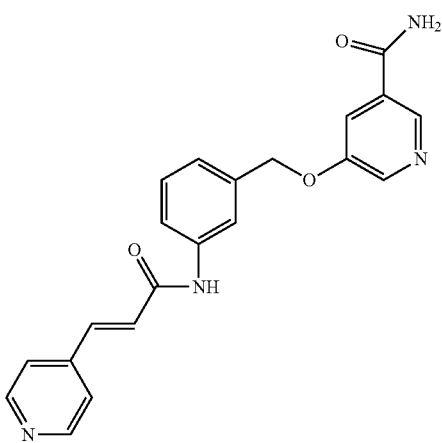

(E)-5-((3-(3-(Pyridin-4-yl)acrylamido)benzyl)oxy)
nicotinamide (A-100)

White solid (35 mg, 45%). $^1$H NMR (DMSO-$d_6$, 600 MHz) δ 10.44 (s, 1H), 8.67-8.61 (m, 3H), 8.49 (d, J=2.4 Hz, 1H), 8.15 (s, 1H), 7.86 (s, 1H), 7.83 (s, 1H), 7.68 (d, J=7.8 Hz, 1H), 7.62 (s, 1H), 7.59-7.53 (m, 3H), 7.39 (dd, J=7.8, 7.8 Hz, 1H), 7.20 (d, J=7.2 Hz, 1H), 7.04 (d, J=15.6 Hz, 1H), 5.25 (s, 2H). HRMS (ESI$^+$) calcd for $C_{21}H_{19}H_4O_3$ (M+H)$^+$ 375.1457, found 375.1459.

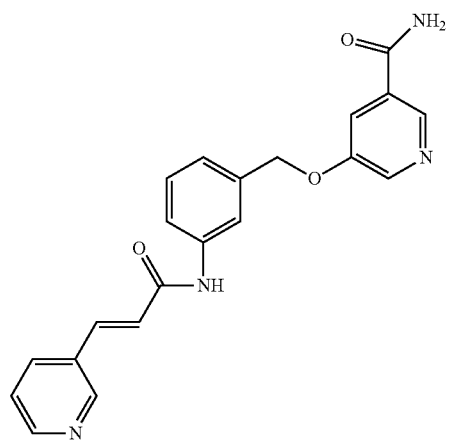 [SMILES: NC(=O)c1cncc(OCc2cccc(NC(=O)/C=C/c3cccnc3)c2)c1]

(E)-5-((3-(3-(Pyridin-3-yl)acrylamido)benzyl)oxy)
nicotinamide (A-99)

White solid (41 mg, 53%). $^1$H NMR (DMSO-$d_6$, 600 MHz) δ 10.35 (s, 1H), 8.82 (d, J=1.8 Hz, 1H), 8.65 (d, J=1.2 Hz, 1H), 8.58 (d, J=4.2 Hz, 1H), 8.49 (d, J=3.0 Hz, 1H), 8.14 (s, 1H), 8.04 (d, J=7.8 Hz, 1H), 7.85 (d, J=2.4 Hz, 1H), 7.83 (s, 1H), 7.68 (d, J=8.4 Hz, 1H), 7.65-7.58 (m, 2H), 7.48 (dd, J=7.8, 4.8 Hz, 1H), 7.38 (dd, J=7.5, 7.5 Hz, 1H), 7.19 (d, J=7.2 Hz, 1H), 6.93 (d, J=15.6 Hz, 1H), 5.25 (s, 2H). HRMS (ESI$^+$) calcd for $C_{21}H_{19}N_4O_3$ (M+H)$^+$ 375.1457, found 375.1457.

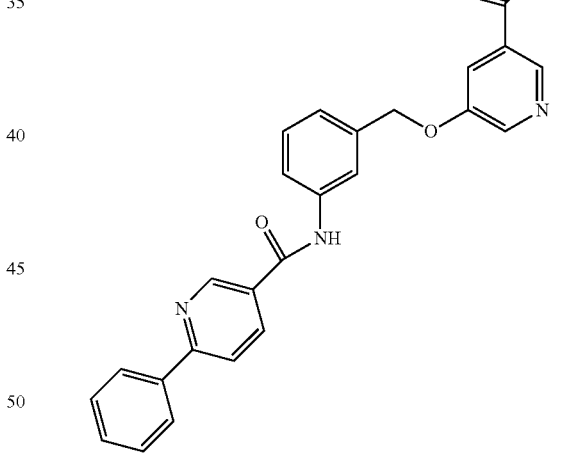

N-(3-(((5-Carbamoylpyridin-3-yl)oxy)methyl)phenyl)-6-phenylnicotinamide (A-101)

White solid (37 mg, 42%). $^1$H NMR (DMSO-$d_6$, 600 MHz) δ 10.53 (s, 1H), 9.20 (d, J=2.4 Hz, 1H), 8.66 (d, J=1.2 Hz, 1H), 8.51 (d, J=2.4 Hz, 1H), 8.40 (dd, J=8.4, 1.8 Hz, 1H), 8.19 (d, J=7.2 Hz, 2H), 8.15 (d, J=8.4 Hz, 2H), 7.95 (s, 1H), 7.89-7.85 (m, 1H), 7.78 (d, J=8.4 Hz, 1H), 7.62 (s, 1H), 7.55 (d, J=7.5, 7.5 Hz, 1H), 7.50 (dd, J=7.2, 7.2 Hz, 2H), 7.42 (dd, J=7.8, 7.8 Hz, 1H), 7.25 (d, J=7.2 Hz, 1H), 5.28 (s, 2H). HRMS (ESI$^+$) calcd for $C_{25}H_{21}N_4O_3$ (M+H)$^+$ 425.1614, found 425.1613.

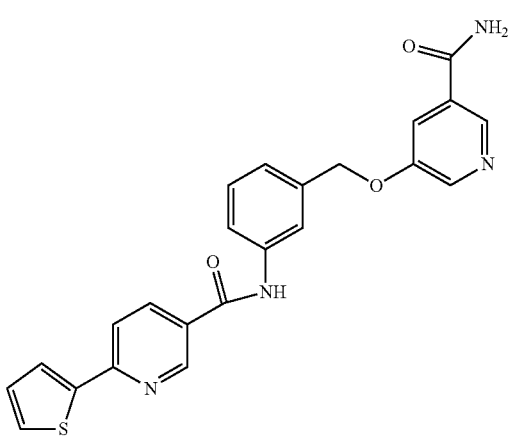 [SMILES: NC(=O)c1cncc(OCc2cccc(NC(=O)c3ccc(-c4cccs4)nc3)c2)c1]

N-(3-(((5-Carbamoylpyridin-3-yl)oxy)methyl)phenyl)-6-(thiophen-2-yl)nicotinamide (A-102)

Pale solid (32 mg, 36%). $^1$H NMR (DMSO-d$_6$, 600 MHz) δ 10.50 (s, 1H), 9.05 (s, 1H), 8.66 (s, 1H), 8.50 (d, J=2.4 Hz, 1H), 8.34 (d, J=7.8 Hz, 1H), 8.14 (s, 1H), 8.08 (d, J=8.4 Hz, 1H), 7.95 (d, J=4.2 Hz, 1H), 7.93 (s, 1H), 7.87 (d, J=1.8 Hz, 1H), 7.78-7.73 (m, 2H), 7.62 (s, 1H), 7.42 (dd, J=8.1, 8.1 Hz, 1H), 7.27-7.21 (m, 2H), 5.27 (s, 2H). HRMS (ESI$^+$) calcd for C$_{23}$H$_{19}$N$_4$O$_3$S (M+H)$^+$ 431.1178, found 431.1171.

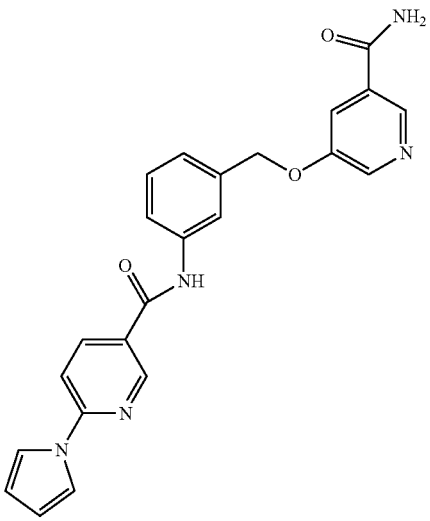 [SMILES: NC(=O)c1cncc(OCc2cccc(NC(=O)c3ccc(-n4cccc4)nc3)c2)c1]

N-(3-(((5-Carbamoylpyridin-3-yl)oxy)methyl)phenyl)-6-(1H-pyrrol-1-yl)nicotinamide (A-104)

Brownish solid (20 mg, 24%). $^1$H NMR (DMSO-d$_6$, 600 MHz) δ 10.45 (s, 1H), 8.99 (s, 1H), 8.66 (s, 1H), 8.50 (s, 1H), 8.42 (d, J=6.6 Hz, 1H), 8.14 (s, 1H), 7.92 (s, 1H), 7.87 (d, J=9.0 Hz, 2H), 7.80-7.73 (m, 3H), 7.62 (s, 1H), 7.41 (dd, J=7.8, 7.8 Hz, 1H), 7.24 (d, J=7.8 Hz, 1H), 6.36 (s, 2H), 5.27 (s, 2H). HRMS (ESI$^+$) calcd for C$_{23}$H$_{20}$N$_5$O$_3$ (M+H)$^+$ 414.1566, found 414.1572.

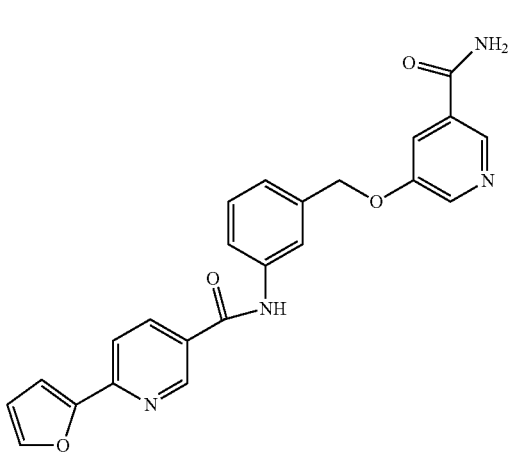

N-(3-(((5-Carbamoylpyridin-3-yl)oxy)methyl)phenyl)-6-(furan-2-yl)nicotinamide (A-103)

Pale solid (24 mg, 28%). $^1$H NMR (DMSO-d$_6$, 600 MHz) δ 10.50 (s, 1H), 9.11 (s, 1H), 8.66 (s, 1H), 8.50 (d, J=3.0 Hz, 1H), 8.38 (d, J=8.4 Hz, 1H), 8.14 (s, 1H), 7.93 (d, J=6.0 Hz, 2H), 7.87 (d, J=8.4 Hz, 2H), 7.76 (d, J=7.8 Hz, 1H), 7.62 (s, 1H), 7.42 (dd, J=8.1, 8.1 Hz, 1H), 7.28 (d, J=3.0 Hz, 1H), 7.24 (d, J=7.2 Hz, 1H), 6.74-6.69 (m, 1H), 5.27 (s, 2H). HRMS (ESI$^+$) calcd for C$_{23}$H$_{19}$N$_4$O$_4$ (M+H)$^+$ 415.1406, found 415.1401.

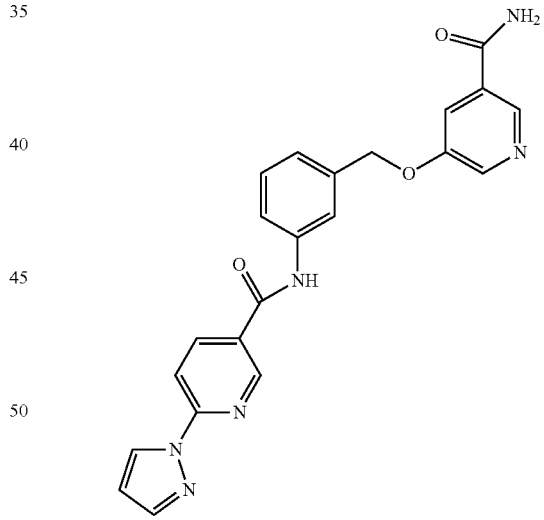

N-(3-(((5-Carbamoylpyridin-3-yl)oxy)methyl)phenyl)-6-(1H-pyrazol-1-yl)nicotinamide (A-105)

Pale solid (35 mg, 41%). $^1$H NMR (DMSO-d$_6$, 600 MHz) δ 10.53 (s, 1H), 9.02 (d, J=1.8 Hz, 1H), 8.71 (d, J=2.4 Hz, 1H), 8.67 (s, 1H), 8.53-8.48 (m, 2H), 8.15 (s, 1H), 8.06 (d, J=9.0 Hz, 1H), 7.91 (d, J=9.6 Hz, 2H), 7.87 (s, 1H), 7.76 (d, J=7.8 Hz, 1H), 7.62 (s, 1H), 7.42 (dd, J=7.5, 7.5 Hz, 1H), 7.24 (d, J=7.2 Hz, 1H), 6.64 (s, 1H), 5.27 (s, 2H). HRMS (ESI$^+$) calcd for C$_{22}$H$_{19}$N$_6$O$_3$ (M+H)$^+$ 415.1519, found 415.1521.

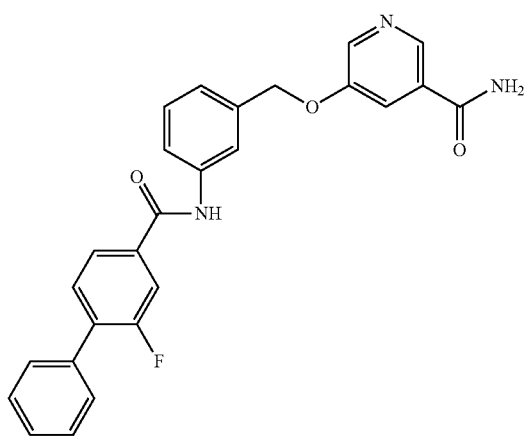 [SMILES: NC(=O)c1cncc(OCc2cccc(NC(=O)c3ccc(-c4ccccc4)c(F)c3)c2)c1]

5-((3-(2-Fluoro-[1,1'-biphenyl]-4-ylcarboxamido)benzyl)oxy)nicotinamide (A-106)

Pale solid (25 mg, 23%). $^1$H NMR (DMSO-d$_6$, 600 MHz) δ 10.42 (s, 1H), 8.66 (s, 1H), 8.50 (d, J=1.2 Hz, 1H), 8.14 (s, 1H), 7.95 (s, 1H), 7.92 (d, J=9.0 Hz, 2H), 7.87 (s, 1H), 7.78 (d, J=8.4 Hz, 1H), 7.72 (dd, J=7.8, 7.8 Hz, 1H), 7.66-7.57 (m, 3H), 7.53 (dd, J=7.2, 7.2 Hz, 2H), 7.47 (dd, J=6.9, 6.9 Hz, 1H), 7.42 (dd, J=8.1, 8.1 Hz, 1H), 7.24 (d, J=6.6 Hz, 1H), 5.27 (s, 2H). HRMS (ESI$^+$) calcd for C$_{26}$H$_{21}$FN$_3$O$_3$ (M+H)$^+$ 442.1567, found 442.1574.

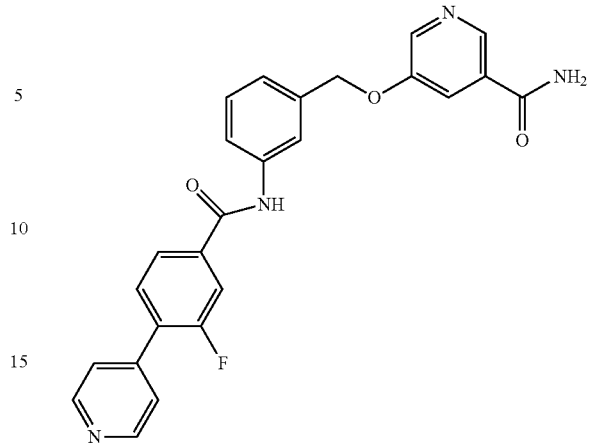

5-((3-(3-Fluoro-4-(pyridin-4-yl)benzamido)benzyl)oxy)nicotinamide (A-108)

Pale solid (35 mg, 32%). $^1$H NMR (DMSO-d$_6$, 600 MHz) δ 10.45 (s, 1H), 8.84 (s, 1H), 8.66 (s, 2H), 8.51 (s, 1H), 8.14 (s, 1H), 8.06 (d, J=7.8 Hz, 1H), 7.98-7.92 (m, 3H), 7.87 (s, 1H), 7.83-7.75 (m, 2H), 7.62 (s, 1H), 7.57 (dd, J=6.0, 6.0 Hz, 1H), 7.42 (dd, J=7.8, 7.8 Hz, 1H), 7.24 (d, J=7.2 Hz, 1H), 5.27 (s, 2H). HRMS (ESI$^+$) calcd for C$_{25}$H$_{20}$FN$_4$O$_3$ (M+H)$^+$ 443.1519, found 443.1522.

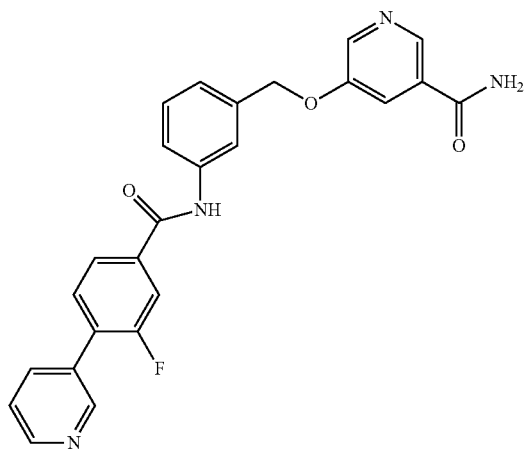 [SMILES: NC(=O)c1cncc(OCc2cccc(NC(=O)c3ccc(-c4cccnc4)c(F)c3)c2)c1]

5-((3-(3-Fluoro-4-(pyridin-3-yl)benzamido)benzyl)oxy)nicotinamide (A-107)

Pale solid (20 mg, 18%). $^1$H NMR (DMSO-d$_6$, 600 MHz) δ 10.47 (s, 1H), 8.72 (d, J=5.4 Hz, 2H), 8.66 (s, 1H), 8.50 (d, J=3.0 Hz, 1H), 8.14 (s, 1H), 7.98-7.92 (m, 3H), 7.87 (s, 1H), 7.83 (dd, J=8.1, 8.1 Hz, 1H), 7.78 (d, J=8.4 Hz, 1H), 7.66 (d, J=4.8 Hz, 2H), 7.62 (s, 1H), 7.42 (dd, J=7.8, 7.8 Hz, 1H), 7.25 (d, J=7.2 Hz, 1H), 5.27 (s, 2H). HRMS (ESI$^+$) calcd for C$_{25}$H$_{20}$FN$_4$O$_3$ (M+H)$^+$ 443.1519, found 443.1520.

5-((3-(4-Bromobenzamido)benzyl)oxy)nicotinamide (A-109)

White solid (850 mg, 61%). $^1$H NMR (DMSO-d$_6$, 600 MHz) δ 10.38 (s, 1H), 8.65 (s, 1H), 8.49 (s, 1H), 8.14 (s, 1H), 7.93-7.89 (m, 3H), 7.86 (s, 1H), 7.77-7.72 (m, 3H), 7.61 (s, 1H), 7.40 (dd, J=8.1, 8.1 Hz, 1H), 7.21 (d, J=7.2 Hz, 1H), 5.25 (s, 2H). HRMS (ESI$^+$) calcd for C$_{20}$H$_{17}$BrN$_3$O$_3$ (M+H)$^+$ 426.0448, found 426.0452.

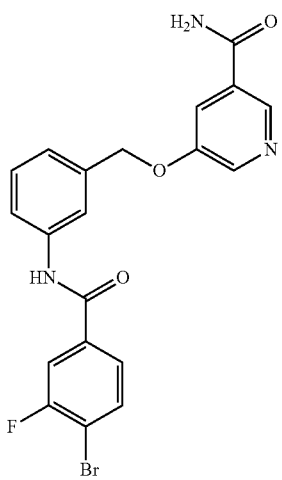 [SMILES: NC(=O)c1cncc(OCc2cccc(NC(=O)c3ccc(Br)c(F)c3)c2)c1]

5-((3-(4-Bromo-3-fluorobenzamido)benzyl)oxy) nicotinamide (A-110)

White solid (240 mg, 54%). $^1$H NMR (DMSO-d$_6$, 600 MHz) δ 10.42 (s, 1H), 8.65 (s, 1H), 8.49 (s, 1H), 8.13 (s, 1H), 7.94 (d, J=9.5 Hz, 1H), 7.91-7.89 (m, 2H), 7.85 (s, 1H), 7.75 (dd, J$_1$=17.3 Hz, J$_2$=8.2 Hz, 2H), 7.61 (s, 1H), 7.40 (t, J=7.8 Hz, 1H), 7.23 (d, J=7.5 Hz, 1H), 5.25 (s, 2H). HRMS (ESI$^+$) calcd for C$_{20}$H$_{16}$BrFN$_3$O$_3$ (M+H)$^+$ 444.0354, found 444.0359.

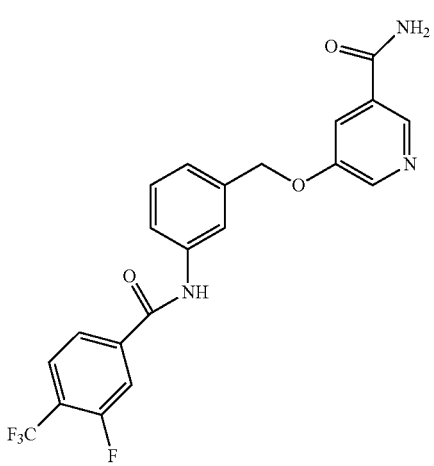

5-((3-(3-Fluoro-4-(trifluoromethyl)benzamido)benzyl)oxy)nicotinamide (A-112)

White solid (50 mg, 56%). $^1$H NMR (DMSO-d$_6$, 600 MHz) δ 10.57 (s, 1H), 8.66 (s, 1H), 8.50 (d, J=2.4 Hz, 1H), 8.14 (s, 1H), 8.06 (d, J=12.0 Hz, 1H), 8.01-7.96 (m, 2H), 7.91 (s, 1H), 7.86 (s, 1H), 7.75 (d, J=7.8 Hz, 1H), 7.62 (s, 1H), 7.42 (dd, J=7.8, 7.8 Hz, 1H), 7.26 (d, J=7.8 Hz, 1H), 5.27 (s, 2H). HRMS (ESI$^+$) calcd for C$_{21}$H$_{16}$F$_4$N$_3$O$_3$ (M+H)$^+$ 434.1122, found 434.1132.

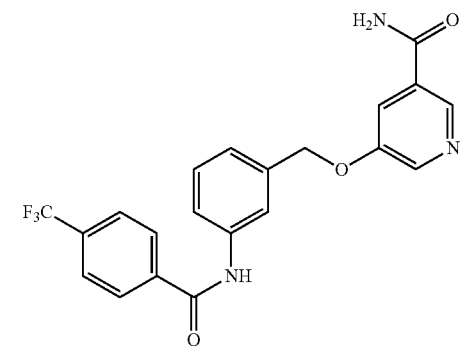 [SMILES: NC(=O)c1cncc(OCc2cccc(NC(=O)c3ccc(C(F)(F)F)cc3)c2)c1]

5-((3-(4-(Trifluoromethyl)benzamido)benzyl)oxy) nicotinamide (A-111)

White solid (40 mg, 40%). $^1$H NMR (DMSO-d$_6$, 600 MHz) δ 10.54 (s, 1H), 8.65 (s, 1H), 8.50 (d, J=2.6 Hz, 1H), 8.15 (d, J=7.8 Hz, 3H), 7.92 (d, J=7.9 Hz, 3H), 7.85 (s, 1H), 7.76 (d, J=8.1 Hz, 1H), 7.63 (s, 1H), 7.40 (t, J=7.8 Hz, 1H), 7.24 (d, J=7.6 Hz, 1H), 5.25 (s, 2H). HRMS (ESI$^+$) calcd for C$_{21}$H$_{17}$F$_3$N$_3$O$_3$ (M+H)$^+$ 416.1217, found 416.1225.

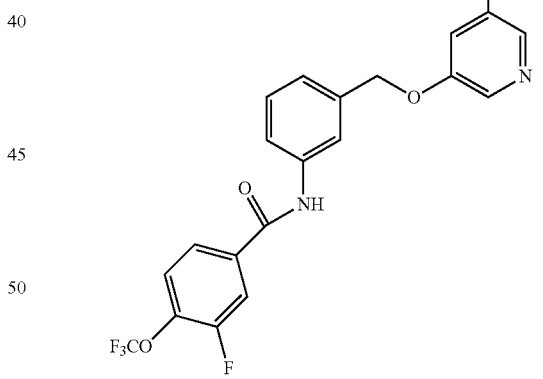

5-((3-(3-Fluoro-4-(trifluoromethoxy)benzamido) benzyl)oxy)nicotinamide (A-113)

White solid (47 mg, 51%). $^1$H NMR (DMSO-d$_6$, 600 MHz) δ 10.46 (s, 1H), 8.65 (s, 1H), 8.49 (d, J=2.4 Hz, 1H), 8.14 (s, 1H), 8.08 (d, J=10.8 Hz, 1H), 7.94-7.88 (m, 2H), 7.86 (s, 1H), 7.79-7.72 (m, 2H), 7.62 (s, 1H), 7.41 (dd, J=8.1, 8.1 Hz, 1H), 7.26 (d, J=6.6 Hz, 1H), 5.26 (s, 2H). HRMS (ESI$^+$) calcd for C$_{21}$H$_{16}$F$_4$N$_3$O$_4$ (M+H)$^+$ 450.1071, found 450.1072.

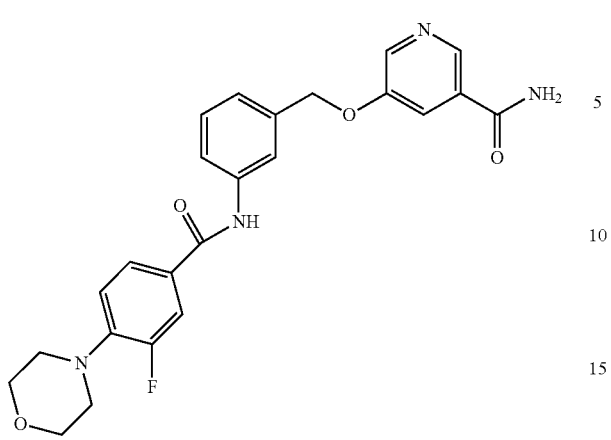

5-((3-(3-Fluoro-4-morpholinobenzamido)benzyl)oxy)nicotinamide (A-114)

White solid (7 mg, 11%). $^1$H NMR (DMSO-$d_6$, 600 MHz) δ 10.17 (s, 1H), 8.65 (s, 1H), 8.49 (s, 1H), 8.14 (s, 1H), 7.91 (s, 1H), 7.86 (s, 1H), 7.82-7.77 (m, 2H), 7.74 (d, J=8.4 Hz, 1H), 7.61 (s, 1H), 7.38 (dd, J=7.8, 7.8 Hz, 1H), 7.20 (d, J=6.6 Hz, 1H), 7.14 (dd, J=9.0, 9.0 Hz, 1H), 5.24 (s, 2H), 3.78-3.73 (m, 4H), 3.15-3.11 (m, 4H). HRMS (ESI$^+$) calcd for $C_{24}H_{24}FN_4O_4$ (M+H)$^+$ 451.1776, found 451.1787.

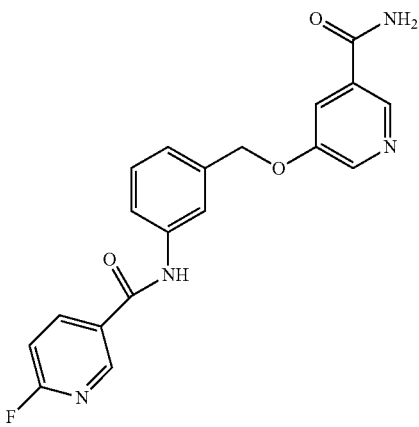 [SMILES: NC(=O)c1cncc(OCc2cccc(NC(=O)c3ccc(F)nc3)c2)c1]

N-(3-(((5-Carbamoylpyridin-3-yl)oxy)methyl)phenyl)-6-fluoronicotinamide (A-116)

Pale solid (100 mg, 67%). $^1$H NMR (DMSO-$d_6$, 600 MHz) δ 10.51 (s, 1H), 8.82 (d, J=1.8 Hz, 1H), 8.65 (s, 1H), 8.52-8.46 (m, 2H), 8.13 (s, 1H), 7.89 (s, 1H), 7.86 (s, 1H), 7.74 (d, J=8.4 Hz, 1H), 7.61 (s, 1H), 7.41 (dd, J=7.8, 7.8 Hz, 1H), 8.37 (dd, J=2.4, 8.4 Hz, 1H), 7.24 (d, J=7.2 Hz, 1H), 5.26 (s, 2H). HRMS (ESI$^+$) calcd for $C_{19}H_{16}FN_4O_3$ (M+H)$^+$ 367.1201, found 367.1203.

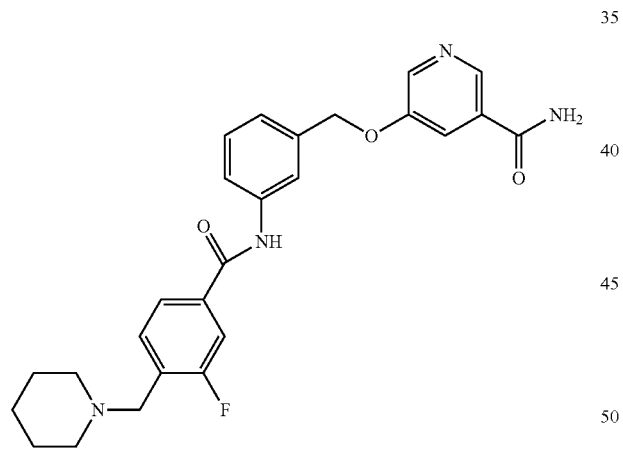

5-((3-(3-Fluoro-4-(piperidin-1-ylmethyl)benzamido)benzyl)oxy)nicotinamide (A-115)

Brownish solid (22 mg, 38%). $^1$H NMR (CD$_3$OD, 600 MHz) δ 8.62 (s, 1H), 8.45 (s, 1H), 7.91 (s, 1H), 7.87 (s, 1H), 7.75 (d, J=7.8 Hz, 1H), 7.70-7.64 (m, 2H), 7.57 (dd, J=7.2, 7.2 Hz, 1H), 7.39 (dd, J=8.1, 8.1 Hz, 1H), 7.26 (d, J=7.8 Hz, 1H), 5.24 (s, 2H), 3.67 (s, 2H), 2.58-2.46 (m, 4H), 1.66-1.58 (m, 4H), 1.50-1.42 (m, 2H). HRMS (ESI$^+$) calcd for $C_{26}H_{28}FN_4O_3$ (M+H)$^+$ 463.2140, found 463.2154.

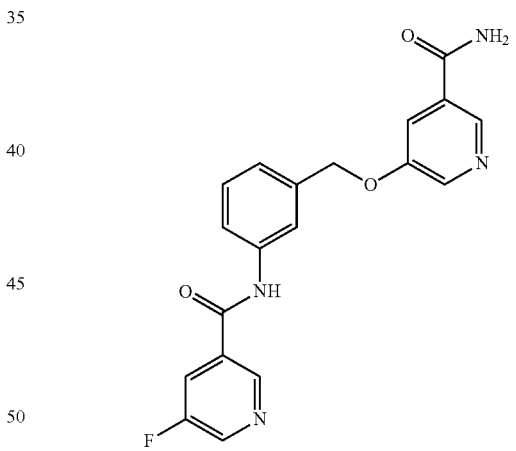

N-(3-(((5-Carbamoylpyridin-3-yl)oxy)methyl)phenyl)-5-fluoronicotinamide (A-117)

White solid (40 mg, 53%). $^1$H NMR (DMSO-$d_6$, 600 MHz) δ 10.56 (s, 1H), 8.99 (s, 1H), 8.80 (d, J=2.4 Hz, 1H), 8.65 (s, 1H), 8.49 (d, J=3.0 Hz, 1H), 8.22 (d, J=9.6 Hz, 1H), 8.14 (s, 1H), 7.90 (s, 1H), 7.86 (s, 1H), 7.74 (d, J=8.4 Hz, 1H), 7.62 (s, 1H), 7.42 (dd, J=7.5, 7.5 Hz, 1H), 7.25 (d, J=7.8 Hz, 1H), 5.27 (s, 2H). HRMS (ESI$^+$) calcd for $C_{19}H_{16}FN_4O_3$ (M+H)$^+$ 367.1201, found 367.1215.

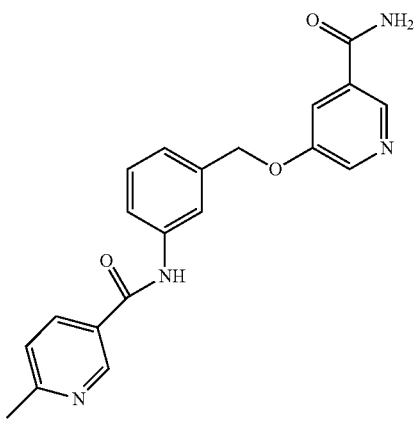 [SMILES: Cc1ccc(C(=O)Nc2cccc(COc3cncc(C(N)=O)c3)c2)cn1]

N-(3-(((5-Carbamoylpyridin-3-yl)oxy)methyl)phenyl)-6-methylnicotinamide (A-118)

White solid (27 mg, 36%). $^1$H NMR (DMSO-d$_6$, 600 MHz) δ 10.41 (s, 1H), 9.00 (s, 1H), 8.65 (s, 1H), 8.49 (d, J=2.4 Hz, 1H), 8.22-8.17 (m, 1H), 8.14 (s, 1H), 7.91 (s, 1H), 7.86 (s, 1H), 7.75 (d, J=8.4 Hz, 1H), 7.61 (s, 1H), 7.44-7.36 (m, 2H), 7.23 (d, J=7.2 Hz, 1H), 5.26 (s, 2H), 2.56 (s, 3H). HRMS (ESI$^+$) calcd for C$_{20}$H$_{19}$H$_4$O$_3$ (M+H)$^+$ 363.1452, found 363.1457.

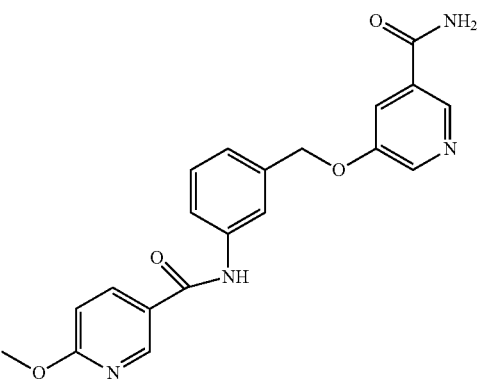

N-(3-(((5-Carbamoylpyridin-3-yl)oxy)methyl)phenyl)-6-methoxynicotinamide (A-120)

White solid (42 mg, 54%). $^1$H NMR (DMSO-d$_6$, 600 MHz) δ 10.31 (s, 1H), 8.79 (s, 1H), 8.65 (s, 1H), 8.49 (d, J=2.4 Hz, 1H), 8.26-8.20 (m, 1H), 8.14 (s, 1H), 7.90 (s, 1H), 7.86 (s, 1H), 7.73 (d, J=7.8 Hz, 1H), 7.61 (s, 1H), 7.39 (dd, J=7.8, 7.8 Hz, 1H), 7.22 (d, J=7.2 Hz, 1H), 6.95 (d, J=9.0 Hz, 1H), 5.25 (s, 2H), 3.94 (s, 3H). HRMS (ESI$^+$) calcd for C$_{20}$H$_{19}$N$_4$O$_4$ (M+H)$^+$ 379.1401, found 379.1400.

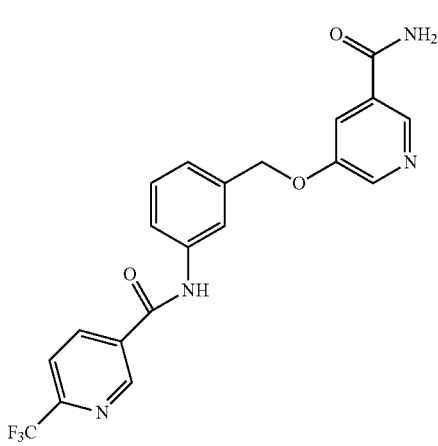 [SMILES: NC(=O)c1cncc(OCc2cccc(NC(=O)c3ccc(C(F)(F)F)nc3)c2)c1]

N-(3-(((5-Carbamoylpyridin-3-yl)oxy)methyl)phenyl)-6-(trifluoromethyl)nicotinamide (A-119)

White solid (44 mg, 51%). $^1$H NMR (DMSO-d$_6$, 600 MHz) δ 10.70 (s, 1H), 9.25 (s, 1H), 8.65 (s, 1H), 8.57 (d, J=7.8 Hz, 1H), 8.50 (d, J=1.8 Hz, 1H), 8.14 (s, 1H), 8.11 (d, J=8.4 Hz, 1H), 7.91 (s, 1H), 7.86 (s, 1H), 7.76 (d, J=7.2 Hz, 1H), 7.62 (s, 1H), 7.43 (dd, J=7.5, 7.5 Hz, 1H), 7.27 (d, J=7.8 Hz, 1H), 5.28 (s, 2H). HRMS (ESI$^+$) calcd for C$_{20}$H$_{16}$F$_3$N$_4$O$_3$ (M+H)$^+$ 417.1169, found 417.1175.

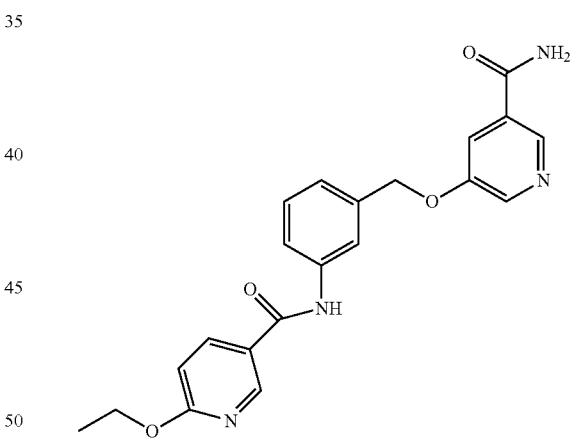

N-(3-(((5-Carbamoylpyridin-3-yl)oxy)methyl)phenyl)-6-ethoxynicotinamide (A-121)

White solid (37 mg, 46%). $^1$H NMR (DMSO-d$_6$, 600 MHz) δ 10.29 (s, 1H), 8.77 (s, 1H), 8.65 (s, 1H), 8.49 (d, J=3.0 Hz, 1H), 8.24-8.20 (m, 1H), 8.14 (s, 1H), 7.90 (s, 1H), 7.86 (s, 1H), 7.73 (d, J=8.4 Hz, 1H), 7.61 (s, 1H), 7.39 (dd, J=7.8, 7.8 Hz, 1H), 7.21 (d, J=7.2 Hz, 1H), 6.92 (d, J=8.4 Hz, 1H), 5.25 (s, 2H), 4.39 (q, J=7.2 Hz, 2H), 1.35 (t, J=7.2 Hz, 3H). HRMS (ESI$^+$) calcd for C$_{21}$H$_{21}$N$_4$O$_4$ (M+H)$^+$ 393.1557, found 393.1566.

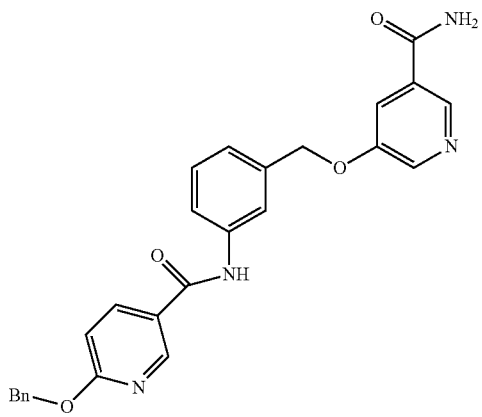 [SMILES: NC(=O)c1cncc(OCc2cccc(NC(=O)c3ccc(OCc4ccccc4)nc3)c2)c1]

6-(Benzyloxy)-N-(3-((5-carbamoylpyridin-3-yl)oxy)methyl)phenyl)nicotinamide (A-122)

White solid (40 mg, 43%). $^1$H NMR (DMSO-$d_6$, 600 MHz) δ 10.32 (s, 1H), 8.79 (s, 1H), 8.65 (s, 1H), 8.49 (s, 1H), 8.25 (d, J=7.8 Hz, 1H), 8.14 (s, 1H), 7.90 (s, 1H), 7.86 (s, 1H), 7.73 (d, J=8.4 Hz, 1H), 7.61 (s, 1H), 7.47 (d, J=8.4 Hz, 2H), 7.39 (dd, J=7.5, 7.5 Hz, 3H), 7.34 (dd, J=6.9, 6.9 Hz, 1H), 7.21 (d, J=7.8 Hz, 1H), 7.02 (d, J=8.4 Hz, 1H), 5.45 (s, 2H), 5.25 (s, 2H). HRMS (ESI$^+$) calcd for $C_{26}H_{23}N_4O_4$ (M+H)$^+$ 455.1714, found 455.1719.

5-((3-(2,6-Difluoroisonicotinamido)benzyl)oxy)nicotinamide (A-124)

White solid (13 mg, 17%). $^1$H NMR (DMSO-$d_6$, 600 MHz) δ 10.67 (s, 1H), 8.65 (s, 1H), 8.49 (d, J=2.4 Hz, 1H), 8.14 (s, 1H), 7.89 (s, 1H), 7.85 (s, 1H), 7.74 (d, J=8.4 Hz, 1H), 7.66 (s, 2H), 7.62 (s, 1H), 7.44 (dd, J=7.2, 7.2 Hz, 1H), 7.28 (d, J=7.8 Hz, 1H), 5.27 (s, 2H). HRMS (ESI$^+$) calcd for $C_{19}H_{15}F_2N_4O_3$ (M+H)$^+$ 385.1107, found 385.1114.

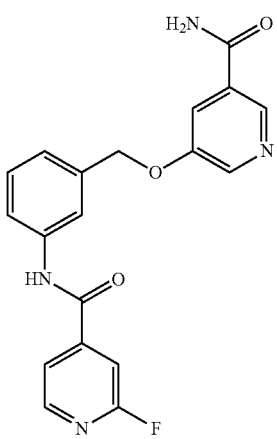 [SMILES: NC(=O)c1cncc(OCc2cccc(NC(=O)c3ccnc(F)c3)c2)c1]

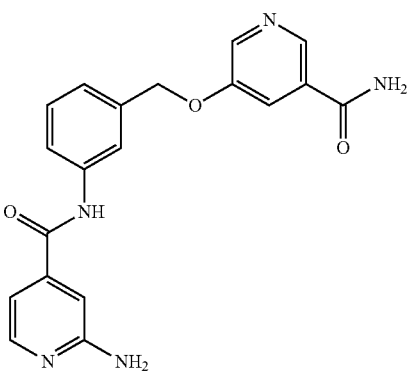 [SMILES: NC(=O)c1cncc(OCc2cccc(NC(=O)c3ccnc(N)c3)c2)c1]

5-((3-(2-Fluoroisonicotinamido)benzyl)oxy)nicotinamide (A-123)

Pale solid (12 mg, 14%). $^1$H NMR (DMSO-$d_6$, 600 MHz) δ 10.63 (s, 1H), 8.65 (s, 1H), 8.49 (s, 1H), 8.45 (d, J=4.9 Hz, 1H), 8.14 (br s, 1H), 7.90 (s, 1H), 7.85 (s, 1H), 7.83 (d, J=4.9 Hz, 1H), 7.74 (d, J=8.0 Hz, 1H), 7.66 (s, 1H), 7.61 (br s, 1H), 7.43 (t, J=8.0 Hz, 1H), 7.27 (d, J=7.6 Hz, 1H), 5.27 (s, 2H). HRMS (ESI$^+$) calcd for $C_{19}H_{16}FN_4O_3$ (M+H)$^+$ 367.1201, found 367.1205.

5-((3-(2-Aminoisonicotinamido)benzyl)oxy)nicotinamide (A-125)

White solid (13 mg, 10%). $^1$H NMR (DMSO-$d_6$, 600 MHz) δ 10.35 (s, 1H), 8.69 (s, 1H), 8.49 (s, 1H), 8.14 (s, 1H), 8.05 (d, J=5.4 Hz, 1H), 7.90 (s, 1H), 7.85 (s, 1H), 7.72 (d, J=7.8 Hz, 1H), 7.61 (s, 1H), 7.39 (dd, J=7.5, 7.5 Hz, 1H), 7.22 (d, J=7.8, 1H), 6.92 (d, J=4.8 Hz, 1H), 6.86 (s, 1H), 6.20 (s, 2H), 5.25 (s, 2H). HRMS (EST$^+$) calcd for $C_{19}H_{18}H_5O_3$ (M+H)$^+$ 364.1404, found 364.1414.

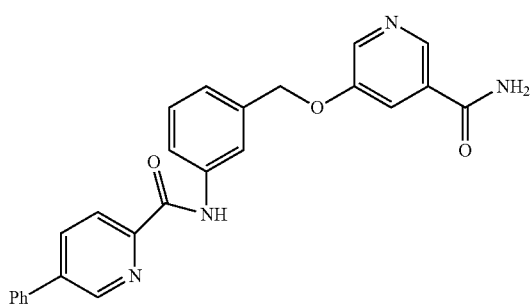 [SMILES: NC(=O)c1cncc(OCc2cccc(NC(=O)c3ccc(-c4ccccc4)cn3)c2)c1]

N-(3-(((5-Carbamoylpyridin-3-yl)oxy)methyl)phenyl)-5-phenylpicolinamide (A-126)

White solid (15 mg, 35%). ¹H NMR (DMSO-d₆, 600 MHz) δ 10.74 (s, 1H), 9.04 (d, J=1.2 Hz, 1H), 8.66 (s, 1H), 8.51 (d, J=3.0 Hz, 1H), 8.37 (d, J=9.0 Hz, 1H), 8.23 (d, J=8.4 Hz, 1H), 8.14 (s, 1H), 8.12 (s, 1H), 7.90-7.86 (m, 2H), 7.84 (d, J=7.8 Hz, 2H), 7.61 (s, 1H), 7.59-7.48 (m, 3H), 7.42 (dd, J=7.8, 7.8 Hz, 1H), 7.24 (d, J=7.8 Hz, 1H), 5.27 (s, 2H). HRMS (ESI⁺) calcd for $C_{25}H_{21}N_4O_3$ (M+H)⁺ 425.1608, found 425.1616.

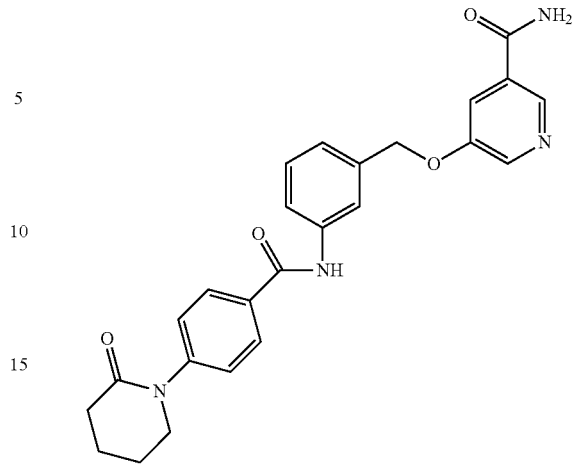

5-((3-(4-(2-Oxopiperidin-1-yl)benzamido)benzyl)oxy)nicotinamide (A-128)

White solid (15.0 mg, 16%). ¹H NMR (DMSO-d₆, 600 MHz) δ 10.30 (s, 1H), 8.65 (d, J=1.2 Hz, 1H), 8.50 (d, J=2.4 Hz, 1H), 8.13 (s, 1H), 7.98-7.92 (m, 3H), 7.86 (s, 1H), 7.75 (d, J=7.2 Hz, 1H), 7.61 (s, 1H), 7.45 (d, J=8.4 Hz, 2H), 7.39 (dd, J=7.8, 7.8 Hz, 1H), 7.21 (d, J=7.2 Hz, 1H), 5.25 (s, 2H), 3.67 (t, J=5.7 Hz, 2H), 2.43 (t, J=6.6 Hz, 2H), 1.93-1.82 (m, 4H). HRMS (ESI⁺) calcd for $C_{25}H_{25}N_4O_4$ (M+H)⁺ 445.1870, found 445.1874.

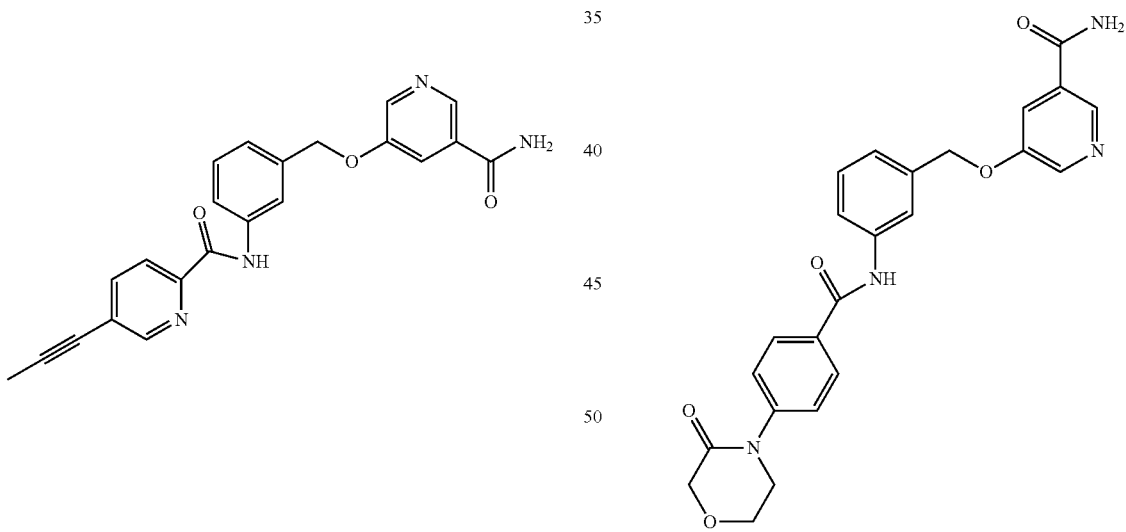

N-(3-(((5-Carbamoylpyridin-3-yl)oxy)methyl)phenyl)-5-(prop-1-yn-1-yl)picolinamide (A-127)

White solid (30 mg, 77%). ¹H NMR (DMSO-d₆, 600 MHz) δ 10.70 (s, 1H), 8.72 (d, J=1.2 Hz, 1H), 8.65 (d, J=1.8 Hz, 1H), 8.50 (d, J=3.0 Hz, 1H), 8.14 (s, 1H), 8.11 (d, J=7.8 Hz, 1H), 8.08 (s, 1H), 8.05 (dd, J=2.4, 8.4 Hz, 1H), 7.88-7.83 (m, 2H), 7.61 (s, 1H), 7.40 (dd, J=7.8, 7.8 Hz, 1H), 7.23 (d, J=7.8 Hz, 1H), 5.25 (s, 2H), 2.14 (s, 3H). HRMS (ESI⁺) calcd for $C_{22}H_{19}N_4O_3$ (M+H)⁺ 387.1452, found 387.1462.

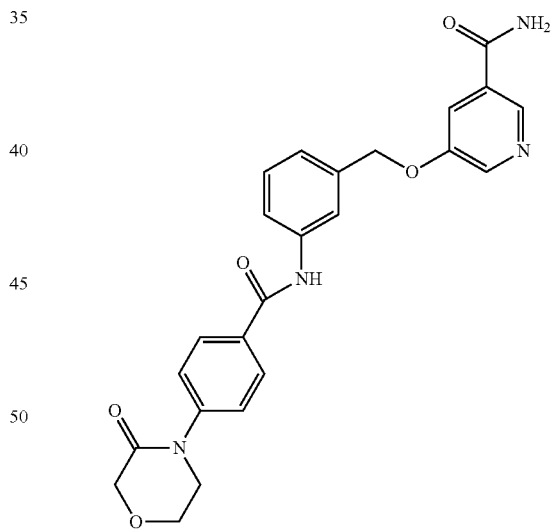

5-((3-(4-(3-Oxomorpholino)benzamido)benzyl)oxy)nicotinamide (A-129)

White solid (7.5 mg, 8.2%). ¹H NMR (DMSO-d₆, 600 MHz) δ 10.33 (s, 1H), 8.65 (s, 1H), 8.49 (s, 1H), 8.14 (s, 1H), 8.00 (d, J=8.4 Hz, 2H), 7.93 (s, 1H), 7.86 (s, 1H), 7.76 (d, J=6.0 Hz, 1H), 7.63-7.57 (m, 3H), 7.39 (dd, J=7.8, 7.8 Hz, 1H), 7.21 (d, J=7.8 Hz, 1H), 5.25 (s, 2H), 4.24 (s, 2H), 4.01 (t, J=4.8 Hz, 2H), 3.82 (t, J=5.1 Hz, 2H). HRMS (ESI⁺) calcd for $C_{24}H_{23}N_4O_5$ (M+H)⁺ 447.1663, found 447.1672.

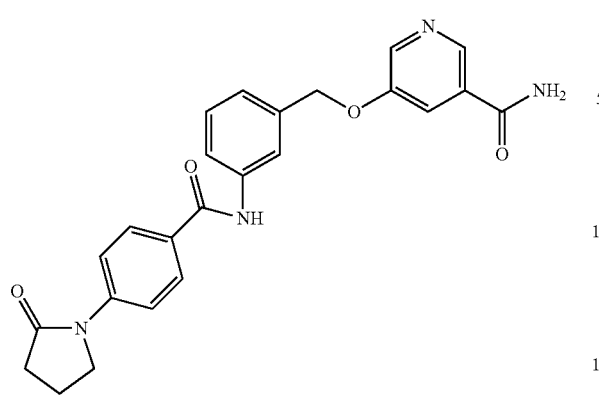

5-((3-(4-(2-Oxopyrrolidin-1-yl)benzamido)benzyl)oxy)nicotinamide (A-130)

White solid (14 mg, 26%). $^1$H NMR (DMSO-d$_6$, 600 MHz) δ 10.24 (s, 1H), 8.65 (d, J=1.2 Hz, 1H), 8.50 (d, J=3.0 Hz, 1H), 8.14 (s, 1H), 7.99 (d, J=9.0 Hz, 2H), 7.92 (s, 1H), 7.86 (dd, J=3.0, 1.8 Hz, 1H), 7.82 (d, J=9.0 Hz, 2H), 7.76 (d, J=7.8 Hz, 1H), 7.61 (s, 1H), 7.39 (dd, J=7.8, 7.8 Hz, 1H), 7.20 (d, J=7.2 Hz, 1H), 5.25 (s, 2H), 3.90 (t, J=7.5 Hz, 2H), 2.53 (t, J=8.4 Hz, 2H), 2.12-2.06 (m, 2H). HRMS (ESI$^+$) calcd for C$_{24}$H$_{23}$N$_4$O$_4$ (M+H)$^+$ 431.1714, found 431.1711.

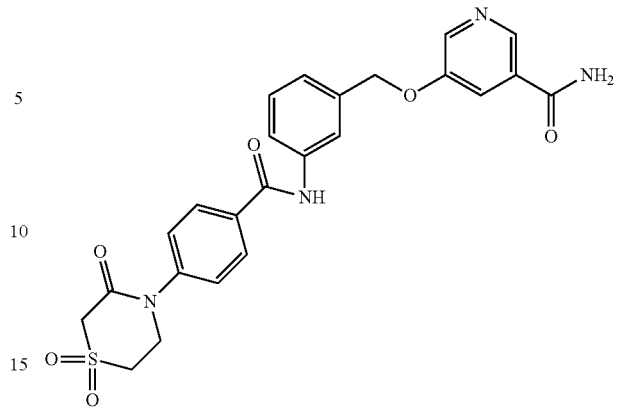

5-((3-(4-(1,1-Dioxido-3-oxothiomorpholino)benzamido)benzyl)oxy)nicotinamide (A-132)

White solid (8.0 mg, 37%). $^1$H NMR (CD$_3$OD, 600 MHz) δ 8.60 (s, 1H), 8.43 (d, J=3.0 Hz, 1H), 8.05 (d, J=9.0 Hz, 3H), 7.90 (dd, J=1.8, 1.8 Hz, 1H), 7.77 (s, 1H), 7.64-7.58 (m, 2H), 7.55-7.49 (m, 2H), 7.38 (dd, J=7.8, 7.8 Hz, 1H), 7.26 (d, J=7.8 Hz, 1H), 6.84 (d, J=9.0 Hz, 2H), 5.23 (s, 2H), 3.86 (t, J=6.9 Hz, 2H), 3.70 (t, J=6.9 Hz, 2H). HRMS (ESI$^+$) calcd for C$_{24}$H$_{23}$H$_4$O$_6$S (M+H)$^+$ 495.1333, found 495.1342.

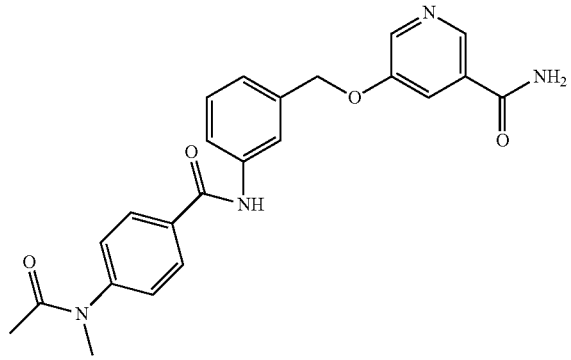 [SMILES: CC(=O)N(C)c1ccc(C(=O)Nc2cccc(COc3cncc(C(N)=O)c3)c2)cc1]

5-((3-(4-(N-Methylacetamido)benzamido)benzyl)oxy)nicotinamide (A-131)

White solid (20 mg, 39%). $^1$H NMR (DMSO-d$_6$, 600 MHz) δ 10.36 (s, 1H), 8.65 (s, 1H), 8.50 (s, 1H), 8.14 (s, 1H), 8.01 (d, J=7.8 Hz, 2H), 7.93 (s, 1H), 7.86 (d, J=1.2 Hz, 1H), 7.75 (d, J=7.8 Hz, 1H), 7.62 (s, 1H), 7.50 (d, J=7.8 Hz, 2H), 7.40 (dd, J=7.8, 7.8 Hz, 1H), 7.20 (d, J=7.2 Hz, 1H), 5.26 (s, 2H), 3.32 (s, 3H), 3.22 (s, 3H). HRMS (ESI$^+$) calcd for C$_{23}$H$_{23}$N$_4$O$_4$ (M+H)$^+$ 419.1714, found 419.1717.

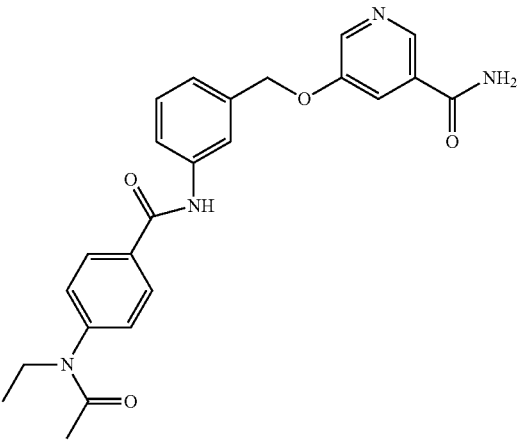 [SMILES: CCN(C(C)=O)c1ccc(C(=O)Nc2cccc(COc3cncc(C(N)=O)c3)c2)cc1]

5-((3-(4-(N-Ethylacetamido)benzamido)benzyl)oxy)nicotinamide (A-133)

White solid (5.0 mg, 17%). $^1$H NMR (CD$_3$OD, 600 MHz) δ 8.63 (s, 1H), 8.47 (d, J=2.4 Hz, 1H), 8.04 (d, J=8.4 Hz, 2H), 7.93 (dd, J=1.8, 1.8 Hz, 1H), 7.89 (s, 1H), 7.69 (d, J=8.4 Hz, 1H), 7.45-7.39 (m, 3H), 7.28 (d, J=7.2 Hz, 1H), 5.27 (s, 2H), 3.79 (q, J=7.2, Hz, 2H), 3.31 (s, 3H), 1.14 (t, J=7.2 Hz, 3H). HRMS (ESI$^+$) calcd for C$_{24}$H$_{25}$N$_4$O$_4$ (M+H)$^+$ 433.1870, found 433.1871.

81

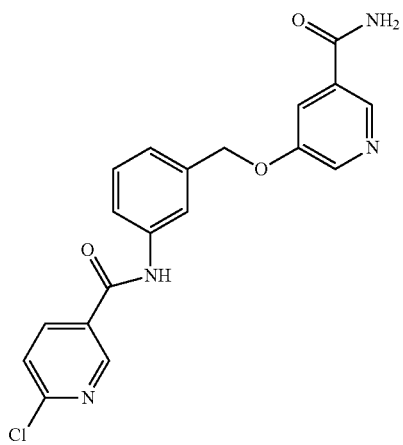 [SMILES: NC(=O)c1cncc(OCc2cccc(NC(=O)c3ccc(Cl)nc3)c2)c1]

N-(3-(((5-Carbamoylpyridin-3-yl)oxy)methyl)phenyl)-6-chloronicotinamide (A-134)

White solid (47 mg, 60%). ¹H NMR (DMSO-d₆, 600 MHz) δ 10.55 (s, 1H), 8.95 (s, 1H), 8.65 (s, 1H), 8.49 (s, 1H), 8.35 (d, J=8.4 Hz, 1H), 8.13 (s, 1H), 7.89 (s, 1H), 7.86 (s, 1H), 7.76-7.68 (m, 2H), 7.61 (s, 1H), 7.42 (dd, J=7.5, 7.5 Hz, 1H), 7.25 (d, J=6.6 Hz, 1H), 5.27 (s, 2H). HRMS (ESI⁺) calcd for $C_{19}H_{16}ClN_4O_3$ (M+H)⁺ 383.0905, found 383.0915.

82

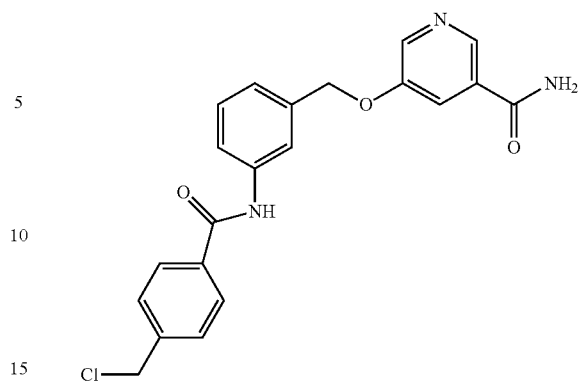

5-((3-(4-(Chloromethyl)benzamido)benzyl)oxy)nicotinamide (A-135)

White solid (130 mg, 53%). ¹H NMR (DMSO-d₆, 600 MHz) δ 10.34 (s, 1H), 8.65 (d, J=1.8 Hz, 1H), 8.49 (d, J=3.0 Hz, 1H), 8.13 (s, 1H), 7.96 (d, J=8.4 Hz, 2H), 7.92 (s, 1H), 7.86 (dd, J=2.4, 2.4 Hz, 1H), 7.75 (d, J=8.4 Hz, 1H), 7.61 (s, 1H), 7.59 (d, J=8.4, 2H), 7.39 (dd, J=7.5, 7.5 Hz, 1H), 7.22 (d, J=7.8 Hz, 1H), 5.25 (s, 2H), 4.85 (s, 2H). HRMS (ESI⁺) calcd for $C_{21}H_{19}ClN_3O_3$ (M+H)⁺ 396.1109, found 396.1110.

Example 2

Representative compounds of formula (I) can be prepared as described below.

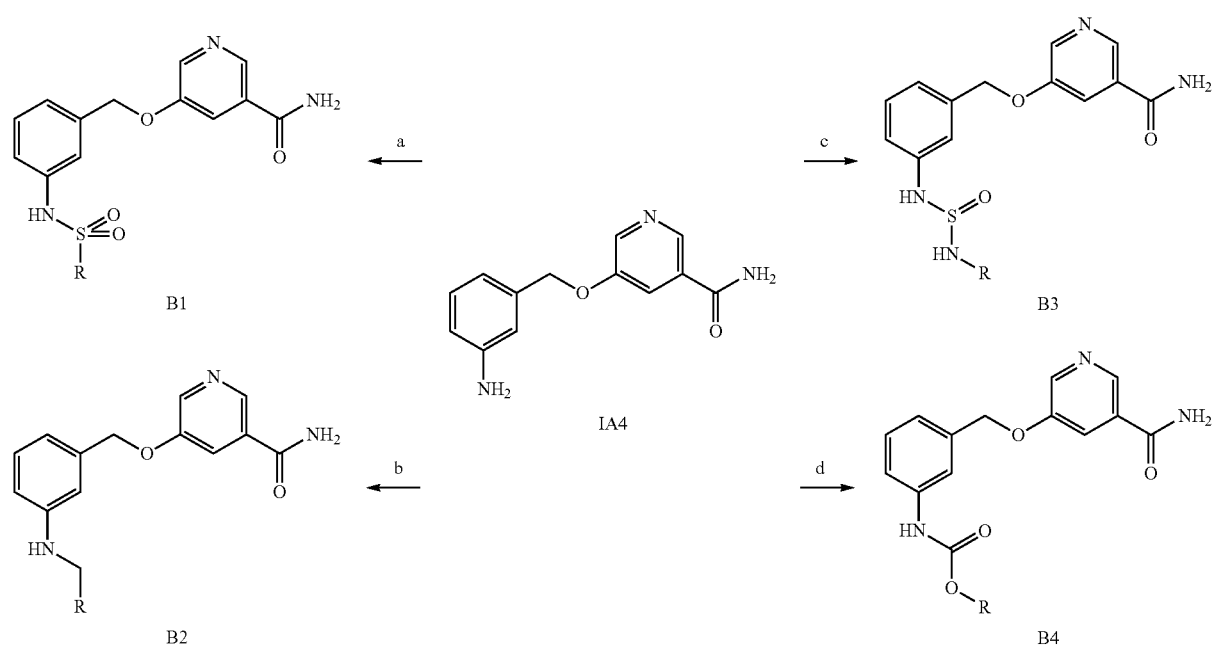

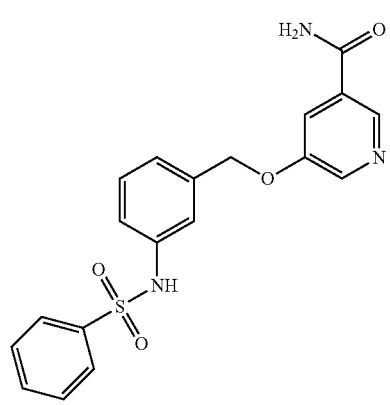

5-((3-(Phenylsulfonamido)benzyl)oxy)nicotinamide (B1-1)

To a solution of intermediate IA4 (60 mg, 0.24 mmol) and DIPEA (87 µL, 0.50 mmol)) in DMF (1 mL) was added benzenesulfonyl chloride (49 µL, 0.38 mmol) and the mixture was allowed to stir at rt overnight. The organic solvent was removed and the resulting residue was purified by flash column chromatography (0-10% MeOH/CH$_2$Cl$_2$) to give compound B1-1 as a white solid (25 mg, 27%). $^1$H NMR (DMSO-d$_6$, 600 MHz) δ 10.36 (br s, 1H), 8.65 (s, 1H), 8.42 (d, J=2.7 Hz, 1H), 8.13 (br s, 1H), 7.79 (s, 1H), 7.73 (d, J=7.8 Hz, 2H), 7.61 (br s, 1H), 7.58 (t, J=7.5 Hz, 1H), 7.50 (t, J=7.5 Hz, 2H), 7.25 (t, J=7.7 Hz, 1H), 7.22 (s, 1H), 7.12 (d, J=7.5 Hz, 1H), 7.04 (d, J=8.0 Hz, 1H), 5.16 (s, 2H). HRMS (ESI$^+$) calcd for C$_{19}$H$_{18}$N$_3$O$_4$S (M+H)$^+$ 384.1013, found 384.1010. Compounds B1-2 to B1-13 were prepared in a manner similar to that described for compound B1-1.

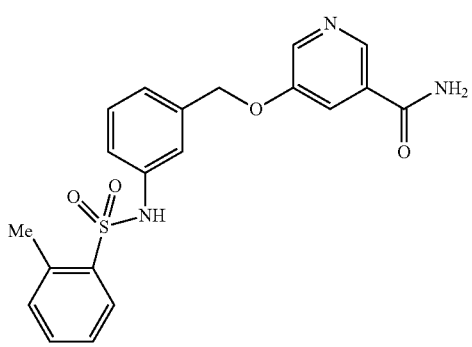 [SMILES: Cc1ccccc1S(=O)(=O)Nc1cccc(COc2cncc(C(N)=O)c2)c1]

5-((3-(2-Methylphenylsulfonamido)benzyl)oxy)nicotinamide (B1-2)

$^1$H NMR (DMSO-d$_6$, 600 MHz) δ 10.41 (s, 1H), 8.65 (s, 1H), 8.41 (s, 1H), 8.13 (s, 1H), 7.84 (d, J=7.2 Hz, 1H), 7.78 (s, 1H), 7.62 (s, 1H), 7.46 (dd, J=7.2, 7.2 Hz, 1H), 7.35-7.27 (m, 2H), 7.23 (dd, J=8.1, 8.1 Hz, 1H), 7.17 (s, 1H), 7.07 (d, J=7.2 Hz, 1H), 7.02 (d, J=7.8 Hz, 1H), 5.14 (s, 2H), 2.56 (s, 3H). HRMS (ESI$^+$) calcd for C$_{20}$H$_{20}$N$_3$O$_4$S (M+H)$^+$ 398.1169, found 398.1172.

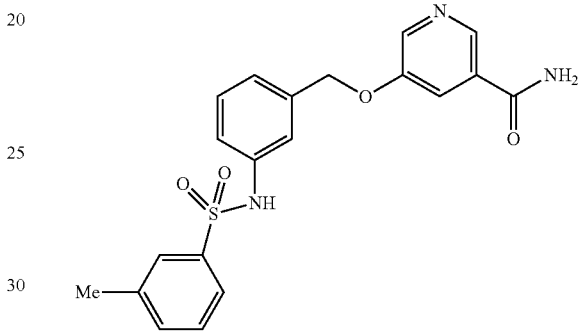

5-((3-(3-Methylphenylsulfonamido)benzyl)oxy)nicotinamide (B1-3)

$^1$H NMR (DMSO-d$_6$, 600 MHz) δ 10.32 (s, 1H), 8.64 (s, 1H), 8.42 (s, 1H), 8.13 (s, 1H), 7.79 (s, 1H), 7.61 (s, 1H), 7.57 (s, 1H), 7.51 (d, J=6.6 Hz, 1H), 7.41-7.34 (m, 2H), 7.25 (dd, J=7.5, 7.5 Hz, 1H), 7.20 (s, 1H), 7.11 (d, J=6.6 Hz, 1H), 7.04 (d, J=8.4 Hz, 1H), 5.16 (s, 2H), 2.31 (s, 3H). HRMS (ESI$^+$) calcd for C$_{20}$H$_{20}$N$_3$O$_4$S (M+H)$^+$ 398.1169, found 398.1179.

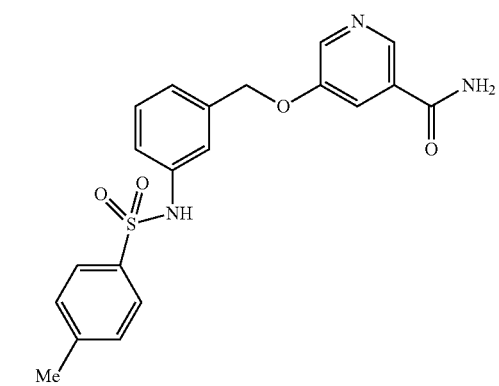 [SMILES: Cc1ccc(S(=O)(=O)Nc2cccc(COc3cncc(C(N)=O)c3)c2)cc1]

5-((3-(4-Methylphenylsulfonamido)benzyl)oxy)nicotinamide (B1-4)

$^1$H NMR (DMSO-d$_6$, 600 MHz) δ 10.29 (s, 1H), 8.65 (s, 1H), 8.42 (d, J=1.2 Hz, 1H), 8.13 (s, 1H), 7.79 (s, 1H), 7.64-7.57 (m, 3H), 7.29 (d, J=7.2 Hz, 2H), 7.24 (dd, J=7.5, 7.5 Hz, 1H), 7.21 (s, 1H), 7.10 (d, J=7.8 Hz, 1H), 7.02 (d,

J=7.8 Hz, 1H), 5.16 (s, 2H), 2.31 (s, 3H). HRMS (ESI⁺) calcd for C₂₀H₂₀N₃O₄S (M+H)⁺ 398.1169, found 398.1173.

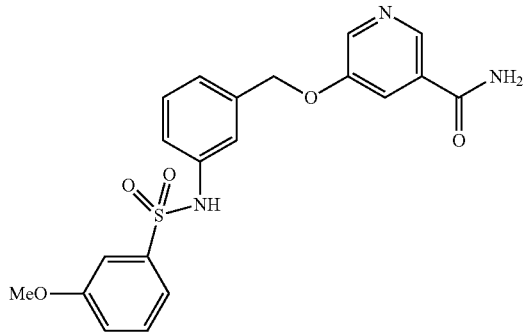 [SMILES: COc1cccc(S(=O)(=O)Nc2cccc(COc3cncc(C(N)=O)c3)c2)c1]

5-((3-(3-Methoxyphenylsulfonamido)benzyl)oxy)nicotinamide (B1-5)

¹H NMR (DMSO-d₆, 600 MHz) δ 10.35 (s, 1H), 8.64 (s, 1H), 8.42 (s, 1H), 8.13 (s, 1H), 7.80 (s, 1H), 7.61 (s, 1H), 7.40 (dd, J=8.1, 8.1 Hz, 1H), 7.30-7.23 (m, 3H), 7.21 (s, 1H), 7.16-7.09 (m, 2H), 7.05 (d, J=8.4 Hz, 1H), 5.15 (s, 2H), 3.74 (s, 3H). HRMS (ESI⁺) calcd for C₂₀H₂₀N₃O₅S (M+H)⁺ 414.1119, found 414.1126.

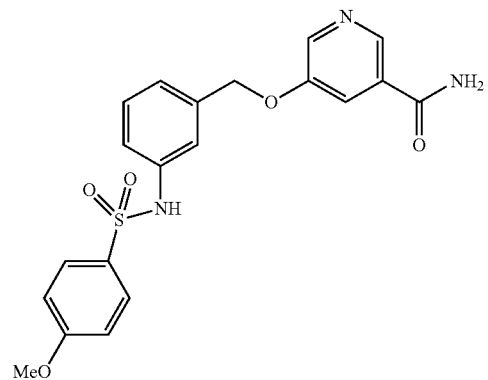 [SMILES: COc1ccc(S(=O)(=O)Nc2cccc(COc3cncc(C(N)=O)c3)c2)cc1]

5-((3-(4-Methoxyphenylsulfonamido)benzyl)oxy)nicotinamide (B1-6)

¹H NMR (DMSO-d₆, 600 MHz) δ 10.23 (s, 1H), 8.65 (s, 1H), 8.42 (d, J=1.8 Hz, 1H), 8.13 (s, 1H), 7.80 (s, 1H), 7.65 (d, J=9.0 Hz, 2H), 7.62 (s, 1H), 7.27-7.20 (m, 2H), 7.10 (d, J=7.2 Hz, 1H), 7.04-6.98 (m, 3H), 5.16 (s, 2H), 3.78 (s, 3H). HRMS (ESI⁺) calcd for C₂₀H₂₀N₃O₅S (M+H)⁺ 414.1118, found 414.1127.

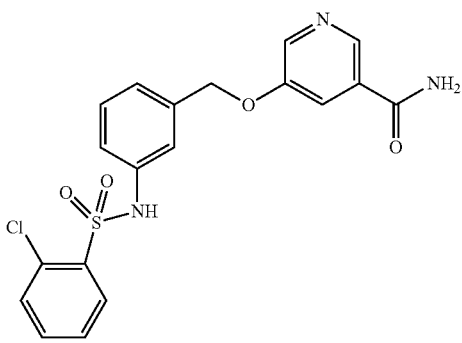 [SMILES: NC(=O)c1cncc(OCc2cccc(NS(=O)(=O)c3ccccc3Cl)c2)c1]

5-((3-(2-Chlorophenylsulfonamido)benzyl)oxy)nicotinamide (B1-7)

¹H NMR (DMSO-d₆, 600 MHz) δ 10.68 (s, 1H), 8.65 (s, 1H), 8.41 (s, 1H), 8.13 (s, 1H), 8.00 (d, J=7.8 Hz, 1H), 7.77 (s, 1H), 7.62 (s, 1H), 7.59 (d, J=4.2 Hz, 2H), 7.49-7.42 (m, 1H), 7.24 (dd, J=7.8, 7.8 Hz, 1H), 7.20 (s, 1H), 7.09 (d, J=7.8 Hz, 1H), 7.05 (d, J=7.8 Hz, 1H), 5.14 (s, 2H). HRMS (ESI⁺) calcd for C₁₉H₁₇ClN₃O₄S (M+H)⁺ 418.0628, found 418.0631.

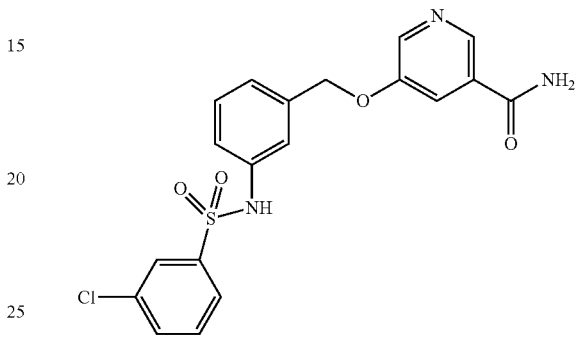

5-((3-(3-Chlorophenylsulfonamido)benzyl)oxy)nicotinamide (B1-8)

¹H NMR (DMSO-d₆, 600 MHz) δ 8.65 (s, 1H), 8.42 (s, 1H), 8.13 (s, 1H), 7.80 (s, 1H), 7.74 (s, 1H), 7.70-7.63 (m, 2H), 7.61 (s, 1H), 7.54 (dd, J=8.1, 8.1 Hz, 1H), 7.29 (dd, J=7.8, 7.8 Hz, 1H), 7.21 (s, 1H), 7.16 (d, J=7.8 Hz, 1H), 7.05 (d, J=8.4 Hz, 1H), 5.17 (s, 2H). HRMS (ESI⁺) calcd for C₁₉H₁₇ClN₃O₄S (M+H)⁺ 418.0623, found 418.0632.

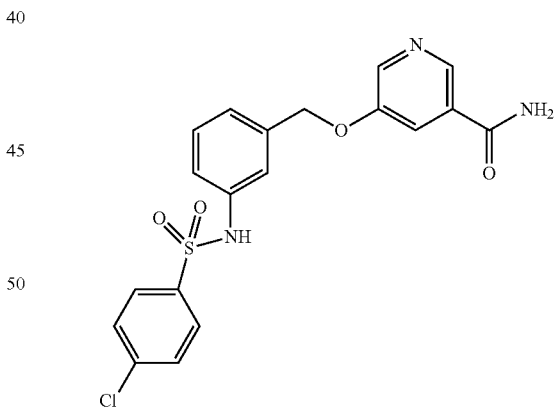

5-((3-(4-Chlorophenylsulfonamido)benzyl)oxy)nicotinamide (B1-9)

¹H NMR (DMSO-d₆, 600 MHz) δ 8.65 (s, 1H), 8.43 (s, 1H), 8.13 (s, 1H), 7.80 (s, 1H), 7.71 (d, J=7.8 Hz, 2H), 7.65-7.56 (m, 3H), 7.27 (dd, J=8.1, 8.1 Hz, 1H), 7.21 (s, 1H), 7.15 (d, J=7.8 Hz, 1H), 7.03 (d, J=8.4 Hz, 1H), 5.17 (s, 2H). HRMS (ESI⁺) calcd for C₁₉H₁₇ClN₃O₄S (M+H)⁺ 418.0623, found 418.0631.

87

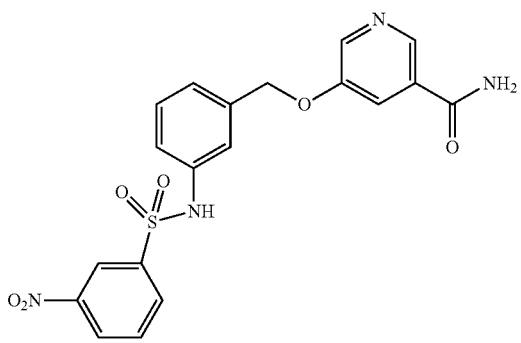 [SMILES: NC(=O)c1cncc(OCc2cccc(NS(=O)(=O)c3cccc([N+](=O)[O-])c3)c2)c1]

5-((3-(3-Nitrophenylsulfonamido)benzyl)oxy)nicotinamide (B1-10)

$^1$H NMR (DMSO-d$_6$, 600 MHz) δ 10.64 (s, 1H), 8.63 (s, 1H), 8.48 (s, 1H), 8.44-8.37 (m, 2H), 8.12 (s, 1H), 8.08 (d, J=7.8 Hz, 1H), 7.80 (dd, J=8.1, 8.1 Hz, 1H), 7.77 (s, 1H), 7.61 (s, 1H), 7.28 (dd, J=8.1, 8.1 Hz, 1H), 7.19 (s, 1H), 7.15 (d, J=7.2 Hz, 1H), 7.06 (d, J=7.2 Hz, 1H), 5.15 (s, 2H). HRMS (ESI$^+$) calcd for C$_{19}$H$_{17}$H$_4$O$_6$S (M+H)$^+$ 429.0863, found 429.0870.

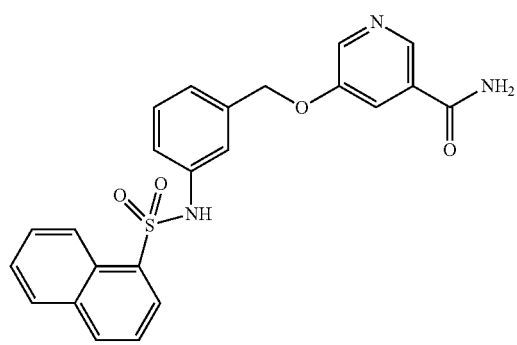 [SMILES: NC(=O)c1cncc(OCc2cccc(NS(=O)(=O)c3cccc4ccccc34)c2)c1]

5-((3-(Naphthalene-1-sulfonamido)benzyl)oxy)nicotinamide (B1-11)

$^1$H NMR (DMSO-d$_6$, 600 MHz) δ 10.76 (s, 1H), 8.71 (d, J=7.8 Hz, 1H), 8.64 (s, 1H), 8.38 (s, 1H), 8.18 (d, J=7.2 Hz, 2H), 8.12 (s, 1H), 8.05 (d, J=8.4 Hz, 1H), 7.75 (s, 1H), 7.72 (dd, J=7.8, 7.8 Hz, 1H), 7.65 (dd, J=7.2, 7.2 Hz, 1H), 7.61 (s, 1H), 7.57 (dd, J=7.5, 7.5 Hz, 1H), 7.20-7.12 (m, 2H), 7.02 (d, J=6.6 Hz, 1H), 6.96 (d, J=8.4 Hz, 1H), 5.09 (s, 2H). HRMS (ESI$^+$) calcd for C$_{23}$H$_{20}$N$_3$O$_4$S (M+H)$^+$ 434.1175, found 434.1170.

88

5-((3-(Naphthalene-2-sulfonamido)benzyl)oxy)nicotinamide (B1-12)

$^1$H NMR (DMSO-d$_6$, 600 MHz) δ 10.47 (s, 1H), 8.64 (s, 1H), 8.43 (s, 1H), 8.38 (s, 1H), 8.16-8.08 (m, 2H), 8.05 (d, J=9.0 Hz, 1H), 7.99 (d, J=8.4 Hz, 1H), 7.79 (s, 1H), 7.75 (d, J=8.4 Hz, 1H), 7.69 (dd, J=7.5, 7.5 Hz, 1H), 7.65-7.58 (m, 2H), 7.27 (s, 1H), 7.22 (dd, J=8.1, 8.1 Hz, 1H), 7.11-7.05 (m, 2H), 5.13 (s, 2H). HRMS (ESI$^+$) calcd for C$_{23}$H$_{20}$H$_3$O$_4$S (M+H)$^+$ 434.1175, found 434.1175.

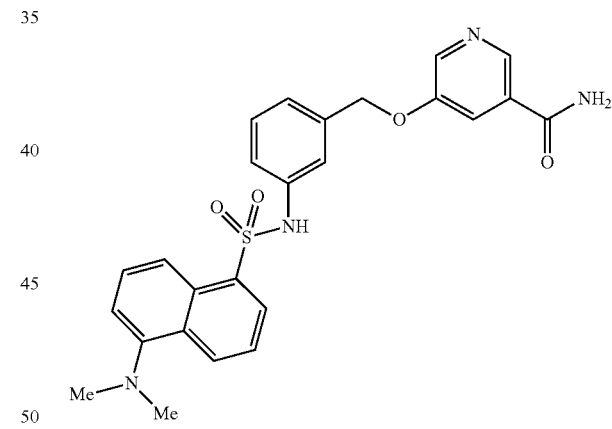

5-((3-(5-(Dimethylamino)naphthalene-1-sulfonamido)benzyl)oxy)nicotinamide (B1-13)

$^1$H NMR (DMSO-d$_6$, 600 MHz) δ 10.75 (s, 1H), 8.64 (s, 1H), 8.41 (d, J=9.0 Hz, 1H), 8.39-8.33 (m, 2H), 8.17 (d, J=7.2 Hz, 1H), 8.12 (s, 1H), 7.76 (s, 1H), 7.65-7.56 (m, 2H), 7.54 (dd, J=8.1, 8.1 Hz, 1H), 7.23 (d, J=7.8 Hz, 1H), 7.20-7.12 (m, 2H), 7.01 (d, J=7.2 Hz, 1H), 6.97 (d, J=7.8 Hz, 1H), 5.09 (s, 2H), 2.79 (s, 6H). HRMS (ESI$^+$) calcd for C$_{25}$H$_{25}$H$_4$O$_4$S (M+H)$^+$ 477.1597, found 477.1604.

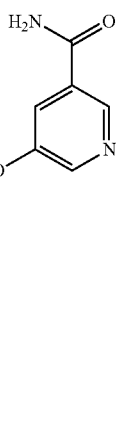

5-((3-(Benzylamino)benzyl)oxy)nicotinamide (B2-1)

To a mixture of intermediate IA4 (60 mg, 0.24 mmol), benzaldehyde (25 μL, 0.24 mmol), and NaBH(OAc)$_3$ (127 mg, 0.60 mmol) in CH$_2$Cl$_2$ (3 mL) was added AcOH (13 μl, 0.23 mmol) and the mixture was allowed to stir at it for 4 h. After the organic solvent was removed, the resulting residue was purified by flash column chromatography to give compound B2-1 as a white solid (30 mg, 37%). $^1$H NMR (DMSO-d$_6$, 600 MHz) δ 8.63 (s, 1H), 8.42 (d, J=2.7 Hz, 1H), 8.12 (br s, 1H), 7.80 (s, 1H), 7.60 (br s, 1H), 7.34 (d, J=7.5 Hz, 2H), 7.30 (t, J=7.5 Hz, 2H), 7.21 (t, J=7.2 Hz, 1H), 7.05 (t, J=7.8 Hz, 1H), 6.69 (s, 1H), 6.60 (d, J=7.5 Hz, 1H), 6.52 (dd, J$_1$=8.2 Hz J$_2$=1.6 Hz, 1H), 6.33 (t, J=6.0 Hz, 1H), 5.07 (s, 2H), 4.26 (d, J=6.1 Hz, 2H). HRMS (ESI$^+$) calcd for C$_{20}$H$_{20}$N$_3$O$_2$ (M+H)$^+$ 334.1550, found 334.1554.

5-((3-(3-Phenylureido)benzyl)oxy)nicotinamide (B3-1)

A solution of intermediate IA4 (60 mg, 0.24 mmol) and phenyl isocyanate (32 μL, 0.29 mmol)) in DMF (1 mL) was allowed to stir at it for 4 h. The organic solvent was removed and the resulting residue was purified by flash column chromatography (0-10% MeOH/CH$_2$Cl$_2$) to give compound B3-1 as a white solid (40 mg, 46%). $^1$H NMR (DMSO-d$_6$, 600 MHz) δ 8.74 (s, 1H), 8.65 (s, 2H), 8.49 (d, J=2.7 Hz, 1H), 8.13 (br s, 1H), 7.85 (t, J=2.1 Hz, 1H), 7.61 (br s, 1H), 7.59 (s, 1H), 7.45 (d, J=8.0 Hz, 2H), 7.40 (d, J=8.0 Hz, 1H), 7.31 (t, J=7.8 Hz, 1H), 7.28 (t, J=7.8 Hz, 2H), 7.07 (d, J=7.4 Hz, 1H), 6.97 (t, J=7.4 Hz, 1H), 5.22 (s, 2H). HRMS (ESI$^+$) calcd for C$_{20}$H$_{19}$N$_4$O$_3$ (M+H)$^+$ 363.1452, found 363.1461.

Compounds B3-2 was prepared in a manner similar to that described for compound B3-1.

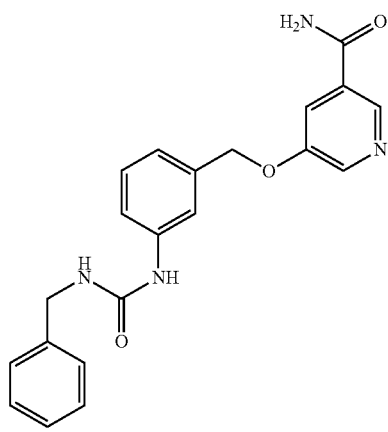 [SMILES: NC(=O)c1cncc(OCc2cccc(NC(=O)NCc3ccccc3)c2)c1]

5-((3-(3-Benzylureido)benzyl)oxy)nicotinamide (B3-2)

White solid (35 mg, 39%). $^1$H NMR (DMSO-d$_6$, 600 MHz) δ 8.65-8.63 (m, 2H), 8.47 (d, J=2.8 Hz, 1H), 8.13 (br s, 1H), 7.84-7.82 (m, 1H), 7.61 (br s, 1H), 7.55 (s, 1H), 7.37-7.28 (m, 5H), 7.27-7.22 (m, 2H), 7.00 (d, J=7.5 Hz, 1H), 6.62 (t, J=5.9 Hz, 1H), 5.18 (s, 2H), 4.30 (d, J=6.0 Hz, 2H). HRMS (ESI$^+$) calcd for C$_{21}$H$_{21}$N$_4$O$_3$ (M+H)$^+$ 377.1608, found 377.1612.

tert-Butyl (3-(((5-carbamoylpyridin-3-yl)oxy)methyl)phenyl)carbamate (B4-1)

A solution of intermediate IA4 (60 mg, 0.24 mmol), di-tert-butyl dicarbonate (83 mg, 0.38 mmol) and DIPEA (87 μL, 0.50 mmol) in CH$_2$Cl$_2$ (1 mL) was allowed to stir at rt overnight. After the organic solvent was removed, the resulting residue was purified by flash column chromatography (0-10% MeOH/CH$_2$Cl$_2$) to give compound B4-1 as a white solid (25 mg, 30%). $^1$H NMR (DMSO-d$_6$, 600 MHz) δ 9.41 (br s, 1H), 8.64 (s, 1H), 8.47 (d, J=2.9 Hz, 1H), 8.13 (br s, 1H), 7.83 (s, 1H), 7.63-7.59 (m, 2H), 7.38 (d, J=8.0 Hz, 1H), 7.27 (t, J=7.8 Hz, 1H), 7.06 (d, J=7.4 Hz, 1H), 5.18 (s, 2H), 1.47 (s, 9H). HRMS (ESI+) calcd for $C_{18}H_{22}N_3O_4$ (M+H)+ 344.1605, found 344.1606.

Compounds B4-2 was prepared in a manner similar to that described for compound B4-1.

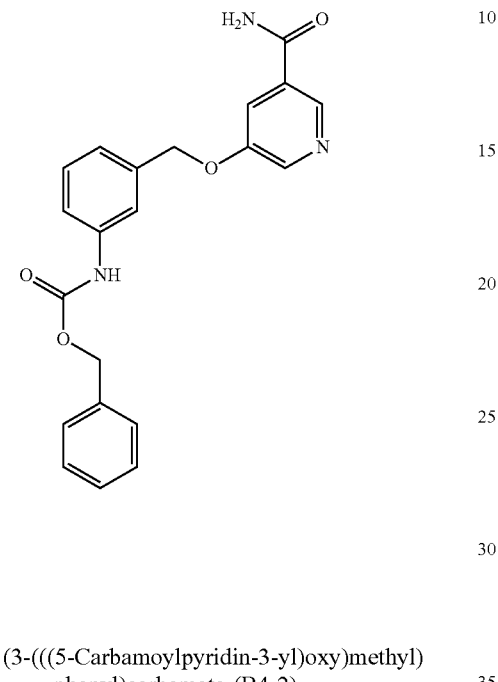

Benzyl (3-(((5-Carbamoylpyridin-3-yl)oxy)methyl) phenyl)carbamate (B4-2)

White solid (45 mg, 50%). 1H NMR (DMSO-d6, 600 MHz) δ 9.84 (br s, 1H), 8.65 (s, 1H), 8.47 (d, J=2.5 Hz, 1H), 8.13 (br s, 1H), 7.84 (s, 1H), 7.61 (s, 2H), 7.43 (s, 1H), 7.42 (s, 2H), 7.39 (t, J=7.5 Hz, 2H), 7.35 (d, J=7.2 Hz, 1H), 7.31 (t, J=7.9 Hz, 1H), 7.10 (d, J=7.5 Hz, 1H), 5.20 (s, 2H), 5.15 (s, 2H). HRMS (ESI+) calcd for $C_{21}H_{20}N_3O_4$ (M+H)+ 378.1448, found 378.1459.

Example 3

Representative compounds of formula (I) can be prepared as described below.

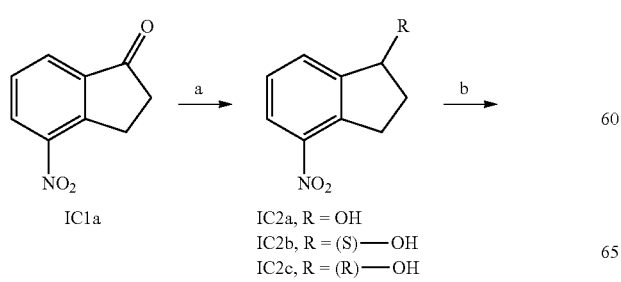

IC1a

IC2a, R = OH
IC2b, R = (S)—OH
IC2c, R = (R)—OH

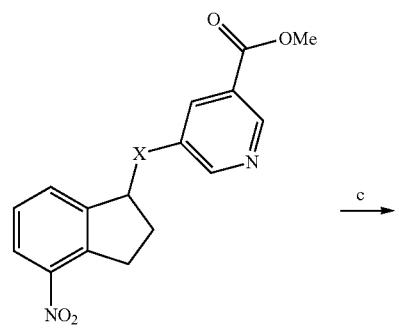

IC3a, X = O
IC3b, X = (S)—O
IC3c, X = (R)—O

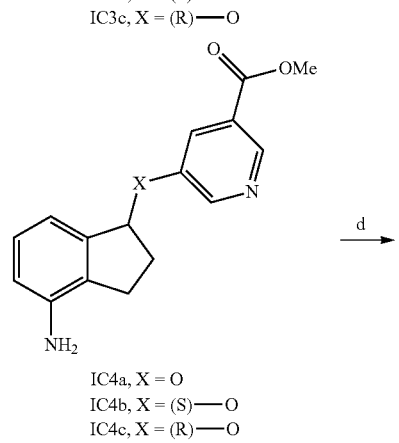

IC4a, X = O
IC4b, X = (S)—O
IC4c, X = (R)—O

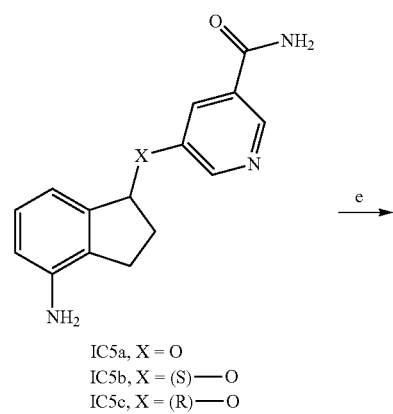

IC5a, X = O
IC5b, X = (S)—O
IC5c, X = (R)—O

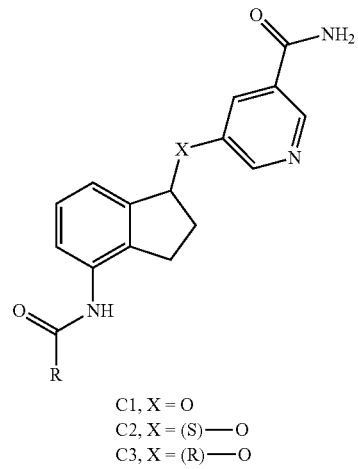

C1, X = O
C2, X = (S)—O
C3, X = (R)—O

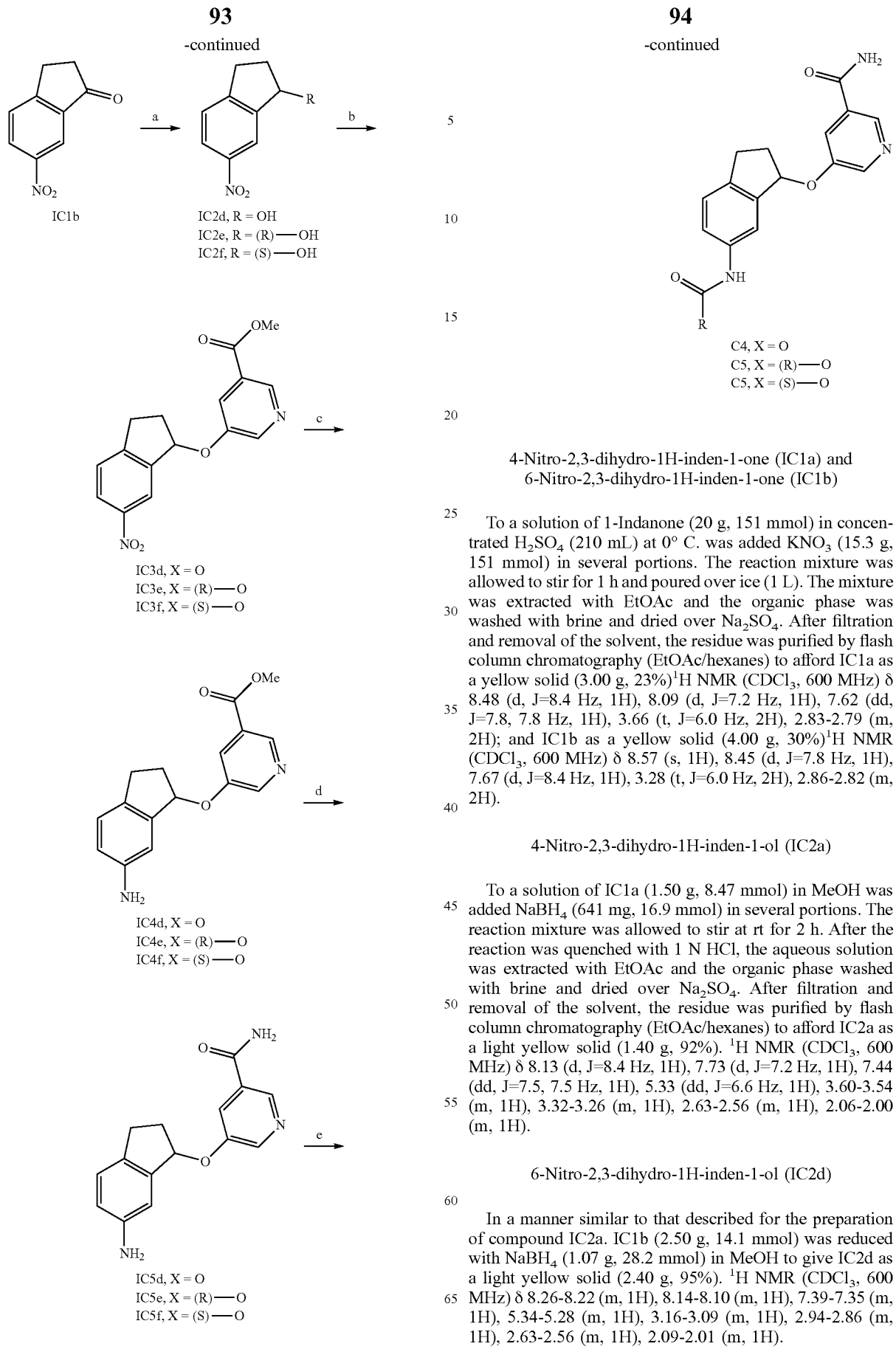

4-Nitro-2,3-dihydro-1H-inden-1-one (IC1a) and 6-Nitro-2,3-dihydro-1H-inden-1-one (IC1b)

To a solution of 1-Indanone (20 g, 151 mmol) in concentrated $H_2SO_4$ (210 mL) at 0° C. was added $KNO_3$ (15.3 g, 151 mmol) in several portions. The reaction mixture was allowed to stir for 1 h and poured over ice (1 L). The mixture was extracted with EtOAc and the organic phase was washed with brine and dried over $Na_2SO_4$. After filtration and removal of the solvent, the residue was purified by flash column chromatography (EtOAc/hexanes) to afford IC1a as a yellow solid (3.00 g, 23%) $^1$H NMR (CDCl$_3$, 600 MHz) δ 8.48 (d, J=8.4 Hz, 1H), 8.09 (d, J=7.2 Hz, 1H), 7.62 (dd, J=7.8, 7.8 Hz, 1H), 3.66 (t, J=6.0 Hz, 2H), 2.83-2.79 (m, 2H); and IC1b as a yellow solid (4.00 g, 30%) $^1$H NMR (CDCl$_3$, 600 MHz) δ 8.57 (s, 1H), 8.45 (d, J=7.8 Hz, 1H), 7.67 (d, J=8.4 Hz, 1H), 3.28 (t, J=6.0 Hz, 2H), 2.86-2.82 (m, 2H).

4-Nitro-2,3-dihydro-1H-inden-1-ol (IC2a)

To a solution of IC1a (1.50 g, 8.47 mmol) in MeOH was added NaBH$_4$ (641 mg, 16.9 mmol) in several portions. The reaction mixture was allowed to stir at rt for 2 h. After the reaction was quenched with 1 N HCl, the aqueous solution was extracted with EtOAc and the organic phase washed with brine and dried over Na$_2$SO$_4$. After filtration and removal of the solvent, the residue was purified by flash column chromatography (EtOAc/hexanes) to afford IC2a as a light yellow solid (1.40 g, 92%). $^1$H NMR (CDCl$_3$, 600 MHz) δ 8.13 (d, J=8.4 Hz, 1H), 7.73 (d, J=7.2 Hz, 1H), 7.44 (dd, J=7.5, 7.5 Hz, 1H), 5.33 (dd, J=6.6 Hz, 1H), 3.60-3.54 (m, 1H), 3.32-3.26 (m, 1H), 2.63-2.56 (m, 1H), 2.06-2.00 (m, 1H).

6-Nitro-2,3-dihydro-1H-inden-1-ol (IC2d)

In a manner similar to that described for the preparation of compound IC2a. IC1b (2.50 g, 14.1 mmol) was reduced with NaBH$_4$ (1.07 g, 28.2 mmol) in MeOH to give IC2d as a light yellow solid (2.40 g, 95%). $^1$H NMR (CDCl$_3$, 600 MHz) δ 8.26-8.22 (m, 1H), 8.14-8.10 (m, 1H), 7.39-7.35 (m, 1H), 5.34-5.28 (m, 1H), 3.16-3.09 (m, 1H), 2.94-2.86 (m, 1H), 2.63-2.56 (m, 1H), 2.09-2.01 (m, 1H).

Methyl 5-((4-Nitro-2,3-dihydro-1H-inden-1-yl)oxy)nicotinate (IC3a)

To a solution of IC2a (1.28 g, 7.16 mmol), methyl 5-hydroxynicotinate (1.32 g, 8.59 mmol), and Ph$_3$P (2.82 g, 10.7 mmol) in anhydrous THF (45 mL) at rt was added DIAD (2.17 g, 10.7 mmol) dropwise. After the mixture was stirred for 12 h and the solvent removed, the residue was purified by flash column chromatography (EtOAc/hexanes) to afford IC3a as a yellow solid (1.70 g, 76%). $^1$H NMR (600 MHz, DMSO) δ 8.74 (s, 1H), 8.61 (d, J=3.0 Hz, 1H), 8.20 (d, J=7.8 Hz, 1H), 7.93 (s, 1H), 7.88 (d, J=6.6 Hz, 1H), 7.59 (dd, J=7.8, 7.8 Hz, 1H), 6.17 (dd, J=4.2, 6.6 Hz, 1H), 3.91 (s, 3H), 3.52-3.45 (m, 1H), 3.40-3.34 (m, 1H), 2.71-2.64 (m, 1H), 2.17-2.10 (m, 1H). HRMS (ESI$^+$) calcd for C$_{16}$H$_{15}$N$_2$O$_5$ (M+H)$^+$ 315.0975, found 315.0983.

Methyl 5-((6-Nitro-2,3-dihydro-1H-inden-1-yl)oxy)nicotinate (IC3d)

In a manner similar to that described for the preparation of compound IC3a, IC3d was prepared from IC2d (1.14 g, 6.34 mmol) as a yellow solid (1.30 g, 65%). $^1$H NMR (600 MHz, CDCl$_3$) δ 8.89 (s, 1H), 8.54 (d, J=3.0 Hz, 1H), 8.28 (s, 1H), 8.23 (dd, J=1.8, 7.8 Hz, 1H), 7.91 (s, 1H), 7.48 (s, 1H), 5.91-5.88 (m, 1H), 3.98 (s, 3H), 3.29-3.23 (m, 1H), 3.11-3.05 (m, 1H), 2.79-2.73 (m, 1H), 2.34-2.28 (m, 1H). HRMS (ESI$^+$) calcd for C$_{16}$H$_{15}$N$_2$O$_5$ (M+H)$^+$ 315.0975, found 315.0988.

Methyl 5-((4-Amino-2,3-dihydro-1H-inden-1-yl)oxy)nicotinate (IC4a)

To a solution of compound IC3a (500 mg, 1.60 mmol) and NiCl$_2$·6H$_2$O (760 mg, 4.48 mmol) in MeOH (800 mL) was slowly added NaBH$_4$ (250 mg, 6.40 mmol) and the mixture was stirred at rt for 2 h. The reaction was quenched with saturated NH$_4$Cl (50 mL) and extracted with EtOAc. The organic phase was washed with water and brine, dried over anhydrous K$_2$CO$_3$, and concentrated in vacuo. The residue was purified by flash column chromatography (EtOAc/hexanes) to afford compound IC4a as a white solid (290 mg, 64%). $^1$H NMR (DMSO-d$_6$, 600 MHz) δ 8.70 (s, 1H), 8.56 (d, J=3.0 Hz, 1H), 7.88-7.86 (m, 1H), 6.93 (dd, J=7.8, 7.8 Hz, 1H), 6.58 (d, J=7.2 Hz, 1H), 6.56 (d, J=8.4 Hz, 1H), 5.95 (dd, J=3.3, 6.6 Hz, 1H), 5.02 (s, 2H), 3.90 (s, 3H), 2.82-2.77 (m, 1H), 2.69-2.64 (m, 1H), 2.57-2.2.51 (m, 1H), 2.05-2.00 (m, 1H). HRMS (ESI$^+$) calcd for C$_{16}$H$_{17}$N$_2$O$_3$ (M+H)$^+$ 285.1234, found 285.1241.

Methyl 5-((6-Amino-2,3-dihydro-1H-inden-1-yl)oxy)nicotinate (IC4d)

In a manner similar to that described for the preparation of compound IC4a, IC3d (500 mg, 1.60 mmol) was reduced to afford IC4d as a light yellow solid (270 mg, 59%). $^1$H NMR (CDCl$_3$, 600 MHz) δ 8.84 (d, J=1.8 Hz, 1H), 8.53 (d, J=3.0 Hz, 1H), 7.89 (dd, J=3.0, 1.8 Hz, 1H), 7.10 (d, J=7.8 Hz, 1H), 6.74 (d, J=2.4 Hz, 1H), 6.69 (dd, J=8.4, 2.4 Hz, 1H), 5.76 (dd, J=6.6, 4.2 Hz, 1H), 3.97 (s, 3H), 3.65 (bs, 2H), 3.08-3.02 (m, 1H), 2.88-2.82 (m, 1H), 2.63-2.56 (m, 1H), 2.02-1.95 (m, 1H). HRMS (ESI$^+$) calcd for C$_{16}$H$_{17}$N$_2$O$_3$ (M+H)$^+$ 285.1234, found 285.1243.

5-((4-Amino-2,3-dihydro-1H-inden-1-yl)oxy)nicotinamide (IC5a)

A solution of methyl ester IC4a (280 mg, 0.98 mmol) in NH$_3$/MeOH (ca. 7N, 10 mL) in a seal tube was heated at 70° C. for 24 h. After the solvent was evaporated in vacuo, the residue was dissolved in EtOAc (150 mL) and the organic layer was washed with H$_2$O (150 mL) and then with brine (100 mL). After the organic layer was dried over Na$_2$SO$_4$ and filtered, the filtrate was concentrated and the residue was purified by flash column chromatography (5% MeOH/CH$_2$Cl$_2$) to afford compound IC5a as a light yellow solid (260 mg, 98%). $^1$H NMR (DMSO-d$_6$, 600 MHz) δ 8.64 (s, 1H), 8.43 (d, J=1.8 Hz, 1H), 8.14 (s, 1H), 7.86 (s, 1H), 7.61 (s, 1H), 6.93 (dd, J=7.5, 7.5 Hz, 1H), 6.58 (d, J=7.8 Hz, 1H), 6.50 (d, J=7.2 Hz, 1H), 5.90 (dd, J=3.6, 6.6 Hz, 1H), 5.02 (s, 2H), 2.82-2.77 (m, 1H), 2.68-2.63 (m, 1H), 2.58-2.52 (m, 1H), 2.04-2.00 (m, 1H). HRMS (ESI$^+$) calcd for C$_{15}$H$_{16}$N$_3$O$_2$ (M+H)$^+$ 270.1237, found 270.1247.

5-((6-Amino-2,3-dihydro-1H-inden-1-yl)oxy)nicotinamide (IC5d)

In a manner similar to that described for the preparation of compound IC5a, aminolysis of IC4d (250 mg, 0.88 mmol) afforded IC5d as a light yellow solid (230 mg, 97%). $^1$H NMR (DMSO-d$_6$, 600 MHz) δ 8.65 (s, 1H), 8.45 (d, J=2.4 Hz, 1H), 8.14 (s, 1H), 7.87 (s, 1H), 7.61 (s, 1H), 6.97 (d, J=7.8 Hz, 1H), 6.59 (s, 1H), 6.56 (d, J=7.2 Hz, 1H), 5.86 (dd, J=5.1, 5.1 Hz, 1H), 4.96 (s, 2H), 2.90-2.85 (m, 1H), 2.75-2.69 (m, 1H), 2.57-2.50 (m, 1H), 2.00-1.95 (m, 1H). HRMS (ESI$^+$) calcd for C$_{15}$H$_{16}$N$_3$O$_2$ (M+H)$^+$ 270.1237, found 270.1237.

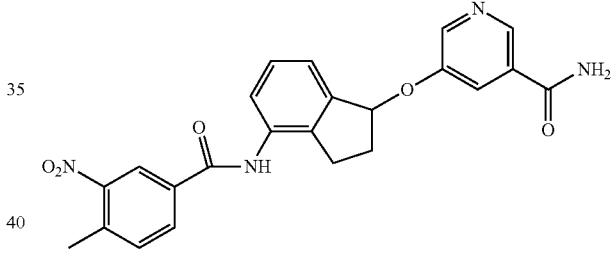

5-((4-(4-Methyl-3-nitrobenzamido)-2,3-dihydro-1H-inden-1-yl)oxy)nicotinamide (C1-1)

To a solution of IC5a (57 mg, 0.21 mmol) and Et$_3$N (33 mg, 0.32 mmol) in anhydrous DMF (2 mL) at rt was added 4-methyl-3-nitrobenzoyl chloride (84 mg, 0.42 mmol) dropwise. After the mixture was allowed to stir at rt for 12 h, the reaction was quenched with saturated NH$_4$Cl (10 mL). The resulting mixture was extracted with EtOAc and the organic phase was washed with water and brine, dried over anhydrous Na$_2$SO$_4$, and concentrated in vacuo. The residue was purified by flash column chromatography (MeOH/CH$_2$Cl$_2$) to afford compound C1-1 as a light yellow solid (37 mg, 42%). $^1$H NMR (DMSO-d$_6$, 600 MHz) δ 10.32 (s, 1H), 8.67 (s, 1H), 8.57 (s, 1H), 8.49 (d, J=2.4 Hz, 1H), 8.22 (d, J=8.4 Hz, 1H), 8.16 (s, 1H), 7.92 (s, 1H), 7.69 (d, J=7.8 Hz, 1H), 7.63 (s, 1H), 7.47-7.43 (m, 1H), 7.34-7.29 (m, 2H), 6.06 (dd, J=3.9, 5.7 Hz, 1H), 3.07-3.01 (m, 1H), 2.92-2.85 (m, 1H), 2.64-2.57 (m, 4H), 2.09-2.03 (m, 1H). HRMS (ESI$^+$) calcd for C$_{23}$H$_{21}$H$_4$O$_5$(M+H)$^+$ 433.1506, found 433.1509.

The following compounds were prepared through an amide formation reaction in a manner similar to that described for the preparation of compound C1-1.

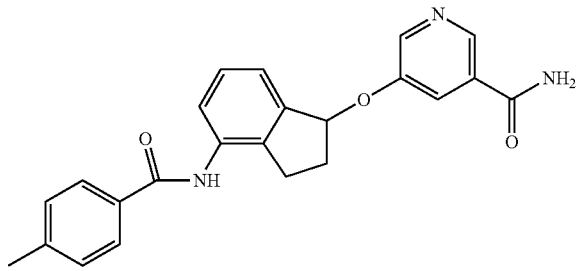 [SMILES: Cc1ccc(C(=O)Nc2cccc3c2CCC3Oc2cncc(C(N)=O)c2)cc1]

5-((4-(4-Methylbenzamido)-2,3-dihydro-1H-inden-1-yl)oxy)nicotinamide (C1-2)

$^1$H NMR (DMSO-d$_6$, 600 MHz) δ 9.95 (s, 1H), 8.66 (s, 1H), 8.49 (d, J=2.4 Hz, 1H), 8.16 (s, 1H), 7.91 (s, 1H), 7.89 (d, J=7.8 Hz, 2H), 7.63 (s, 1H), 7.47 (dd, J=4.2, 4.2 Hz, 1H), 7.34 (d, J=7.8 Hz, 2H), 7.30-7.26 (m, 2H), 6.05 (dd, J=3.6, 6.0 Hz, 1H), 3.07-3.01 (m, 1H), 2.92-2.85 (m, 1H), 2.62-2.56 (m, 1H), 2.39 (s, 3H), 2.09-2.03 (m, 1H). HRMS (ESI$^+$) calcd for C$_{23}$H$_{22}$N$_3$O$_3$ (M+H)$^+$ 388.1656, found 388.1654.

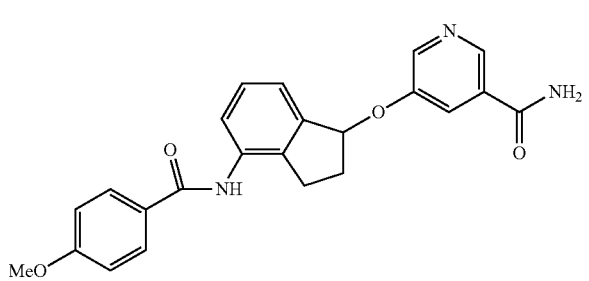 [SMILES: COc1ccc(C(=O)Nc2cccc3c2CCC3Oc2cncc(C(N)=O)c2)cc1]

5-((4-(4-Methoxybenzamido)-2,3-dihydro-1H-inden-1-yl)oxy)nicotinamide (C1-3)

$^1$H NMR (DMSO-d$_6$, 600 MHz) δ 9.88 (s, 1H), 8.66 (s, 1H), 8.49 (d, J=3.0 Hz, 1H), 8.16 (s, 1H), 7.97 (d, J=8.4 Hz, 2H), 7.91 (s, 1H), 7.63 (s, 1H), 7.47-7.44 (m, 1H), 7.30-7.23 (m, 2H), 7.06 (d, J=8.4 Hz, 2H), 6.05 (dd, J=3.6, 6.0 Hz, 1H), 3.84 (s, 3H), 3.06-3.00 (m, 1H), 2.91-2.85 (m, 1H), 2.62-2.56 (m, 1H), 2.09-2.03 (m, 1H). HRMS (ESI$^+$) calcd for C$_{23}$H$_{22}$N$_3$O$_4$ (M+H)$^+$ 404.1605, found 404.1613.

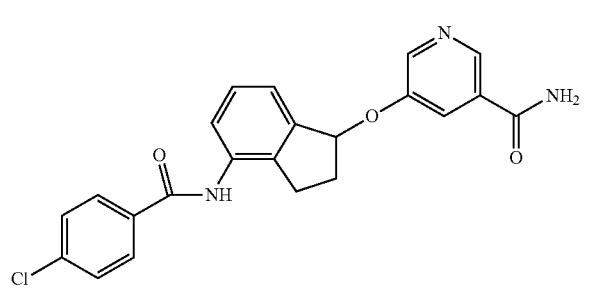 [SMILES: NC(=O)c1cncc(OC2CCc3c(NC(=O)c4ccc(Cl)cc4)cccc32)c1]

5-((4-(4-Chlorobenzamido)-2,3-dihydro-1H-inden-1-yl)oxy)nicotinamide (C1-4)

$^1$H NMR (DMSO-d$_6$, 600 MHz) δ 10.13 (s, 1H), 8.66 (s, 1H), 8.49 (d, J=3.0 Hz, 1H), 8.16 (s, 1H), 8.00 (d, J=9.0 Hz, 2H), 7.91 (s, 1H), 7.65-7.60 (m, 3H), 7.48-7.45 (m, 1H), 7.32-7.28 (m, 2H), 6.07-6.04 (m, 1H), 3.06-3.00 (m, 1H), 2.91-2.85 (m, 1H), 2.63-2.56 (m, 1H), 2.09-2.03 (m, 1H). HRMS (ESI$^+$) calcd for C$_{22}$H$_{19}$ClN$_3$O$_3$ (M+H)$^+$ 408.1109, found 408.1116.

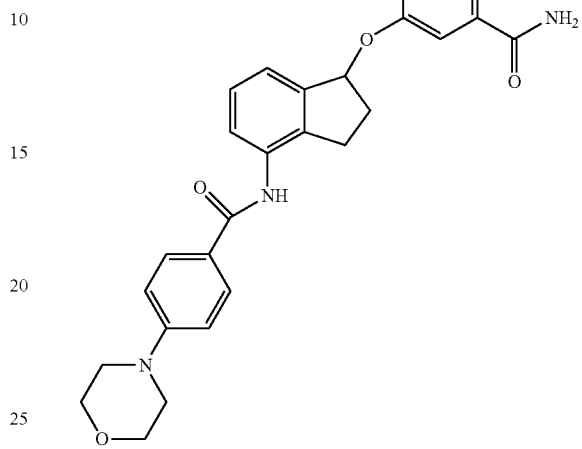

5-((4-(4-Morpholinobenzamido)-2,3-dihydro-1H-inden-1-yl)oxy)nicotinamide (C1-5)

$^1$H NMR (DMF-d$_7$, 600 MHz) δ 9.77 (s, 1H), 8.85 (s, 1H), 8.57 (s, 1H), 8.36 (s, 1H), 8.09 (s, 1H), 8.07-8.02 (m, 2H), 7.68 (d, J=7.8 Hz, 1H), 7.64 (s, 1H), 7.38-7.32 (m, 2H), 7.12 (d, J=9.0 Hz, 2H), 6.15-6.11 (m, 1H), 3.87-3.80 (m, 4H), 3.36-3.30 (m, 4H), 3.25-3.18 (m, 1H), 3.08-3.01 (m, 1H), 2.76-2.68 (m, 1H), 2.22-2.14 (m, 1H). HRMS (ESI$^+$) calcd for C$_{26}$H$_{27}$N$_4$O$_4$ (M+H)$^+$ 459.2027, found 459.2036.

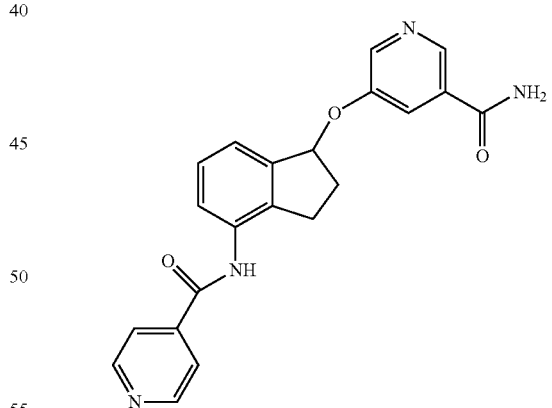

5-((4-(Isonicotinamido)-2,3-dihydro-1H-inden-1-yl)oxy)nicotinamide (C1-6)

$^1$H NMR (DMSO-d$_6$, 600 MHz) δ 10.32 (s, 1H), 8.80 (d, J=5.4 Hz, 2H), 8.67 (s, 1H), 8.49 (d, J=3.0 Hz, 1H), 8.16 (s, 1H), 7.91 (s, 1H), 7.88 (d, J=4.8 Hz, 2H), 7.62 (s, 1H), 7.50-7.47 (m, 1H), 7.34-7.30 (m, 2H), 6.08-6.04 (m, 1H), 3.08-3.02 (m, 1H), 2.92-2.86 (m, 1H), 2.64-2.57 (m, 1H), 2.10-2.03 (m, 1H). HRMS (ESI$^+$) calcd for C$_{21}$H$_{19}$N$_4$O$_3$ (M+H)$^+$ 375.1452, found 375.1463.

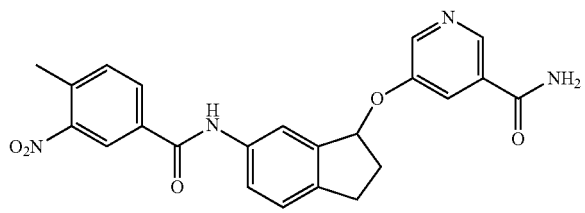 [SMILES: Cc1ccc(C(=O)Nc2ccc3c(c2)C(Oc2cncc(C(N)=O)c2)CC3)cc1[N+](=O)[O-]]

5-((6-(4-Methyl-3-nitrobenzamido)-2,3-dihydro-1H-inden-1-yl)oxy)nicotinamide (C4-1)

$^1$H NMR (DMSO-$d_6$, 600 MHz) δ 10.48 (s, 1H), 8.67 (s, 1H), 8.56 (d, J=1.2 Hz, 1H), 8.50 (d, J=2.4 Hz, 1H), 8.20 (d, J=6.6 Hz, 1H), 8.16 (s, 1H), 7.90 (s, 1H), 7.85 (s, 1H), 7.74 (d, J=7.8 Hz, 1H), 7.68 (d, J=8.4 Hz, 1H), 7.63 (s, 1H), 7.35 (d, J=9.0 Hz, 1H), 6.05 (dd, J=3.6, 3.6 Hz, 1H), 3.07-3.01 (m, 1H), 2.92-2.86 (m, 1H), 2.69-2.63 (m, 1H), 2.59 (s, 3H), 2.09-2.04 (m, 1H). HRMS (ESI$^+$) calcd for $C_{23}H_{21}N_4O_5$ (M+H)$^+$ 433.1506, found 433.1509.

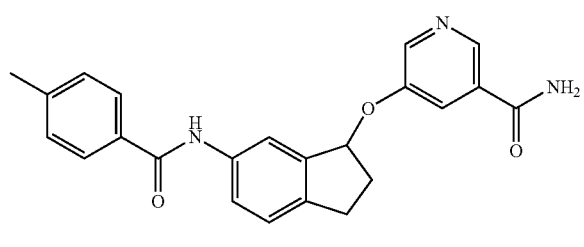 [SMILES: Cc1ccc(C(=O)Nc2ccc3c(c2)C(Oc2cncc(C(N)=O)c2)CC3)cc1]

5-((6-(4-Methylbenzamido)-2,3-dihydro-1H-inden-1-yl)oxy)nicotinamide (C4-2)

$^1$H NMR (DMSO-$d_6$, 600 MHz) δ 10.17 (s, 1H), 8.67 (s, 1H), 8.49 (d, J=2.4 Hz, 1H), 8.16 (s, 1H), 7.90 (s, 1H), 7.88-7.86 (m, 2H), 7.85 (s, 1H), 7.73 (d, J=8.4 Hz, 1H), 7.63 (s, 1H), 7.34-7.30 (m, 3H), 6.02 (dd, J=5.4, 5.4 Hz, 1H), 3.06-3.00 (m, 1H), 2.91-2.85 (m, 1H), 2.68-2.61 (m, 1H), 2.38 (s, 3H), 2.09-2.03 (m, 1H). HRMS (ESI$^+$) calcd for $C_{23}H_{22}N_3O_3$ (M+H)$^+$ 388.1656, found 388.1655.

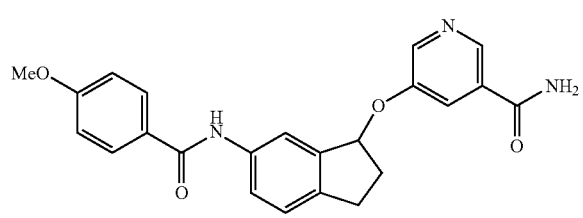 [SMILES: COc1ccc(C(=O)Nc2ccc3c(c2)C(Oc2cncc(C(N)=O)c2)CC3)cc1]

5-((6-(4-Methoxybenzamido)-2,3-dihydro-1H-inden-1-yl)oxy)nicotinamide (C4-3)

$^1$H NMR (DMSO-$d_6$, 600 MHz) δ 10.10 (s, 1H), 8.67 (s, 1H), 8.49 (d, J=2.4 Hz, 1H), 8.15 (s, 1H), 7.95 (d, J=9.0 Hz, 2H), 7.90 (s, 1H), 7.86 (s, 1H), 7.72 (d, J=7.2 Hz, 1H), 7.63 (s, 1H), 7.31 (d, J=8.4 Hz, 1H), 7.05 (d, J=9.0 Hz, 2H), 6.02 (dd, J=5.4, 5.4 Hz, 1H), 3.83 (s, 3H), 3.06-3.00 (m, 1H), 2.91-2.85 (m, 1H), 2.68-2.61 (m, 1H), 2.09-2.03 (m, 1H). HRMS (ESI$^+$) calcd for $C_{23}H_{22}N_3O_4$ (M+H)$^+$ 404.1605, found 404.1609.

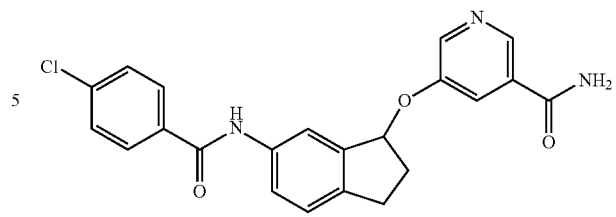

5-((6-(4-Chlorobenzamido)-2,3-dihydro-1H-inden-1-yl)oxy)nicotinamide (C4-4)

$^1$H NMR (DMSO-$d_6$, 600 MHz) δ 10.33 (s, 1H), 8.67 (s, 1H), 8.49 (d, J=3.0 Hz, 1H), 8.16 (s, 1H), 7.97 (d, J=8.4 Hz, 2H), 7.90 (s, 1H), 7.86 (s, 1H), 7.72 (dd, J=1.2, 8.4 Hz, 2H), 7.63 (s, 1H), 7.60 (d, J=9.6 Hz, 1H), 7.33 (d, J=8.4 Hz, 1H), 6.03 (dd, J=4.5, 6.3 Hz, 1H), 3.06-3.00 (m, 1H), 2.92-2.85 (m, 1H), 2.68-2.60 (m, 1H), 2.09-2.03 (m, 1H). HRMS (ESI$^+$) calcd for $C_{22}H_{19}ClN_3O_3$ (M+H)$^+$ 408.1109, found 408.1113.

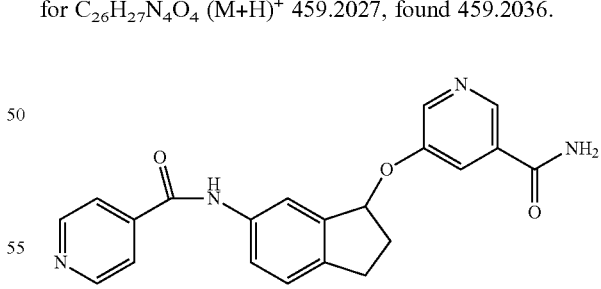

5-((6-(4-Morpholinobenzamido)-2,3-dihydro-1H-inden-1-yl)oxy)nicotinamide (C4-5)

$^1$H NMR (DMSO-$d_6$, 600 MHz) δ 9.98 (s, 1H), 8.67 (s, 1H), 8.49 (s, 1H), 8.16 (s, 1H), 7.93-7.83 (m, 4H), 7.72 (d, J=8.4 Hz, 1H), 7.63 (s, 1H), 7.29 (d, J=7.8 Hz, 1H), 7.01 (d, J=8.4 Hz, 2H), 6.03-5.98 (m, 1H), 3.78-3.70 (m, 4H), 3.28-3.21 (m, 4H), 3.06-2.98 (m, 1H), 2.92-2.83 (m, 1H), 2.68-2.60 (m, 1H), 2.10-2.02 (m, 1H). HRMS (ESI$^+$) calcd for $C_{26}H_{27}N_4O_4$ (M+H)$^+$ 459.2027, found 459.2036.

5-((6-(Isonicotinamido)-2,3-dihydro-1H-inden-1-yl)oxy)nicotinamide (C4-6)

$^1$H NMR (DMSO-$d_6$, 600 MHz) δ 10.51 (s, 1H), 8.77 (d, J=6.0 Hz, 2H), 8.67 (s, 1H), 8.49 (d, J=2.4 Hz, 1H), 8.15 (s, 1H), 7.90 (s, 1H), 7.88-7.83 (m, 3H), 7.73 (d, J=7.8 Hz, 1H), 7.62 (s, 1H), 7.35 (d, J=7.8 Hz, 1H), 6.06-6.02 (m, 1H), 3.08-3.02 (m, 1H), 2.94-2.86 (m, 1H), 2.68-2.62 (m, 1H), 2.10-2.03 (m, 1H). HRMS (ESI+) calcd for $C_{21}H_{19}N_4O_3$ (M+H)+ 375.1452, found 375.1458.

(S)-4-Nitro-2,3-dihydro-1H-inden-1-ol (IC2b)

To a solution of compound IC1a (1.00 g, 5.65 mmol) and (R)-CBS (78 mg, 0.28 mmol) in DCM (20 mL) at −20° C. was slowly added $BH_3.SMe_2$ (0.57 mL, 5.65 mmol) and the mixture was stirred at this temperature for 1 h. After the reaction was quenched with saturated $NH_4Cl$ (20 mL) and stirred at rt for 3 h, the mixture was extracted with EtOAc. The organic phase was washed with water and brine, dried over anhydrous $Na_2SO_4$, and concentrated in vacuo. The residue was purified by flash column chromatography (EtOAc/hexanes) to afford compound IC2b as a light yellow solid (900 mg, 89%). $^1$H NMR (CDCl$_3$, 600 MHz) δ 8.13 (d, J=8.4 Hz, 1H), 7.73 (d, J=7.2 Hz, 1H), 7.44 (dd, J=7.5, 7.5 Hz, 1H), 5.33 (dd, J=6.6, 6.6 Hz, 1H), 3.60-3.52 (m, 1H), 3.32-3.24 (m, 1H), 2.63-2.56 (m, 1H), 2.06-2.00 (m, 1H).

(R)-4-Nitro-2,3-dihydro-1H-inden-1-ol (IC2c)

In a manner similar to that described for the preparation of compound IC2b, IC1a (1.77 g, 10.0 mmol) was reduced with $BH_3.SMe_2$ (1.00 mL, 10.0 mmol) in the presence of (S)-CBS (139 mg, 0.50 mmol) to give IC2c as a white solid (1.61 g, 90%). $^1$H NMR (CDCl$_3$, 600 MHz) δ 8.12 (d, J=8.4 Hz, 1H), 7.72 (d, J=7.2 Hz, 1H), 7.43 (dd, J=7.5, 7.5 Hz, 1H), 5.32 (dd, J=6.6, 6.6 Hz, 1H), 3.60-3.52 (m, 1H), 3.32-3.24 (m, 1H), 2.63-2.56 (m, 1H), 2.06-2.00 (m, 1H).

(R)-6-Nitro-2,3-dihydro-1H-inden-1-ol (IC2e)

In a manner similar to that described for the preparation of compound IC2b, IC1b (1.00 g, 5.65 mmol) was reduced with $BH_3SMe_2$ (0.57 mL, 5.65 mmol) in the presence of (S)-CBS (78 mg, 0.28 mmol) in DCM to give IC2e (850 mg, 84%) as a light yellow solid. $^1$H NMR (CDCl$_3$, 600 MHz) δ 8.26-8.22 (m, 1H), 8.14 (dd, J=2.4, 8.4 Hz, 1H), 7.37 (d, J=7.8 Hz, 1H), 5.32 (dd, J=6.6, 6.6 Hz, 1H), 3.16-3.09 (m, 1H), 2.94-2.86 (m, 1H), 2.64-2.58 (m, 1H), 2.09-2.01 (m, 1H).

(S)-6-Nitro-2,3-dihydro-1H-inden-1-ol (IC2f)

In a manner similar to that described for the preparation of compound IC2b. IC1b (1.00 g, 5.65 mmol) was reduced with $BH_3SMe_2$ (0.57 mL, 5.65 mmol) in the presence of (R)-CBS (78 mg, 0.25 mmol) to give IC2f as a light yellow solid (900 mg, 89%). $^1$H NMR (CDCl$_3$, 600 MHz) δ 8.26-8.22 (m, 1H), 8.14 (dd, J=2.4, 8.4 Hz, 1H), 7.37 (d, J=7.8 Hz, 1H), 5.32 (dd, J=6.6, 6.6 Hz, 1H), 3.16-3.09 (m, 1H), 2.94-2.86 (m, 1H), 2.64-2.58 (m, 1H), 2.09-2.01 (m, 1H).

(S)-Methyl 5-((4-Nitro-2,3-dihydro-1H-inden-1-yl)oxy)nicotinate (IC3b)

In a manner similar to that described for the preparation of compound IC3a, IC2c (500 mg, 2.79 mmol) and methyl 5-hydroxynicotinate (513 g, 3.35 mmol) were treated with DIAD and Ph$_3$P to afford IC3b as a yellow solid (580 g, 66%). $^1$H NMR (CDCl$_3$, 600 MHz) δ 8.84 (s, 1H), 8.52 (d, J=2.4 Hz, 1H), 7.90 (s, 1H), 7.11 (dd, J=7.8, 7.8 Hz, 1H), 6.85 (d, J=7.8 Hz, 1H), 6.68 (d, J=7.2 Hz, 1H), 5.82 (dd, J=3.6, 6.6 Hz, 1H), 3.96 (s, 3H), 3.00-2.92 (m, 1H), 2.80-2.73 (m, 1H), 2.66-2.60 (m, 1H), 2.28-2.22 (m, 1H). HRMS (ESI+) calcd for $C_{16}H_{15}N_2O_5$ (M+H)+ 315.0975, found 315.0984.

(R)-Methyl 5-((4-Nitro-2,3-dihydro-1H-inden-1-yl)oxy)nicotinate (IC3c)

In a manner similar to that described for the preparation of compound IC3a, IC2b (500 mg, 2.79 mmol) and methyl 5-hydroxynicotinate (513 g, 3.35 mmol) were treated with DIAD and Ph$_3$P to afford IC3c as a yellow solid (560 g, 64%). $^1$H NMR (CDCl$_3$, 600 MHz) δ 8.84 (s, 1H), 8.52 (s, 1H), 7.90 (s, 1H), 7.11 (dd, J=7.8, 7.8 Hz, 1H), 6.85 (d, J=7.8 Hz, 1H), 6.68 (d, J=7.2 Hz, 1H), 5.82 (dd, J=3.6, 6.6 Hz, 1H), 3.96 (s, 3H), 3.00-2.92 (m, 1H), 2.80-2.73 (m, 1H), 2.66-2.60 (m, 1H), 2.28-2.22 (m, 1H). HRMS (ESI+) calcd for $C_{16}H_{15}N_2O_5$ (M+H)+ 315.0975, found 315.0985.

(R)-Methyl 5-((6-Nitro-2,3-dihydro-1H-inden-1-yl)oxy)nicotinate (IC3e)

In a manner similar to that described for the preparation of compound IC3a, IC2f (550 mg, 3.07 mmol) and methyl 5-hydroxynicotinate (554 g, 3.68 mmol) were treated with DIAD and Ph$_3$P to afford IC3e as a yellow solid (629 g, 64%). $^1$H NMR (CDCl$_3$, 600 MHz) δ 8.84 (s, 1H), 8.52 (d, J=3.0 Hz, 1H), 7.89 (dd, J=2.4, 2.4 Hz, 1H), 7.10 (d, J=7.8 Hz, 1H), 6.74 (s, 1H), 6.69 (dd, J=1.8, 8.1 Hz, 1H), 5.76 (dd, J=4.2, 6.0 Hz, 1H), 3.97 (s, 3H), 3.08-3.02 (m, 1H), 2.88-2.82 (m, 1H), 2.63-2.56 (m, 1H), 2.22-2.14 (m, 1H). HRMS (ESI+) calcd for $C_{16}H_{15}N_2O_5$ (M+H)+ 315.0975, found 315.0981.

(S)-Methyl 5-((6-Nitro-2,3-dihydro-1H-inden-1-yl)oxy)nicotinate (IC3f)

In a manner similar to that described for the preparation of compound IC3a, IC2e (700 mg, 3.91 mmol) and methyl 5-hydroxynicotinate (718 g, 4.69 mmol) were treated with DIAD and Ph$_3$P to afford IC3f as a yellow solid (800 g, 65%). $^1$H NMR (CDCl$_3$, 600 MHz) δ 8.84 (s, 1H), 8.52 (d, J=2.4 Hz, 1H), 7.89 (s, 1H), 7.10 (d, J=7.8 Hz, 1H), 6.74 (s, 1H), 6.69 (d, J=8.4 Hz, 1H), 5.88-5.74 (m, 1H), 3.97 (s, 3H), 3.08-3.02 (m, 1H), 2.88-2.82 (m, 1H), 2.63-2.56 (m, 1H), 2.22-2.14 (m, 1H). HRMS (ESI+) calcd for $C_{16}H_{15}N_2O_5$ (M+H)+ 315.0975, found 315.0986.

(S)-Methyl 5-((4-Amino-2,3-dihydro-1H-inden-1-yl)oxy)nicotinate (IC4b)

In a manner similar to that described for the preparation of compound IC4a, IC3d (250 mg, 0.80 mmol) was reduced to afford IC4b as a light yellow solid (180 mg, 80%). $^1$H NMR (CDCl$_3$, 600 MHz) 8.84 (s, 1H), 8.52 (d, J=2.4 Hz, 1H), 7.90 (dd, J=1.8, 1.8 Hz, 1H), 7.11 (dd, J=7.8, 7.8 Hz, 1H), 6.85 (d, J=7.8 Hz, 1H), 6.68 (d, J=7.8 Hz, 1H), 5.83 (dd, J=6.0, 3.6 Hz, 1H), 3.96 (s, 3H), 3.00-2.92 (m, 1H), 2.80-2.73 (m, 1H), 2.67-2.60 (m, 1H), 2.28-2.22 (m, 1H). HRMS (ESI+) calcd for $C_{16}H_{17}N_2O_3$ (M+H)+ 285.1234, found 285.1237.

(R)-Methyl 5-((4-Amino-2,3-dihydro-1H-inden-1-yl)oxy)nicotinate (IC4c)

In a manner similar to that described for the preparation of compound IC4a, IC3c (250 mg, 0.80 mmol) was reduced to afford IC4c as a light yellow solid (160 mg, 70%). $^1$H NMR (CDCl$_3$, 600 MHz) δ 8.84 (s, 1H), 8.52 (s, 1H), 7.90 (s, 1H), 7.11 (dd, J=7.8, 7.8 Hz, 1H), 6.85 (d, J=7.2 Hz, 1H), 6.67 (d, J=7.8 Hz, 1H), 5.84-5.80 (m, 1H), 3.96 (s, 3H), 3.00-2.92 (m, 1H), 2.80-2.73 (m, 1H), 2.67-2.59 (m, 1H), 2.29-2.22 (m, 1H). HRMS (ESI$^+$) calcd for C$_{16}$H$_{17}$N$_2$O$_3$ (M+H)$^+$ 285.1234, found 285.1241.

(R)-Methyl 5-((6-Amino-2,3-dihydro-1H-inden-1-yl)oxy)nicotinate (IC4e)

In a manner similar to that described for the preparation of compound IC4a, IC3e (314 mg, 1.00 mmol) was reduced to afford IC4e as a yellow solid (200 mg, 70%). $^1$H NMR (CDCl$_3$, 600 MHz) δ 8.84 (s, 1H), 8.52 (d, J=2.4 Hz, 1H), 7.89 (s, 1H), 7.10 (d, J=7.8 Hz, 1H), 6.74 (s, 1H), 6.69 (d, J=8.4 Hz, 1H), 5.77-5.74 (m, 1H), 3.96 (s, 3H), 3.08-3.01 (m, 1H), 2.88-2.81 (m, 1H), 2.64-2.56 (m, 1H), 2.22-2.14 (m, 1H). HRMS (ESI$^+$) calcd for C$_{16}$H$_{17}$N$_2$O$_3$ (M+H)$^+$ 285.1234, found 285.1239.

(S)-Methyl 5-((6-Amino-2,3-dihydro-1H-inden-1-yl)oxy)nicotinate (IC4f)

In a manner similar to that described for the preparation of compound IC4a, IC3f (314 mg, 1.00 mmol) was reduced to afford IC4f as a yellow solid (220 mg, 77%). $^1$H NMR (CDCl$_3$, 600 MHz) δ 8.84 (d, J=1.2 Hz, 1H), 8.52 (d, J=3.0 Hz, 1H), 7.89 (dd, J=2.4, 2.4 Hz, 1H), 7.10 (d, J=7.8 Hz, 1H), 6.74 (d, J=1.8 Hz, 1H), 6.69 (dd, J=7.8, 1.8 Hz, 1H), 5.76 (dd, J=6.0, 3.6 Hz, 1H), 3.97 (s, 3H), 3.07-3.02 (m, 1H), 2.88-2.82 (m, 1H), 2.63-2.56 (m, 1H), 2.21-2.14 (m, 1H). HRMS (ESI$^+$) calcd for C$_{16}$H$_{17}$N$_2$O$_3$ (M+H)$^+$ 285.1234, found 285.1239.

(S)-5-((4-Amino-2,3-dihydro-1H-inden-1-yl)oxy)nicotinamide (IC5b)

In a manner similar to that described for the preparation of compound IC5a, aminolysis of IC4b (180 mg, 0.63 mmol) afforded IC5b as a white solid (160 mg, 94%). $^1$H NMR (CDCl$_3$, 600 MHz) δ 8.57 (d, J=1.8 Hz, 1H), 8.50 (d, J=3.0 Hz, 1H), 7.81 (dd, J=2.4, 2.4 Hz, 1H), 7.11 (dd, J=7.8 Hz, 1H), 6.86 (d, J=7.8 Hz, 1H), 6.68 (d, J=7.2 Hz, 1H), 5.84 (dd, J=6.6, 3.6 Hz, 1H), 2.99-2.92 (m, 1H), 2.80-2.73 (m, 1H), 2.68-2.61 (m, 1H), 2.28-2.22 (m, 1H). HRMS (ESI$^+$) calcd for C$_{15}$H$_{16}$N$_3$O$_2$ (M+H)$^+$ 270.1237, found 270.1249.

(R)-5-((4-Amino-2,3-dihydro-1H-inden-1-yl)oxy)nicotinamide (IC5c)

In a manner similar to that described for the preparation of compound IC5a, aminolysis of IC4c (160 mg, 0.56 mmol) afforded IC5c as a white solid (140 mg, 93%). $^1$H NMR (CDCl$_3$, 600 MHz) δ 8.59 (d, J=1.8 Hz, 1H), 8.48 (d, J=3.0 Hz, 1H), 7.81 (dd, J=2.4, 2.4 Hz, 1H), 7.11 (dd, J=7.8 Hz, 1H), 6.85 (d, J=7.8 Hz, 1H), 6.67 (d, J=7.8 Hz, 1H), 5.83 (dd, J=7.2, 3.6 Hz, 1H), 2.98-2.91 (m, 1H), 2.78-2.72 (m, 1H), 2.66-2.60 (m, 1H), 2.27-2.21 (m, 1H). HRMS (ESI$^+$) calcd for C$_{15}$H$_{16}$N$_3$O$_2$ (M+H)$^+$ 270.1237, found 270.1235.

(R)-5-((6-Amino-2,3-dihydro-1H-inden-1-yl)oxy)nicotinamide (IC5e)

In a manner similar to that described for the preparation of compound IC5a, aminolysis of IC4e (220 mg, 0.77 mmol) afforded IC5e as a light yellow solid (180 mg, 86%). $^1$H NMR (CDCl$_3$, 600 MHz) δ 8.57 (s, 1H), 8.50 (d, J=3.0 Hz, 1H), 7.81 (s, 1H), 7.10 (d, J=7.8 Hz, 1H), 6.74 (s, 1H), 6.69 (d, J=8.4 Hz, 1H), 5.77 (dd, J=4.8, 4.8 Hz, 1H), 3.08-3.01 (m, 1H), 2.88-2.82 (m, 1H), 2.63-2.56 (m, 1H), 2.20-2.14 (m, 1H). HRMS (ESI$^+$) calcd for C$_{15}$H$_{16}$N$_3$O$_2$ (M+H)$^+$ 270.1237, found 270.1240.

(S)-5-((6-Amino-2,3-dihydro-1H-inden-1-yl)oxy)nicotinamide (IC5f)

In a manner similar to that described for the preparation of compound IC5a, aminolysis of IC4f (200 mg, 0.70 mmol) afforded IC5f as a light yellow solid (150 mg, 79%). $^1$H NMR (CDCl$_3$, 600 MHz) δ 8.58 (d, J=1.2 Hz, 1H), 8.49 (d, J=3.0 Hz, 1H), 7.80 (dd, J=2.4, 2.4 Hz, 1H), 7.10 (d, J=7.8 Hz, 1H), 6.74 (s, 1H), 6.69 (dd, J=8.4, 2.4 Hz, 1H), 5.77 (dd, J=6.0, 4.2 Hz, 1H), 3.07-3.00 (m, 1H), 2.87-2.81 (m, 1H), 2.62-2.55 (m, 1H), 2.20-2.13 (m, 1H). HRMS (ESI$^+$) calcd for C$_{15}$H$_{16}$N$_3$O$_2$ (M+H)$^+$ 270.1237, found 270.1249.

The following compounds were prepared through an amide formation reaction in a manner similar to that described for the preparation of compound C1-1.

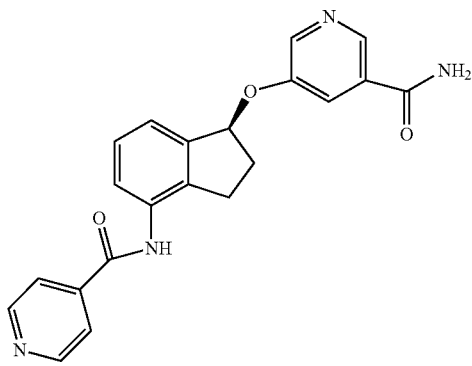 [SMILES: NC(=O)c1cncc(O[C@H]2CCc3c(NC(=O)c4ccncc4)cccc32)c1]

(S)-5-((4-(Isonicotinamido)-2,3-dihydro-1H-inden-1-yl)oxy)nicotinamide (C2-1)

$^1$H NMR (DMSO-d$_6$, 600 MHz) δ 10.32 (s, 1H), 8.80 (d, J=5.4 Hz, 2H), 8.67 (s, 1H), 8.49 (d, J=2.4 Hz, 1H), 8.16 (s, 1H), 7.91 (s, 1H), 7.88 (d, J=4.8 Hz, 2H), 7.63 (s, 1H), 7.51-7.47 (m, 1H), 7.35-7.30 (m, 2H), 6.06 (dd, J=3.6, 6.0 Hz, 1H), 3.08-3.01 (m, 1H), 2.93-2.85 (m, 1H), 2.65-2.56 (m, 1H), 2.11-2.03 (m, 1H). HRMS (ESI$^+$) calcd for C$_{21}$H$_{19}$N$_4$O$_3$ (M+H)$^+$ 375.1452, found 375.1460.

105

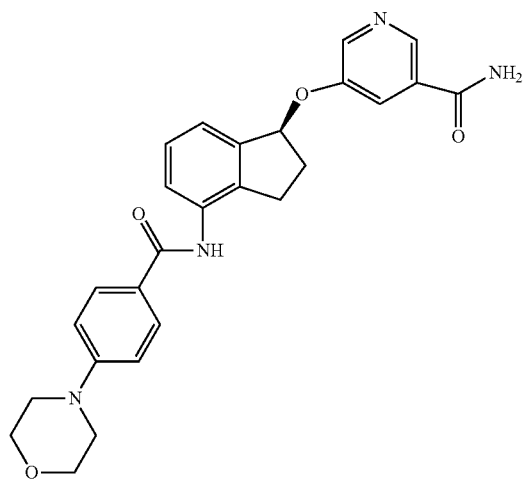 [SMILES: NC(=O)c1cncc(O[C@H]2CCc3c(NC(=O)c4ccc(N5CCOCC5)cc4)cccc32)c1]

(S)-5-((4-(4-Morpholinobenzamido)-2,3-dihydro-1H-inden-1-yl)oxy)nicotinamide (C2-2)

$^1$H NMR (CD$_3$OD, 600 MHz) δ 8.65 (s, 1H), 8.45 (s, 1H), 7.97 (s, 1H), 7.89 (d, J=8.4 Hz, 2H), 7.44 (d, J=7.2 Hz, 1H), 7.34-7.26 (m, 2H), 7.03 (d, J=8.4 Hz, 2H), 6.04-5.99 (m, 1H), 3.88-3.78 (m, 4H), 3.35-3.25 (m, 4H), 3.16-3.08 (m, 1H), 3.00-2.92 (m, 1H), 2.72-2.62 (m, 1H), 2.24-2.16 (m, 1H). HRMS (ESI$^+$) calcd for C$_{26}$H$_{27}$N$_4$O$_4$ (M+H)$^+$ 459.2027, found 459.2031.

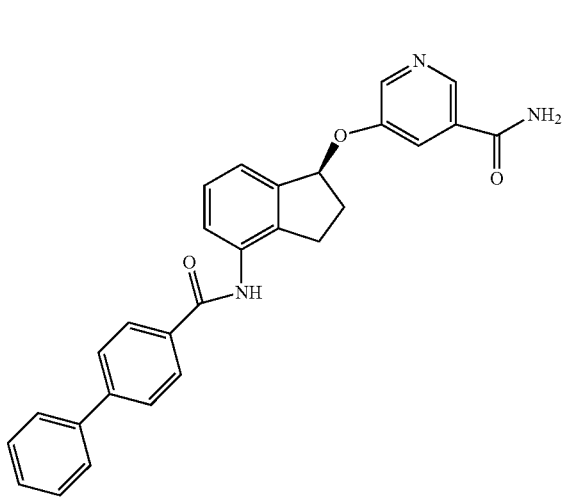 [SMILES: NC(=O)c1cncc(O[C@H]2CCc3c(NC(=O)c4ccc(-c5ccccc5)cc4)cccc32)c1]

(S)-5-((4-([1,1'-Biphenyl]-4-ylcarboxamido)-2,3-dihydro-1H-inden-1-yl)oxy)nicotinamide (C2-3)

$^1$H NMR (DMSO-d$_6$, 600 MHz) δ 10.10 (s, 1H), 8.67 (s, 1H), 8.50 (d, J=1.8 Hz, 1H), 8.17 (s, 1H), 8.08 (d, J=8.4 Hz, 2H), 7.92 (s, 1H), 7.84 (d, J=7.8 Hz, 2H), 7.76 (d, J=7.8 Hz, 2H), 7.63 (s, 1H), 7.55-7.47 (m, 3H), 7.43 (dd, J=7.2, 7.2 Hz, 1H), 7.34-7.28 (m, 2H), 6.08-6.04 (m, 1H), 3.10-3.02 (m, 1H), 2.95-2.88 (m, 1H), 2.65-2.56 (m, 1H), 2.11-2.03 (m, 1H). HRMS (ESI$^+$) calcd for C$_{28}$H$_{24}$N$_3$O$_3$ (M+H)$^+$ 450.1812, found 450.1812.

106

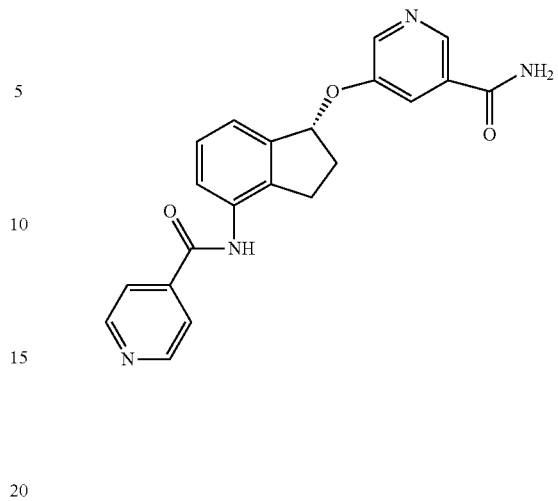

(R)-5-((4-(Isonicotinamido)-2,3-dihydro-1H-inden-1-yl)oxy)nicotinamide (C3-1)

$^1$H NMR (DMSO-d$_6$, 600 MHz) δ 10.33 (s, 1H), 8.80 (d, J=4.2 Hz, 2H), 8.67 (s, 1H), 8.49 (s, 1H), 8.16 (s, 1H), 7.91 (s, 1H), 7.88 (d, J=4.2 Hz, 2H), 7.63 (s, 1H), 7.49 (d, J=4.8 Hz, 1H), 7.35-7.30 (m, 2H), 6.08-6.04 (m, 1H), 3.08-3.01 (m, 1H), 2.93-2.85 (m, 1H), 2.65-2.56 (m, 1H), 2.11-2.03 (m, 1H). HRMS (ESI$^+$) calcd for C$_{21}$H$_{19}$N$_4$O$_3$ (M+H)$^+$ 375.1452, found 375.1465.

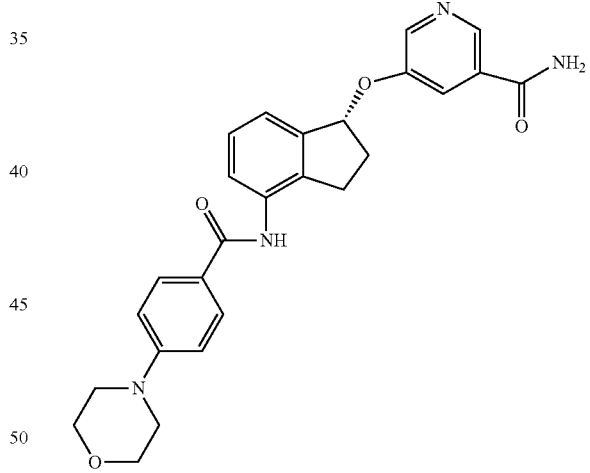

(R)-5-((4-(4-Morpholinobenzamido)-2,3-dihydro-1H-inden-1-yl)oxy)nicotinamide (C3-2)

$^1$H NMR (DMSO-d$_6$, 600 MHz) δ 9.75 (s, 1H), 8.67 (s, 1H), 8.49 (s, 1H), 8.16 (s, 1H), 7.93-7.85 (m, 3H), 7.63 (s, 1H), 7.46 (d, J=7.2 Hz, 1H), 7.29-7.23 (m, 2H), 7.03 (d, J=9.0 Hz, 2H), 6.06-6.02 (m, 1H), 3.79-3.72 (m, 4H), 3.28-3.22 (m, 4H), 3.08-3.00 (m, 1H), 2.91-2.84 (m, 1H), 2.63-2.55 (m, 1H), 2.09-2.02 (m, 1H). HRMS (ESI$^+$) calcd for C$_{26}$H$_{27}$N$_4$O$_4$ (M+H)$^+$ 459.2027, found 459.2039.1.

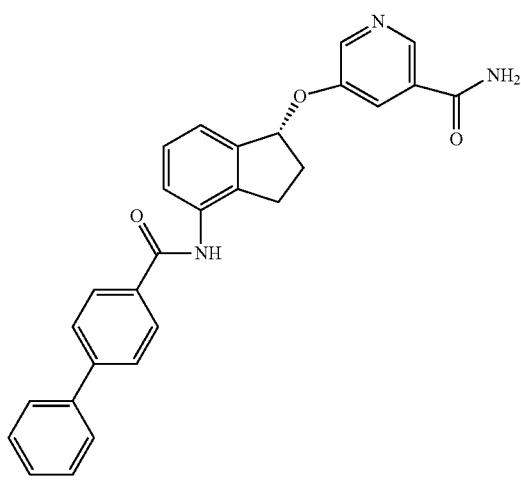 [SMILES: NC(=O)c1cncc(O[C@@H]2CCc3c(NC(=O)c4ccc(-c5ccccc5)cc4)cccc32)c1]

(R)-5-((4-([1,1'-Biphenyl]-4-carboxamido)-2,3-dihydro-1H-inden-1-yl)oxy)nicotinamide (C3-3)

White solid (4.0 mg, 5%). $^1$H NMR (CD$_3$OD, 600 MHz) δ 8.65 (s, 1H), 8.46 (s, 1H), 8.06 (d, J=7.8 Hz, 2H), 7.99 (s, 1H), 7.79 (d, J=8.4 Hz, 2H), 7.70 (d, J=8.4 Hz, 2H), 7.52-7.46 (m, 3H), 7.42-7.39 (m, 1H), 7.38-7.32 (m, 2H), 6.06-6.02 (m, 1H), 3.20-3.13 (m, 1H), 3.03-2.96 (m, 1H), 2.74-2.66 (m, 1H), 2.26-2.19 (m, 1H). HRMS (ESI$^+$) calcd for C$_{28}$H$_{24}$N$_3$O$_3$ (M+H)$^+$ 450.1812, found 450.1819.

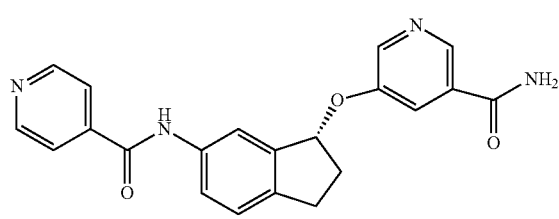 [SMILES: NC(=O)c1cncc(O[C@@H]2CCc3ccc(NC(=O)c4ccncc4)cc32)c1]

(R)-5-((6-(Isonicotinamido)-2,3-dihydro-1H-inden-1-yl)oxy)nicotinamide (C5-1)

$^1$H NMR (DMSO-d$_6$, 600 MHz) δ 10.51 (s, 1H), 8.77 (d, J=6.0 Hz, 2H), 8.67 (s, 1H), 8.50 (s, 1H), 8.16 (s, 1H), 7.90 (s, 1H), 7.88-7.82 (m, 3H), 7.73 (d, J=8.4 Hz, 1H), 7.63 (s, 1H), 7.35 (d, J=8.4 Hz, 1H), 6.06-6.01 (m, 1H), 3.08-3.01 (m, 1H), 2.94-2.86 (m, 1H), 2.68-2.62 (m, 1H), 2.10-2.03 (m, 1H). HRMS (ESI$^+$) calcd for C$_{21}$H$_{19}$N$_4$O$_3$ (M+H)$^+$ 375.1452, found 375.1461.

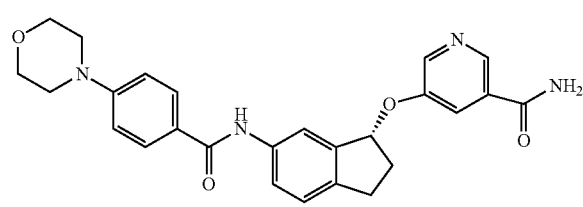 [SMILES: NC(=O)c1cncc(O[C@@H]2CCc3ccc(NC(=O)c4ccc(N5CCOCC5)cc4)cc32)c1]

(R)-5-((6-(4-Morpholinobenzamido)-2,3-dihydro-1H-inden-1-yl)oxy)nicotinamide (C5-2)

$^1$H NMR (DMSO-d$_6$, 600 MHz) δ 9.98 (s, 1H), 8.67 (s, 1H), 8.49 (s, 1H), 8.16 (s, 1H), 7.93-7.83 (m, 4H), 7.72 (d, J=8.4 Hz, 1H), 7.63 (s, 1H), 7.29 (d, J=7.8 Hz, 1H), 7.01 (d, J=7.8 Hz, 2H), 6.03-5.98 (m, 1H), 3.78-3.71 (m, 4H), 3.27-3.20 (m, 4H), 3.06-2.98 (m, 1H), 2.92-2.83 (m, 1H), 2.68-2.60 (m, 1H), 2.10-2.02 (m, 1H). HRMS (ESI$^+$) calcd for C$_{26}$H$_{27}$N$_4$O$_4$ (M+H)$^+$ 459.2027, found 459.2034.

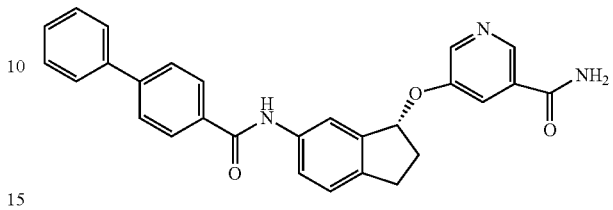

(R)-5-((6-([1,1-Biphenyl]-4-ylcarboxamido)-2,3-dihydro-1H-inden-1-yl)oxy)nicotinamide (C5-3)

$^1$H NMR (DMSO-d$_6$, 600 MHz) δ 10.32 (s, 1H), 8.68 (s, 1H), 8.51 (s, 1H), 8.16 (s, 1H), 8.05 (d, J=7.8 Hz, 2H), 7.91 (s, 2H), 7.83 (d, J=8.4 Hz, 2H), 7.78-7.73 (m, 3H), 7.63 (s, 1H), 7.51 (dd, J=7.2, 7.2 Hz, 2H), 7.45-7.40 (m, 1H), 7.34 (d, J=7.8 Hz, 1H), 6.06-6.02 (m, 1H), 3.08-3.01 (m, 1H), 2.93-2.85 (m, 1H), 2.70-2.62 (m, 1H), 2.11-2.03 (m, 1H). HRMS (ESI$^+$) calcd for C$_{28}$H$_{24}$N$_3$O$_3$ (M+H)$^+$ 450.1812, found 450.1820.

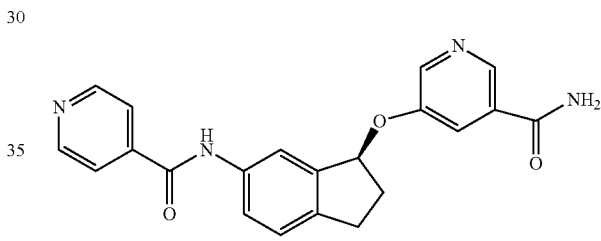

(S)-5-((6-(Isonicotinamido)-2,3-dihydro-1H-inden-1-yl)oxy)nicotinamide (C6-1)

$^1$H NMR (CD$_3$OD, 600 MHz) δ 8.72 (d, J=5.4 Hz, 2H), 8.65 (s, 1H), 8.45 (s, 1H), 7.99-7.96 (m, 1H), 7.87 (d, J=5.4 Hz, 2H), 7.83 (s, 1H), 7.68-7.64 (m, 1H), 7.35 (d, J=8.4 Hz, 1H), 6.01-5.97 (m, 1H), 3.17-3.10 (m, 1H), 3.00-2.93 (m, 1H), 2.74-2.67 (m, 1H), 2.26-2.19 (m, 1H). HRMS (ESI$^+$) calcd for C$_{21}$H$_{19}$N$_4$O$_3$ (M+H)$^+$ 375.1452, found 375.1465.

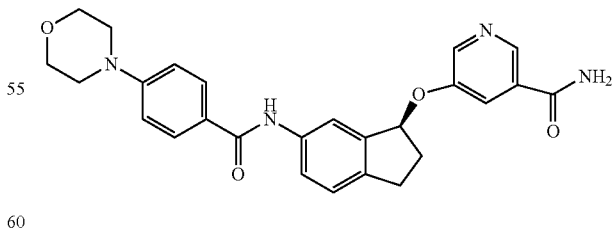

(S)-5-((6-(4-Morpholinobenzamido)-2,3-dihydro-1H-inden-1-yl)oxy)nicotinamide (C6-2)

$^1$H NMR (DMSO-d$_6$, 600 MHz) δ 9.98 (s, 1H), 8.67 (s, 1H), 8.49 (s, 1H), 8.16 (s, 1H), 7.93-7.83 (m, 4H), 7.72 (d, J=8.4 Hz, 1H), 7.63 (s, 1H), 7.29 (d, J=7.8 Hz, 1H), 7.01 (d,

J=8.4 Hz, 2H), 6.03-5.98 (m, 1H), 3.78-3.70 (m, 4H), 3.28-3.21 (m, 4H), 3.06-2.98 (m, 1H), 2.92-2.83 (m, 1H), 2.68-2.60 (m, 1H), 2.10-2.02 (m, 1H). HRMS (ESI+) calcd for $C_{26}H_{27}H_4O_4$ (M+H)+ 459.2027, found 459.2037.
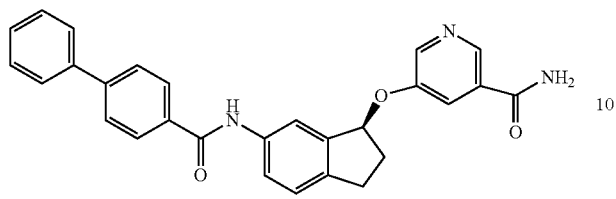
(S)-5-(((6-([1,1'-Biphenyl]-4-ylcarboxamido)-2,3-dihydro-1H-inden-1-yl)oxy)nicotinamide (C6-3)
$^1$H NMR (DMSO-$d_6$, 600 MHz) δ 10.32 (s, 1H), 8.67 (s, 1H), 8.51 (s, 1H), 8.17 (s, 1H), 8.05 (d, J=8.4 Hz, 2H), 7.91 (s, 2H), 7.83 (d, J=8.4 Hz, 2H), 7.78-7.73 (m, 3H), 7.63 (s, 1H), 7.51 (dd, J=7.5, 7.5 Hz, 2H), 7.45-7.41 (m, 1H), 7.34 (d, J=7.2 Hz, 1H), 6.06-6.02 (m, 1H), 3.08-3.01 (m, 1H), 2.93-2.85 (m, 1H), 2.70-2.62 (m, 1H), 2.11-2.03 (m, 1H). HRMS (ESI+) calcd for $C_{28}H_{24}N_3O_3$ (M+H)+ 450.1812, found 450.1820.
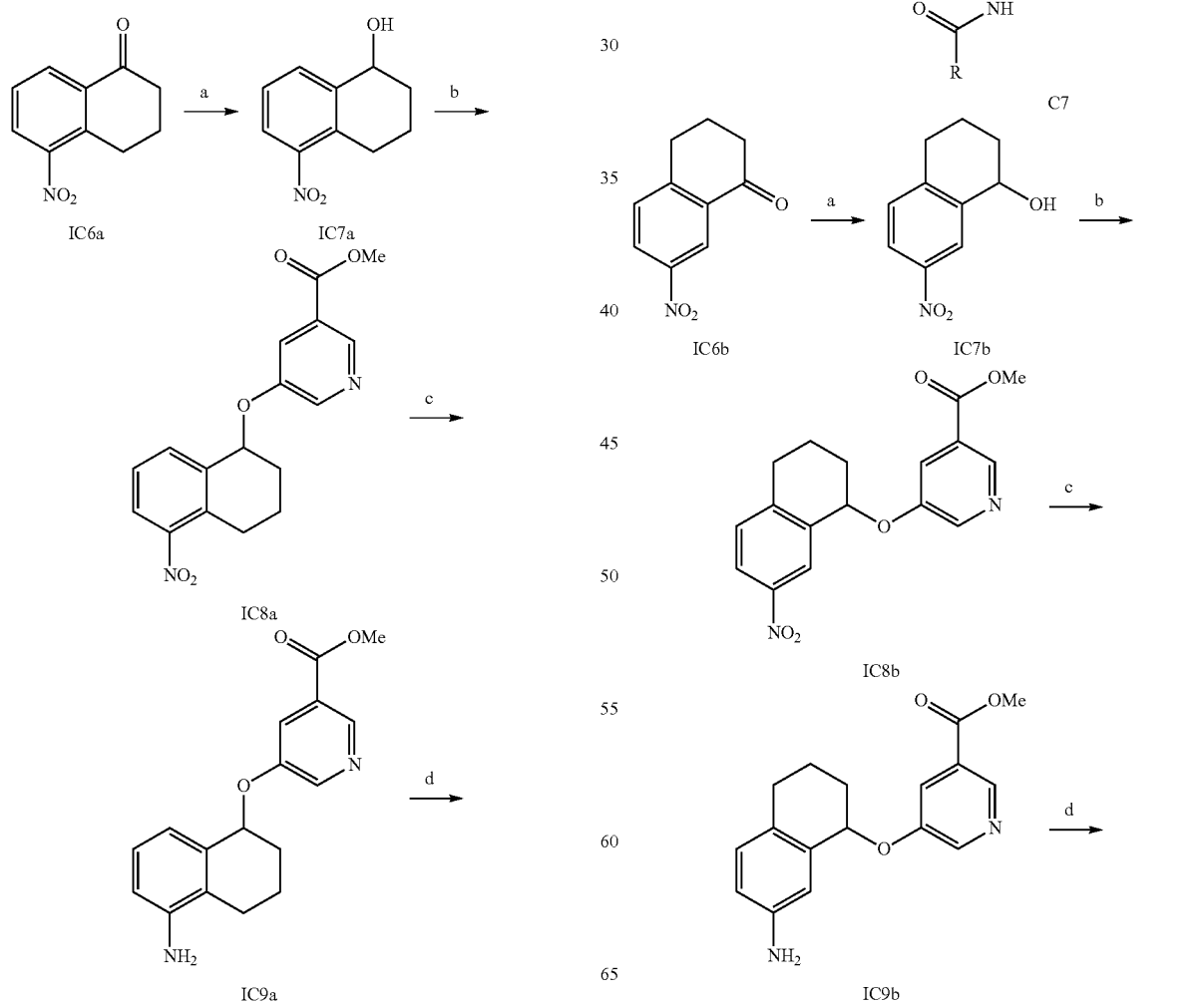

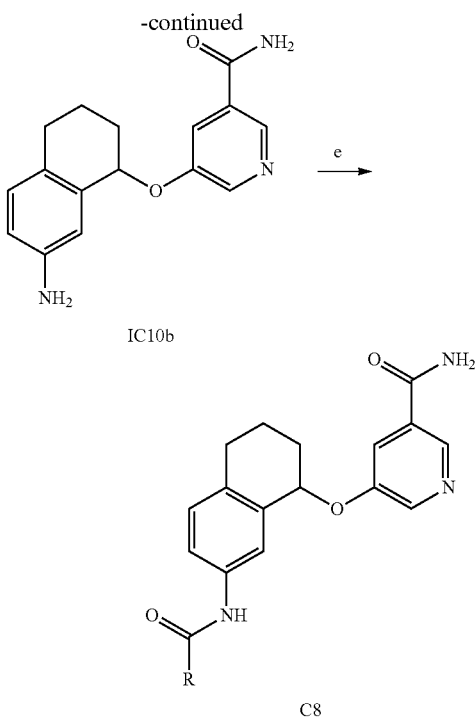

5-Nitro-3,4-dihydronaphthalen-1(2H)-one (IC6a) and 7-Nitro-3,4-dihydronaphthalen-1(2H)-one (IC6b)

In a manner similar to that described for the preparation of compounds IC1a and IC1b, tetralone (5.53 g, 37.8 mmol) was subjected to a nitration reaction to afford IC6a as a yellow solid (1.48 g, 20%) $^1$H NMR (DMSO-d$_6$, 600 MHz) δ 8.22 (d, J=7.8 Hz, 1H), 8.19 (d, J=8.4 Hz, 1H), 7.61 (dd, J=7.5, 7.5 Hz, 1H), 3.09 (t, J=6.3 Hz, 2H), 2.68 (t, J=6.9 Hz, 2H), 2.06 (p, J=6.3 Hz, 2H). HRMS (ESL) calcd for C$_{10}$H$_8$NO$_3$ (M–H)$^-$ 190.0510, found 190.0505; and IC6b as a yellow solid (4.00 g, 55%) $^1$H NMR (DMSO-d$_6$, 600 MHz) δ 8.54 (s, 1H), 8.36 (d, J=8.4 Hz, 1H), 7.67 (d, J=8.4 Hz, 1H), 3.08 (t, J=5.7 Hz, 2H), 2.70 (t, J=6.6 Hz, 2H), 2.09 (p, J=6.3 Hz, 2H). HRMS (ESL) calcd for C$_{10}$H$_8$NO$_3$ (M–H)$^-$ 190.0510, found 190.0511.

5-Nitro-1,2,3,4-tetrahydronaphthalen-1-ol (IC7a)

In a manner similar to that described for the preparation of compound IC2a, IC6a (1.35 g, 7.06 mmol) was reduced with NaBH$_4$ to afford IC7a as a light yellow solid (1.25 g, 92%). $^1$H NMR (DMSO-d$_6$, 600 MHz) δ 8.26 (s, 1H), 7.99 (d, J=8.4 Hz, 1H), 7.35 (d, J=8.4 Hz, 1H), 5.55 (d, J=6.0 Hz, 1H), 4.66-4.61 (m, 1H), 2.88-2.75 (m, 2H), 2.01-1.94 (m, 1H), 1.93-1.85 (m, 1H), 1.76-1.62 (m, 2H). HRMS (ESI") calcd for C$_{10}$H$_{10}$NO$_3$ (M–H)$^-$ 192.0666, found 192.0659.

7-Nitro-1,2,3,4-tetrahydronaphthalen-1-ol (IC7b)

In a manner similar to that described for the preparation of compound IC2a, IC6b (1.50 g, 7.85 mmol) was reduced with NaBH$_4$ to give IC7b as a white solid (1.40 g, 92%). $^1$H NMR (DMSO-d$_6$, 600 MHz) δ 7.76 (d, J=7.8 Hz, 2H), 7.42 (dd, J=7.8, 7.8 Hz, 1H), 5.43 (d, J=5.4 Hz, 1H), 4.65-4.60 (m, 1H), 2.89-2.82 (m, 1H), 2.80-2.73 (m, 1H), 1.96-1.84 (m, 2H), 1.74-1.64 (m, 2H). HRMS (ESL) calcd for C$_{10}$H$_{10}$NO$_3$ (M–H)$^-$ 192.0666, found 192.0669.

Methyl 5-((5-Nitro-1,2,3,4-tetrahydronaphthalen-1-yl)oxy)nicotinate (IC8a)

In a manner similar to that described for the preparation of compound IC3a, IC7a (468 mg, 2.42 mmol) and methyl 5-hydroxynicotinate (371 mg, 2.42 mmol) were treated with DIAD and Ph$_3$P to afford IC8a as a yellow solid (600 mg, 75%). $^1$H NMR (CDCl$_3$, 600 MHz) δ 8.88 (s, 1H), 8.53 (d, J=3.0 Hz, 1H), 7.91 (s, 1H), 7.88 (d, J=8.4 Hz, 1H), 7.61 (d, J=7.8 Hz, 1H), 7.38 (dd, J=8.1, 8.1 Hz, 1H), 5.50 (dd, J=4.8, 4.8 Hz, 1H), 3.98 (s, 3H), 3.17-3.11 (m, 1H), 3.04-2.96 (m, 1H), 2.22-2.15 (m, 1H), 2.12-1.98 (m, 2H), 1.93-1.86 (m, 1H). HRMS (ESI$^+$) calcd for C$_{17}$H$_{17}$N$_2$O$_5$ (M+H)$^+$ 329.1132, found 329.1139.

Methyl 5-((7-Nitro-1,2,3,4-tetrahydronaphthalen-1-yl)oxy)nicotinate (IC8b)

In a manner similar to that described for the preparation of compound IC3a, IC7b (505 mg, 3.30 mmol) and methyl 5-hydroxynicotinate (638 mg, 3.30 mmol) were treated with DIAD and Ph$_3$P to afford IC8b as a yellow solid (810 mg, 75%). $^1$H NMR (CDCl$_3$, 600 MHz) 8.89 (s, 1H), 8.55 (d, J=2.4 Hz, 1H), 8.24 (s, 1H), 8.12 (d, J=9.0 Hz, 1H), 7.92 (s, 1H), 7.35 (d, J=8.4 Hz, 1H), 5.51 (dd, J=4.8, 4.8 Hz, 1H), 3.98 (s, 3H), 3.05-2.99 (m, 1H), 2.91-2.85 (m, 1H), 2.17-2.10 (m, 2H), 2.08-2.02 (m, 1H), 1.93-1.87 (m, 1H). HRMS (ESI$^+$) calcd for C$_{17}$H$_{17}$N$_2$O$_5$ (M+H)$^+$ 329.1132, found 329.1134.

Methyl 5-((5-Amino-1,2,3,4-tetrahydronaphthalen-1-yl)oxy)nicotinate (IC9a)

In a manner similar to that described for the preparation of compound IC4a, IC8a (737 mg, 2.24 mmol) was reduced to afford IC9a as a light yellow solid (620 mg, 94%). $^1$H NMR (CDCl$_3$, 600 MHz) δ 8.84 (s, 1H), 8.53 (s, 1H), 7.91 (s, 1H), 7.06 (dd, J=7.8, 7.8 Hz, 1H), 6.78 (d, J=7.8 Hz, 1H), 6.68 (d, J=8.4 Hz, 1H), 5.45-5.40 (m, 1H), 3.96 (s, 3H), 3.68 (bs, 2H), 2.64-2.57 (m, 1H), 2.49-2.41 (m, 1H), 2.19-2.06 (m, 2H), 2.03-1.95 (m, 1H), 1.94-1.86 (m, 1H). HRMS (ESI$^+$) calcd for C$_{17}$H$_{19}$N$_2$O$_3$ (M+H)$^+$ 299.1390, found 299.1400.

Methyl 5-((7-Amino-1,2,3,4-tetrahydronaphthalen-1-yl)oxy)nicotinate (IC9b)

In a manner similar to that described for the preparation of compound IC4a, IC8b (682 mg, 2.08 mmol) was reduced to afford IC9b as a white solid (580 mg, 94%). $^1$H NMR (CDCl$_3$, 600 MHz) δ 8.83 (s, 1H), 8.53 (s, 1H), 7.90 (s, 1H), 6.96 (d, J=8.4 Hz, 1H), 6.66-6.61 (m, 2H), 5.38-5.34 (m, 1H), 3.96 (s, 3H), 3.60 (bs, 2H), 2.81-2.75 (m, 1H), 2.71-2.63 (m, 1H), 2.12-2.05 (m, 1H), 2.04-1.92 (m, 2H), 1.81-1.74 (m, 1H). HRMS (ESI$^+$) calcd for C$_{17}$H$_{19}$N$_2$O$_3$ (M+H)$^+$ 299.1390, found 299.1390.

5-((5-Amino-1,2,3,4-tetrahydronaphthalen-1-yl)oxy)nicotinamide (IC10a)

In a manner similar to that described for the preparation of compound IC5a, aminolysis of methyl ester IC9a (400 mg, 1.34 mmol) in the presence of CaCl$_2$ (149 mg, 1.34 mmol) afforded IC10a as a white solid (320 mg, 84%). $^1$H NMR (CD$_3$OD, 600 MHz) δ 8.62 (s, 1H), 8.40 (s, 1H), 7.95 (s, 1H), 6.95 (dd, J=7.5, 7.5 Hz, 1H), 6.71 (d, J=7.8 Hz, 1H), 6.68 (d, J=7.2 Hz, 1H), 5.54-5.48 (m, 1H), 2.67-2.60 (m, 1H), 2.50-2.42 (m, 1H), 2.16-2.01 (m, 2H), 2.00-1.95 (m, 1H), 1.92-1.80 (m, 1H). HRMS (ESI$^+$) calcd for C$_{16}$H$_{18}$N$_3$O$_2$ (M+H)$^+$ 284.1394, found 284.1397.

5-((7-Amino-1,2,3,4-tetrahydronaphthalen-1-yl)oxy)nicotinamide (IC10b)

In a manner similar to that described for the preparation of compound IC5a, aminolysis of methyl ester IC9b (500 mg, 1.73 mmol) in the presence of CaCl$_2$ (192 mg, 1.73 mmol) afforded IC10b as a white solid (410 mg, 85%). $^1$H NMR (DMSO-d$_6$, 600 MHz) δ 8.64 (d, J=1.8 Hz, 1H), 8.45 (d, J=3.0 Hz, 1H), 8.14 (s, 1H), 7.89 (dd, J=1.8, 1.8 Hz, 1H), 7.61 (s, 1H), 6.82 (d, J=8.4 Hz, 1H), 6.52-6.47 (m, 2H), 5.49 (t, J=4.8 Hz, 1H), 4.86 (s, 2H), 2.68-2.62 (m, 1H), 2.60-2.53 (m, 1H), 1.96-1.91 (m, 2H), 1.86-1.79 (m, 1H), 1.73-1.66 (m, 1H). HRMS (ESI$^+$) calcd for C$_{16}$H$_{18}$N$_3$O$_2$ (M+H)$^+$ 284.1394, found 284.1399.

The following compounds were prepared through an amide formation reaction in a manner similar to that described for the preparation of compound C1-1.

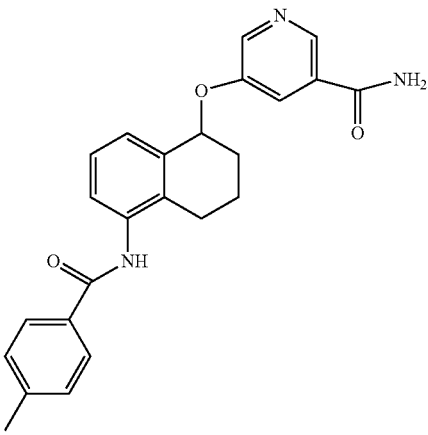 [SMILES: Cc1ccc(C(=O)Nc2cccc3c2CCCC3Oc2cncc(C(N)=O)c2)cc1]

5-((5-(4-Methylbenzamido)-1,2,3,4-tetrahydronaphthalen-1-yl)oxy)nicotinamide (C7-2)

$^1$H NMR (CD$_3$OD, 600 MHz) δ 8.65 (s, 1H), 8.44 (s, 1H), 7.99 (s, 1H), 7.87 (d, J=7.2 Hz, 2H), 7.36-7.30 (m, 4H), 7.27 (dd, J=7.8, 7.8 Hz, 1H), 5.66 (dd, J=4.2, 4.2 Hz, 1H), 2.92-2.86 (m, 1H), 2.75-2.68 (m, 1H), 2.43 (s, 3H), 2.19-2.13 (m, 1H), 2.10-1.97 (m, 2H), 1.89-1.83 (m, 1H). HRMS (ESI$^+$) calcd for C$_{24}$H$_{24}$N$_3$O$_3$ (M+H)$^+$ 402.1812, found 402.1817.

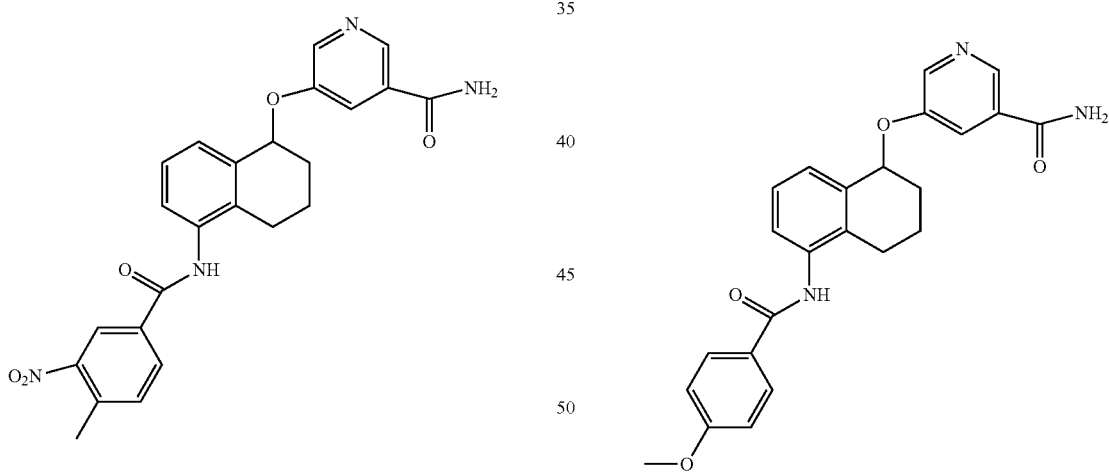

5-((5-(4-Methyl-3-nitrobenzamido)-1,2,3,4-tetrahydronaphthalen-1-yl)oxy)nicotinamide (C7-1)

$^1$H NMR (DMSO-d$_6$, 600 MHz) δ 10.14 (s, 1H), 8.66 (s, 1H), 8.58 (s, 1H), 8.50 (s, 1H), 8.22 (d, J=7.8 Hz, 1H), 8.16 (s, 1H), 7.95 (s, 1H), 7.69 (d, J=7.8 Hz, 1H), 7.63 (s, 1H), 7.36-7.30 (m, 2H), 7.29-7.25 (m, 1H), 5.73-5.69 (m, 1H), 2.84-2.76 (m, 1H), 2.67-2.59 (m, 4H), 2.06-1.93 (m, 2H), 1.90-1.81 (m, 1H), 1.80-1.73 (m, 1H). HRMS (ESI$^+$) calcd for C$_{24}$H$_{23}$N$_4$O$_5$ (M+H)$^+$ 447.1663, found 447.1667.

5-((5-(4-Methoxybenzamido)-1,2,3,4-tetrahydronaphthalen-1-yl)oxy)nicotinamide (C7-3)

$^1$H NMR (CD$_3$OD, 600 MHz) δ 8.65 (s, 1H), 8.44 (s, 1H), 7.99 (s, 1H), 7.96 (d, J=8.4 Hz, 2H), 7.34 (d, J=7.8 Hz, 1H), 7.31 (d, J=7.8 Hz, 1H), 7.27 (dd, J=7.5, 7.5 Hz, 1H), 7.05 (d, J=8.4 Hz, 2H), 5.67 (dd, J=4.2, 4.2 Hz, 1H), 3.88 (s, 3H), 2.94-2.85 (m, 1H), 2.75-2.68 (m, 1H), 2.20-2.14 (m, 1H), 2.11-1.97 (m, 2H), 1.90-1.83 (m, 1H). HRMS (ESI$^+$) calcd for C$_{24}$H$_{24}$N$_3$O$_4$ (M+H)$^+$ 418.1761, found 418.1773.

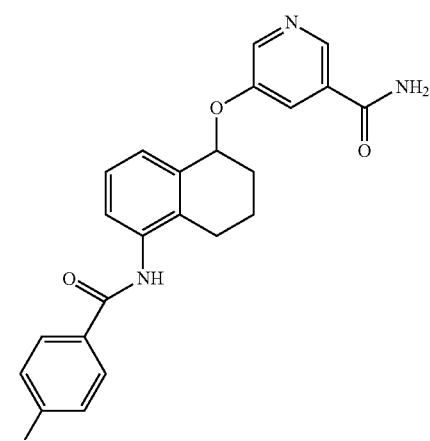

5-((5-(4-Chlorobenzamido)-1,2,3,4-tetrahydronaphthalen-1-yl)oxy)nicotinamide (C7-4)

¹H NMR (DMSO-d₆, 600 MHz) δ 9.95 (s, 1H), 8.66 (s, 1H), 8.49 (d, J=1.8 Hz, 1H), 8.16 (s, 1H), 8.01 (d, J=9.0 Hz, 2H), 7.95 (s, 1H), 7.65-7.59 (m, 3H), 7.34 (dd, J=6.0, 6.0 Hz, 1H), 7.30 (d, J=7.8 Hz, 1H), 7.26 (dd, J=7.8, 7.8 Hz, 1H), 5.72-5.69 (m, 1H), 2.85-2.77 (m, 1H), 2.67-2.59 (m, 1H), 2.06-1.93 (m, 2H), 1.91-1.82 (m, 1H), 1.81-1.74 (m, 1H). HRMS (ESI⁺) calcd for $C_{23}H_{21}ClN_3O_3$ (M+H)⁺ 422.1266, found 422.1275.

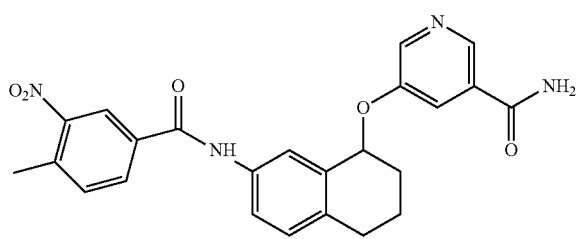 [SMILES: Cc1ccc(C(=O)Nc2ccc3c(c2)C(Oc2cncc(C(N)=O)c2)CCC3)cc1[N+](=O)[O-]]

5-((7-(4-Methyl-3-nitrobenzamido)-1,2,3,4-tetrahydronaphthalen-1-yl)oxy)nicotinamide (C8-1)

¹H NMR (DMSO-d₆, 600 MHz) δ 10.41 (s, 1H), 8.66 (s, 1H), 8.55 (s, 1H), 8.51 (s, 1H), 8.18 (d, J=8.4 Hz, 1H), 8.15 (s, 1H), 7.94 (s, 1H), 7.75-7.00 (m, 2H), 7.66 (d, J=7.2 Hz, 1H), 7.63 (s, 1H), 7.19 (d, J=8.4 Hz, 1H), 5.68-5.64 (m, 1H), 2.86-2.79 (m, 1H), 2.76-2.68 (m, 1H), 2.58 (s, 3H), 2.07-1.95 (m, 2H), 1.92-1.83 (m, 1H), 1.82-1.74 (m, 1H). HRMS (ESI⁺) calcd for $C_{23}H_{21}ClN_3O_3$ (M+H)⁺ 447.1663, found 447.1671.

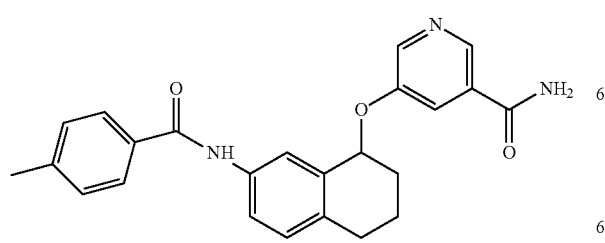

5-((7-(4-Methylbenzamido)-1,2,3,4-tetrahydronaphthalen-1-yl)oxy)nicotinamide (C8-2)

¹H NMR (DMSO-d₆, 600 MHz) δ 10.01 (s, 1H), 8.66 (s, 1H), 8.50 (s, 1H), 8.15 (s, 1H), 7.96-7.92 (m, 1H), 7.85 (d, J=7.2 Hz, 2H), 7.76 (s, 1H), 7.71 (d, J=7.2 Hz, 1H), 7.62 (s, 1H), 7.31 (d, J=6.6 Hz, 2H), 7.15 (d, J=7.8 Hz, 1H), 5.66-5.62 (m, 1H), 2.84-2.78 (m, 1H), 2.75-2.67 (m, 1H), 2.37 (s, 3H), 2.04-1.96 (m, 2H), 1.92-1.83 (m, 1H), 1.82-1.74 (m, 1H). HRMS (ESI⁺) calcd for $C_{24}H_{24}N_3O_3$ (M+H)⁺ 402.1812, found 402.1815.

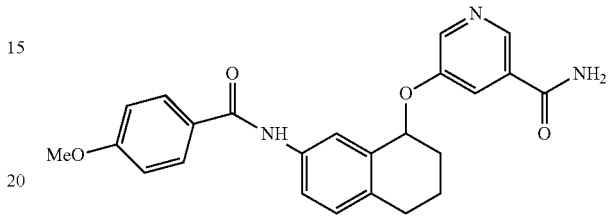

5-((7-(4-Methoxybenzamido)-1,2,3,4-tetrahydronaphthalen-1-yl)oxy)nicotinamide (C8-3)

¹H NMR (DMSO-d₆, 600 MHz) δ 10.03 (s, 1H), 8.66 (s, 1H), 8.50 (s, 1H), 8.15 (s, 1H), 7.96-7.90 (m, 3H), 7.75 (s, 1H), 7.70 (d, J=7.8 Hz, 1H), 7.62 (s, 1H), 7.15 (d, J=7.2 Hz, 1H), 7.03 (d, J=8.4 Hz, 2H), 5.66-5.62 (m, 1H), 3.82 (s, 3H), 2.84-2.78 (m, 1H), 2.75-2.67 (m, 1H), 2.04-1.96 (m, 2H), 1.92-1.83 (m, 1H), 1.82-1.74 (m, 1H). HRMS (ESI⁺) calcd for $C_{24}H_{24}N_3O_4$ (M+H)⁺ 418.1761, found 418.1759.

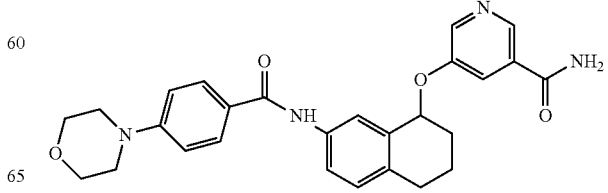

5-((7-(4-Chlorobenzamido)-1,2,3,4-tetrahydronaphthalen-1-yl)oxy)nicotinamide (C8-4)

¹H NMR (DMSO-d₆, 600 MHz) δ 10.26 (s, 1H), 8.66 (s, 1H), 8.50 (d, J=2.4 Hz, 1H), 8.16 (s, 1H), 7.98-7.91 (m, 3H), 7.74 (s, 1H), 7.70 (d, J=7.8 Hz, 1H), 7.63 (s, 1H), 7.58 (d, J=8.4 Hz, 2H), 7.17 (d, J=8.4 Hz, 1H), 5.67-5.63 (m, 1H), 2.85-2.78 (m, 1H), 2.76-2.68 (m, 1H), 2.06-1.95 (m, 2H), 1.92-1.83 (m, 1H), 1.82-1.74 (m, 1H). HRMS (ESI⁺) calcd for $C_{23}H_{21}ClN_3O_3$ (M+H)⁺ 422.1266, found 422.1268.

5-((7-(4-Morpholinobenzamido)-1,2,3,4-tetrahydronaphthalen-1-yl)oxy)nicotinamide (C8-5)

$^1$H NMR (CD$_3$OD, 600 MHz) δ 8.63 (s, 1H), 8.44 (d, J=2.4 Hz, 1H), 7.98 (s, 1H), 7.82 (d, J=9.0 Hz, 2H), 7.67 (s, 1H), 7.56 (d, J=7.8 Hz, 1H), 7.15 (d, J=9.0 Hz, 1H), 6.97 (d, J=9.0 Hz, 2H), 5.59-5.55 (m, 1H), 3.81 (t, J=4.8 Hz, 4H), 3.25 (t, J=4.8 Hz, 4H), 2.90-2.84 (m, 1H), 2.80-2.73 (m, 1H), 2.15-2.08 (m, 2H), 2.05-1.96 (m, 1H), 1.88-1.81 (m, 1H). HRMS (ESI$^+$) calcd for C$_{27}$H$_{29}$H$_4$O$_4$ (M+H)$^+$ 473.2183, found 473.2195.

Example 4

Representative compounds of formula (I) can be prepared as described below.

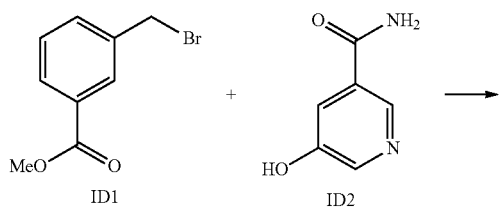

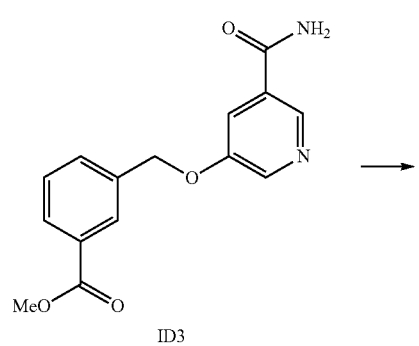

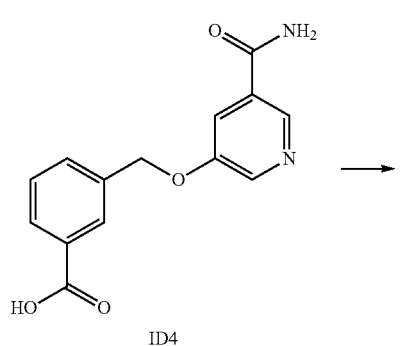

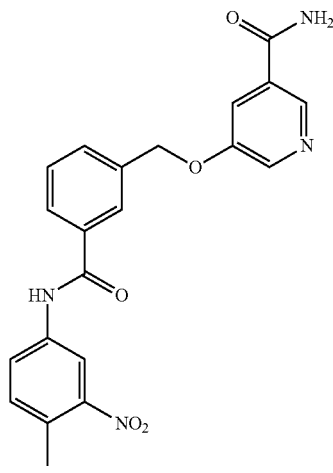 [SMILES: Cc1ccc(NC(=O)c2cccc(COc3cncc(C(N)=O)c3)c2)cc1[N+](=O)[O-]]

D1-1

Methyl 3-(((5-Carbamoylpyridin-3-yl)oxy)methyl)benzoate (ID3)

A mixture of methyl 3-(bromomethyl)benzoate (ID1, 1.14 g, 4.98 mmol), 5-hydroxynicotinamide (ID2, 760 mg, 5.50 mmol) and Cs$_2$CO$_3$ (3.27 g, 10.0 mmol) was allowed to stir at rt for 20 h and then poured into ice-water (300 mL). The resulting mixture was extracted with EtOAc (300 mL) and the organic layer was washed with brine (100 mL) and dried over anhydrous Na$_2$SO$_4$. After filtration, the filtrate was concentrated and the residue was purified by the flash column chromatography (0-10% MeOH/CH$_2$Cl$_2$) to give compound ID3 as a pale solid (335 mg, 23%). $^1$H NMR (DMSO-d$_6$, 600 MHz) δ 8.66 (d, J=1.8 Hz, 1H), 8.50 (d, J=2.4 Hz, 1H), 8.13 (brs, 1H), 8.08 (s, 1H), 7.76 (d, J=8.4 Hz, 1H), 7.87 (dd, J=2.1, 2.1 Hz, 1H), 7.76 (d, J=8.4 Hz, 1H), 7.61 (brs, 1H), 7.58 (dd, J=7.8, 7.8 Hz, 1H), 5.33 (s, 2H), 3.87 (s, 3H). HRMS (ESI$^+$) calcd for C$_{15}$H$_{15}$N$_2$O$_4$ (M+H)$^+$ 287.1026, found 287.1023.

3-(((5-Carbamoylpyridin-3-yl)oxy)methyl)benzoic acid (ID4)

A mixture of ID3 (300 mg, 1.05 mmol) in THF (6 mL), MeOH (3 mL) and 1 N NaOH (6 mL) was allowed to stir at rt for 16 h. After the organic solvents were removed in vacuo, the mixture was acidified with 1 N HCl to pH=5 and the precipitate was collected, washed with water and dried to give compound ID4 as a white solid (146 mg, 51%). $^1$H NMR (DMSO-d$_6$, 600 MHz) δ 8.66 (d, J=1.8 Hz, 1H), 8.50 (d, J=3.0 Hz, 1H), 8.14 (brs, 1H), 8.06 (s, 1H), 7.92 (d, J=7.8 Hz, 1H), 7.87 (dd, J=2.4, 2.4 Hz, 1H), 7.72 (d, J=7.8 Hz, 1H), 7.62 (brs, 1H), 7.54 (dd, J=7.8, 7.8 Hz, 1H), 5.32 (s, 2H). HRMS (ESI$^+$) calcd for C$_{14}$H$_{13}$N$_2$O$_4$ (M+H)$^+$ 273.0870, found 273.0871.

5-((3-((4-Methyl-3-nitrophenyl)carbamoyl)benzyl)oxy)nicotinamide (D1-1)

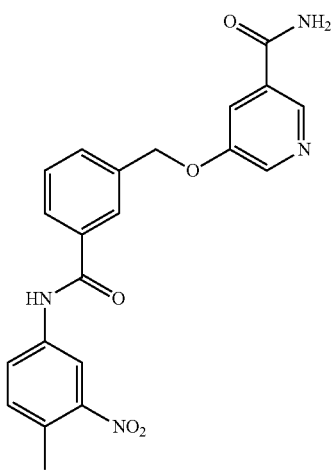

A mixture of ID4 (120 mg, 0.44 mmol), PyBOP (345 mg, 0.66 mmol), DIPEA (350 µL, 2.01 mmol) and 4-methyl-3-nitroaniline (101 mg, 0.66 mmol) in DMF (5 mL) was allowed to stir at rt for 20 h. After DMF was removed, the residue was dissolved in EtOAc (100 mL) and the solution was washed with water (40×2 mL) and brine (40 mL). The organic layer was dried over $Na_2SO_4$ and filtered and the filtrate was concentrated. The residue was purified by the flash column chromatography (0-10% $MeOH/CH_2Cl_2$) to give compound D1-1 as a pale solid (33 mg, 18%). $^1H$ NMR (DMSO-$d_6$, 600 MHz) δ 10.65 (s, 1H), 8.67 (d, J=1.2 Hz, 1H), 8.55 (d, J=2.4 Hz, 1H), 8.52 (d, J=3.0 Hz, 1H), 8.14 (brs, 1H), 8.09 (s, 1H), 8.00 (dd, J=8.7, 2.1 Hz, 1H), 7.97 (d, J=7.8 Hz, 1H), 7.89 (s, 1H), 7.72 (d, J=7.8 Hz, 1H), 7.64-7.58 (m, 2H), 7.50 (d, J=8.4 Hz, 1H), 5.34 (s, 2H), 2.50 (s, 3H). HRMS (ESI$^+$) calcd for $C_{21}H_{19}N_4O_5$ $(M+H)^+$ 407.1350, found 407.1343.

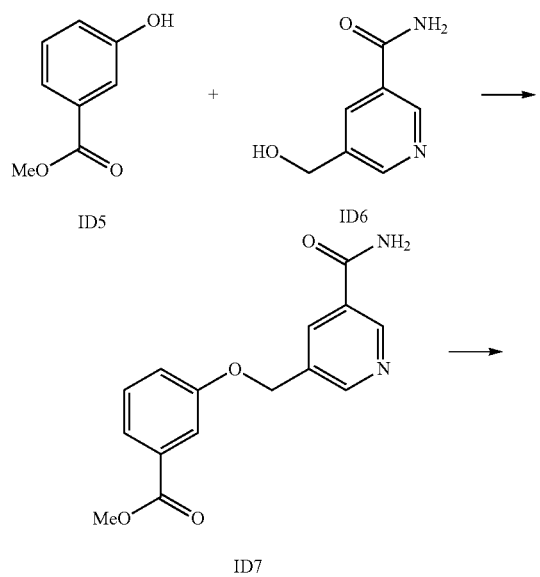

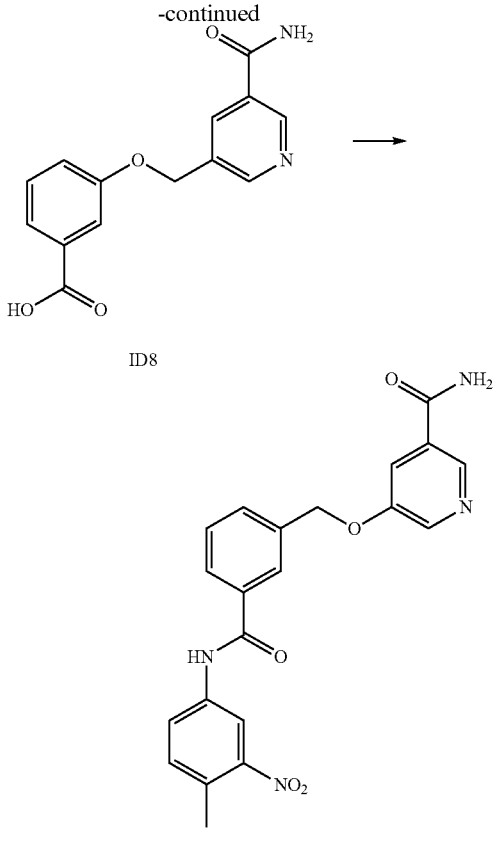

Methyl 3-((5-Carbamoylpyridin-3-yl)methoxy)benzoate (ID7)

A To a solution of methyl 3-hydroxybenzoate (ID5, 350 mg, 2.30 mmol), 5-(hydroxymethyl)nicotinamide (ID6, 290 mg, 1.91 mmol) and $PPh_3$ (758 mg, 2.89 mmol) in THF (10 mL) at rt was slowly added DIAD (0.56 mL, 2.89 mmol) and the resulting mixture was allowed to stir for 24 h. After the organic solvent was removed, the residue was purified by the flash column chromatography (0-5% $MeOH/CH_2Cl_2$) to give compound ID7 as a white solid (193 mg, 35%). $^1H$ NMR (DMSO-$d_6$, 600 MHz) δ 9.01 (d, J=1.8 Hz, 1H), 8.81 (d, J=1.8 Hz, 1H), 8.31 (s, 1H), 8.21 (brs, 1H), 7.64 (brs, 1H), 7.60-7.55 (m, 2H), 7.48 (dd, J=7.8, 7.8 Hz, 1H), 7.37-7.33 (m, 1H), 5.29 (s, 2H), 3.85 (s, 3H). HRMS (ESI$^+$) calcd for $C_{15}H_{15}N_2O_4$ $(M+H)^+$ 287.1026, found 287.1031.

3-((5-Carbamoylpyridin-3-yl)methoxy)benzoic acid (ID8)

Compound ID8 was prepared in a manner similar to that described for compound ID4. White solid (145 mg, 89%). $^1H$ NMR (DMSO-$d_6$, 600 MHz) δ 13.13 (brs, 1H), 9.04 (s, 0.3H), 9.00 (d, J=1.8 Hz, 0.7H), 8.89 (d, J=1.8 Hz, 0.3H), 8.81 (d, J=1.2 Hz, 0.7 Hz), 8.35 (s, 0.3H), 8.31 (s, 0.7H), 8.21 (brs, 1H), 7.63 (brs, 1H), 7.59-7.54 (m, 2H), 7.44 (dd, J=8.4, 8.4 Hz, 1H), 7.31, (dd, J=8.4, 1.8 Hz, 1H), 5.31 (s, 0.6H), 5.28 (s, 1.4H). HRMS (ESI$^+$) calcd for $C_{14}H_{13}N_2O_4$ $(M+H)^+$ 273.0870, found 273.0871.

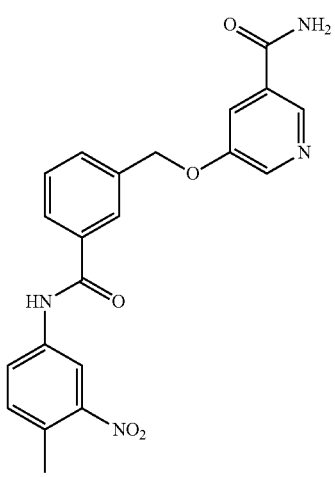 [SMILES: Cc1ccc(NC(=O)c2cccc(COc3cncc(C(N)=O)c3)c2)cc1[N+](=O)[O-]]

5-((3-((4-Methyl-3-nitrophenyl)carbamoyl)phenoxy)methyl)nicotinamide (D2-1)

Compound D2-1 was prepared in a manner similar to that described for compound D1-1. Yellow solid (35 mg, 20%). $^1$H NMR (DMSO-d$_6$, 600 MHz) δ 10.56 (s, 1H), 9.02 (d, J=1.8 Hz, 1H), 8.83 (d, J=1.8 Hz, 1H), 8.55 (d, J=1.8 Hz, 1H), 8.34 (s, 1H), 8.22 (brs, 1H), 8.00 (dd, J=8.4, 2.4 Hz, 1H), 7.67-7.63 (m, 2H), 7.61 (d, J=7.2 Hz, 1H), 7.53-7.47 (m, 2H), 7.32 (dd, J=8.4, 2.4 Hz, 1H), 5.31 (s, 2H), 2.50 (s, 3H). HRMS (ESI$^+$) calcd for C$_{21}$H$_{19}$N$_4$O$_5$ (M+H)$^+$ 407.1350, found 407.1348.

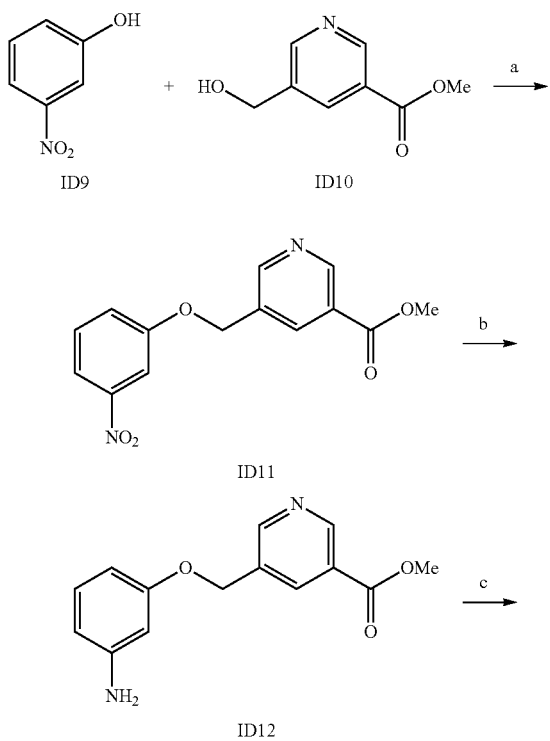

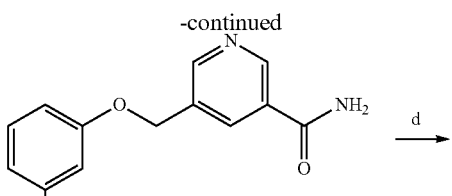

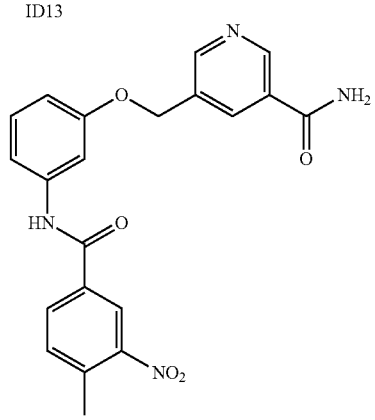

Methyl 5-((3-Nitrophenoxy)methyl)nicotinate (ID11)

To a solution of 3-nitrophenol (ID9, 900 mg, 6.46 mmol), methyl 5-(hydroxymethyl) nicotinate (ID10, 900 mg, 5.38 mmol), and Ph$_3$P (2.12 g, 8.07 mmol) in anhydrous CH$_2$Cl$_2$ (40 mL) at rt was added DIAD (1.63 g, 8.07 mmol) dropwise. The mixture was allowed to stir at rt for 12 h and concentrated. The residue was purified by flash column chromatography to afford ID11 as a light yellow solid (340 mg, 22%). $^1$H NMR (CDCl$_3$, 600 MHz) δ 9.23 (d, J=2.4 Hz, 1H), 8.88 (d, J=2.4 Hz, 1H), 8.41 (dd, J=1.8, 1.8 Hz, 1H), 7.90 (dd, J=8.4, 1.2 Hz, 1H), 7.85 (dd, J=2.4, 2.4 Hz, 1H), 7.50 (dd, J=8.4, 8.4 Hz, 1H), 7.32 (dd, J=7.8, 1.8 Hz, 1H), 5.22 (s, 2H), 3.99 (s, 3H). HRMS (ESI$^+$) calcd for C$_{14}$H$_{13}$N$_2$O$_5$ (M+H)$^+$ 289.0819, found 289.0820.

Methyl 5-((3-Aminophenoxy)methyl)nicotinate (ID12)

To a solution of ID11 (312 mg, 1.09 mmol) in anhydrous EtOH (40 mL) at rt was added tin (II) chloride (1.50 g, 7.92 mmol) and the mixture was heated at 70° C. for 12 h. The reaction was quenched with saturated NaHCO$_3$ (150 mL) and the mixture was extracted with EtOAc. The organic phase was washed with water and brine, dried over anhydrous Na$_2$SO$_4$, and concentrated in vacuo. The residue was purified by flash column chromatography (MeOH/CH$_2$Cl$_2$) to afford compound ID12 as a light yellow oil (200 mg, 71%). $^1$H NMR (CDCl$_3$, 600 MHz) δ 9.17 (d, J=1.8 Hz, 1H), 8.82 (d, J=1.8 Hz, 1H), 8.37-8.35 (m, 1H), 7.06 (t, J=8.1 Hz, 1H), 6.37 (dd, J$_1$=8.1 Hz, J$_2$=2.2 Hz, 1H), 6.34-6.30 (m, 2H), 5.06 (s, 2H), 3.96 (s, 3H), 3.73 (br s, 2H). HRMS (ESI$^+$) calcd for C$_{14}$H$_{15}$N$_2$O$_3$ (M+H)$^+$ 259.1077, found 259.1082.

5-((3-Aminophenoxy)methyl)nicotinamide (ID13)

A solution of ID12 (200 mg, 0.77 mmol) in NH$_3$/MeOH (ca. 7 N, 5 mL) in a seal tube was heated at 70° C. for 24 h. After the solvent was evaporated in vacuo, the residue was dissolved in EtOAc (100 mL) and the solution was washed with H₂O (150 mL) and brine (100 mL). The organic layer was dried over Na₂SO₄, concentrated, and the residue was purified by flash column chromatography (5% MeOH/ CH₂Cl₂) to afford ID13 as a light brownish solid (56 mg, 30%). ¹H NMR (CD₃OD, 600 MHz) δ 8.96 (d, J=1.8 Hz, 1H), 8.75 (d, J=1.8 Hz, 1H), 8.35 (t, J=1.8 Hz, 1H), 7.00 (t, J=8.1 Hz, 1H), 6.41-6.40 (m, 1H), 6.38-6.34 (m, 2H), 5.14 (s, 2H). HRMS (ESI⁺) calcd for $C_{13}H_{14}H_{3}O_{2}$ (M+H)⁺ 244.1081, found 244.1077.

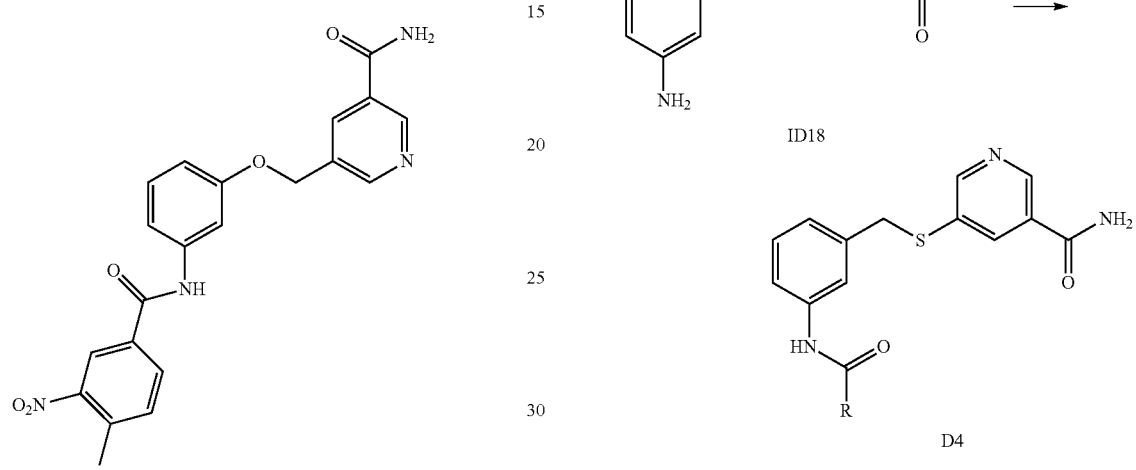

5-((3-(4-Methyl-3-nitrobenzamido)phenoxy)methyl) nicotinamide (D3-1)

Compound D3-1 was prepared from ID13 in a manner similar to that described for compound A-1. ¹H NMR (DMSO-d₆, 600 MHz) δ 10.46 (s, 1H), 9.01 (s, 1H), 8.81 (s, 1H), 8.56 (s, 1H), 8.31 (s, 1H), 8.24-8.18 (m, 2H), 7.68 (d, J=8.4 Hz, 1H), 7.64 (s, 1H), 7.59 (s, 1H), 7.38 (d, J=7.8 Hz, 1H), 7.30 (dd, J=7.8, 7.8 Hz, 1H), 6.84 (d, J=8.4 Hz, 1H), 5.23 (s, 2H), 2.60 (s, 3H). HRMS (ESI⁺) calcd for $C_{21}H_{19}N_{4}O_{5}$ (M+H)⁺ 407.1350, found 407.1358.

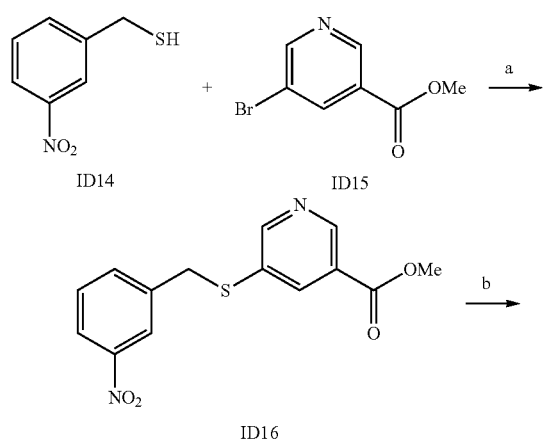

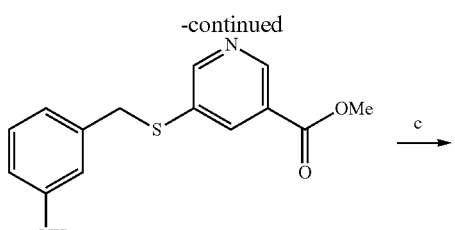

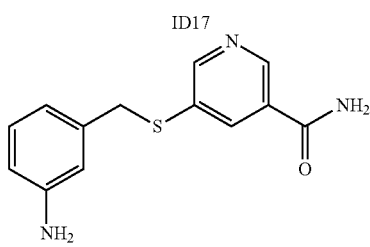

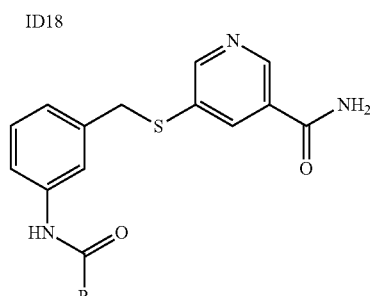

Methyl 5-((3-Nitrobenzyl)thio)nicotinate (ID16)

To a mixture of (3-nitrobenzyl) mercaptan (ID14, 350 mg, 2.00 mmol), methyl 5-bromonicotinate (ID15, 432 mg, 2.00 mmol), Pd₂(dba)₃ (46 mg, 0.05 mmol), and Xantphos (58 mg, 0.10 mmol) in 1,4-dioxane (10 mL) was added DIPEA (517 mg, 4.0 mmol) dropwise under Ar protection. The reaction mixture was allowed to stir at 110° C. for 16 h and concentrated in vacuo. The residue was purified by flash column chromatography (EtOAc/hexanes) to afford ID16 as a light yellow solid (490 mg, 81%). ¹H NMR (CDCl₃, 600 MHz) δ 8.09 (d, J=1.8 Hz, 1H), 8.63 (d, J=2.4 Hz, 1H), 8.18 (dd, J=2.4, 2.4 Hz, 1H), 8.15 (s, 1H), 8.13 (d, J=7.8 Hz, 1H), 7.60 (d, J=7.2 Hz, 1H), 7.48 (dd, J=7.8, 7.8 Hz, 1H), 4.22 (s, 2H), 3.95 (s, 3H). HRMS (ESI⁺) calcd for $C_{14}H_{13}N_{2}O_{5}S$ (M+H)⁺ 305.0591, found 305.0595.

Methyl 5-((3-Aminobenzyl)thio)nicotinate (ID17)

To a solution of ID16 (490 mg, 1.60 mmol) and NiCl₂.6H2O (761 mg, 3.20 mmol) in MeOH (100 mL) was slowly added NaBH₄ (242 mg, 6.40 mmol) and the mixture was allowed to stir at rt for 3 h. The reaction was quenched with saturated NH₄Cl (50 mL) and the mixture was extracted with EtOAc. The organic phase washed with water and brine, dried over anhydrous K₂CO₃, and concentrated in vacuo. The residue was purified by flash column chromatography (EtOAc/hexanes) to afford ID17 as a white solid (120 mg, 27%). ¹H NMR (CDCl₃, 600 MHz) δ 8.98 (d, J=1.8 Hz, 1H), 8.62 (d, J=2.3 Hz, 1H), 8.19-8.18 (m, 1H), 7.07 (t, J=7.6 Hz, 1H), 6.66 (d, J=7.6 Hz, 1H), 6.63-6.62 (m, 1H), 6.58-6.55 (m, 1H), 4.06 (s, 2H), 3.94 (s, 3H), 3.67 (br s, 2H). HRMS (ESI⁺) calcd for $C_{14}H_{15}N_{2}O_{2}S$ (M+H)⁺ 275.0849, found 275.0848.

5-((3-Aminobenzyl)thio)nicotinamide (ID18)

In a manner similar to that described for the preparation of compound ID13, aminolysis of ID17 afforded compound ID18 as a light brownish solid (80 mg, 70%). $^1$H NMR (CD$_3$OD, 600 MHz) δ 8.77 (s, 1H), 8.51 (s, 1H), 8.19 (s, 1H), 6.99 (m, 1H), 6.70 (s, 1H), 6.61 (d, J=7.2 Hz, 1H), 6.59 (d, J=7.7 Hz, 1H), 4.13 (s, 2H). HRMS (ESI$^+$) calcd for C$_{13}$H$_{14}$H$_3$OS (M+H)$^+$ 260.0852, found 260.0849.

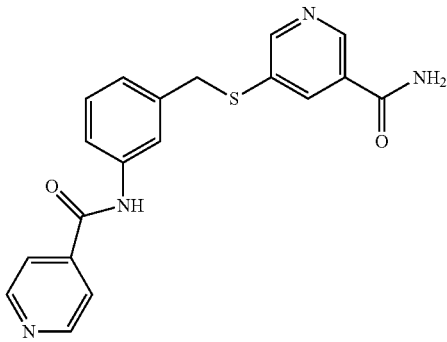 [SMILES: NC(=O)c1cncc(SCc2cccc(NC(=O)c3ccncc3)c2)c1]

5-((3-(Isonicotinamido)benzyl)thio)nicotinamide (D4-1)

Compound D4-1 was prepared from ID18 through an amide formation reaction in a manner similar to that described for compound A-1. $^1$H NMR (DMSO-d$_6$, 600 MHz) δ 10.51 (s, 1H), 8.82-8.75 (m, 2H), 8.62 (s, 1H), 8.17 (d, J=15.6 Hz, 2H), 7.89-7.82 (m, 3H), 7.64 (s, 2H), 7.30 (dd, J=7.5, 7.5 Hz, 1H), 7.12 (d, J=7.2 Hz, 1H), 4.38 (s, 2H). HRMS (ESI$^+$) calcd for C$_{19}$H$_{17}$N$_4$O$_2$S (M+H)$^+$ 365.1067, found 365.1074.

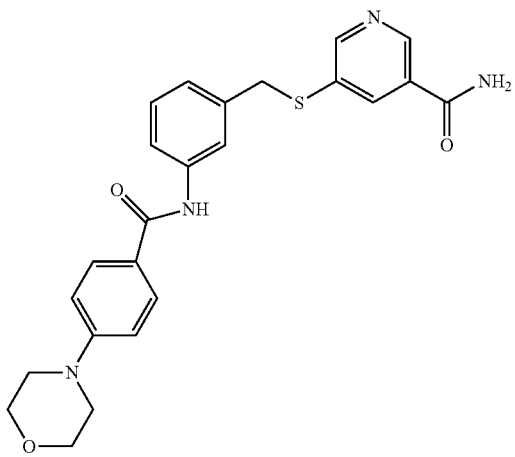 [SMILES: NC(=O)c1cncc(SCc2cccc(NC(=O)c3ccc(N4CCOCC4)cc3)c2)c1]

5-((3-(4-Morpholinobenzamido)benzyl)thio)nicotinamide (D4-2)

Compound D4-2 was prepared from ID18 through an amide formation reaction in a manner similar to that described for compound A-1. $^1$H NMR (DMSO-d$_6$, 600 MHz) δ 9.97 (s, 1H), 8.80 (s, 1H), 8.62 (s, 1H), 8.20-8.12 (m, 2H), 7.90-7.84 (m, 3H), 7.67-7.60 (m, 2H), 7.25 (dd, J=7.8, 7.8 Hz, 1H), 7.07-6.99 (m, 3H), 4.35 (s, 2H), 3.75 (t, J=4.5 Hz, 4H), 3.25 (t, J=4.5 Hz, 4H). HRMS (ESI$^+$) calcd for C$_{24}$H$_{25}$N$_4$O$_3$S (M+H)$^+$ 449.1642, found 449.1646.

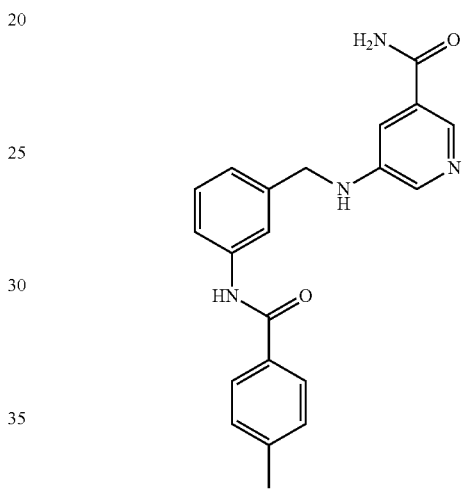

5-((3-(4-Methylbenzamido)benzyl)amino)nicotinamide (D5-1)

$^1$H NMR (DMSO-d$_6$, 600 MHz) δ 10.16 (s, 1H), 8.22 (s, 1H), 8.09 (s, 1H), 7.94 (br s, 1H), 7.86 (d, J=7.8 Hz, 2H), 7.81 (s, 1H), 7.66 (d, J=8.1 Hz, 1H), 7.39 (s, 1H), 7.34-7.28 (m, 4H), 7.10 (d, J=7.5 Hz, 1H), 6.73 (t, J=5.8 Hz, 1H), 4.34 (d, J=5.8 Hz, 2H), 2.38 (s, 3H). HRMS (ESI$^+$) calcd for C$_{21}$H$_{21}$N$_4$O$_2$ (M+H)$^+$ 361.1659, found 361.1660.

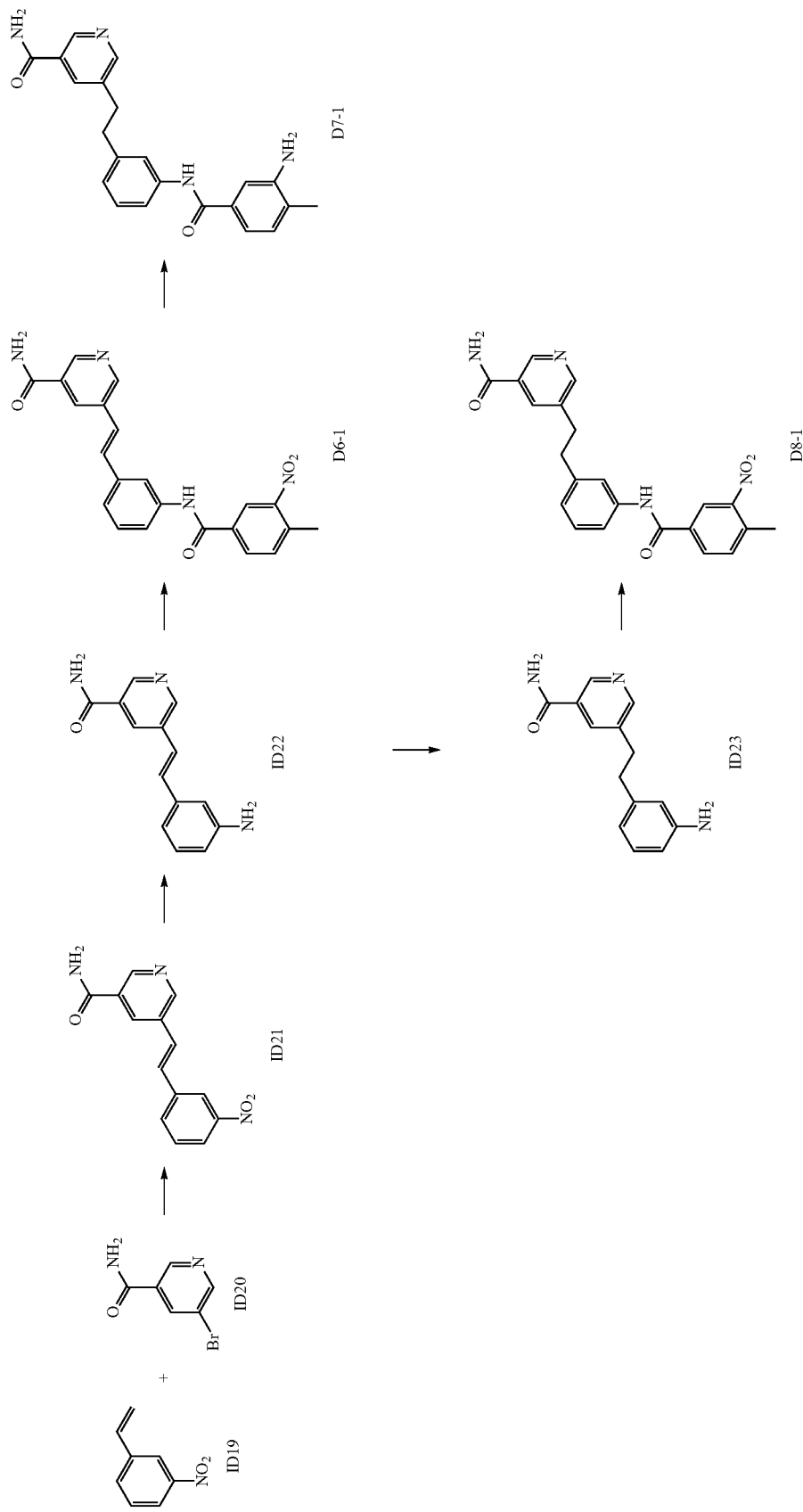

(E)-5-(3-Nitrostyryl)nicotinamide (ID21)

A mixture of 5-bromonicotinamide (ID20, 1.61 g, 8.01 mmol), Pd(OAc)$_2$ (36 mg, 0.16 mmol), P(O-tolyl)$_3$ (146 mg, 0.48 mmol) and NaOAc (1.32 g, 16.1 mmol) in anhydrous DMF (16 mL) was evacuated and back-filled with argon and 1-nitro-3-vinylbenzene (ID19, 1.35 mL, 9.68 mmol) was added. The resulting mixture was heated at 130° C. for 25 h, cooled to rt, and then poured to ice-water (250 mL). The solid formed was filtered, washed with water, and dried to give compound ID21 as a pale solid (1.71 g, 79%). $^1$H NMR (DMSO-d$_6$, 600 MHz) δ 8.93 (s, 1H), 8.92 (s, 1H), 8.52 (s, 1H), 8.48 (s, 1H), 8.20 (s, 1H), 8.15 (d, J=7.2 Hz, 1H), 8.10 (d, J=7.2 Hz, 1H), 7.76-7.55 (m, 4H). HRMS (ESI$^+$) calcd for C$_{14}$H$_{12}$N$_3$O$_3$ (M+H)$^+$ 270.0873, found 270.0876.

(E)-5-(3-Aminostyryl)nicotinamide (ID22)

To a suspension of compound ID21 (1.56 g, 5.79 mmol) in EtOH (200 mL) was added SnCl$_2$ (7.71 g, 40.7 mmol) and the resulting mixture was heated at 70° C. for 22 h and cooled to rt. After addition of water (150 mL), sat. NaHCO$_3$ (150 mL) and subsequently EtOAc (100 mL), the solid formed was collected and washed with EtOAc. Another portion of compound ID22 was also obtained from the filtrate in a similar manner to give compound ID22 in total as a yellow solid (1.19 g, 86%). $^1$H NMR (DMSO-d$_6$, 600 MHz) δ 8.87 (d, J=2.4 Hz, 1H), 8.85 (d, J=1.8 Hz, 1H), 8.44 (dd, J=1.8, 1.8 Hz, 1H), 8.18 (brs, 1H), 7.63 (brs, 1H), 7.31 (d, J=16.8 Hz, 1H), 7.14 (d, J=16.2 Hz, 1H), 7.05 (dd, J=7.5, 7.5 Hz, 1H), 6.82-6.78 (m, 2H), 6.54 (dd, J=9.0, 1.8 Hz, 1H), 5.12 (s, 2H). HRMS (ESI$^+$) calcd for C$_{14}$H$_{14}$N$_3$O (M+H)$^+$ 240.1131, found 240.1128.

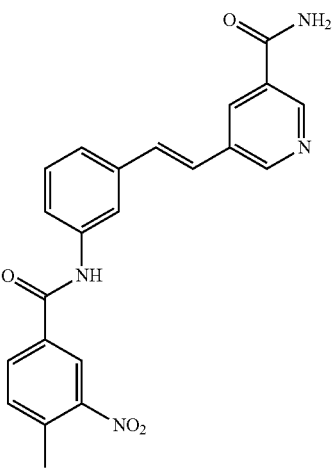 [SMILES: Cc1ccc(C(=O)Nc2cccc(/C=C/c3cncc(C(N)=O)c3)c2)cc1[N+](=O)[O-]]

(E)-5-(3-(4-Methyl-3-nitrobenzamido)styryl)nicotinamide (D6-1)

A solution of compound ID22 (600 mg, 2.51 mmol), 4-methyl-3-nitrobenzoyl chloride (0.55 mL, 3.78 mmol) and DIPEA (0.87 mL, 4.99 mmol) in CH$_2$Cl$_2$ (25 mL) and DMF (5 mL) was allowed to stir at rt for 16 h. After the organic solvents were removed, the residue was diluted with water (50 mL) and EtOAc (50 mL) and the resulting mixture was allowed to stir vigorously for 30 min. The solid formed was collected, washed with water, and triturated with hot MeOH (100 mL) to give compound D6-1 as a yellow solid (744 mg, 74%). $^1$H NMR (DMSO-d$_6$, 600 MHz) δ 10.54 (s, 1H), 8.90 (s, 2H), 8.61 (s, 1H), 8.50 (d, J=1.2 Hz, 1H), 8.23 (s, 1H), 8.20 (s, 1H), 8.09 (s, 1H), 7.74-7.60 (m, 3H), 7.52-7.38 (m, 3H), 7.30 (d, J=16.2 Hz, 1H), 2.61 (s, 3H). HRMS (ESI$^+$) calcd for C$_{22}$H$_{19}$N$_4$O$_4$ (M+H)$^+$ 403.1401, found 403.1396.

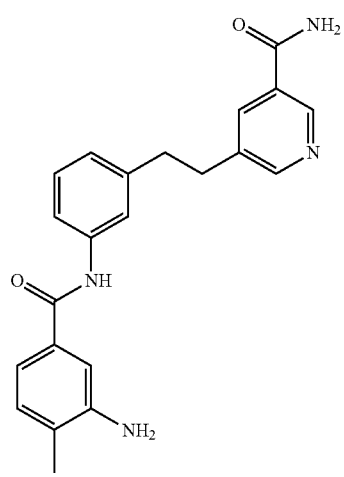 [SMILES: Cc1ccc(C(=O)Nc2cccc(CCc3cncc(C(N)=O)c3)c2)cc1[N+](=O)[O-]]

5-(3-(3-Amino-4-methylbenzamido)phenethyl)nicotinamide (D7-1)

A mixture of compound D6-1 (205 mg, 0.51 mmol) and 10% Pd/C (33 mg) in anhydrous DMF (10 mL) was hydrogenated (balloon) at rt for 6 h and filtered. The filtrate was concentrated and the residue was purified by the flash column chromatography (0-10% MeOH/CH$_2$Cl$_2$) to give compound D7-1 as a pale solid (85 mg, 44%). $^1$H NMR (DMSO-d$_6$, 600 MHz) δ 9.94 (s, 1H), 8.85 (d, J=1.2 Hz, 1H), 8.55 (d, J=1.2 Hz, 1H), 8.12 (s, 2H), 7.69 (s, 1H), 7.60-7.54 (m, 2H), 7.22 (dd, J=7.8, 7.8 Hz, 1H), 7.16 (s, 1H), 7.07 (d, J=7.8 Hz, 1H), 7.04 (d, J=7.8 Hz, 1H), 6.93 (d, J=7.8 Hz, 1H), 5.06 (brs, 2H), 3.00-2.94 (m, 2H), 2.94-2.88 (m, 2H), 2.11 (s, 3H). HRMS (ESI$^+$) calcd for C$_{22}$H$_{23}$N$_4$O$_2$ (M+H)$^+$ 375.1816, found 375.1816.

5-(3-Aminophenethyl)nicotinamide (ID23)

A mixture of compound ID22 (303 mg, 1.27 mmol) in MeOH (20 mL) was hydrogenated (balloon) in the presence of 10% Pd/C (35 mg) to give compound ID23 as a white solid (293 mg, 96%). $^1$H NMR (DMSO-d$_6$, 600 MHz) δ 8.84 (d, J=2.4 Hz, 1H), 8.51 (d, J=1.8 Hz, 1H), 8.11 (brs, 1H), 8.08 (dd, J=2.1, 2.1 Hz, 1H), 7.55 (brs, 1H), 6.90 (dd, J=7.8, 7.8 Hz, 1H), 6.24 (s, 1H), 6.40-6.34 (m, 2H), 4.93 (s, 2H), 2.90 (dd, J=7.8, 7.8 Hz, 2H), 2.75 (dd, J=8.1, 8.1 Hz, 2H). HRMS (ESI$^+$) calcd for C$_{14}$H$_{16}$N$_3$O (M+H)$^+$ 242.1288, found 242.1286.

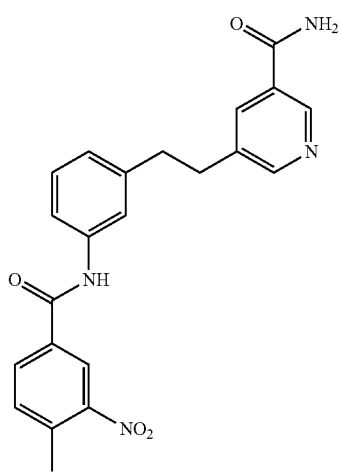

5-(3-(4-Methyl-3-nitrobenzamido)phenethyl)nicotinamide (D8-1)

Compound D8-1 was prepared from compound ID23 in a manner similar to that described for compound D6-1. Pale solid (127 mg, 76%). $^1$H NMR (DMSO-$d_6$, 600 MHz) δ 10.41 (s, 1H), 8.85 (d, J=1.8 Hz, 1H), 8.58 (d, J=1.2 Hz, 1H), 8.55 (d, J=1.8 Hz, 1H), 8.21 (dd, J=7.5, 1.5 Hz, 1H), 8.14-8.08 (m, 2H), 7.72-7.66 (m, 2H), 7.60 (d, J=7.8 Hz, 1H), 7.56 (brs, 1H), 7.28 (dd, J=7.8, 7.8 Hz, 1H), 7.00 (d, J=7.8 Hz, 1H), 3.01-2.96 (m, 2H), 2.96-2.91 (m, 2H), 2.60 (s, 3H). HRMS (ESI$^+$) calcd for $C_{22}H_{21}N_4O_4$ (M+H)$^+$ 405.1557, found 405.1563.

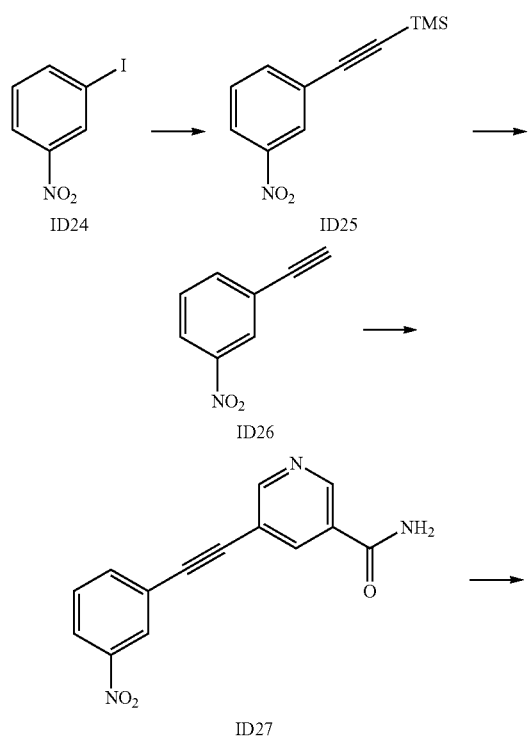

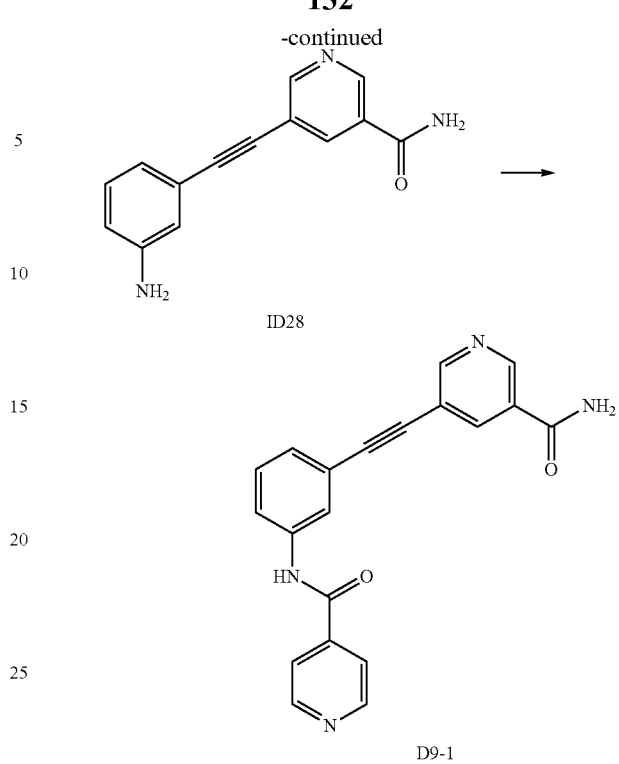

Trimethyl((3-nitrophenyl)ethynyl)silane (ID25)

To a mixture of 1-iodo-3-nitrobenzene (ID24, 1.5 g, 6.00 mmol), ethynyltrimethylsilane (706 mg, 7.20 mmol), Pd(PPh$_3$)$_2$Cl$_2$ (84 mg, 0.12 mmol), CuI (23 mg, 0.12 mmol), and PPh$_3$ (63 mg, 0.24 mmol) in toluene (15 mL) was added DIPEA (2 mL) under Ar protection. The reaction mixture was allowed to stir at 80° C. for 16 h and concentrated in vacuo. The residue was purified by flash column chromatography (EtOAc/hexanes) to afford ID25 as a light yellow oil (1.28 g, 93%). $^1$H NMR (CDCl$_3$, 600 MHz) δ 8.31 (s, 1H), 8.17 (d, J=7.8 Hz, 1H), 7.76 (d, J=7.2 Hz, 1H), 7.49 (dd, J=8.1, 8.1 Hz, 1H), 0.28 (s, 9H).

1-Ethynyl-3-nitrobenzene (ID26)

A mixture of ID25 (1.20 g, 5.47 mmol) and K$_2$CO$_3$ (1.50 g, 10.9 mmol) in MeOH (30 mL) and THF (30 mL) was allowed to stir at rt for 3 h. After the solvent was evaporated in vacuo, the residue was dissolved in EtOAc (100 mL) and the solution was washed with H$_2$O (150 mL) and brine (100 mL) The organic layer was dried over Na$_2$SO$_4$, filtered, and concentrated to afford ID26 as a light yellow oil (790 mg, 98%). $^1$H NMR (CDCl$_3$, 600 MHz) δ 8.32 (s, 1H), 8.21 (d, J=8.4 Hz, 1H), 7.80 (d, J=8.4 Hz, 1H), 7.54 (dd, J=8.1, 8.1 Hz, 1H), 3.26 (s, 1H); $^{13}$C NMR (CDCl$_3$, 150 MHz) δ 148.17, 137.93, 129.56, 127.06, 124.03, 123.70, 81.22, 80.113.

5-((3-Nitrophenyl)ethynyl)nicotinamide (ID27)

A Sonogashira coupling reaction of ID26 (518 mg, 3.52 mmol) and methyl 5-bromonicotinate (653 mg, 2.93 mmol) followed by aminolysis afforded ID27 as a light yellow solid (500 mg, 64% over two steps). $^1$H NMR (DMSO-$d_6$, 600 MHz) δ 9.04 (s, 1H), 8.94 (s, 1H), 8.45 (s, 1H), 8.42 (s, 1H), 8.30 (d, J=7.2 Hz, 1H), 8.25 (s, 1H), 8.05 (d, J=7.8 Hz, 1H), 7.79-7.71 (m, 2H). HRMS (ESI$^+$) calcd for C$_{14}$H$_{10}$N$_3$O$_3$ (M+H)$^+$ 268.0717, found 268.0725.

5-((3-Aminophenyl)ethynyl)nicotinamide (ID28)

In a manner similar to that described for the preparation of compound ID17, reduction of ID27 afforded compound ID28 as a white solid (150 mg, 33%). $^1$H NMR (CD$_3$OD, 600 MHz) δ 8.95 (d, J=1.8 Hz, 1H), 8.79 (d, J=1.8 Hz, 1H), 8.35 (dd, J=1.8, 1.8 Hz, 1H), 7.12 (dd, J=7.8, 7.8 Hz, 1H), 6.90 (s, 1H), 6.87 (d, J=7.2 Hz, 1H), 6.76 (dd, J=7.8, 1.8 Hz, 1H). HRMS (ESI$^+$) calcd for C$_{14}$H$_{12}$N$_3$O (M+H)$^+$ 238.0975, found 238.0982.

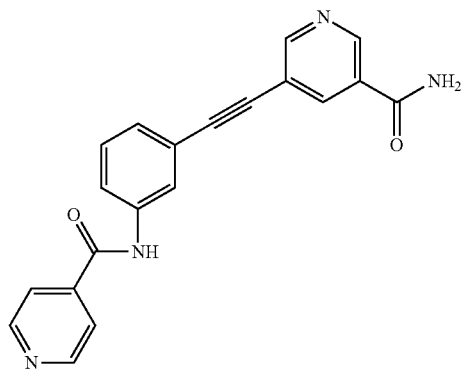 [SMILES: NC(=O)c1cncc(C#Cc2cccc(NC(=O)c3ccncc3)c2)c1]

5-((3-(Isonicotinamido)phenyl)ethynyl)nicotinamide (D9-1)

Compound D9-1 was prepared from ID28 through an amide formation reaction in a manner similar to that described for compound A-1. Light yellow solid (10 mg, 12%). $^1$H NMR (DMSO-d$_6$, 600 MHz) δ 10.69 (s, 1H), 9.01 (s, 1H), 8.90 (s, 1H), 8.80 (d, J=3.6 Hz, 2H), 8.41 (s, 1H), 8.25 (s, 1H), 8.13 (s, 1H), 7.89 (d, J=4.2 Hz, 2H), 7.82 (d, J=8.4 Hz, 1H), 7.71 (s, 1H), 7.48 (dd, J=8.1, 8.1 Hz, 1H), 7.39 (d, J=7.2 Hz, 1H). HRMS (ESI$^+$) calcd for C$_{20}$H$_{15}$N$_4$O$_2$ (M+H)$^+$ 343.1190, found 343.1195.

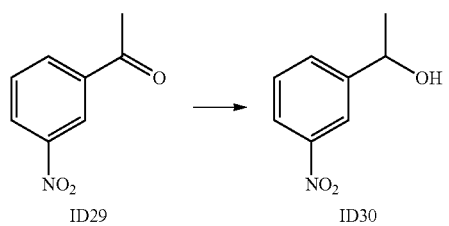

ID29     ID30

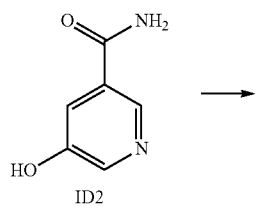

ID2

-continued

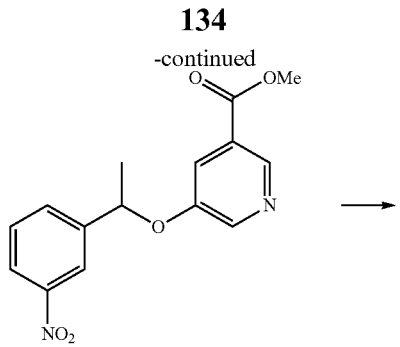

ID31

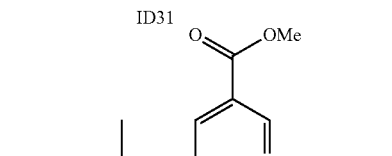

ID32

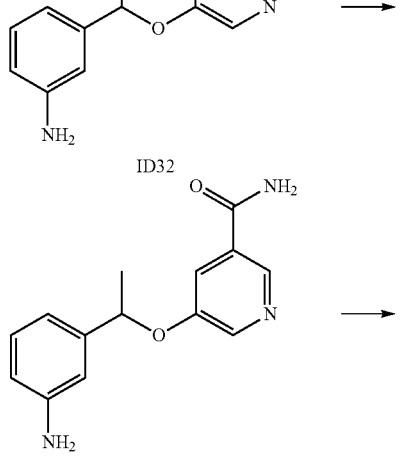

ID33

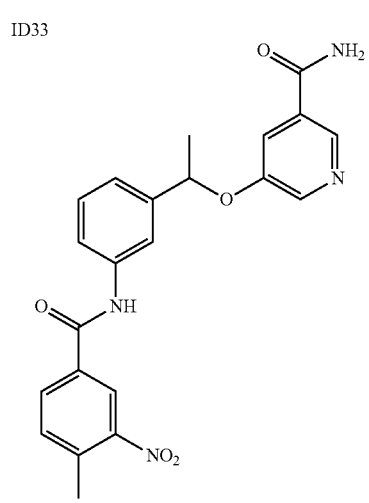

D10-1

1-(3-Nitrophenyl)ethanol (ID30)

To a solution of 1-(3-nitrophenyl)ethanone (ID29, 2.32 g, 14.0 mmol) in MeOH (100 mL) at 0° C. was added NaBH$_4$ (2.20 g, 58.2 mmol) and the resulting mixture was allowed to stir at 0° C. for 1 h. After concentration, the residue was diluted with EtOAc (150 mL) and water (50 mL) and the organic layer was washed with water (50 mL), brine (50 mL), and dried over Na$_2$SO$_4$. After filtration, the filtrate was concentrated and the residue was dried in vacuo to give compound ID30 as a yellowish oil (2.23 g, 95%). $^1$H NMR (CDCl$_3$, 600 MHz) δ 8.25 (s, 1H), 8.12 (ddd, J=8.4, 1.2, 1.2 Hz, 1H), 7.72 (d, J=7.2 Hz, 1H), 7.52 (dd, J=8.1, 8.1 Hz, 1H), 5.02 (q, J=6.6 Hz, 1H), 2.07 (s, 1H), 1.54 (d, J=6.6 Hz, 3H).

Methyl 5-(1-(3-Nitrophenyl)ethoxy)nicotinate (ID31)

To a solution of compound ID30 (1.02 g, 6.10 mmol), 5-hydroxynicotinamide (ID2, 766 mg, 5.00 mmol) and PPh$_3$ (1.97 g, 7.51 mmol) in anhydrous THF (40 mL) at 0° C. was slowly added DIAD (1.45 mL, 7.49 mmol). The resulting mixture was allowed to stir at 0° C. for 1 h and then at rt for 16 h. After concentration, the oily residue was triturated with Et$_2$O and hexanes and the organic solvents were pooled and concentration. The residue was purified by the flash column chromatography (0-40% EtOAc/hexanes) to give compound ID31 as a pale solid (1.46 g, 96%). $^1$H NMR (CDCl$_3$, 600 MHz) δ 8.80 (d, J=1.2 Hz, 1H), 8.46 (d, J=2.4 Hz, 1H), 8.27 (dd, J=2.1, 2.1 Hz, 1H), 8.16 (ddd, J=8.4, 2.4, 1.2 Hz, 1H), 7.74-7.70 (m, 2H), 7.56 (dd, J=8.1, 8.1 Hz, 1H), 5.52 (q, J=6.6 Hz, 1H), 3.92 (s, 3H), 1.72 (d, J=6.6 Hz, 3H). HRMS (ESI$^+$) calcd for C$_{15}$H$_{15}$N$_2$O$_5$ (M+H)$^+$ 303.0975, found 303.0969.

Methyl 5-(1-(3-Aminophenyl)ethoxy)nicotinate (ID32)

Compound ID32 was prepared from compound ID31 in a manner similar to that described for ID22. Clear syrup (231 mg, 18%). $^1$H NMR (CDCl$_3$, 600 MHz) δ 8.60 (d, J=1.8 Hz, 1H), 8.37 (d, J=3.0 Hz, 1H), 7.79 (dd, J=3.0, 1.8 Hz, 1H), 7.07 (dd, J=7.8, 7.8 Hz, 1H), 6.76 (s, 1H), 6.71 (d, J=7.8 Hz, 1H), 6.61 (dd, J=8.1, 1.5 Hz, 1H), 5.40 (q, J=6.6 Hz, 1H), 3.89 (s, 3H), 1.63 (d, J=6.0 Hz, 3H). HRMS (ESI$^+$) calcd for C$_{15}$H$_{17}$N$_2$O$_3$ (M+H)$^+$ 273.1234, found 273.1237.

5-(1-(3-Aminophenyl)ethoxy)nicotinamide (ID33)

Compound ID32 (221 mg, 0.81 mmol) was treated with 7 N NH$_3$/MeOH (20 mL) at 70° C. for 22 h to give compound ID33 as a white solid (177 mg, 85%). $^1$H NMR (CD$_3$OD, 600 MHz) δ 8.51 (d, J=1.8 Hz, 1H), 8.30 (d, J=3.0 Hz, 1H), 7.74 (dd, J=3.0, 1.8 Hz, 1H), 7.07 (dd, J=7.8, 7.8 Hz, 1H), 6.76 (dd, J=2.1, 2.1 Hz, 1H), 6.72 (d, J=7.8 Hz, 1H), 6.63-6.60 (m, 1H), 5.40 (q, J=6.6 Hz, 1H), 1.63 (d, J=6.6 Hz, 3H). HRMS (ESI$^+$) calcd for C$_{14}$H$_{16}$N$_3$O$_2$ (M+H)$^+$ 258.1237, found 258.1236.

5-(1-(3-(4-Methyl-3-nitrobenzamido)phenyl)ethoxy) nicotinamide (D10-1)

Compound D10-1 was prepared from compound ID33 through an amide formation reaction in a manner similar to that described for compound A-1. White solid (45 mg, 25%). $^1$H NMR (DMSO-d$_6$, 600 MHz) δ 10.48 (s, 1H), 8.57 (s, 1H), 8.56 (s, 1H), 8.40 (d, J=2.4 Hz, 1H), 8.19 (d, J=8.4 Hz, 1H), 8.09 (s, 1H), 7.86 (s, 1H), 7.74-7.69 (m, 2H), 7.67 (d, J=8.4 Hz, 1H), 7.57 (s, 1H), 7.37 (dd, J=7.8, 7.8 Hz, 1H), 7.21 (d, J=7.8 Hz, 1H), 5.67 (q, J=6.6 Hz, 1H), 2.59 (s, 3H), 1.61 (d, J=6.0 Hz, 3H). HRMS (ESI$^+$) calcd for C$_{22}$H$_{21}$N$_4$O$_5$ (M+H)$^+$ 421.1506, found 421.1505.

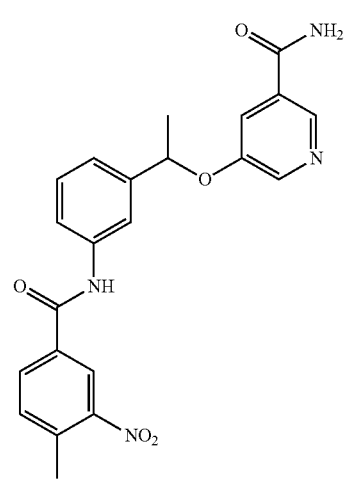 [SMILES: Cc1ccc(C(=O)Nc2cccc(C(C)Oc3cncc(C(N)=O)c3)c2)cc1[N+](=O)[O-]]

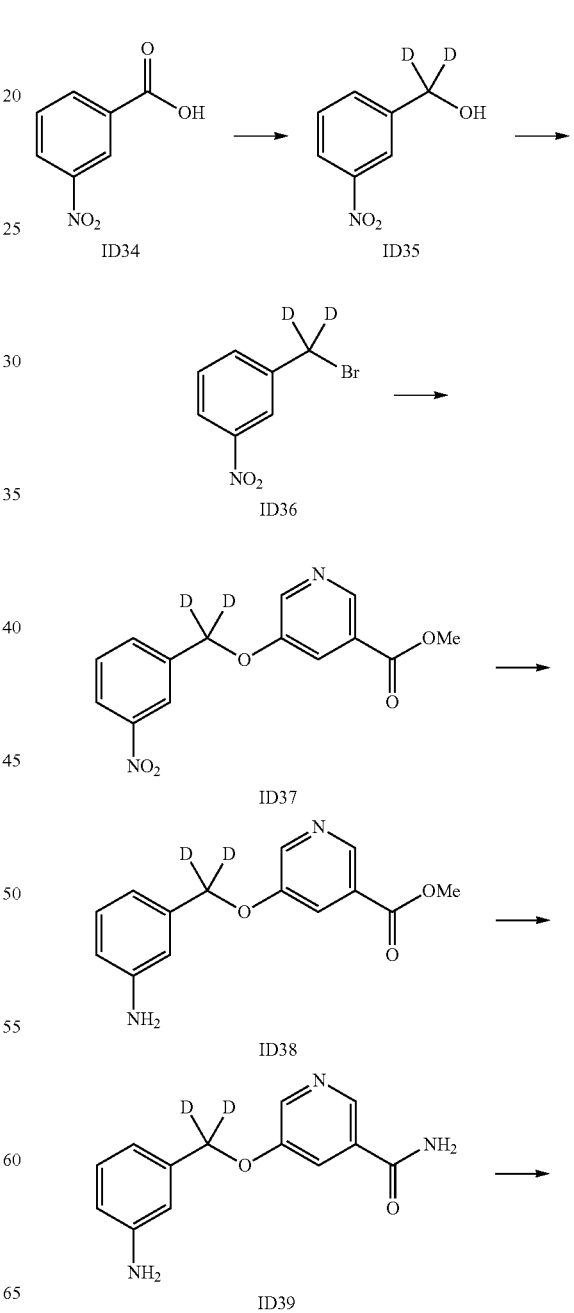

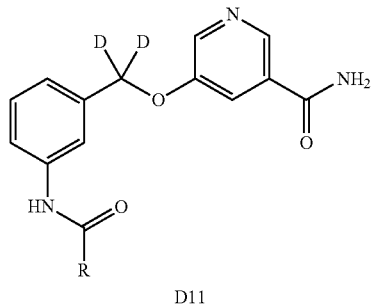

D11

ID35

To a mixture of 3-nitrobenzoic acid (1.33 g, 7.96 mmol) and N-methylmorpholine (886 mg, 8.75 mmol) in THF (20 mL) at 0° C. was added ethyl chloroformate (950 mg, 8.75 mmol). After being stirred for an additional 30 min at 0° C., the mixture was filtered and the insoluble salt was washed with THF (5 mL×3). To the filtrate were added $D_2O$ (10 mL) followed by $NaBD_4$ (1.00 g, 23.9 mmol) and the mixture was allowed to stir at rt for 2 h. The reaction was quenched with saturated $NH_4Cl$ (50 mL) and the resulting mixture was extracted with EtOAc. The organic phase was washed with water and brine, dried over anhydrous $K_2CO_3$, and concentrated in vacuo. The residue was purified by flash column chromatography (EtOAc/hexanes) to afford compound ID35 as a light yellow oil (1.10 g, 89%). $^1H$ NMR (CDCl$_3$, 600 MHz) δ 8.22 (s, 1H), 8.12 (d, J=8.4 Hz, 1H), 7.69 (d, J=7.2 Hz, 1H), 7.52 (dt, J=8.1, 2.1 Hz, 1H).

ID36

To a mixture of ID35 (1.10 g, 7.09 mmol) and $CBr_4$ (2.82 g, 8.51 mmol) in $CH_2Cl_2$ (100 mL) was added $Ph_3P$ (2.23 g, 8.51 mmol) and the reaction mixture was allowed to stir at rt for 12 h. After removal of the solvent, the residue was purified by flash column chromatography (EtOAc/hexanes) to afford ID36 as a yellow oil (1.33 g, 86%). $^1H$ NMR (CDCl$_3$, 600 MHz) δ 8.65 (s, 1H), 8.55 (d, J=8.4 Hz, 1H), 8.11 (d, J=7.2 Hz, 1H), 7.52 (dd, J=7.8, 7.8 Hz, 1H).

ID37

A mixture of methyl 5-hydroxynicotinate (1.03 g, 6.10 mmol), $CsCO_3$ (3.97 g, 12.2 mmol) and ID36 (1.33 g, 6.10 mmol) in DMF (80 mL) was allowed to stir at rt for 12 h. After water (200 mL) was added, the precipitate was filtered, washed with hexanes, and dried in vacuo to afford ID37 as a white solid (1.40 g, 79%). $^1H$ NMR (CDCl$_3$, 600 MHz) δ 8.89 (d, J=1.8 Hz, 1H), 8.57 (d, J=3.0 Hz, 1H), 8.35 (dd, J=1.8, 1.8 Hz, 1H), 8.24 (dd, J=7.8, 1.8 Hz, 1H), 7.87 (dd, J=3.0, 1.8 Hz, 1H), 7.79 (d, J=7.8 Hz, 1H), 7.62 (dd, J=8.1, 8.1 Hz, 1H), 3.97 (s, 3H). HRMS (ESI$^+$) calcd for $C_{14}H_{11}D_2N_2O_5$ (M+H)$^+$ 291.0945, found 291.0955.

ID38

To a solution of ID37 (800 mg, 2.76 mmol) and $NiCl_2 \cdot 6H_2O$ (1.31 g, 5.52 mmol) in MeOH (100 mL) was slowly added $NaBH_4$ (420 mg, 11.04 mmol) and the mixture was allowed to stir at rt for 3 h. The reaction was quenched with saturated $NH_4Cl$ (50 mL) and the mixture was extracted with EtOAc. The organic phase was washed with water and brine, dried over anhydrous $K_2CO_3$, and concentrated in vacuo. The residue was purified by flash column chromatography (EtOAc/hexanes) to afford ID38 as a light yellow solid (500 mg, 70%). $^1H$ NMR (CDCl$_3$, 600 MHz) δ 8.82 (d, J=1.8 Hz, 1H), 8.53 (d, J=3.0 Hz, 1H), 7.83 (dd, J=3.0, 1.8 Hz, 1H), 7.18 (dd, J=7.8, 7.8 Hz, 1H), 6.80 (d, J=7.8 Hz, 1H), 6.75 (dd, J=1.8, 1.8 Hz, 1H), 6.66 (dd, J=6.6, 2.1 Hz, 1H), 3.95 (s, 3H). HRMS (ESI$^+$) calcd for $C_{14}H_{13}D_2N_2O_3$ (M+H)$^+$ 261.1203, found 261.1211.

ID39

A solution of ID38 (500 mg, 1.92 mmol) in $NH_3$/MeOH (ca. 7N, 5 mL) in a seal tube was heated at 70° C. for 24 h. After the solvent was evaporated in vacuo, the residue was dissolved in EtOAc (100 mL) and the resulting solution was washed with $H_2O$ (150 mL) and brine (100 mL). The organic layer was dried over $Na_2SO_4$ and concentrated, and the residue was purified by flash column chromatography (5% MeOH/CH$_2$Cl$_2$) to afford ID39 as a light brownish solid (430 mg, 91%). $^1H$ NMR (DMSO-d$_6$, 600 MHz) δ 8.63 (s, 1H), 8.44 (d, J=3.0 Hz, 1H), 8.12 (s, 1H), 7.82-7.78 (m, 1H), 7.60 (s, 1H), 7.02 (dd, J=7.5, 7.5 Hz, 1H), 6.63 (s, 1H), 6.57 (d, J=7.8 Hz, 1H), 6.52 (dd, J=7.8, 1.2 Hz, 1H), 5.13 (s, 2H). HRMS (ESI$^+$) calcd for $C_{13}H_{12}D_2N_3O_2$ (M+H)$^+$ 246.1206, found 246.1210.

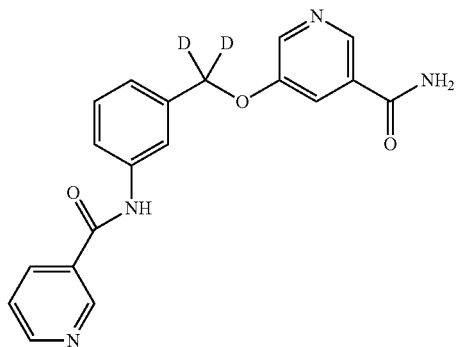 [SMILES: [2H]C([2H])(Oc1cncc(C(N)=O)c1)c1cccc(NC(=O)c2cccnc2)c1]

D11-1

Compound D11-1 was prepared from compound ID39 through an amide formation reaction in a manner similar to that described for compound A-1. $^1H$ NMR (DMSO-d$_6$, 600 MHz) δ 10.51 (s, 1H), 9.11 (s, 1H), 8.76 (d, J=3.6 Hz, 1H), 8.65 (s, 1H), 8.49 (s, 1H), 8.29 (d, J=7.8 Hz, 1H), 8.14 (s, 1H), 7.92 (s, 1H), 7.86 (s, 1H), 7.75 (d, J=7.8 Hz, 1H), 7.61 (s, 1H), 7.57 (dd, J=4.8, 6.6 Hz, 1H), 7.41 (dd, J=7.8, 7.8 Hz, 1H), 7.24 (d, J=7.2 Hz, 1H). HRMS (ESI$^+$) calcd for $C_{19}H_{15}D_2N_4O_3$ (M+H)$^+$ 351.1421, found 351.1428.

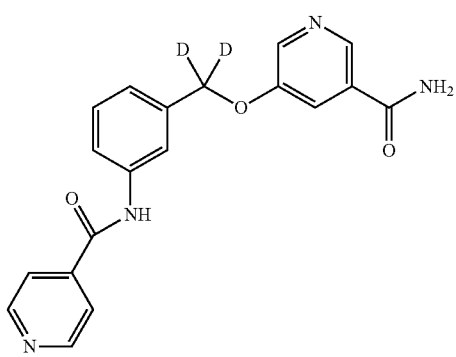 [SMILES: [2H]C([2H])(Oc1cncc(C(N)=O)c1)c1cccc(NC(=O)c2ccncc2)c1]

D11-2

Compound D11-2 was prepared from compound ID39 through an amide formation reaction in a manner similar to that described for compound A-1. $^1$H NMR (DMSO-d$_6$, 600 MHz) δ 10.56 (s, 1H), 8.83-8.65 (m, 2H), 8.65 (s, 1H), 8.50 (s, 1H), 8.13 (s, 1H), 7.92 (s, 1H), 7.89-7.84 (m, 3H), 7.75 (d, J=7.2 Hz, 1H), 7.61 (s, 1H), 7.42 (dd, J=8.1, 8.1, Hz, 1H), 7.25 (d, J=7.2 Hz, 1H). HRMS (ESI$^+$) calcd for C$_{19}$H$_{15}$D$_2$N$_4$O$_3$ (M+H)$^+$ 351.1421, found 351.1428.

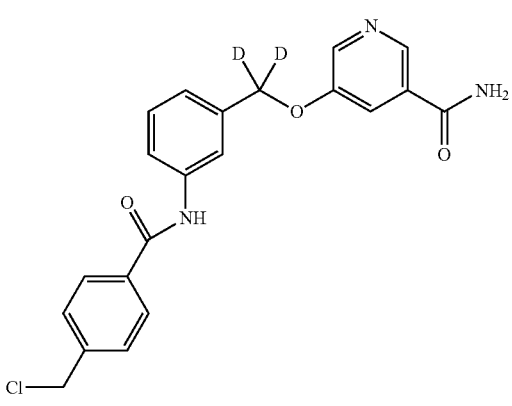 [SMILES: [2H]C([2H])(Oc1cncc(C(N)=O)c1)c1cccc(NC(=O)c2ccc(CCl)cc2)c1]

D11-3

Compound D11-3 was prepared from compound ID39 through an amide formation reaction in a manner similar to that described for compound A-1. $^1$H NMR (DMSO-d$_6$, 600 MHz) δ 10.34 (s, 1H), 8.65 (d, J=1.8 Hz, 1H), 8.49 (d, J=2.4 Hz, 1H), 8.14 (s, 1H), 7.96 (d, J=8.4 Hz, 2H), 7.92 (s, 1H), 7.86 (dd, J=1.8, 1.8 Hz, 1H), 7.75 (d, J=7.8 Hz, 1H), 7.61 (s, 1H), 7.59 (d, J=8.4 Hz, 2H), 7.39 (dd, J=7.5, 7.5 Hz, 1H), 7.22 (d, J=7.8 Hz, 1H), 4.85 (s, 2H). HRMS (ESI$^+$) calcd for C$_{21}$H$_{17}$D$_2$ClN$_3$O$_3$ (M+H)$^+$ 398.1235, found 398.1236.

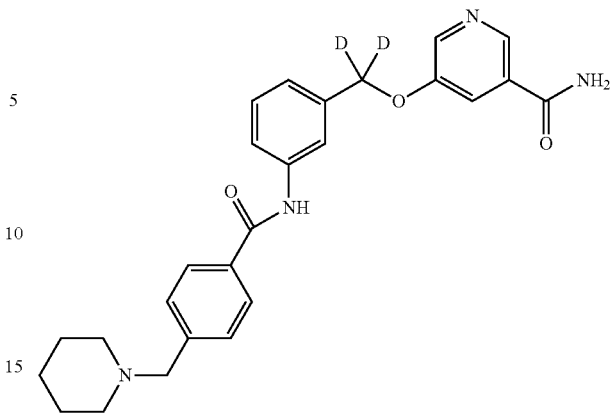

D11-4

A solution of D11-3 (18 mg, 0.045 mmol), piperidine (5 mg, 0.068 mmol), and DIPEA (9 mg, 0.065 mmol) in DMF (2 mL) was heated at 50° C. for 12 h. After the reaction was quenched with saturated NH$_4$Cl (10 mL), the mixture was extracted with EtOAc. The organic phase was washed with water and brine, dried over anhydrous Na$_2$SO$_4$, and concentrated in vacuo. The residue was purified by flash column chromatography (MeOH/CH$_2$Cl$_2$) to afford compound D11-4 as a white solid (20 mg, 94%). $^1$H NMR (CD$_3$OD, 600 MHz) δ 8.62 (d, J=1.2 Hz, 1H), 8.45 (d, J=2.4 Hz, 1H), 7.94-7.89 (m, 3H), 7.87 (s, 1H), 7.67 (dd, J=8.3, 1.2 Hz, 1H), 7.49 (d, J=8.4 Hz, 2H), 7.39 (dd, J=7.5, 7.5 Hz, 1H), 7.26 (d, J=7.8 Hz, 1H), 3.62 (s, 2H), 2.56-2.44 (m, 4H), 1.62 (quin, J=6.0 Hz, 4H), 1.53-1.45 (m, 2H). HRMS (ESI$^+$) calcd for C$_{26}$H$_{27}$D$_2$N$_4$O$_3$ (M+H)$^+$ 447.2360, found 447.2360.

The following compounds were prepared through a displacement reaction of D11-3 in a manner similar to that described for compound D11-4.

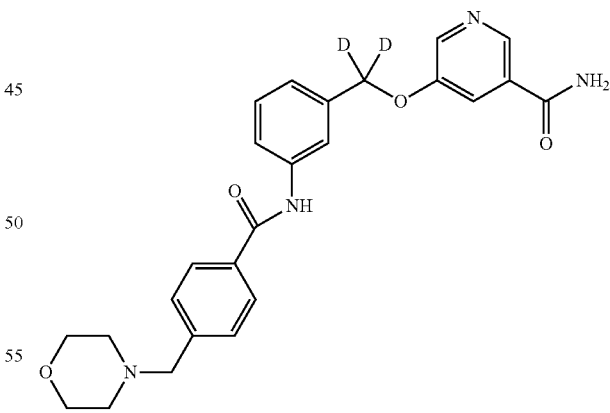

D11-5

$^1$H NMR (CD$_3$OD, 600 MHz) δ 8.62 (s, 1H), 8.46 (d, J=2.4 Hz, 1H), 7.93-7.89 (m, 3H), 7.87 (s, 1H), 7.67 (d, J=8.4 Hz, 1H), 7.50 (d, J=7.8 Hz, 2H), 7.40 (dd, J=8.1, 8.1 Hz, 1H), 7.26 (d, J=7.8 Hz, 1H), 3.70 (t, J=4.5 Hz, 4H), 3.60 (s, 2H), 2.52-2.44 (m, 4H). HRMS (ESI$^+$) calcd for C$_{25}$H$_{25}$D$_2$N$_4$O$_4$ (M+H)$^+$ 449.2152, found 449.2153.

141

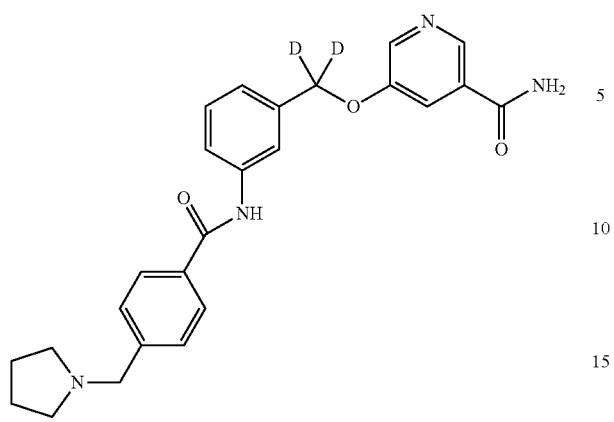

D11-6

¹H NMR (CD₃OD, 600 MHz) δ 8.62 (s, 1H), 8.45 (s, 1H), 7.94-7.90 (m, 3H), 7.87 (s, 1H), 7.67 (d, J=8.4 Hz, 1H), 7.51 (d, J=7.2 Hz, 2H), 7.40 (dd, J=7.8, 7.8 Hz, 1H), 7.26 (d, J=7.2 Hz, 1H), 3.80 (s, 2H), 2.69-2.62 (m, 4H), 1.89-1.82 (m, 4H). HRMS (ESI⁺) calcd for $C_{25}H_{25}D_2N_4O_3$ (M+H)⁺ 433.2203, found 433.2205.

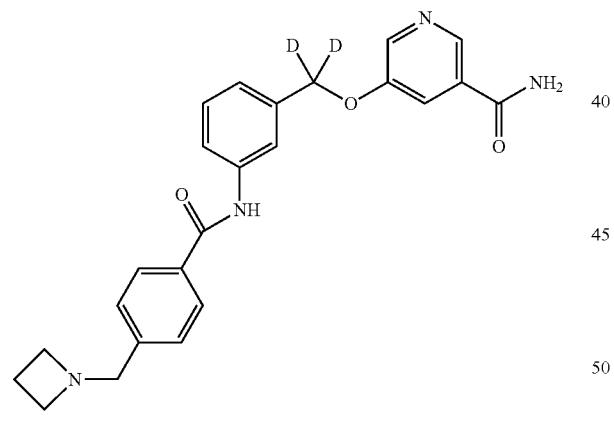

D11-7

¹H NMR (CD₃OD, 600 MHz) δ 8.62 (d, J=1.2 Hz, 1H), 8.46 (d, J=3.0 Hz, 1H), 7.95 (d, J=8.4 Hz, 2H), 7.92 (dd, J=2.1, 2.1 Hz, 1H), 7.87 (s, 1H), 7.68 (d, J=7.2 Hz, 1H), 7.50 (d, J=8.4 Hz, 2H), 7.40 (dd, J=7.8, 7.8 Hz, 1H), 7.27 (d, J=7.8 Hz, 1H), 3.97 (s, 2H), 3.63 (t, J=7.5 Hz, 4H), 2.28 (q, J=7.8 Hz, 2H). HRMS (ESI⁺) calcd for $C_{24}H_{23}D_2N_4O_3$ (M+H)⁺ 419.2047, found 419.2057.

142

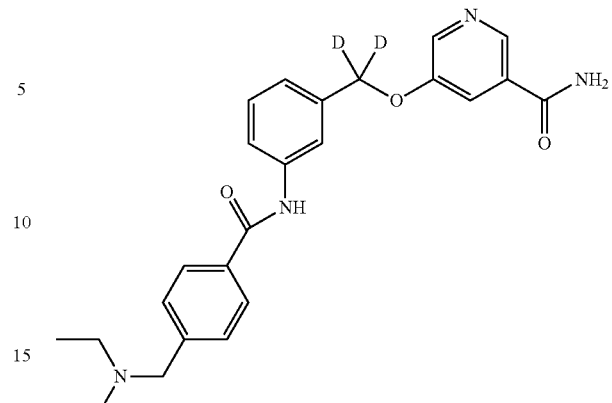

D11-8

¹H NMR (CD₃OD, 600 MHz) δ 8.62 (d, J=2.4 Hz, 1H), 8.45 (d, J=3.0 Hz, 1H), 7.93-7.89 (m, 3H), 7.87 (s, 1H), 7.67 (d, J=8.4 Hz, 1H), 7.50 (d, J=7.8 Hz, 2H), 7.39 (dd, J=8.1, 8.1 Hz, 1H), 7.26 (d, J=7.8 Hz, 1H), 3.73 (s, 2H), 2.62 (q, J=7.2 Hz, 4H), 1.11 (t, J=7.2 Hz, 6H). HRMS (ESI⁺) calcd for $C_{25}H_{27}D_2N_4O_3$ (M+H)⁺ 435.2360, found 435.2366.

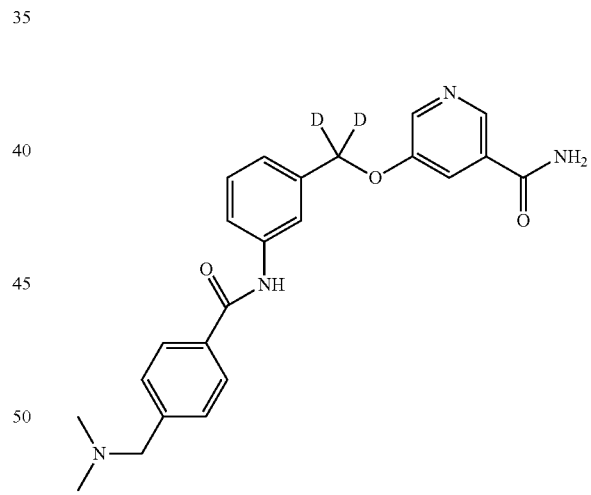

D11-9

¹H NMR (CD₃OD, 600 MHz) δ 8.62 (s, 1H), 8.46 (d, J=2.4 Hz, 1H), 7.96-7.91 (m, 3H), 7.88 (s, 1H), 7.68 (dd, J=8.4, 1.2 Hz, 1H), 7.50 (d, J=8.4 Hz, 2H), 7.40 (dd, J=8.1, 8.1 Hz, 1H), 7.27 (d, J=7.8 Hz, 1H), 3.68 (d, J=3.0 Hz, 2H), 2.36 (s, 6H). HRMS (ESI⁺) calcd for $C_{23}H_{23}D_2N_4O_3$ (M+H)⁺ 407.2047, found 407.2053.

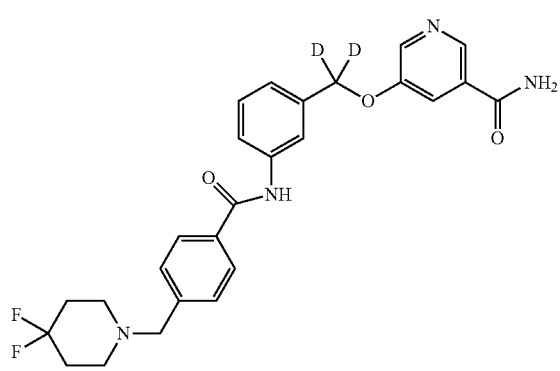 [SMILES: [2H]C([2H])(Oc1cncc(C(N)=O)c1)c1cccc(NC(=O)c2ccc(CN3CCC(F)(F)CC3)cc2)c1]

D11-10

¹H NMR (CD₃OD, 600 MHz) δ 8.62 (s, 1H), 8.45 (d, J=1.8 Hz, 1H), 7.93-7.89 (m, 3H), 7.87 (s, 1H), 7.67 (d, J=7.8 Hz, 1H), 7.49 (d, J=7.8 Hz, 2H), 7.39 (dd, J=8.1, 8.1 Hz, 1H), 7.26 (d, J=7.8 Hz, 1H), 3.65 (s, 2H), 2.62-2.54 (m, 4H), 2.04-1.95 (m, 4H). HRMS (ESI⁺) calcd for C₂₆H₂₅D₂F₂N₄O₃ (M+H)⁺ 483.2171, found 483.2179.

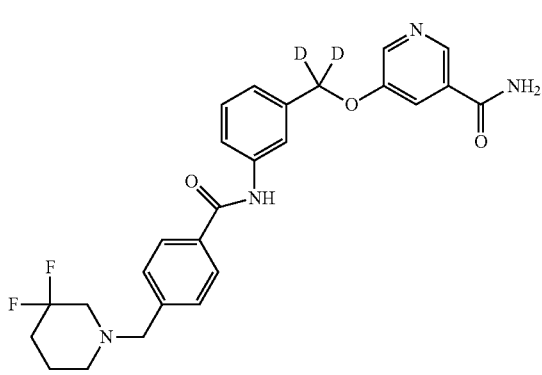 [SMILES: [2H]C([2H])(Oc1cncc(C(N)=O)c1)c1cccc(NC(=O)c2ccc(CN3CCCC(F)(F)C3)cc2)c1]

D11-11

¹H NMR (CD₃OD, 600 MHz) δ 8.62 (s, 1H), 8.45 (d, J=2.4 Hz, 1H), 7.93-7.89 (m, 3H), 7.87 (s, 1H), 7.67 (d, J=8.4 Hz, 1H), 7.48 (d, J=7.8 Hz, 2H), 7.39 (dd, J=8.1, 8.1 Hz, 1H), 7.25 (d, J=7.8 Hz, 1H), 3.65 (s, 2H), 2.61 (t, J=11.4 Hz, 2H), 2.51-2.44 (m, 2H), 1.92-1.84 (m, 2H), 1.79-1.73 (m, 2H). HRMS (ESI⁺) calcd for C₂₆H₂₅D₂F₂N₄O₃ (M+H)⁺ 483.2171, found 483.2184.

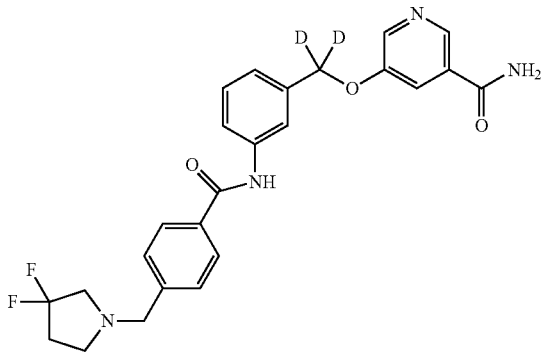 [SMILES: [2H]C([2H])(Oc1cncc(C(N)=O)c1)c1cccc(NC(=O)c2ccc(CN3CCC(F)(F)C3)cc2)c1]

D11-12

¹H NMR (CD₃OD, 600 MHz) δ 8.62 (d, J=1.8 Hz, 1H), 8.45 (d, J=2.4 Hz, 1H), 7.93-7.89 (m, 3H), 7.87 (s, 1H), 7.67 (d, J=9.0 Hz, 1H), 7.49 (d, J=8.4 Hz, 2H), 7.39 (dd, J=7.8, 7.8 Hz, 1H), 7.26 (d, J=7.8 Hz, 1H), 3.72 (s, 2H), 2.89 (t, J=13.2 Hz, 2H), 2.78 (t, J=6.9 Hz, 2H), 2.52-2.43 (m, 2H). HRMS (ESI⁺) calcd for C₂₅H₂₃D₂F₂N₄O₃ (M+H)⁺ 469.2015, found 469.2023.

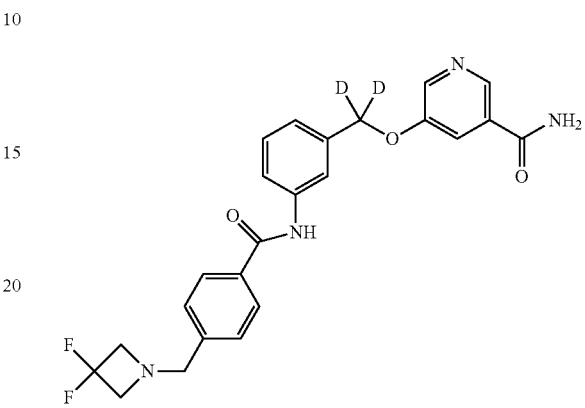

D11-13

¹H NMR (CD₃OD, 600 MHz) δ 8.62 (d, J=1.2 Hz, 1H), 8.45 (d, J=3.0 Hz, 1H), 7.94-7.89 (m, 3H), 7.87 (s, 1H), 7.67 (d, J=8.4 Hz, 1H), 7.47 (d, J=7.8 Hz, 2H), 7.39 (dd, J=8.1, 8.1 Hz, 1H), 7.25 (d, J=7.8 Hz, 1H), 3.84 (s, 2H), 3.65 (t, J=12.0 Hz, 4H). HRMS (ESI⁺) calcd for C₂₄H₂₁D₂F₂N₄O₃ (M+H)⁺ 455.1858, found 455.1867.

Example 5

Representative compounds of formula (I) can be prepared as described below.

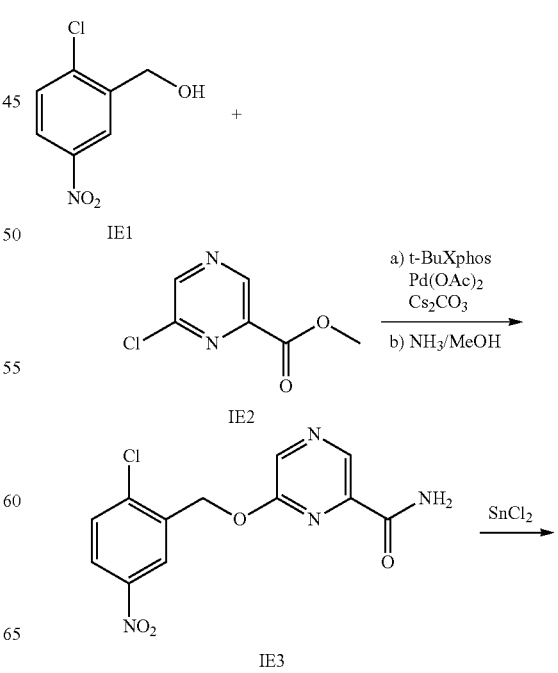

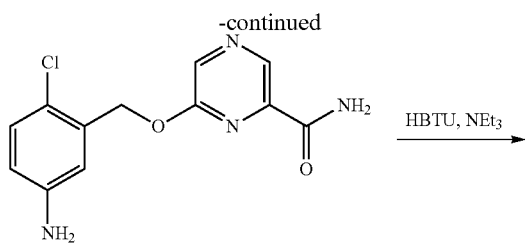

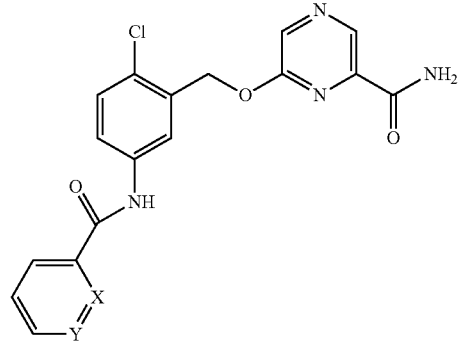

E3-1, X = CH, Y = N
E3-2, X = N, Y = CH

6-((2-Chloro-5-nitrobenzyl)oxy)pyrazine-2-carboxamide (IE3)

An oven-dried seal tube was charged with Pd(OAc)$_2$ (4.4 mg, 0.02 mmol, 1 mol %), t-Bu-Xphos (17 mg, 0.04 mmol, 2 mol %) and Cs$_2$CO$_3$ (980 mg, 3.0 mmol, 1.5 equiv). The seal tube was sealed with a septum, evacuated and backfilled with argon. Toluene (10 mL), methyl 6-chloro-2-pyrazinecarboxylate (IE2, 340 mg, 2.0 mmol), and 2-chloro-5-nitrobenzyl alcohol (IE1, 1.13 g, 6.0 mmol) were added via syringe. The reaction mixture was heated at 100° C. for 24 h, then cooled to room temperature, diluted with EtOAc (20 mL), filtered through a pad of Celite, and concentrated. The residue was purified by flash column chromatography (0-50% EtOAc/hexanes) to afford an inseparable mixture of IE1 and the coupling product. This mixture in NH$_3$/MeOH (ca. 7 N, 20 mL) in a seal tube was heated at 70° C. for 24 h. After the solvent was evaporated in vacuo, the residue was dissolved in EtOAc (150 mL) and the resulting solution was washed with H$_2$O (150 mL) and brine (100 mL). After the organic layer was dried over Na$_2$SO$_4$ and filtered, the filtrate was concentrated and the residue was purified by flash column chromatography (0-15% MeOH/CH$_2$Cl$_2$) to afford compound IE3 as a light yellow solid (100 mg, 16% over two steps). $^1$H NMR (CDCl$_3$, 600 MHz) δ 9.06 (s, 1H), 8.60 (s, 1H), 8.47 (d, J=2.4 Hz, 1H), 8.19 (dd, J=9.0, 2.4 Hz, 1H), 7.63 (d, J=9.0 Hz, 1H), 5.59 (s, 2H). HRMS (ESI$^+$) calcd for C$_{12}$H$_{10}$ClN$_4$O$_4$ (M+H)$^+$ 309.0385, found 309.0392.

6-((5-Amino-2-chlorobenzyl)oxy)pyrazine-2-carboxamide (IE4)

A solution of IE3 (100 mg, 0.323 mmol) and SnCl$_2$ (442 mg, 2.33 mmol) in MeOH (20 mL) was heated at 70° C. for 16 h. After the solvent was evaporated in vacuo, the residue was quenched with NaHCO$_3$ (sat.) and EtOAc (50 mL) was added. The solid formed was filtered and the organic layer was washed with H$_2$O (150 mL) and brine (100 mL) and then concentrated. The residue was purified by flash column chromatography (0-15% MeOH/CH$_2$Cl$_2$) to afford compound IE4 as a light yellow solid (25 mg, 25%). $^1$H NMR (DMSO-d$_6$, 600 MHz) δ 8.75 (s, 1H), 8.53 (s, 1H), 8.20 (s, 1H), 7.85 (s, 1H), 7.10 (d, J=9.0 Hz, 1H), 6.76 (d, J=2.4 Hz, 1H), 6.56 (dd, J=8.4, 2.4 Hz, 1H), 5.45 (s, 2H), 5.31 (s, 2H). HRMS (ESI$^+$) calcd for C$_{12}$H$_{12}$ClN$_4$O$_2$ (M+H)$^+$ 279.0643, found 279.0639.

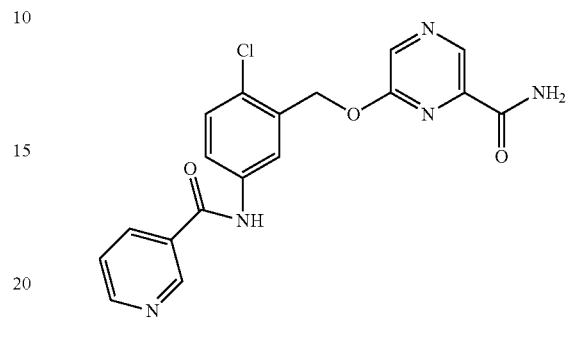

6-((2-Chloro-5-(nicotinamido)benzyl)oxy)pyrazine-2-carboxamide (E3-1)

Compound E3-1 was prepared from intermediate IE4 and nicotinic acid via an HBTU-mediated amide formation. Light yellow solid (10.7 mg, 87%). $^1$H NMR (DMSO-d$_6$, 600 MHz) δ 10.57 (s, 1H), 9.07 (s, 1H), 8.78-8.71 (m, 2H), 8.55 (s, 1H), 8.25 (d, J=7.8 Hz, 1H), 8.19 (s, 1H), 8.01 (s, 1H), 7.85 (s, 1H), 7.80 (d, J=7.8 Hz, 1H), 7.54 (dd, J=6.6 Hz, 1H), 7.51 (d, J=9.0 Hz, 1H), 5.60 (s, 2H). HRMS (ESI$^+$) calcd for C$_{18}$H$_{15}$ClN$_5$O$_{11}$ (M+H)$^+$ 384.0858, found 384.0858.

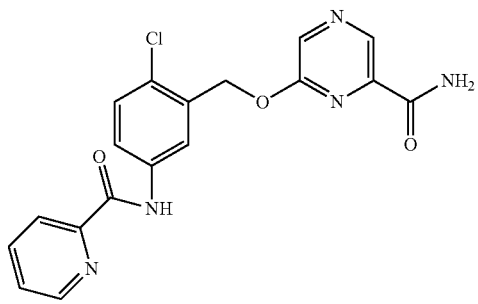 [SMILES: NC(=O)c1cncc(OCc2cc(NC(=O)c3ccccn3)ccc2Cl)n1]

6-((2-Chloro-5-(picolinamido)benzyl)oxy)pyrazine-2-carboxamide (E3-2)

Compound E3-2 was prepared from intermediate IE4 and picolinic acid via an HBTU-mediated amide formation. White solid (12.0 mg, 98%). $^1$H NMR (DMSO-d$_6$, 600 MHz) δ 10.84 (s, 1H), 8.77 (s, 1H), 8.74 (d, J=4.2 Hz, 1H), 8.59 (s, 1H), 8.26-8.20 (m, 2H), 8.16 (d, J=7.8 Hz, 1H), 8.07 (dd, J=7.2, 7.2 Hz, 1H), 7.99 (dd, J=8.4, 3.0 Hz, 1H), 7.88 (s, 1H), 7.69 (dd, J=6.0, 6.0 Hz, 1H), 7.54 (d, J=7.8 Hz, 1H), 5.62 (s, 2H). HRMS (ESI$^+$) calcd for C$_{18}$H$_{15}$ClN$_5$O$_{11}$ (M+H)$^+$ 384.0858, found 384.0850.

The following compounds were prepared through a reaction sequence similar to that described for the preparation of compound E3-1.

6-((3-(Isonicotinamido)benzyl)oxy)pyrazine-2-carboxamide (E1-1)

$^1$H NMR (CD$_3$OD, 600 MHz) δ 8.80 (s, 1H), 8.47 (s, 1H), 7.96 (s, 1H), 7.63 (d, J=7.8 Hz, 2H), 7.42 (dd, J=7.8, 7.8 Hz, 1H), 7.39-7.33 (m, 2H), 7.19 (d, J=7.2 Hz, 2H), 5.55 (s, 2H). HRMS (ESI$^+$) calcd for C$_{18}$H$_{16}$N$_5$O$_3$ (M+H)$^+$ 350.1248, found 350.1256.

6-((3-(Isonicotinamido)benzyl)oxy)pyridazine-4-carboxamide (E2-1)

$^1$H NMR (DMF-d$_7$, 600 MHz) δ 10.64 (s, 1H), 9.33 (s, 1H), 8.84-8.78 (m, 2H), 8.53 (s, 1H), 8.08 (s, 1H), 7.98-7.95 (m, 3H), 7.92 (d, J=7.8 Hz, 1H), 7.68 (s, 1H), 7.46 (dd, J=7.8, 7.8 Hz, 1H), 7.36 (d, J=6.0 Hz, 1H), 5.67 (s, 2H). HRMS (ESI$^+$) calcd for C$_{18}$H$_{16}$N$_5$O$_3$ (M+H)$^+$ 350.1248, found 350.1252.

Example 6

Representative compounds of formula (I) can be prepared as described below.

IF4a, R$^1$ = Me, R$^2$ = H, R$^3$ = H, R$^4$ = H
IF4b, R$^1$ = F, R$^2$ = H, R$^3$ = H, R$^4$ = H
IF4c, R$^1$ = Cl, R$^2$ = H, R$^3$ = H, R$^4$ = H
IF4d, R$^1$ = CF$_3$, R$^2$ = H, R$^3$ = H, R$^4$ = H
IF4e, R$^1$ = OMe, R$^2$ = H, R$^3$ = H, R$^4$ = H
IF4g, R$^1$ = H, R$^2$ = F, R$^3$ = H, R$^4$ = H
IF4l, R$^1$ = F, R$^2$ = F, R$^3$ = H, R$^4$ = H

IF1a, R$^1$ = Me, R$^2$ = H, R$^3$ = H, R$^4$ = H
IF1d, R$^1$ = CF$_3$, R$^2$ = H, R$^3$ = H, R$^4$ = H
IF1e, R$^1$ = OMe, R$^2$ = H, R$^3$ = H, R$^4$ = H
IF1g, R$^1$ = H, R$^2$ = F, R$^3$ = H, R$^4$ = H
IF1l, R$^1$ = F, R$^2$ = F, R$^3$ = H, R$^4$ = H

IF2a, R$^1$ = Me, R$^2$ = H, R$^3$ = H, R$^4$ = H
IF2b, R$^1$ = F, R$^2$ = H, R$^3$ = H, R$^4$ = H
IF2c, R$^1$ = Cl, R$^2$ = H, R$^3$ = H, R$^4$ = H
IF2d, R$^1$ = CF$_3$, R$^2$ = H, R$^3$ = H, R$^4$ = H
IF2e, R$^1$ = OMe, R$^2$ = H, R$^3$ = H, R$^4$ = H
IF2g, R$^1$ = H, R$^2$ = F, R$^3$ = H, R$^4$ = H
IF2l, R$^1$ = F, R$^2$ = F, R$^3$ = H, R$^4$ = H

IF3a, R$^1$ = Me, R$^2$ = H, R$^3$ = H, R$^4$ = H
IF3b, R$^1$ = F, R$^2$ = H, R$^3$ = H, R$^4$ = H
IF3c, R$^1$ = Cl, R$^2$ = H, R$^3$ = H, R$^4$ = H
IF3d, R$^1$ = CF$_3$, R$^2$ = H, R$^3$ = H, R$^4$ = H
IF3e, R$^1$ = OMe, R$^2$ = H, R$^3$ = H, R$^4$ = H
IF3g, R$^1$ = H, R$^2$ = F, R$^3$ = H, R$^4$ = H
IF3l, R$^1$ = F, R$^2$ = F, R$^3$ = H, R$^4$ = H

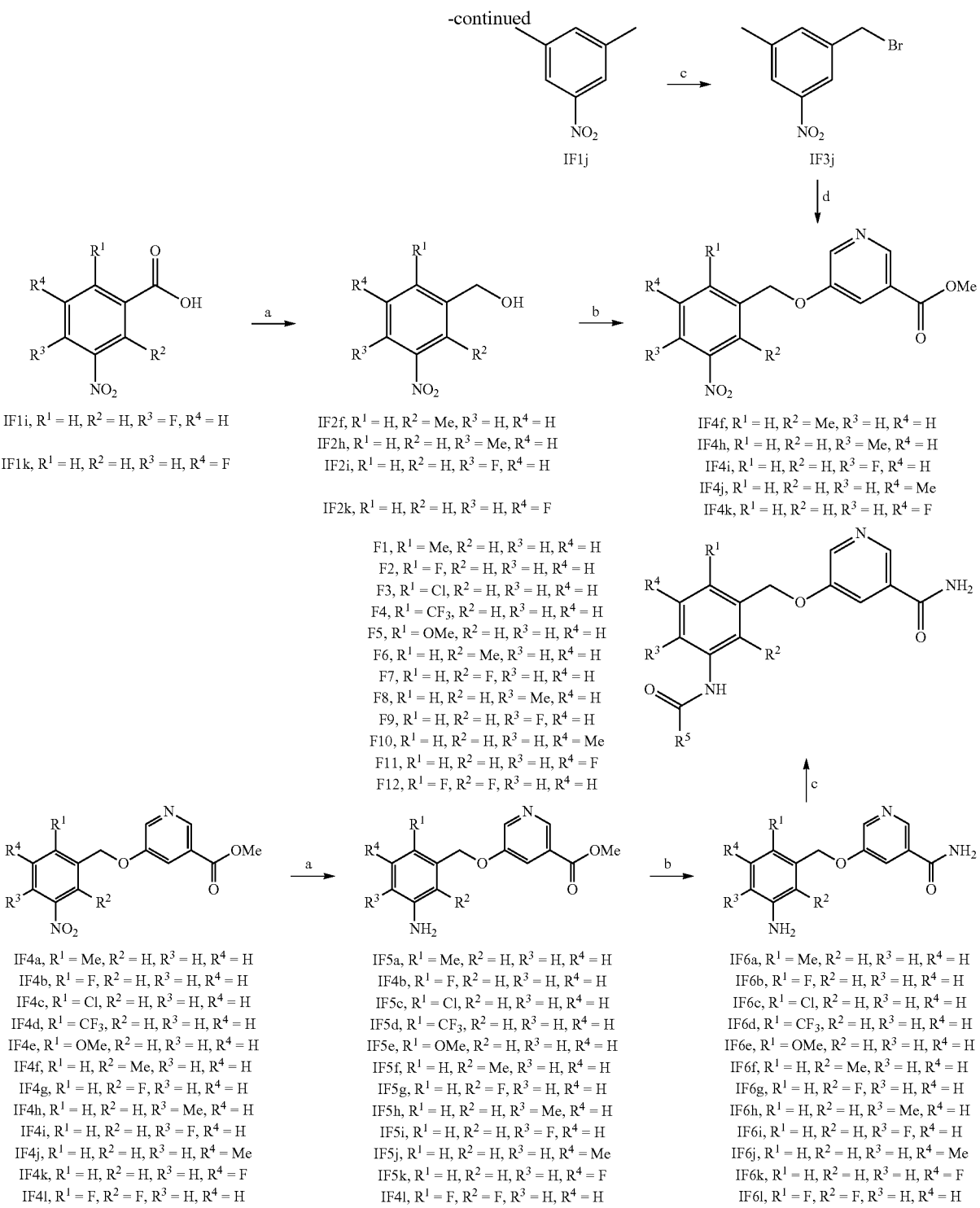

IF2a

To a mixture of carboxylic acid IF1a (1.81 g, 10.0 mmol) and N-methylmorpholine (1.11 g, 11.0 mmol) in THF (20 mL) at 0° C. was added ethyl chloroformate (1.19 g, 11.0 mmol). The mixture was allowed to stir at 0° C. for an additional 30 min and filtered. The insoluble salt was washed with THF (5 mL×3). To the filtrate was added NaBH$_4$ (1.13 g, 30 mmol) and the resulting mixture was then stirred at rt for 2 h. The reaction mixture was quenched with saturated NH$_4$Cl (50 mL) and extracted with EtOAc. The organic phase was washed with water and brine, dried over anhydrous K$_2$CO$_3$, and concentrated in vacuo. The residue was purified by flash column chromatography (EtOAc/hexanes) to afford compound IF2a as a colorless oil (1.60 g, 94%). $^1$H NMR (CDCl$_3$, 600 MHz) δ 8.31 (d, J=2.4 Hz, 1H), 8.06 (dd, J=8.1, 2.7 Hz, 1H), 7.32 (d, J=9.0 Hz, 1H), 4.79 (d, J=4.8 Hz, 2H), 1.57 (s, 3H).

IF2d

In a manner similar to that described for the preparation of compound IF2a, IF1d (2.35 g, 10.0 mmol) was reduced to alcohol IF2d as a light yellow solid (1.70 g, 77%). $^1$H NMR (CDCl$_3$, 600 MHz) δ 8.69 (s, 1H), 8.23 (d, J=7.2 Hz, 1H), 7.84 (d, J=9.0 Hz, 1H), 5.01 (d, J=4.8 Hz, 2H).

IF2e

In a manner similar to that described for the preparation of compound IF2a, IF1e (1.97 g, 10.0 mmol) was reduced to alcohol IF2e as a white solid (1.60 g, 87%). $^1$H NMR (CDCl$_3$, 600 MHz) δ 8.29 (d, J=3.0 Hz, 1H), 8.21 (dd, J=9.0, 3.0 Hz, 1H), 7.84 (d, J=9.0 Hz, 1H), 4.75 (s, 2H), 3.97 (s, 3H).

IF2g

In a manner similar to that described for the preparation of compound IF2a, IF1g (1.85 g, 10.0 mmol) was reduced to alcohol IF2g as a light yellow oil (1.54 g, 90%). $^1$H NMR (CDCl$_3$, 600 MHz) δ 7.97 (dd, J=7.8, 7.8 Hz, 1H), 7.80 (dd, J=7.2, 7.2 Hz, 1H), 7.31 (dd, J=7.8, 7.8 Hz, 1H), 4.86 (s, 2H).

IF2i

In a manner similar to that described for the preparation of compound IF2a, IF1i (2.50 g, 13.5 mmol) was reduced to alcohol IF2i as a yellow oil (1.37 g, 59%). $^1$H NMR (CDCl$_3$, 600 MHz) δ 8.08 (dd, J$_1$=7.0 Hz, J$_2$=2.2 Hz, 1H), 7.66-7.62 (m, 1H), 7.29 (dd, J$_1$=10.5 Hz, J$_2$=8.6 Hz, 1H), 4.77 (d, J=5.7 Hz, 2H), 1.98 (t, J=5.7 Hz, 1H).

IF2k

In a manner similar to that described for the preparation of compound IF2a, IF1k (1.00 g, 5.40 mmol) was reduced to alcohol IF2k as a yellow oil (346 mg, 37%). $^1$H NMR (CDCl$_3$, 600 MHz) δ 8.05 (s, 1H), 7.84 (dt, J$_1$=8.2 Hz, J$_2$=2.1 Hz, 1H), 7.47 (d, J=8.4 Hz, 1H), 4.84 (d, J=5.7 Hz, 2H), 1.98 (t, J=5.7 Hz, 1H).

IF2l

In a manner similar to that described for the preparation of compound IF2a, IF1l (1.00 g, 5.78 mmol) was reduced to alcohol IF2l as a light yellow oil (700 mg, 76%). $^1$H NMR (CDCl$_3$, 600 MHz) δ 8.14-8.08 (m, 1H), 7.10-7.05 (m, 1H), 4.84 (s, 2H).

IF3a

A mixture of IF2a (1.60 g, 9.58 mmol), CBr$_4$ (3.81 g, 11.50 mmol) and Ph$_3$P (3.02 g, 11.50 mmol) in CH$_2$Cl$_2$ (100 mL) was allowed to stir at rt for 12 h. After removal of the solvent, the residue was purified by flash column chromatography (EtOAc/hexanes) to afford IF3a as a white solid (1.22 g, 55%). $^1$H NMR (CDCl$_3$, 600 MHz) δ 8.20 (d, J=1.2 Hz, 1H), 8.08 (dd, J=8.4, 2.4 Hz, 1H), 7.36 (d, J=9.0 Hz, 1H), 4.53 (s, 2H), 1.58 (s, 3H).

IF3b

In a manner similar to that described for the preparation of compound IF3a, bromination of IF2b (1.71 g, 10.0 mmol) afforded IF3b as a white solid (2.00 g, 85%). $^1$H NMR (CDCl$_3$, 600 MHz) δ 8.36 (dd, J$_1$=6.4 Hz, J$_2$=2.8 Hz, 1H), 8.25-8.21 (m, 1H), 7.25 (t, J=8.8 Hz, 1H), 4.54 (s, 2H).

IF3c

In a manner similar to that described for the preparation of compound IF3a, bromination of IF2c (1.88 g, 10.0 mmol) afforded IF3b as a white solid (1.96 g, 78%). $^1$H NMR (CDCl$_3$, 600 MHz) δ 8.35 (d, J=2.5 Hz, 1H), 8.13 (dd, J$_1$=8.8 Hz, J$_2$=2.5 Hz, 1H), 7.59 (d, J=8.8 Hz, 1H), 4.62 (s, 2H).

IF3d

In a manner similar to that described for the preparation of compound IF3a, bromination of IF2d (1.70 g, 7.70 mmol) afforded IF3d as a colorless oil (1.50 g, 69%). $^1$H NMR (CDCl$_3$, 600 MHz) δ 8.48 (s, 1H), 8.26 (d, J=9.0 Hz, 1H), 7.88 (d, J=8.4 Hz, 1H), 4.68 (s, 2H).

IF3e

In a manner similar to that described for the preparation of compound IF3a, bromination of IF2e (1.60 g, 8.70 mmol) afforded IF3e as a white solid (1.50 g, 70%). $^1$H NMR (CDCl$_3$, 600 MHz) δ 8.26 (d, J=3.0 Hz, 1H), 8.22 (dd, J=9.0, 3.0 Hz, 1H), 6.97 (d, J=9.0 Hz, 1H), 4.54 (s, 2H), 4.02 (s, 3H).

IF3g

In a manner similar to that described for the preparation of compound IF3a, bromination of IF2g (1.54 g, 9.00 mmol) afforded IF3g as a brownish oil (1.54 g, 73%). $^1$H NMR (CDCl$_3$, 600 MHz) δ 8.02 (dd, J=6.6, 6.6 Hz, 1H), 7.73 (dd, J=6.6, 6.6 Hz, 1H), 7.31 (dd, J=7.8, 7.8 Hz, 1H), 4.56 (s, 2H).

IF3j

To a solution of 1,3-dimethyl-5-nitrobenzene (IF1j, 2.00 g, 13.2 mmol) and NBS (2.35 g, 13.2 mmol) in CCl$_4$ (50 mL) was added AIBN (217 mg, 1.32 mmol) and the mixture was allowed to reflux overnight. The organic solvent was removed and the resulting residue was purified by flash column chromatography to give IF3j as a white solid (1.30 g, 43%). $^1$H NMR (CDCl$_3$, 600 MHz) δ 8.06 (s, 1H), 7.98 (s, 1H), 7.53 (s, 1H), 4.50 (s, 2H), 2.47 (s, 3H).

IF3l

In a manner similar to that described for the preparation of compound IF3a, bromination of IF2l (700 mg, 4.40 mmol) afforded IF3l as a colorless oil (700 mg, 72%). $^1$H NMR (CDCl$_3$, 600 MHz) δ 8.16-8.10 (m, 1H), 7.09 (dd, J=8.4, 8.4 Hz, 1H), 4.54 (s, 2H).

IF4a

A mixture of methyl 5-hydroxynicotinate (0.893 g, 5.83 mmol), Cs$_2$CO$_3$ (3.45 g, 10.6 mmol) and IF3a (1.22 g, 5.30 mmol) in DMF (80 mL) was allowed to stir at rt for 12 h. After water (200 mL) was added, the solid precipitate was filtered, washed with hexanes, and dried under vacuum to afford IF4a as a light yellow solid (1.14 g, 71%). $^1$H NMR (CDCl$_3$, 600 MHz) δ 8.90 (d, J=1.8 Hz, 1H), 8.59 (d, J=3.0

Hz, 1H), 8.35 (d, J=2.4 Hz, 1H), 8.15 (dd, J=7.8, 2.4 Hz, 1H), 7.90 (dd, J=3.0, 1.8 Hz, 1H), 7.41 (d, J=7.8 Hz, 1H), 5.18 (s, 2H), 3.98 (s, 3H), 2.49 (s, 3H). HRMS (ESI$^+$) calcd for $C_{15}H_{15}N_2O_5$ (M+H)$^+$ 303.0976, found 303.0985.

IF4b

In a manner similar to that described for the preparation of compound IF4a, coupling of IF3b (2.00 g, 8.55 mmol) afforded IF4b as a light yellow solid (1.43 g, 55%). $^1$H NMR (CDCl$_3$, 600 MHz) δ 8.91 (d, J=1.5 Hz, 1H), 8.60 (d, J=2.9 Hz, 1H), 8.50 (dd, J$_1$=6.0 Hz, J$_2$=2.9 Hz, 1H), 8.31-8.27 (m, 1H), 7.90 (dd, J$_1$=2.9 Hz, J$_2$=1.8 Hz, 1H), 7.30 (t, J=8.9 Hz, 1H), 5.27 (s, 2H), 3.98 (s, 3H). HRMS (ESI$^+$) calcd for $C_{14}H_{12}FN_2O_5$ (M+H)$^+$ 307.0725, found 307.0721.

IF4c

In a manner similar to that described for the preparation of compound IF4a, coupling of IF3c (1.96 g, 7.82 mmol) afforded IF4c as a brownish solid (1.65 g, 65%). $^1$H NMR (CDCl$_3$, 600 MHz) δ 8.92 (d, J=1.5 Hz, 1H), 8.63 (d, J=2.9 Hz, 1H), 8.50 (d, J=2.6 Hz, 1H), 8.20 (dd, J$_1$=8.8 Hz, J$_2$=2.6 Hz, 1H), 7.92 (dd, J$_1$=2.9 Hz, J$_2$=1.8 Hz, 1H), 7.63 (d, J=8.8 Hz, 1H), 5.29 (s, 2H), 3.98 (s, 3H). HRMS (ESI$^+$) calcd for $C_{14}H_{12}ClN_2O_5$ (M+H)$^+$ 323.0429, found 323.0433.

IF4d

In a manner similar to that described for the preparation of compound IF4a, coupling of IF3d (1.50 g, 5.28 mmol) afforded IF4d as a light yellow solid (1.30 g, 69%). $^1$H NMR (CDCl$_3$, 600 MHz) δ 8.92 (s, 1H), 8.66 (s, 1H), 8.61 (d, J=2.4 Hz, 1H), 8.33 (d, J=8.4 Hz, 1H), 7.95 (d, J=9.0 Hz, 1H), 7.89 (s, 1H), 5.41 (s, 2H), 3.98 (s, 3H). HRMS (ESI$^+$) calcd for $C_{15}H_{12}F_3N_2O_5$ (M+H)$^+$ 357.0693, found 357.0695.

IF4e

In a manner similar to that described for the preparation of compound IF4a, coupling of IF3e (1.50 g, 6.10 mmol) afforded IF4e as a light brownish solid (1.50 g, 77%). $^1$H NMR (CDCl$_3$, 600 MHz) δ 8.88 (s, 1H), 8.59 (d, J=2.4 Hz, 1H), 8.41 (d, J=3.0 Hz, 1H), 8.27 (dd, J=9.0, 3.0 Hz, 1H), 7.90 (dd, J=3.0, 1.8 Hz, 1H), 7.01 (d, J=8.4 Hz, 1H), 5.20 (s, 2H), 4.02 (s, 3H), 3.97 (s, 3H). HRMS (ESI$^+$) calcd for $C_{15}H_{15}N_2O_6$ (M+H)$^+$ 319.0925, found 319.0931.

IF4f

To a solution of IF2f (700 mg, 4.19 mmol) and methyl 5-hydroxynicotinate (706 mg, 4.61 mmol) and Ph$_3$P (1.65 g, 6.29 mmol) in anhydrous THF (40 mL) at rt was added DIAD (1.27 g, 6.29 mmol) dropwise. After the mixture was allowed to stir at rt for 12 h and the solvent removed, the resulting residue was purified by flash column chromatography (EtOAc/hexanes) to afford IF4f as a yellow solid (320 mg, 255). $^1$H NMR (CDCl$_3$, 600 MHz) δ 7.88 (d, J=7.8 Hz, 1H), 7.82 (s, 1H), 7.61 (s, 1H), 7.45 (dd, J=7.8, 7.8 Hz, 1H), 7.40 (s, 1H), 7.35 (d, J=7.8 Hz, 1H), 5.40 (s, 2H), 3.93 (s, 3H), 2.42 (s, 3H). HRMS (ESI$^+$) calcd for $C_{15}H_{15}N_2O_5$ (M+H)$^+$ 303.0976, found 303.0980.

IF4g

In a manner similar to that described for the preparation of compound IF4a, coupling of IF3g (1.54 g, 6.58 mmol) afforded IF4g as a light yellow solid (1.42 g, 70%). $^1$H NMR (CDCl$_3$, 600 MHz) δ 8.90 (s, 1H), 8.57 (d, J=2.4 Hz, 1H), 8.08 (dd, J=7.8, 7.8 Hz, 1H), 8.89 (s, 1H), 7.85 (dd, J=6.6, 6.6 Hz, 1H), 7.38 (dd, J=7.8, 7.8 Hz, 1H), 5.30 (s, 2H), 3.97 (s, 3H). HRMS (ESI$^+$) calcd for $C_{14}H_{12}FN_2O_5$ (M+H)$^+$ 307.0725, found 307.0733.

IF4h

In a manner similar to that described for the preparation of compound IF4f, a Mitsunobu reaction of IF2h (500 mg, 3.00 mmol) afforded IF4h as a light yellow solid (400 mg, 44%). $^1$H NMR (DMSO-d$_6$, 600 MHz) δ 8.24 (s, 1H), 8.08 (s, 1H), 7.80 (s, 1H), 7.78 (d, J=8.4 Hz, 1H), 7.55 (d, J=8.4 Hz, 1H), 7.27 (s, 1H), 5.54 (s, 2H), 3.84 (s, 3H), 3.33 (s, 3H). HRMS (ESI$^+$) calcd for $C_{15}H_{15}N_2O_5$ (M+H)$^+$ 303.0976, found 303.0976.

IF4i

In a manner similar to that described for the preparation of compound IF4f, a Mitsunobu reaction of IF2i (1.18 g, 6.88 mmol) afforded IF4i as a yellow solid (490 mg, 23%). $^1$H NMR (CDCl$_3$, 600 MHz) δ 8.89 (d, J=1.4 Hz, 1H), 8.56 (d, J=3.0 Hz, 1H), 8.18 (dd, J$_1$=7.0 Hz, J$_2$=2.3 Hz, 1H), 7.85 (dd, J$_1$=2.9 Hz, J$_2$=1.8 Hz, 1H), 7.74-7.71 (m, 1H), 7.36 (dd, J$_1$=10.2 Hz, J$_2$=8.7 Hz, 1H), 5.19 (s, 2H), 3.97 (s, 3H). HRMS (ESI$^+$) calcd for $C_{14}H_{12}FN_2O_5$ (M+H)$^+$ 307.0725, found 307.0731.

IF4j

In a manner similar to that described for the preparation of compound IF4a, coupling of IF3j (1.28 g, 5.56 mmol) afforded IF4j as a white solid (540 mg, 32%). $^1$H NMR (CDCl$_3$, 600 MHz) δ 8.88 (d, J=1.2 Hz, 1H), 8.57 (d, J=2.9 Hz, 1H), 8.13 (s, 1H), 8.04 (s, 1H), 7.86 (dd, J$_1$=2.9 Hz, J$_2$=1.8 Hz, 1H), 7.59 (s, 1H), 5.20 (s, 2H), 3.97 (s, 3H), 2.51 (s, 3H). HRMS (ESI$^+$) calcd for $C_{15}H_{15}N_2O_5$ (M+H)$^+$ 303.0976, found 303.0967.

IF4k

In a manner similar to that described for the preparation of compound IF4f, a Mitsunobu reaction of IF2k (322 mg, 1.88 mmol) afforded IF4k as a white solid (286 mg, 49%). $^1$H NMR (CDCl$_3$, 600 MHz) δ 8.90 (d, J=1.4 Hz, 1H), 8.59 (d, J=2.9 Hz, 1H), 8.16 (s, 1H), 7.93 (dt, J$_1$=8.1 Hz, J$_2$=2.1 Hz, 1H), 7.87 (dd, J$_1$=2.9 Hz, J$_2$=1.7 Hz, 1H), 7.56 (d, J=8.2 Hz, 1H), 5.25 (s, 2H), 3.97 (s, 3H). HRMS (ESI$^+$) calcd for $C_{14}H_{12}FN_2O_5$ (M+H)+307.0725, found 307.0729.

IF4l

In a manner similar to that described for the preparation of compound IF4a, coupling of IF3l (700 mg, 3.15 mmol) afforded IF4l as a light yellow solid (600 mg, 62%). $^1$H NMR (CDCl$_3$, 600 MHz) δ 8.90 (s, 1H), 8.53 (d, J=3.0 Hz, 1H), 8.25-8.20 (m, 1H), 7.92 (dd, J=3.0, 1.8 Hz, 1H), 7.15 (dd, J=9.0, 9.0 Hz, 1H), 5.27 (s, 2H), 3.98 (s, 3H). HRMS (ESI$^+$) calcd for $C_{14}H_{11}F_2N_2O_5$ (M+H)$^+$ 325.0631, found 325.0639.

IF5a

To a solution of IF4a (1.14 g, 3.77 mmol) and NiCl$_2$.6H$_2$O (1.79 g, 7.54 mmol) in MeOH (150 mL) was slowly added NaBH$_4$ (570 mg, 15.1 mmol) and the mixture was allowed to stir at rt for 3 h. After the reaction was quenched with saturated NH$_4$Cl (50 ml), the mixture was extracted with EtOAc. The organic phase washed with water and brine, dried over anhydrous K$_2$CO$_3$, and concentrated in vacuo. The residue was purified by flash column chromatography (EtOAc/hexanes) to afford IF5a as a brownish solid (700 mg, 68%). $^1$H NMR (CDCl$_3$, 600 MHz) δ 8.84 (s, 1H), 8.54 (d, J=3.0 Hz, 1H), 7.85 (d, J=1.8 Hz, 1H), 7.01 (d, J=7.8 Hz, 1H), 7.76 (d, J=2.4 Hz, 1H), 6.62 (dd, J=8.4, 2.4 Hz, 1H), 5.04 (s, 2H), 3.96 (s, 3H), 3.61 (brs, 2H), 2.26 (s, 3H). HRMS (ESI$^+$) calcd for C$_{15}$H$_{17}$N$_2$O$_3$ (M+H)$^+$ 273.1234, found 273.1236.

IF5b

In a manner similar to that described for the preparation of compound IF5a, reduction of IF4b (1.43 g, 4.67 mmol) afforded IF5b as a light yellow solid (980 mg, 76%). $^1$H NMR (CDCl$_3$, 600 MHz) δ 8.84 (s, 1H), 8.53 (d, J=2.6 Hz, 1H), 7.86 (s, 1H), 6.90 (t, J=9.2 Hz, 1H), 6.77 (dd, J$_1$=5.6 Hz, J$_2$=2.7 Hz, 1H), 6.64-6.59 (m, 1H), 5.13 (s, 2H), 3.95 (s, 3H), 3.63 (br s, 2H). HRMS (ESI$^+$) calcd for C$_{14}$H$_{14}$FN$_2$O$_3$ (M+H)$^+$ 277.0983, found 277.0980.

IF5c

In a manner similar to that described for the preparation of compound IF5a, reduction of IF4c (1.65 g, 5.11 mmol) afforded IF5c as a light yellow solid (1.10 g, 74%). $^1$H NMR (CDCl$_3$, 600 MHz) δ 8.85 (d, J=1.7 Hz, 1H), 8.55 (d, J=2.9 Hz, 1H), 7.86-7.84 (m, 1H), 7.16 (d, J=8.6 Hz, 1H), 6.83 (d, J=2.9 Hz, 1H), 6.59 (dd, J$_1$=8.6 Hz, J$_2$=2.9 Hz, 1H), 5.15 (s, 2H), 3.95 (s, 3H), 3.75 (br s, 2H). HRMS (ESI$^+$) calcd for C$_{14}$H$_{14}$ClN$_2$O$_3$ (M+H)$^+$ 293.0687, found 293.0686.

IF5d

In a manner similar to that described for the preparation of compound IF5a, reduction of IF4d (1.30 g, 3.65 mmol) afforded IF5d as a light yellow solid (800 mg, 67%). $^1$H NMR (CDCl$_3$, 600 MHz) δ 8.86 (s, 1H), 8.54 (s, 1H), 7.83 (s, 1H), 7.47 (d, J=8.4 Hz, 1H), 6.91 (s, 1H), 6.63 (d, J=8.4 Hz, 1H), 5.25 (s, 2H), 4.02 (s, 2H), 3.95 (s, 3H). HRMS (ESI$^+$) calcd for C$_{15}$H$_{14}$F$_3$N$_2$O$_3$ (M+H)$^+$ 327.0952, found 327.0961.

IF5e

In a manner similar to that described for the preparation of compound IF5a, reduction of IF4e (1.50 g, 4.70 mmol) afforded IF5e as a light yellow solid (1.00 g, 74%). $^1$H NMR (CDCl$_3$, 600 MHz) δ 8.82 (d, J=1.2 Hz, 1H), 8.53 (d, J=3.0 Hz, 1H), 7.88 (dd, J=3.0, 1.8 Hz, 1H), 6.82 (d, J=3.0 Hz, 1H), 6.76 (d, J=9.0 Hz, 1H), 6.66 (dd, J=8.4, 3.0 Hz, 1H), 5.14 (s, 2H), 3.95 (s, 3H), 3.82 (s, 3H). HRMS (ESI$^+$) calcd for C$_{15}$H$_{17}$N$_2$O$_4$ (M+H)$^+$ 289.1183, found 289.1183.

IF5g

In a manner similar to that described for the preparation of compound IF5a, reduction of IF4g (1.42 g, 4.64 mmol) afforded IF5g as a light yellow solid (1.00 g, 78%). $^1$H NMR (CDCl$_3$, 600 MHz) δ 8.84 (d, J=1.2 Hz, 1H), 8.54 (d, J=3.0 Hz, 1H), 7.87 (dd, J=1.8, 1.8 Hz, 1H), 6.96 (dd, J=7.2, 7.2 Hz, 1H), 6.84-6.77 (m, 2H), 5.17 (s, 2H), 3.96 (s, 3H). HRMS (ESI$^+$) calcd for C$_{14}$H$_{14}$FN$_2$O$_3$ (M+H)$^+$ 277.0983, found 277.0988.

IF5h

In a manner similar to that described for the preparation of compound IF5a, reduction of IF4h (2.47 g, 8.18 mmol) afforded IF5h as a light yellow oil (1.77 g, 80%). $^1$H NMR (DMSO-d$_6$, 600 MHz) δ 7.86 (s, 1H), 7.63 (s, 1H), 7.25 (s, 1H), 6.93 (d, J=7.8 Hz, 1H), 6.59 (s, 1H), 6.55 (d, J=7.2 Hz, 1H), 5.30 (s, 2H), 4.99 (s, 2H), 3.84 (s, 3H), 2.02 (s, 3H). HRMS (ESI$^+$) calcd for C$_{15}$H$_{17}$N$_2$O$_3$ (M+H)$^+$ 273.1234, found 273.1239.

IF5i

In a manner similar to that described for the preparation of compound IF5a, reduction of IF4i (490 mg, 1.60 mmol) afforded IF5i as a white solid (150 mg, 34%). $^1$H NMR (CDCl$_3$, 600 MHz) δ 8.83 (s, 1H), 8.51 (d, J=2.4 Hz, 1H), 7.83-7.81 (m, 1H), 6.99 (dd, J$_1$=10.9 Hz, J$_2$=8.3 Hz, 1H), 6.85 (dd, J$_1$=8.5 Hz, J$_2$=2.0 Hz, 1H), 6.75-6.72 (m, 1H), 5.02 (s, 2H), 3.95 (s, 3H), 3.81 (br s, 2H). HRMS (ESI$^+$) calcd for C$_{14}$H$_{14}$FN$_2$O$_3$ (M+H)±277.0983, found 277.0982.

IF5j

A solution of IF4j (540 mg, 1.79 mmol) and SnCl$_2$ (2.37 g, 12.5 mmol) in MeOH (10 mL) in a seal tube was heated at 75° C. for 2 h before it was quenched with saturated Na$_2$CO$_3$. The mixture was filtered and the filtrate was diluted with water. The resulting mixture was extracted with EtOAc and the organic phase was washed with water and brine, dried over anhydrous Na$_2$SO$_4$, and concentrated in vacuo. The residue was purified by flash column chromatography (EtOAc/hexanes) to afford IF5j as a white solid (103 mg, 21%). $^1$H NMR (CDCl$_3$, 600 MHz) δ 8.82 (d, J=1.8 Hz, 1H), 8.53 (d, J=2.9 Hz, 1H), 7.83 (dd, J$_1$=2.9 Hz, J$_2$=1.8 Hz, 1H), 6.63 (s, 1H), 6.55 (s, 1H), 6.48 (s, 1H), 5.01 (s, 2H), 3.94 (s, 3H), 3.68 (br s, 2H), 2.27 (s, 3H). HRMS (ESI$^+$) calcd for C$_{15}$H$_{17}$N$_2$O$_3$ (M+H)+273.1234, found 273.1225.

IF5k

In a manner similar to that described for the preparation of compound IF5a, reduction of IF4k (286 mg, 0.94 mmol) afforded IF5k as a white solid (92 mg, 35%). $^1$H NMR (CDCl$_3$, 600 MHz) δ 8.84 (s, 1H), 8.52 (d, J=2.8 Hz, 1H), 7.82-7.80 (m, 1H), 6.52-6.49 (m, 2H), 6.34 (dt, J$_1$=10.4 Hz, J$_2$=2.0 Hz, 1H), 5.03 (s, 2H), 3.95 (s, 3H), 3.85 (br s, 2H). HRMS (ESI$^+$) calcd for C$_{14}$H$_{14}$FN$_2$O$_3$ (M+H)$^+$ 277.0983, found 277.0983.

IF5l

In a manner similar to that described for the preparation of compound IF5a, reduction of IF4l (600 mg, 1.94 mmol) afforded IF5l as a light brownish oil (300 mg, 53%). $^1$H NMR (CDCl$_3$, 600 MHz) δ 8.86 (d, J=1.2 Hz, 1H), 8.53 (d, J=3.0 Hz, 1H), 7.92 (dd, J=2.4, 1.2 Hz, 1H), 6.81-6.76 (m, 2H), 5.20 (s, 2H), 3.96 (s, 3H). HRMS (ESI$^+$) calcd for C$_{14}$H$_{13}$F$_2$N$_2$O$_3$ (M+H)$^+$ 295.0889, found 295.0893.

IF6a

A solution of IF5a (700 mg, 2.57 mmol) in NH$_3$/MeOH (ca. 7N, 10 mL) in a seal tube was heated at 70° C. for 24 h. After the solvent was evaporated in vacuo, the residue was dissolved in EtOAc (100 mL) and the solution was washed with H$_2$O (150 mL) and then with brine (100 mL). The organic layer was dried over Na$_2$SO$_4$, concentrated, and the residue was purified by flash column chromatography (5% MeOH/CH$_2$Cl$_2$) to afford IF6a as a light brownish solid (250 mg, 38%). $^1$H NMR (DMSO-d$_6$, 600 MHz) δ 8.64 (d, J=1.2 Hz, 1H), 8.46 (d, J=2.4 Hz, 1H), 8.14 (s, 1H), 7.83 (d, J=1.8 Hz, 1H), 7.61 (s, 1H), 6.87 (d, J=8.4 Hz, 1H), 6.64 (d, J=1.8 Hz, 1H), 6.46 (dd, J=7.8, 2.4 Hz, 1H), 5.06 (s, 2H), 4.89 (s, 2H), 2.15 (s, 3H). HRMS (ESI$^+$) calcd for C$_{14}$H$_{16}$N$_3$O$_2$ (M+H)$^+$ 258.1237, found 258.1239.

IF6b

In a manner similar to that described for the preparation of compound IF6a, aminolysis of IF5b (980 mg, 3.55 mmol) afforded IF6b as a light yellow solid (600 mg, 65%). $^1$H NMR (DMSO-d$_6$, 600 MHz) δ 8.65 (s, 1H), 8.46 (d, J=2.4 Hz, 1H), 8.14 (s, 1H), 7.84 (s, 1H), 7.61 (s, 1H), 6.90 (dd, J=9.0, 9.0 Hz, 1H), 6.69-6.65 (m, 1H), 6.57-6.52 (m, 1H), 5.13 (s, 2H), 5.03 (s, 2H). HRMS (ESI$^+$) calcd for C$_{13}$H$_{13}$FN$_3$O$_2$ (M+H)$^+$ 262.0986, found 262.0992.

IF6c

In a manner similar to that described for the preparation of compound IF6a, aminolysis of IF5c (1.10 g, 3.76 mmol) afforded IF6b as an off-white solid (800 mg, 77%). $^1$H NMR (DMSO-d$_6$, 600 MHz) δ 8.66 (s, 1H), 8.46 (d, J=2.4 Hz, 1H), 8.15 (s, 1H), 7.83 (s, 1H), 7.62 (s, 1H), 7.10 (d, J=9.0 Hz, 1H), 6.75 (d, J=3.0 Hz, 1H), 6.55 (dd, J=9.0, 3.0 Hz, 1H), 5.33 (s, 2H), 5.13 (s, 2H). HRMS (ESI$^+$) calcd for C$_{13}$H$_{13}$ClN$_3$O$_2$ (M+H)$^+$ 278.0691, found 278.0696.

IF6d

In a manner similar to that described for the preparation of compound IF6a, aminolysis of IF5d (800 mg, 2.45 mmol) afforded IF6d as a light brownish solid (400 mg, 52%). $^1$H NMR (DMSO-d$_6$, 600 MHz) δ 8.67 (s, 1H), 8.44 (s, 1H), 8.17 (s, 1H), 7.81 (s, 1H), 7.63 (s, 1H), 7.38 (d, J=8.4 Hz, 1H), 6.82 (s, 1H), 6.60 (d, J=8.4 Hz, 1H), 5.92 (s, 2H), 5.18 (s, 2H). HRMS (ESI$^+$) calcd for C$_{14}$H$_{13}$F$_3$N$_3$O$_2$ (M+H)$^+$ 312.0954, found 312.0965.

IF6e

In a manner similar to that described for the preparation of compound IF6a, aminolysis of IF5e (1.00 g, 3.47 mmol) afforded IF6e as a light brownish solid (400 mg, 42%). $^1$H NMR (DMSO-d$_6$, 600 MHz) δ 8.63 (s, 1H), 8.43 (s, 1H), 8.14 (s, 1H), 7.81 (s, 1H), 7.59 (s, 1H), 6.77 (d, J=9.0 Hz, 1H), 6.65 (d, J=3.0 Hz, 1H), 6.54 (dd, J=9.0, 3.0 Hz, 1H), 5.07 (s, 2H), 4.70 (s, 2H), 3.70 (s, 3H). HRMS (ESI$^+$) calcd for C$_{14}$H$_{16}$N$_3$O$_3$ (M+H)$^+$ 274.1186, found 274.1197.

IF6f

In a manner similar to that described for the preparation of compound IF6a, aminolysis of IF5f (2.00 g, 7.34 mmol) afforded IF6f as a light yellow solid (1.60 g, 85%). $^1$H NMR (DMSO-d$_6$, 600 MHz) δ 8.63 (s, 1H), 8.46 (d, J=2.4 Hz, 1H), 8.13 (s, 1H), 7.84 (s, 1H), 7.60 (s, 1H), 6.89 (dd, J=7.5, 7.5 Hz, 1H), 6.65 (d, J=7.8 Hz, 2H), 5.12 (s, 2H), 4.90 (s, 2H), 2.03 (s, 3H). HRMS (ESI$^+$) calcd for C$_{14}$H$_{16}$N$_3$O$_2$ (M+H)$^+$ 258.1237, found 258.1238.

IF6g

In a manner similar to that described for the preparation of compound IF6a, aminolysis of IF5g (1.00 g, 3.62 mmol) afforded IF6G as a light yellow solid (600 mg, 64%). $^1$H NMR (DMSO-d$_6$, 600 MHz) δ 8.65 (s, 1H), 8.47 (d, J=2.4 Hz, 1H), 8.14 (s, 1H), 7.86 (s, 1H), 7.61 (s, 1H), 6.88 (dd, J=7.2. 7.2 Hz, 1H), 6.77 (dd, J=8.4, 8.4 Hz, 1H), 6.65 (dd, J=6.6, 6.6 Hz, 1H) 5.20 (s, 2H), 5.18 (s, 2H). HRMS (ESI$^+$) calcd for C$_{13}$H$_{13}$FN$_3$O$_2$ (M+H)$^+$ 262.0986, found 262.0992.

IF6h

In a manner similar to that described for the preparation of compound IF6a, aminolysis of IF5h (20 mg, 0.07 mmol) afforded IF6h as a light yellow solid (15 mg, 83%). $^1$H NMR (DMSO-d$_6$, 600 MHz) δ 8.05 (s, 1H), 7.73 (s, 1H), 7.59 (s, 1H), 7.51 (s, 1H), 7.33 (s, 1H), 6.93 (d, J=7.8 Hz, 1H), 6.59 (s, 1H), 6.54 (d, J=6.0 Hz, 1H), 5.24 (s, 2H), 4.99 (s, 2H), 2.02 (s, 3H). HRMS (ESI$^+$) calcd for C$_{14}$H$_{16}$N$_3$O$_2$ (M+H)$^+$ 258.1237, found 258.1257.

IF6i

In a manner similar to that described for the preparation of compound IF6a, aminolysis of IF5i (175 mg, 0.63 mmol) afforded IF6i as a white solid (141 mg, 85%). $^1$H NMR (CD$_3$OD, 600 MHz) δ 8.60 (d, J=1.8 Hz, 1H), 8.38 (d, J=2.7 Hz, 1H), 7.85 (t, J=2.3 Hz, 1H), 6.94-6.90 (m, 2H), 6.71-6.67 (m, 1H), 5.04 (s, 2H). HRMS (ESI$^+$) calcd for C$_{13}$H$_{13}$FN$_3$O$_2$ (M+H)$^+$ 262.0986, found 262.0991.

IF6j

In a manner similar to that described for the preparation of compound IF6a, aminolysis of IF5j (100 mg, 0.37 mmol) afforded IF6j as a white solid (77 mg, 81%). $^1$H NMR (CDCl$_3$, 600 MHz) δ 8.58 (d, J=1.8 Hz, 1H), 8.44 (d, J=2.9 Hz, 1H), 7.73-7.71 (m, 1H), 6.73 (br s, 1H), 6.58 (s, 1H), 6.51 (s, 1H), 6.45 (s, 1H), 6.44 (br s, 1H), 4.96 (s, 2H), 3.67 (br s, 2H), 2.24 (s, 3H). HRMS (ESI$^+$) calcd for C$_{14}$H$_{16}$N$_3$O$_2$ (M+H)$^+$ 258.1237, found 258.1234.

IF6k

In a manner similar to that described for the preparation of compound IF6a, aminolysis of IF5k (82 mg, 0.30 mmol) afforded IF6k as a white solid (75 mg, 96%). $^1$H NMR (CD$_3$OD, 600 MHz) δ 8.61 (d, J=1.8 Hz, 1H), 8.41 (d, J=2.9 Hz, 1H), 7.86 (t, J=2.1 Hz, 1H), 6.56 (s, 1H), 6.42 (d, J=9.5 Hz, 1H), 6.34 (dt, J$_1$=11.2 Hz, J$_2$=2.0 Hz, 1H), 5.08 (s, 2H). HRMS (ESI$^+$) calcd for C$_{13}$H$_{13}$FN$_3$O$_2$ (M+H)$^+$ 262.0986, found 262.0990.

IF6l

In a manner similar to that described for the preparation of compound IF6a, aminolysis of IF5l (300 mg, 1.02 mmol) afforded IF6l as a brown solid (250 mg, 88%). $^1$H NMR (DMSO-d$_6$, 600 MHz) δ 8.68 (s, 1H), 8.47 (d, J=2.4 Hz, 1H), 8.13 (s, 1H), 7.90 (s, 1H), 7.62 (s, 1H), 6.90-6.80 (m, 2H), 5.19 (s, 2H), 5.10 (s, 2H). HRMS (ESI$^+$) calcd for C$_{13}$H$_{12}$F$_2$N$_3$O$_2$ (M+H)$^+$ 280.0892, found 280.0895.

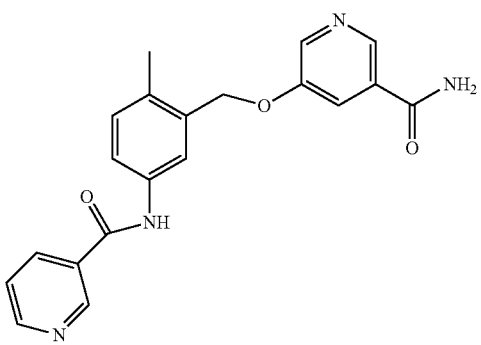 [SMILES: Cc1ccc(NC(=O)c2cccnc2)cc1COc1cncc(C(N)=O)c1]

N-(3-(((5-Carbamoylpyridin-3-yl)oxy)methyl)-4-methylphenyl)nicotinamide (F1-1)

A mixture of IF6a (39 mg, 0.15 mmol), nicotinic acid (23 mg, 0.18 mmol) and EDC·HCl (36 mg, 0.18 mmol) in CH$_2$Cl$_2$/DMF (1:1, 8 mL) was allowed to stir at rt for 12 h. After the reaction was quenched with saturated NH$_4$Cl (10 mL), the mixture was extracted with EtOAc and the organic phase was washed with water and brine, dried over anhydrous Na$_2$SO$_4$, and concentrated in vacuo. The residue was purified by flash column chromatography (MeOH/CH$_2$Cl$_2$) to afford compound F1-1 as a white solid (36 mg, 65%). $^1$H NMR (DMSO-d$_6$, 600 MHz) δ 10.42 (s, 1H), 9.10 (s, 1H), 8.75 (d, J=4.2 Hz, 1H), 8.67 (s, 1H), 8.52 (s, 1H), 8.28 (d, J=7.8 Hz, 1H), 8.15 (s, 1H), 7.89 (s, 1H), 7.83 (s, 1H), 7.69 (d, J=8.4 Hz, 1H), 7.63 (s, 1H), 7.58-7.52 (m, 1H), 7.24 (d, J=7.8 Hz, 1H), 5.23 (s, 2H), 2.32 (s, 3H). HRMS (ESI$^+$) calcd for C$_{20}$H$_{19}$N$_4$O$_3$ (M+H)$^+$ 363.1452, found 363.1460.

The following compounds were prepared through an amide formation reaction in a manner similar to that described for the preparation of compound F1-1.

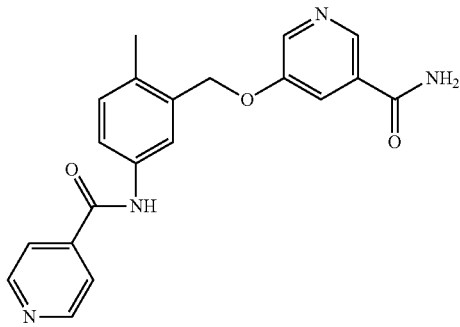 [SMILES: Cc1ccc(NC(=O)c2ccncc2)cc1COc1cncc(C(N)=O)c1]

5-((5-(Isonicotinamido)-2-methylbenzyl)oxy)nicotinamide (F1-2)

White solid (35 mg, 62%). $^1$H NMR (DMSO-d$_6$, 600 MHz) δ 10.49 (s, 1H), 8.78 (d, J=6.0 Hz, 2H), 8.67 (d, J=1.8 Hz, 1H), 8.51 (d, J=3.0 Hz, 1H), 8.15 (s, 1H), 7.88 (dd, J=2.4, 2.4 Hz, 1H), 7.85 (d, J=5.4 Hz, 2H), 7.83 (d, J=1.8 Hz, 1H), 7.69 (dd, J=8.4, 1.8 Hz, 1H), 7.63 (s, 1H), 7.25 (d, J=7.8, 1H), 5.23 (s, 2H), 2.32 (s, 3H). HRMS (ESI$^+$) calcd for C$_{20}$H$_{19}$N$_4$O$_3$ (M+H)$^+$ 363.1452, found 363.1457.

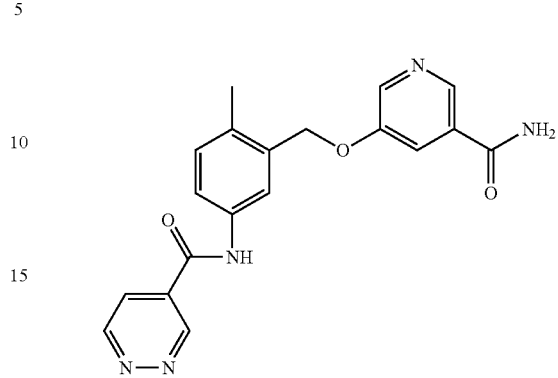

N-(3-(((5-Carbamoylpyridin-3-yl)oxy)methyl)-4-methylphenyl)pyridazine-4-carboxamide (F1-3)

White solid (43 mg, 76%). $^1$H NMR (DMSO-d$_6$, 600 MHz) δ 10.70 (s, 1H), 9.64 (s, 1H), 9.48 (d, J=5.4 Hz, 1H), 8.67 (s, 1H), 8.51 (d, J=2.4 Hz, 1H), 8.15 (s, 1H), 8.11 (d, J=3.0 Hz, 1H), 7.88 (s, 1H), 7.82 (s, 1H), 7.69 (d, J=7.8 Hz, 1H), 7.63 (s, 1H), 7.27 (d, J=8.4 Hz, 1H), 5.24 (s, 2H), 2.33 (s, 3H). HRMS (ESI$^+$) calcd for C$_{19}$H$_{18}$N$_5$O$_3$ (M+H)$^+$ 364.1404, found 364.1413.

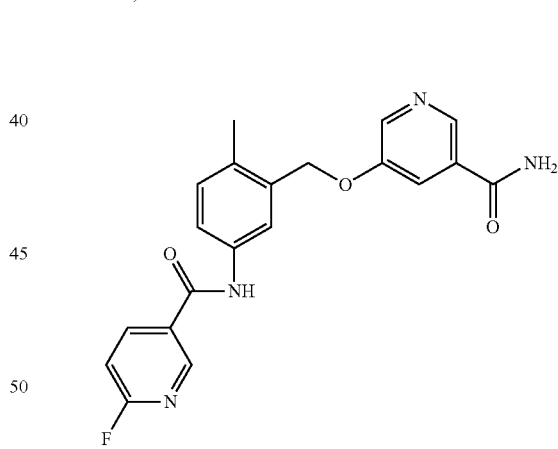

N-(3-(((5-Carbamoylpyridin-3-yl)oxy)methyl)-4-methylphenyl)-6-fluoronicotinamide (F1-4)

White solid (50 mg, 85%). $^1$H NMR (DMSO-d$_6$, 600 MHz) δ 10.47 (s, 1H), 8.81 (s, 1H), 8.67 (s, 1H), 8.54-8.46 (m, 2H), 8.17 (s, 1H), 7.89 (s, 1H), 7.82 (s, 1H), 7.68 (d, J=7.8 Hz, 1H), 7.63 (s, 1H), 7.35 (d, J=8.4 Hz, 1H), 7.24 (d, J=8.4 Hz, 1H), 5.23 (s, 2H), 2.32 (s, 3H). HRMS (ESI$^+$) calcd for C$_{20}$H$_{18}$FN$_4$O$_3$ (M+H)$^+$ 381.1357, found 381.1368.

161

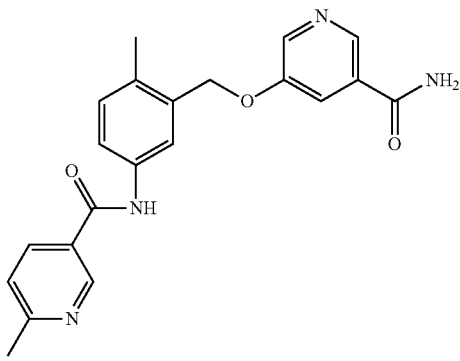 [SMILES: Cc1ccc(C(=O)Nc2ccc(C)c(COc3cncc(C(N)=O)c3)c2)cn1]

N-(3-(((5-Carbamoylpyridin-3-yl)oxy)methyl)-4-methylphenyl)-6-methylnicotinamide (F1-5)

White solid (32 mg, 55%). $^1$H NMR (DMSO-$d_6$, 600 MHz) δ 10.33 (s, 1H), 8.99 (d, J=2.8 Hz, 1H), 8.67 (s, 1H), 8.51 (s, 1H), 8.19 (dd, J=8.1, 2.1 Hz, 1H), 8.15 (s, 1H), 7.88 (s, 1H), 7.82 (d, J=1.8 Hz, 1H), 7.67 (dd, J=7.8, 2.4 Hz, 1H), 7.63 (s, 1H), 7.41 (d, J=8.4 Hz, 1H), 7.24 (d, J=8.4 Hz, 1H), 5.22 (s, 2H), 2.55 (s, 3H), 2.32 (s, 3H). HRMS (ESI$^+$) calcd for $C_{21}H_{21}N_4O_3$ (M+H)$^+$ 377.1608, found 377.1617.

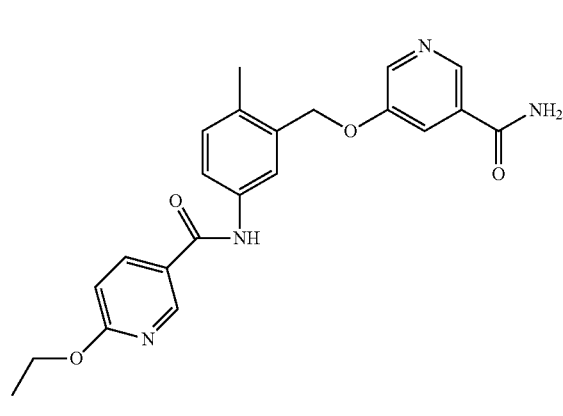 [SMILES: CCOc1ccc(C(=O)Nc2ccc(C)c(COc3cncc(C(N)=O)c3)c2)cn1]

N-(3-(((5-Carbamoylpyridin-3-yl)oxy)methyl)-4-methylphenyl)-6-ethoxynicotinamide (F1-6)

White solid (10 mg, 17%). $^1$H NMR (DMSO-$d_6$, 600 MHz) δ 10.21 (s, 1H), 8.76 (d, J=2.4 Hz, 1H), 8.67 (d, J=1.2 Hz, 1H), 8.51 (d, J=2.4 Hz, 1H), 8.21 (dd, J=2.4, 8.4 Hz, 1H), 8.15 (s, 1H), 7.88 (dd, J=2.1, 2.1 Hz, 1H), 7.81 (d, J=1.8 Hz, 1H), 7.66 (dd, J=1.8, 7.8 Hz, 1H), 7.62 (s, 1H), 7.22 (d, J=8.4 Hz, 1H), 6.91 (d, J=8.4 Hz, 1H), 5.22 (s, 2H), 4.39 (q, J=7.2 Hz, 2H), 2.31 (s, 3H), 1.34 (t, J=7.2 Hz, 3H). HRMS (ESI$^+$) calcd for $C_{22}H_{23}H_4O_4$ (M+H)$^+$ 407.1714, found 407.1721.

162

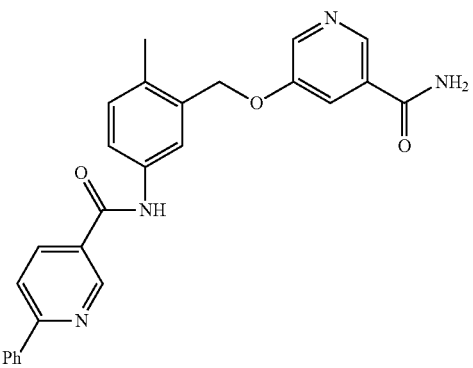 [SMILES: Cc1ccc(NC(=O)c2ccc(-c3ccccc3)nc2)cc1COc1cncc(C(N)=O)c1]

N-(3-(((5-Carbamoylpyridin-3-yl)oxy)methyl)-4-methylphenyl)-6-phenylnicotinamide (F1-7)

White solid (40 mg, 59%). $^1$H NMR (DMSO-$d_6$, 600 MHz) δ 10.45 (s, 1H), 9.19 (s, 1H), 8.67 (s, 1H), 8.52 (s, 1H), 8.39 (d, J=10.2 Hz, 1H), 8.20-8.12 (m, 4H), 7.89 (s, 1H), 7.86 (s, 1H), 7.72 (d, J=6.6 Hz, 1H), 7.63 (s, 1H), 7.57-7.47 (m, 3H), 7.26 (d, J=7.2 Hz, 1H), 5.24 (s, 2H), 2.33 (s, 3H). HRMS (ESI$^+$) calcd for $C_{26}H_{23}N_4O_3$ (M+H)$^+$ 439.1765, found 439.1775.

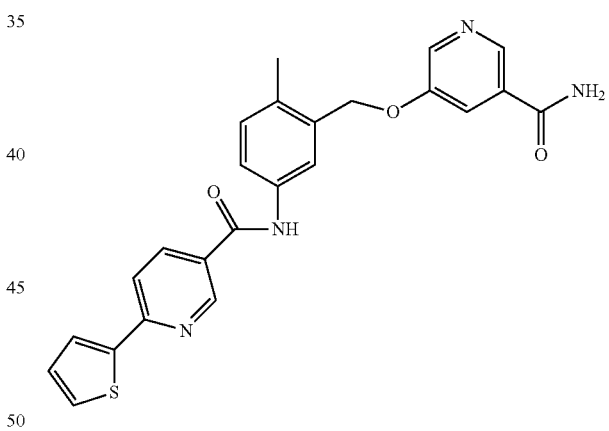

N-(3-(((5-carbamoylpyridin-3-yl)oxy)methyl)-4-methylphenyl)-6-(thiophen-2-yl)nicotinamide (F1-8)

White solid (50 mg, 74%). $^1$H NMR (DMSO-$d_6$, 600 MHz) δ 10.39 (s, 1H), 9.04 (d, J=1.2 Hz, 1H), 8.67 (s, 1H), 8.52 (d, J=3.0 Hz, 1H), 8.33 (dd, J=2.4, 8.4 Hz, 1H), 8.15 (s, 1H), 8.07 (d, J=7.8 Hz, 1H), 7.95 (d, J=2.4 Hz, 1H), 7.89 (s, 1H), 7.84 (s, 1H), 7.74 (d, J=5.4 Hz, 1H), 7.72-7.67 (m, 1H), 7.63 (s, 1H), 7.25 (d, J=7.8 Hz, 1H), 7.22 (dd, J=4.5, 4.5 Hz, 1H), 5.24 (s, 2H), 2.33 (s, 3H). HRMS (ESI$^+$) calcd for $C_{24}H_{21}H_4O_3S$ (M+H)$^+$ 445.1329, found 445.1336.

163

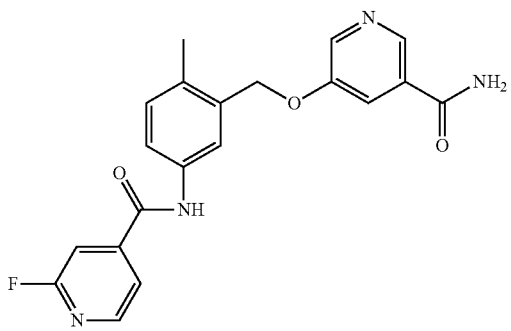 [SMILES: Cc1ccc(NC(=O)c2ccnc(F)c2)cc1COc1cncc(C(N)=O)c1]

5-((5-(2-Fluoroisonicotinamido)-2-methylbenzyl)oxy)nicotinamide (F1-9)

White solid (50 mg, 85%). $^1$H NMR (DMSO-d$_6$, 600 MHz) δ 10.55 (s, 1H), 8.67 (s, 1H), 8.51 (d, J=3.0 Hz, 1H), 8.44 (d, J=4.8 Hz, 1H), 8.15 (s, 1H), 7.88 (s, 1H), 7.84-7.80 (m, 2H), 7.69 (d, J=8.4 Hz, 1H), 7.66 (s, 1H), 7.63 (s, 1H), 7.26 (d, J=8.4 Hz, 1H), 5.24 (s, 2H), 2.33 (s, 3H). HRMS (ESI$^+$) calcd for $C_{20}H_{18}FN_4O_3$ (M+H)$^+$ 381.1357, found 381.1367.

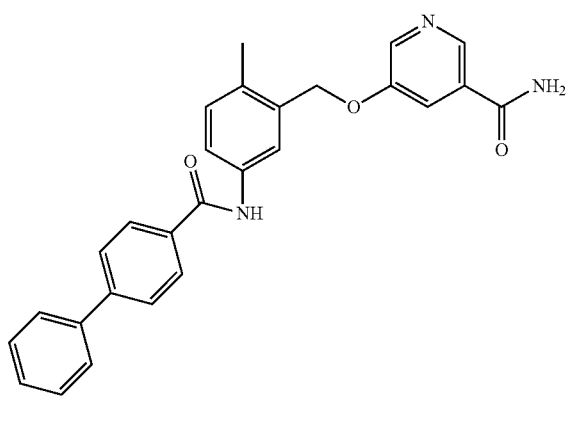 [SMILES: Cc1ccc(NC(=O)c2ccc(-c3ccccc3)cc2)cc1COc1cncc(C(N)=O)c1]

5-((5-([1,1'-Biphenyl]-4-ylcarboxamido)-2-methylbenzyl)oxy)nicotinamide (F1-10)

White solid (25 mg, 37%). $^1$H NMR (DMSO-d$_6$, 600 MHz) δ 10.28 (s, 1H), 8.67 (d, J=1.2 Hz, 1H), 8.52 (d, J=2.4 Hz, 1H), 8.15 (s, 1H), 8.06 (d, J=8.4 Hz, 2H), 7.89 (s, 1H), 7.87 (d, J=1.8 Hz, 1H), 7.83 (d, J=9.0 Hz, 2H), 7.76 (d, J=6.6 Hz, 2H), 7.72 (dd, J=8.4, 1.8 Hz, 1H), 7.63 (s, 1H), 7.51 (dd, J=7.8, 7.8 Hz, 2H), 7.43 (dd, J=7.2, 7.2 Hz, 1H), 7.24 (d, J=8.4 Hz, 1H), 5.23 (s, 2H), 2.33 (s, 3H). HRMS (ESI$^+$) calcd for $C_{27}H_{24}N_3O_3$ (M+H)$^+$ 438.1812, found 438.1821.

164

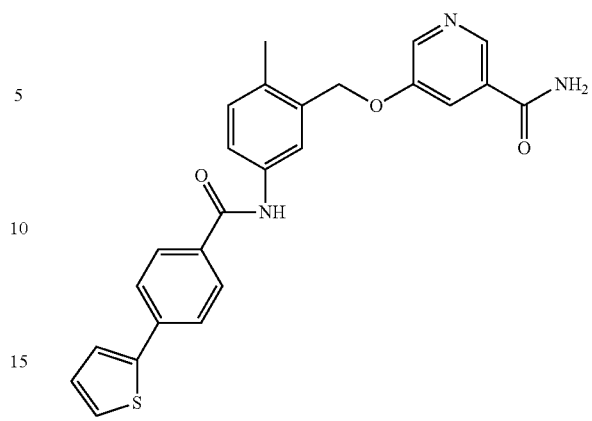

5-(((2-Methyl-5-(4-(thiophen-2-yl)benzamido)benzyl)oxy)nicotinamide (F1-11)

White solid (30 mg, 44%). $^1$H NMR (DMSO-d$_6$, 600 MHz) δ 10.26 (s, 1H), 8.67 (s, 1H), 8.52 (d, J=3.0 Hz, 1H), 8.15 (s, 1H), 8.01 (d, J=8.4 Hz, 2H), 7.89 (s, 1H), 7.85 (s, 1H), 7.81 (d, J=8.4 Hz, 2H), 7.70 (d, J=8.4 Hz, 1H), 7.68 (d, J=3.6 Hz, 1H), 7.65 (d, J=5.4 Hz, 1H), 7.63 (s, 1H), 7.23 (d, J=8.4 Hz, 1H), 7.19 (dd, J=4.2 Hz, 1H), 5.23 (s, 2H), 2.32 (s, 3H). HRMS (ESP) calcd for $C_{25}H_{22}N_3O_3S$ (M+H)$^+$ 444.1376, found 444.1382.

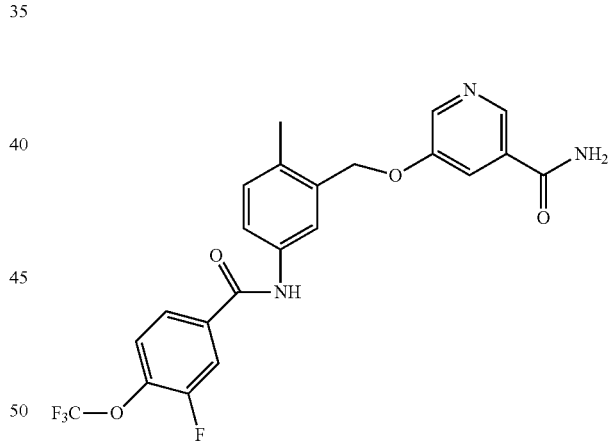

5-((5-(3-Fluoro-4-(trifluoromethoxy)benzamido)-2-methylbenzyl)oxy)nicotinamide (F1-12)

White solid (52 mg, 73%). $^1$H NMR (DMSO-do, 600 MHz) δ 10.39 (s, 1H), 8.67 (s, 1H), 8.51 (d, J=2.4 Hz, 1H), 8.15 (s, 1H), 8.08-8.04 (m, 1H), 7.92-7.86 (m, 2H), 7.81 (s, 1H), 7.75 (dd, J=8.1, 8.1 Hz, 1H), 7.68 (dd, J=1.8, 8.4 Hz, 1H), 7.63 (s, 1H), 7.25 (d, J=7.8 Hz, 1H), 5.23 (s, 2H), 2.32 (s, 3H). HRMS (ESI$^+$) calcd for $C_{22}H_{18}F_4N_3O_4$ (M+H)$^+$ 464.1228, found 464.1236.

165

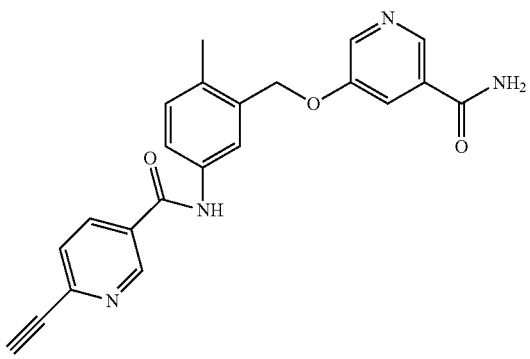 [SMILES: C#Cc1ccc(C(=O)Nc2ccc(C)c(COc3cncc(C(N)=O)c3)c2)cn1]

N-(3-(((5-Carbamoylpyridin-3-yl)oxy)methyl)-4-methylphenyl)-6-ethynylnicotinamide (F1-13)

Pale solid (17 mg, 37%). $^1$H NMR (DMSO-d$_6$, 600 MHz) δ 10.47 (s, 1H), 9.07 (s, 1H), 8.67 (s, 1H), 8.51 (s, 1H), 8.31 (d, J=7.8 Hz, 1H), 8.15 (s, 1H), 7.88 (s, 1H), 7.82 (s, 1H), 7.73 (d, J=8.4 Hz, 1H), 7.69 (d, J=9.0 Hz, 1H), 7.63 (s, 1H), 7.25 (d, J=7.8 Hz, 1H), 5.23 (s, 2H), 4.55 (s, 1H), 2.32 (s, 3H). HRMS (ESI$^+$) calcd for C$_{22}$H$_{19}$N$_4$O$_3$ (M+H)$^+$ 387.1452, found 387.1454.

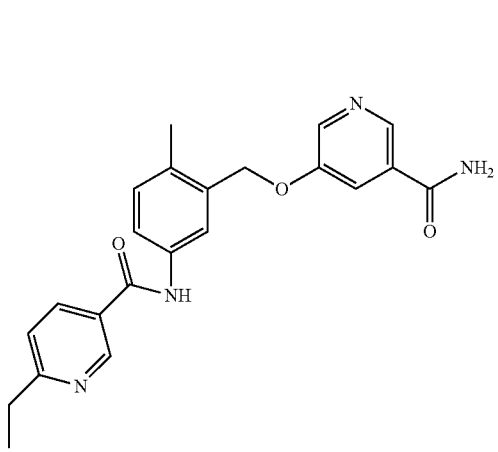 [SMILES: CCc1ccc(C(=O)Nc2ccc(C)c(COc3cncc(C(N)=O)c3)c2)cn1]

N-(3-(((5-Carbamoylpyridin-3-yl)oxy)methyl)-4-methylphenyl)-6-ethylnicotinamide (F1-14)

White solid (30 mg, 66%). $^1$H NMR (DMSO-d$_6$, 600 MHz) δ 10.33 (s, 1H), 9.00 (s, 1H), 8.67 (s, 1H), 8.51 (s, 1H), 8.20 (d, J=8.4 Hz, 1H), 8.15 (s, 1H), 7.88 (s, 1H), 7.83 (s, 1H), 7.68 (d, J=9.9 Hz, 1H), 7.63 (s, 1H), 7.42 (d, J=8.4 Hz, 1H), 7.24 (d, J=8.4 Hz, 1H), 5.23 (s, 2H), 2.83 (q, J=7.8 Hz, 2H), 2.32 (s, 3H), 1.26 (t, J=7.8 Hz, 3H). HRMS (ESI$^+$) calcd for C$_{22}$H$_{23}$N$_4$O$_3$ (M+H)$^+$ 391.1765, found 391.1765.

166

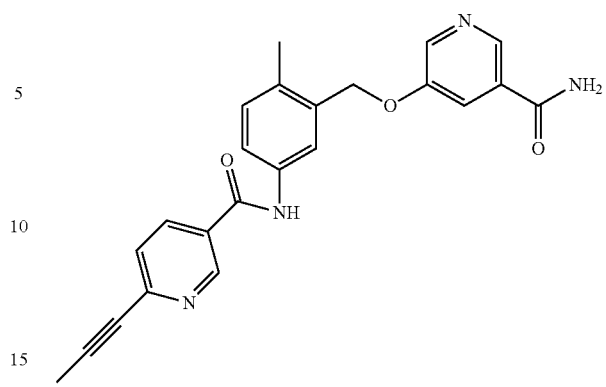

N-(3-(((5-Carbamoylpyridin-3-yl)oxy)methyl)-4-methylphenyl)-6-(prop-1-yn-1-yl)nicotinamide (F1-15)

Pale solid (21 mg, 45%). $^1$H NMR (DMSO-d$_6$, 600 MHz) δ 10.42 (s, 1H), 9.03 (s, 1H), 8.67 (s, 1H), 8.51 (s, 1H), 8.26 (d, J=8.4 Hz, 1H), 8.15 (s, 1H), 7.88 (s, 1H), 7.82 (s, 1H), 7.68 (d, J=8.4 Hz, 1H), 7.63 (s, 1H), 7.59 (d, J=8.4 Hz, 1H), 7.24 (d, J=9.0 Hz, 1H), 5.23 (s, 2H), 2.32 (s, 3H), 2.12 (s, 3H). HRMS (ESI$^+$) calcd for C$_{23}$H$_{21}$N$_4$O$_3$ (M+H)$^+$ 401.1608, found 401.1612.

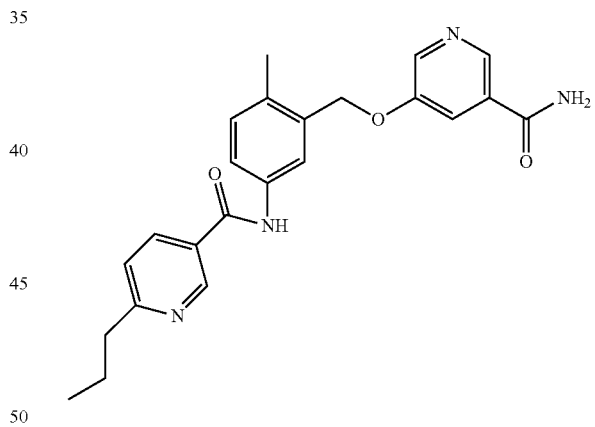

N-(3-(((5-Carbamoylpyridin-3-yl)oxy)methyl)-4-methylphenyl)-6-propylnicotinamide (F1-16)

White solid (21 mg, 43%). $^1$H NMR (DMSO-d$_6$, 600 MHz) δ 10.34 (s, 1H), 9.00 (s, 1H), 8.67 (s, 1H), 8.51 (s, 1H), 8.19 (d, J=7.8 Hz, 1H), 8.15 (s, 1H), 7.88 (s, 1H), 7.82 (s, 1H), 7.68 (d, J=7.8 Hz, 1H), 7.63 (s, 1H), 7.40 (d, J=8.4 Hz, 1H), 7.24 (d, J=8.4 Hz, 1H), 5.23 (s, 2H), 2.78 (t, J=8.1 Hz, 2H), 2.32 (s, 3H), 1.76-1.67 (m, 2H), 0.91 (t, J=7.2 Hz, 3H). HRMS (ESI$^+$) calcd for C$_{23}$H$_{25}$N$_4$O$_3$ (M+H)$^+$ 405.1921, found 405.1929.

167

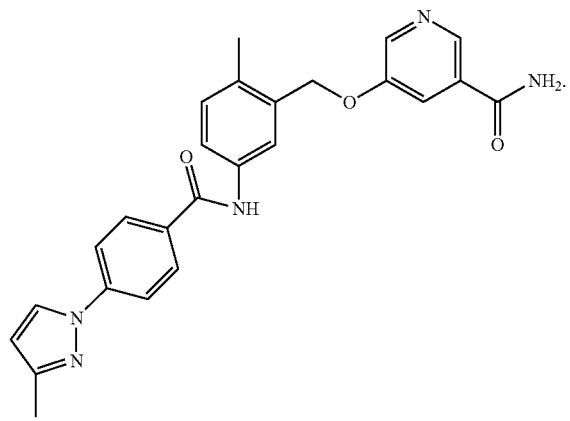 [SMILES: Cc1ccn(-c2ccc(C(=O)Nc3ccc(C)c(COc4cncc(C(N)=O)c4)c3)cc2)n1]

5-((2-Methyl-5-(4-(3-methyl-1H-pyrazol-1-yl)benzamido)benzyl)oxy)nicotinamide (F1-17)

White solid (33 mg, 64%). $^1$H NMR (DMSO-d$_6$, 600 MHz) δ 10.25 (s, 1H), 8.67 (s, 1H), 8.51 (d, J=7.8 Hz, 2H), 8.15 (s, 1H), 8.07 (d, J=7.8 Hz, 2H), 7.94 (d, J=7.2 Hz, 2H), 7.89 (s, 1H), 7.85 (s, 1H), 7.70 (d, J=8.4 Hz, 1H), 7.63 (s, 1H), 7.23 (d, J=8.4 Hz, 1H), 6.40 (s, 1H), 5.23 (s, 2H), 2.32 (s, 3H), 2.29 (s, 3H). HRMS (ESI$^+$) calcd for C$_{25}$H$_{24}$N$_5$O$_3$ (M+H)$^+$ 442.1874, found 442.1883.

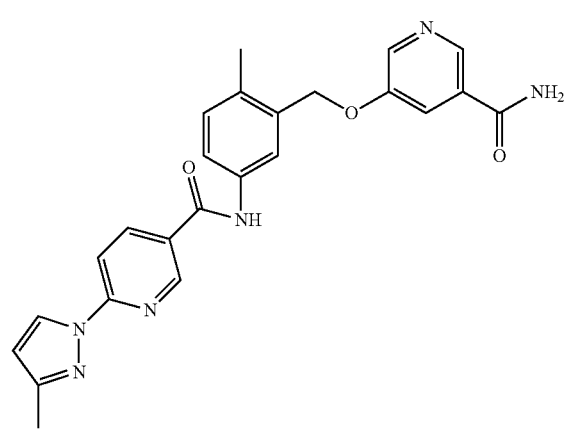 [SMILES: Cc1ccn(-c2ccc(C(=O)Nc3ccc(C)c(COc4cncc(C(N)=O)c4)c3)cn2)n1]

N-(3-(((5-Carbamoylpyridin-3-yl)oxy)methyl)-4-methylphenyl)-6-(3-methyl-1H-pyrazol-1-yl)nicotinamide (F1-18)

White solid (28 mg, 39%). $^1$H NMR (DMSO-d$_6$, 600 MHz) δ 10.41 (s, 1H), 8.97 (s, 1H), 8.67 (s, 1H), 8.58 (s, 1H), 8.52 (s, 1H), 8.47 (d, J=8.4 Hz, 1H), 8.15 (s, 1H), 7.96 (d, J=9.0 Hz, 1H), 7.89 (s, 1H), 7.83 (s, 1H), 7.70 (d, J=8.4 Hz, 1H), 7.63 (s, 1H), 7.25 (d, J=7.8 Hz, 1H), 6.45 (s, 1H), 5.24 (s, 2H), 2.33 (s, 3H), 2.32 (s, 3H). HRMS (ESI$^+$) calcd for C$_{24}$H$_{23}$N$_6$O$_3$ (M+H)$^+$ 443.1826, found 443.1829.

168

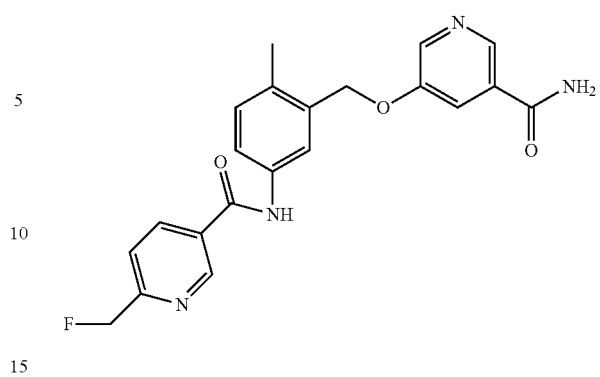

N-(3-(((5-Carbamoylpyridin-3-yl)oxy)methyl)-4-methylphenyl)-6-(fluoromethyl)nicotinamide (F1-19)

White solid (14 mg, 36%). $^1$H NMR (CD$_3$OD, 600 MHz) δ 9.07 (s, 1H), 8.64 (s, 1H), 8.48 (s, 1H), 8.39 (d, J=8.4 Hz, 1H), 7.96 (s, 1H), 7.82 (s, 1H), 7.67 (d, J=7.8 Hz, 1H), 7.63 (d, J=7.8 Hz, 1H), 7.27 (d, J=8.4 Hz, 1H), 5.54 (d, J=46.8 Hz, 2H), 5.26 (s, 2H), 2.40 (s, 3H). HRMS (ESI$^+$) calcd for C$_{21}$H$_{20}$FN$_4$O$_3$ (M+H)$^+$ 395.1514, found 395.1512.

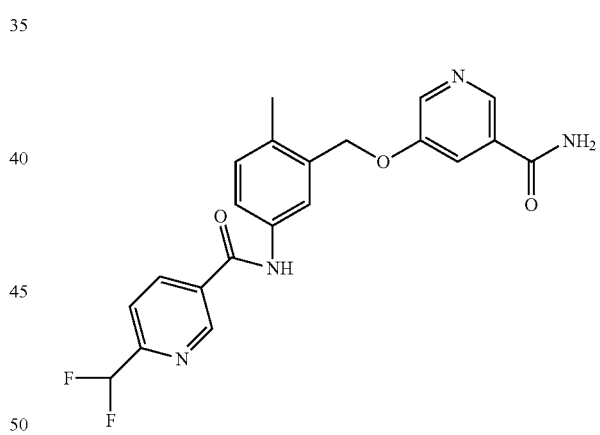

N-(3-(((5-Carbamoylpyridin-3-yl)oxy)methyl)-4-methylphenyl)-6-(difluoromethyl)nicotinamide (F1-20)

White solid (32 mg, 77%). $^1$H NMR (DMSO-d$_6$, 600 MHz) δ 10.55 (s, 1H), 9.17 (s, 1H), 8.67 (s, 1H), 8.51 (d, J=1.8 Hz, 1H), 8.48 (d, J=7.8 Hz, 1H), 8.15 (s, 1H), 7.89 (s, 1H), 7.87 (d, J=8.4 Hz, 1H), 7.83 (s, 1H), 7.70 (d, J=7.8 Hz, 1H), 7.63 (s, 1H), 7.26 (d, J=8.4 Hz, 1H), 7.07 (t, J=54.9 Hz, 1H), 5.76 (s, 2H), 2.33 (s, 3H). HRMS (ESI$^+$) calcd for C$_{21}$H$_{19}$F$_2$N$_4$O$_3$ (M+H)$^+$ 413.1420, found 413.1428.

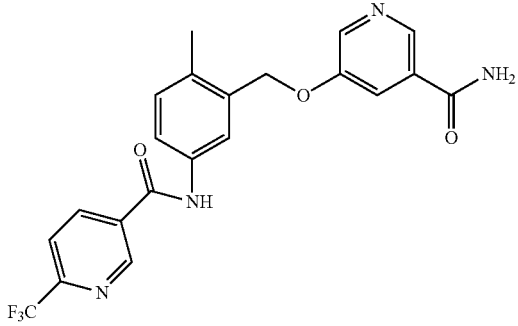 [SMILES: Cc1ccc(NC(=O)c2ccc(C(F)(F)F)nc2)cc1COc1cncc(C(N)=O)c1]

N-(3-(((5-Carbamoylpyridin-3-yl)oxy)methyl)-4-methylphenyl)-6-(trifluoromethyl)nicotinamide (F1-21)

White solid (20 mg, 39%). $^1$H NMR (DMSO-d$_6$, 600 MHz) δ 10.62 (s, 1H), 9.24 (s, 1H), 8.67 (s, 1H), 8.56 (d, J=8.4 Hz, 1H), 8.52 (s, 1H), 8.15 (s, 1H), 8.10 (d, J=8.4 Hz, 1H), 7.88 (s, 1H), 7.82 (s, 1H), 7.70 (d, J=9.0 Hz, 1H), 7.63 (s, 1H), 7.27 (d, J=8.4 Hz, 1H), 5.24 (s, 2H), 2.33 (s, 3H). HRMS (ESI$^+$) calcd for C$_{21}$H$_{18}$F$_3$N$_4$O$_3$ (M+H)$^+$ 431.1326, found 431.1326.

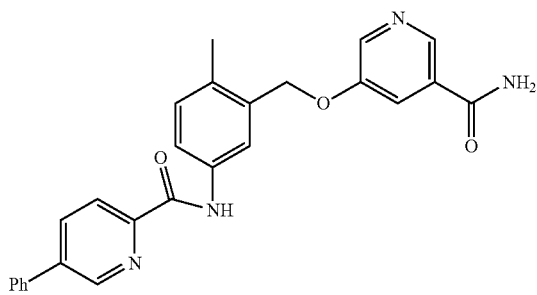 [SMILES: Cc1ccc(NC(=O)c2ccc(-c3ccccc3)cn2)cc1COc1cncc(C(N)=O)c1]

N-(3-(((5-Carbamoylpyridin-3-yl)oxy)methyl)-4-methylphenyl)-5-phenylpicolinamide (F1-22)

White solid (25 mg, 57%). $^1$H NMR (DMSO-d$_6$, 600 MHz) δ 10.65 (s, 1H), 9.02 (d, J=2.4 Hz, 1H), 8.67 (d, J=1.2 Hz, 1H), 8.53 (d, J=3.0 Hz, 1H), 8.35 (dd, J=2.4, 7.8 Hz, 1H), 8.22 (d, J=7.8 Hz, 1H), 8.16 (s, 1H), 8.30 (d, J=1.8 Hz, 1H), 7.90 (dd, J=2.4, 2.4 Hz, 1H), 7.86-7.81 (m, 3H), 7.63 (s, 1H), 7.57 (dd, J=7.5, 7.5 Hz, 2H), 7.50 (dd, J=7.5, 7.5 Hz, 1H), 7.25 (d, J=7.8 Hz, 1H), 5.23 (s, 2H), 2.33 (s, 3H). HRMS (ESI$^+$) calcd for C$_{26}$H$_{23}$N$_4$O$_3$ (M+H)$^+$ 439.1765, found 439.1775.

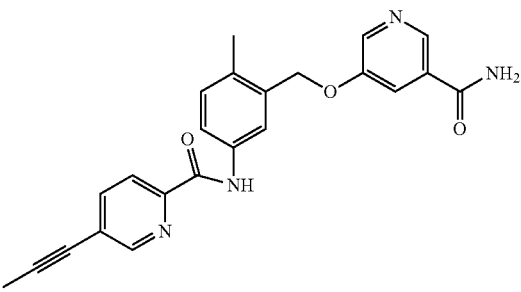 [SMILES: CC#Cc1ccc(C(=O)Nc2ccc(C)c(COc3cncc(C(N)=O)c3)c2)nc1]

N-(3-(((5-Carbamoylpyridin-3-yl)oxy)methyl)-4-methylphenyl)-5-(prop-1-yn-1-yl)picolinamide (F1-23)

White solid (22 mg, 55%). $^1$H NMR (DMSO-d$_6$, 600 MHz) δ 10.61 (s, 1H), 8.71 (s, 1H), 8.66 (s, 1H), 8.52 (d, J=2.4 Hz, 1H), 8.15 (s, 1H), 8.10 (d, J=8.4 Hz, 1H), 8.05 (dd, J=1.8, 8.4 Hz, 1H), 7.99 (s, 1H), 7.89 (s, 1H), 7.79 (d, J=8.4 Hz, 1H), 7.62 (s, 1H), 7.23 (d, J=7.8 Hz, 1H), 5.22 (s, 2H), 2.32 (s, 3H), 2.14 (s, 3H). HRMS (ESI$^+$) calcd for C$_{23}$H$_{21}$N$_4$O$_3$ (M+H)$^+$ 401.1608, found 401.1612.

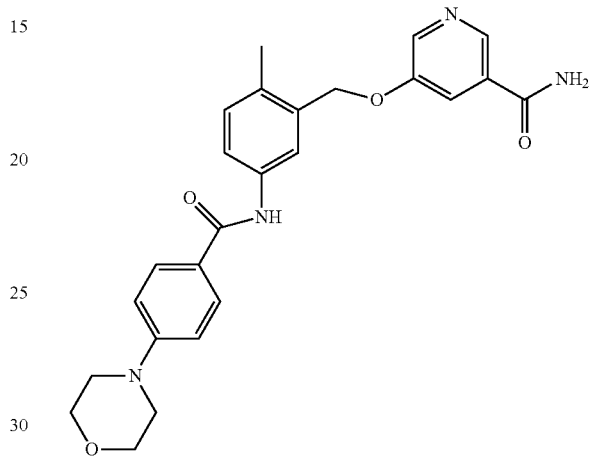

5-((2-Methyl-5-(4-morpholinobenzamido)benzyl)oxy)nicotinamide (F1-24)

Pale solid (20 mg, 38%). $^1$H NMR (DMSO-d$_6$, 600 MHz) δ 9.94 (s, 1H), 8.72 (s, 1H), 8.58 (s, 1H), 8.15 (s, 1H), 7.93-7.85 (m, 3H), 7.83 (s, 1H), 7.67 (d, J=8.4 Hz, 1H), 7.63 (s, 1H), 7.19 (d, J=8.4 Hz, 1H), 7.01 (d, J=9.0 Hz, 2H), 5.21 (s, 2H), 3.74 (t, J=4.2 Hz, 4H), 3.25 (t, J=4.2 Hz, 4H), 2.30 (s, 3H). HRMS (ESI$^+$) calcd for C$_{25}$H$_{27}$N$_4$O$_4$ (M+H)$^+$ 447.2027, found 447.2035.

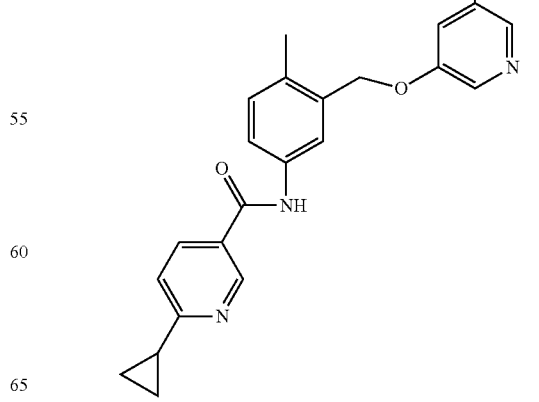

171

N-(3-(((5-Carbamoylpyridin-3-yl)oxy)methyl)-4-methylphenyl)-6-cyclopropylnicotinamide (F1-25)

Yellow solid (6.0 mg, 27%). $^1$H NMR (MeOH-d$_4$, 600 MHz) δ 8.90 (s, 1H), 8.64 (s, 1H), 8.48 (s, 1H), 8.20-8.15 (m, 1H), 7.95 (s, 1H), 7.79 (s, 1H), 7.60 (d, J=8.4 Hz, 1H), 7.35 (d, J=8.4 Hz, 1H), 7.25 (d, J=8.4 Hz, 1H), 5.25 (s, 2H), 2.39 (s, 3H), 2.20-2.14 (m, 1H), 1.13-1.02 (m, 4H). HRMS (ESI$^+$) calcd for C$_{23}$H$_{23}$N$_4$O$_3$ (M+H)$^+$ 403.1765, found 403.1765.

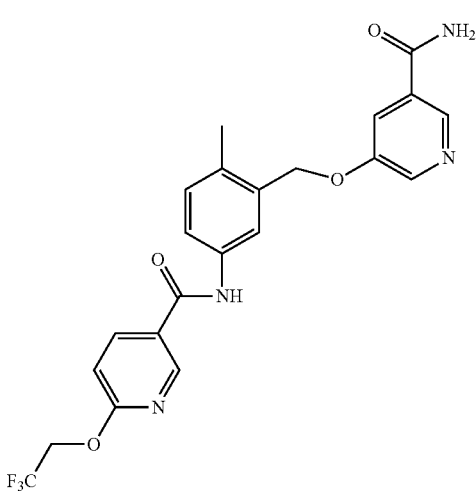 [SMILES: Cc1ccc(NC(=O)c2ccc(OCC(F)(F)F)nc2)cc1COc1cncc(C(N)=O)c1]

N-(3-(((5-Carbamoylpyridin-3-yl)oxy)methyl)-4-methylphenyl)-6-(2,2,2-trifluoroethoxy)nicotinamide (F1-26)

Yellow solid (8.4 mg, 30%). $^1$H NMR (DMSO-d$_6$, 600 MHz) δ 10.31 (s, 1H), 8.79 (s, 1H), 8.67 (s, 1H), 8.51 (s, 1H), 8.32 (d, J=8.4 Hz, 1H), 8.15 (s, 1H), 7.88 (s, 1H), 7.81 (s, 1H), 7.67 (d, J=7.8 Hz, 1H), 7.63 (s, 1H), 7.24 (d, J=8.4 Hz, 1H), 7.13 (d, J=8.4 Hz, 1H), 5.23 (s, 2H), 5.09 (q, J=9.0 Hz, 2H), 2.32 (s, 3H). HRMS (ESI$^+$) calcd for C$_{22}$H$_{20}$F$_3$N$_4$O$_4$ (M+H)$^+$ 461.1431, found 461.1436.

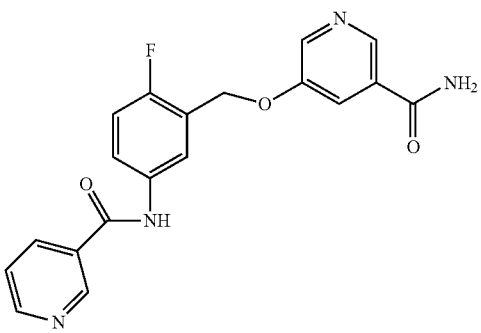 [SMILES: NC(=O)c1cncc(OCc2cc(NC(=O)c3cccnc3)ccc2F)c1]

172

N-(3-(((5-Carbamoylpyridin-3-yl)oxy)methyl)-4-fluorophenyl)nicotinamide (F2-1)

White solid (25 mg, 36%). $^1$H NMR (DMSO-d$_6$, 600 MHz) δ 10.55 (s, 1H), 9.13 (s, 1H), 8.78 (s, 1H), 8.69 (s, 1H), 8.53 (s, 1H), 8.29 (d, J=7.8 Hz, 1H), 8.15 (s, 1H), 7.98 (d, J=4.8 Hz, 1H), 7.90 (s, 1H), 7.83-7.78 (m, 1H), 7.63 (s, 1H), 7.60-7.54 (m, 1H), 7.30 (dd, J=9.0, 9.0 Hz, 1H), 5.30 (s, 2H). HRMS (ESI$^+$) calcd for C$_{19}$H$_{16}$FN$_4$O$_3$ (M+H)$^+$ 367.1201, found 367.1208.

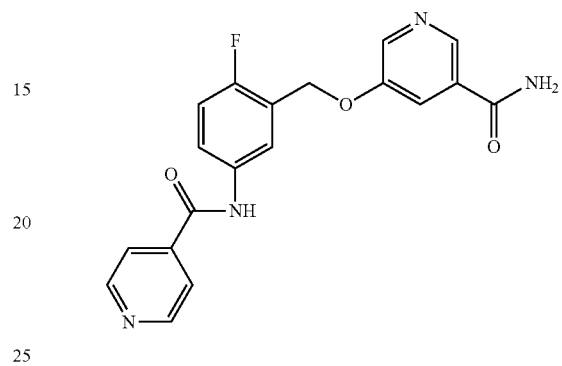

5-((2-Fluoro-5-(isonicotinamido)benzyl)oxy)nicotinamide (F2-2)

White solid (23 mg, 41%). $^1$H NMR (DMSO-d$_6$, 600 MHz) δ 10.61 (s, 1H), 8.79 (d, J=6.0 Hz, 2H), 8.67 (s, 1H), 8.51 (d, J=3.0 Hz, 1H), 8.15 (s, 1H), 7.97 (d, J=4.2 Hz, 1H), 7.89 (s, 1H), 7.86 (d, J=6.0 Hz, 2H), 7.83-7.79 (m, 1H), 7.63 (s, 1H), 7.31 (dd, J=9.6, 9.6 Hz, 1H), 5.30 (s, 2H). HRMS (ESI$^+$) calcd for C$_{19}$H$_{16}$FN$_4$O$_3$ (M+H)$^+$ 367.1201, found 367.1212.

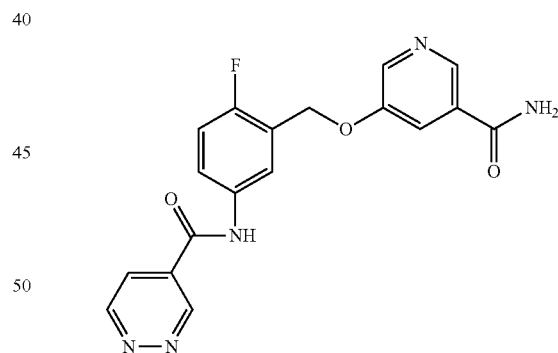

N-(3-(((5-Carbamoylpyridin-3-yl)oxy)methyl)-4-fluorophenyl)pyridazine-4-carboxamide (F2-3)

White solid (30 mg, 53%). $^1$H NMR (DMSO-d$_6$, 600 MHz) δ 10.82 (s, 1H), 9.64 (s, 1H), 9.49 (d, J=5.4 Hz, 1H), 8.68 (s, 1H), 8.51 (d, J=3.0 Hz, 1H), 8.15 (s, 1H), 8.11 (dd, J=5.4, 1.8 Hz, 1H), 7.98-7.93 (m, 1H), 7.89 (s, 1H), 7.83-7.79 (m, 1H), 7.63 (s, 1H), 7.33 (dd, J=9.3, 9.3 Hz, 1H), 5.32 (s, 2H). HRMS (ESI$^+$) calcd for C$_{18}$H$_{15}$FN$_5$O$_3$ (M+H)$^+$ 368.1153, found 368.1162.

173

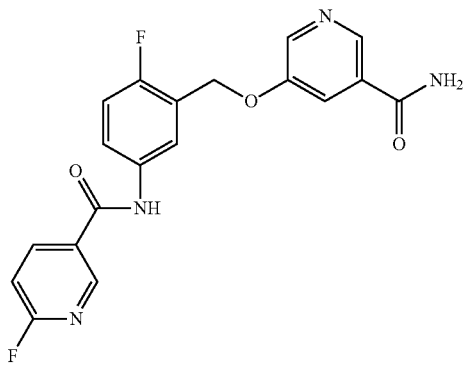 [SMILES: NC(=O)c1cncc(OCc2cc(NC(=O)c3ccc(F)nc3)ccc2F)c1]

N-(3-(((5-Carbamoylpyridin-3-yl)oxy)methyl)-4-fluorophenyl)-6-fluoronicotinamide (F2-4)

White solid (38 mg, 66%). $^1$H NMR (DMSO-d$_6$, 600 MHz) δ 10.55 (s, 1H), 8.81 (d, J=2.4 Hz, 1H), 8.67 (d, J=1.8 Hz, 1H), 8.52-8.46 (m, 2H), 8.15 (s, 1H), 7.94 (dd, J=6.0, 1.8 Hz, 1H), 7.89 (dd, J=2.1, 2.1 Hz, 1H), 7.81-7.78 (m, 1H), 7.63 (s, 1H), 7.37 (dd, J=8.4, 2.4 Hz, 1H), 7.31 (dd, J=9.6, 9.6 Hz, 1H), 5.30 (s, 2H). HRMS (ESI$^+$) calcd for C$_{19}$H$_{15}$F$_2$N$_4$O$_3$ (M+H)$^+$ 385.1107, found 385.1111.

174

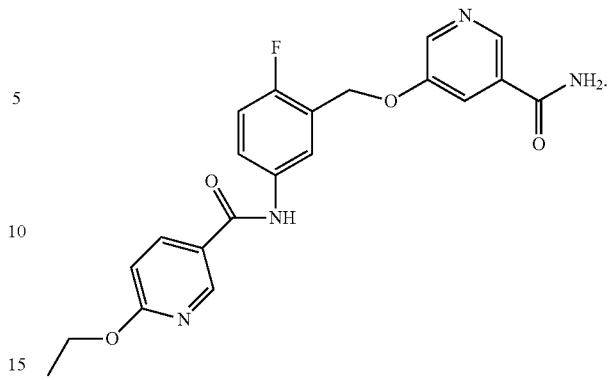

N-(3-(((5-Carbamoylpyridin-3-yl)oxy)methyl)-4-fluorophenyl)-6-ethoxynicotinamide (F2-6)

White solid (23 mg, 37%). $^1$H NMR (DMSO-d$_6$, 600 MHz) δ 10.34 (s, 1H), 8.76 (s, 1H), 8.67 (s, 1H), 8.50 (d, J=2.4 Hz, 1H), 8.21 (dd, J=1.8, 8.1 Hz, 1H), 8.15 (s, 1H), 7.95 (d, J=4.2 Hz, 1H), 7.89 (s, 1H), 7.78 (d, J=3.9, 3.9 Hz, 1H), 7.63 (s, 1H), 7.28 (dd, J=9.3, 9.3, Hz, 1H), 6.92 (d, J=8.4 Hz, 1H), 5.29 (s, 2H), 4.39 (q, J=7.2 Hz, 2H), 1.34 (t, J=7.2 Hz, 3H). HRMS (ESI$^+$) calcd for C$_{21}$H$_{20}$FN$_4$O$_4$ (M+H)$^+$ 411.1463, found 411.1467.

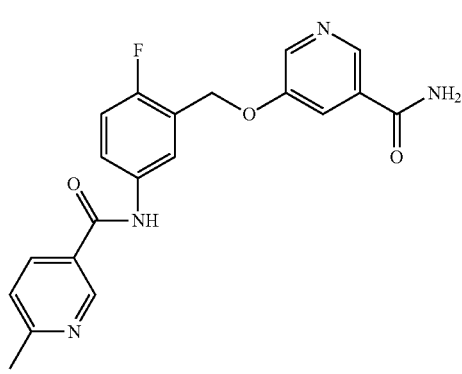 [SMILES: Cc1ccc(C(=O)Nc2ccc(F)c(COc3cncc(C(N)=O)c3)c2)cn1]

N-(3-(((5-Carbamoylpyridin-3-yl)oxy)methyl)-4-fluorophenyl)-6-methylnicotinamide (F2-5)

White solid (35 mg, 60%). $^1$H NMR (DMSO-d$_6$, 600 MHz) δ 10.45 (s, 1H), 8.99 (d, J=2.4 Hz, 1H), 8.67 (d, J=1.8 Hz, 1H), 8.51 (d, J=3.0 Hz, 1H), 8.19 (dd, J=8.4, 2.4 Hz, 1H), 8.15 (s, 1H), 7.96 (dd, J=6.6, 2.4 Hz, 1H), 7.92-7.88 (m, 1H), 7.82-7.78 (m, 1H), 7.63 (s, 1H), 7.42 (d, J=8.4, 1H), 7.29 (dd, J=9.3, 9.3 Hz, 1H), 5.30 (s, 2H), 2.55 (s, 3H). HRMS (ESI$^+$) calcd for C$_{20}$H$_{18}$FN$_4$O$_3$ (M+H)$^+$ 381.1357, found 381.1366.

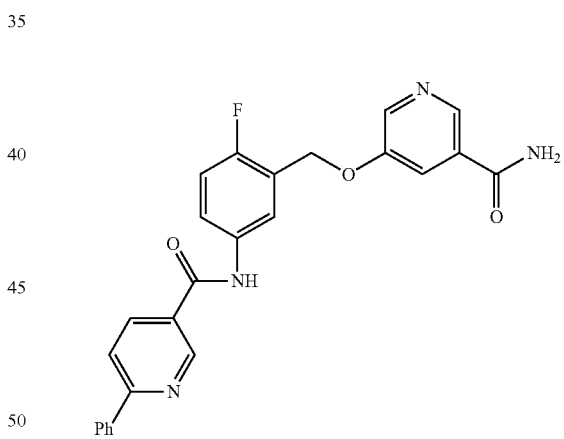

N-(3-(((5-Carbamoylpyridin-3-yl)oxy)methyl)-4-fluorophenyl)-6-phenylnicotinamide (F2-7)

White solid (43 mg, 64%). $^1$H NMR (DMSO-d$_6$, 600 MHz) δ 10.57 (s, 1H), 9.19 (d, J=2.4 Hz, 1H), 8.68 (d, J=0.6 Hz, 1H), 8.52 (d, J=3.0 Hz, 1H), 8.39 (dd, J=8.1, 2.1 Hz, 1H), 8.20-8.13 (m, 4H), 8.00 (dd, J=6.6, 2.4 Hz, 1H), 7.91-7.89 (m, 1H), 7.86-7.82 (m, 1H), 7.63 (s, 1H), 7.57-7.49 (m, 3H), 7.31 (dd, J=9.3, 9.3 Hz, 1H), 5.31 (s, 2H). HRMS (ESI$^+$) calcd for C$_{25}$H$_{20}$FN$_4$O$_3$ (M+H)$^+$ 443.1514, found 443.1511.

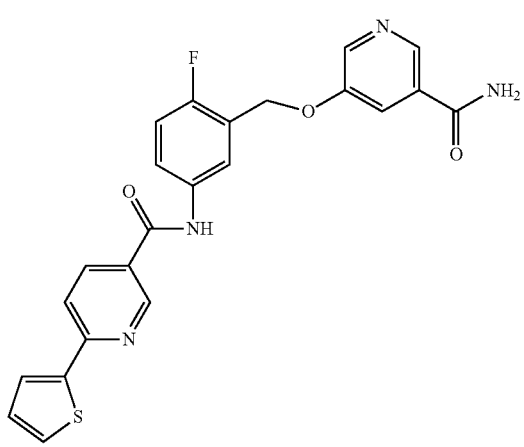 [SMILES: NC(=O)c1cncc(OCc2cc(NC(=O)c3ccc(-c4cccs4)nc3)ccc2F)c1]

N-(3-(((5-Carbamoylpyridin-3-yl)oxy)methyl)-4-fluorophenyl)-6-(thiophen-2-yl)nicotinamide (F2-8)

Pale solid (23 mg, 34%). $^1$H NMR (DMSO-d$_6$, 600 MHz) δ 10.51 (s, 1H), 9.04 (s, 1H), 8.68 (s, 1H), 8.52 (d, J=2.4 Hz, 1H), 8.33 (dd, J=1.8, 8.4 Hz, 1H), 8.16 (s, 1H), 8.08 (d, J=8.4 Hz, 1H), 7.98 (d, J=4.2 Hz, 1H), 7.95 (d, J=3.6 Hz, 1H), 7.90 (s, 1H), 7.84-7.79 (m, 1H), 7.74 (d, J=5.4 Hz, 1H), 7.63 (s, 1H), 7.31 (dd, J=9.3, 9.3 Hz, 1H), 7.22 (dd, J=4.2, 4.2 Hz, 1H), 5.31 (s, 2H). HRMS (ESI$^+$) calcd for C$_{23}$H$_{18}$FN$_4$O$_3$S (M+H)$^+$ 449.1078, found 449.1088.

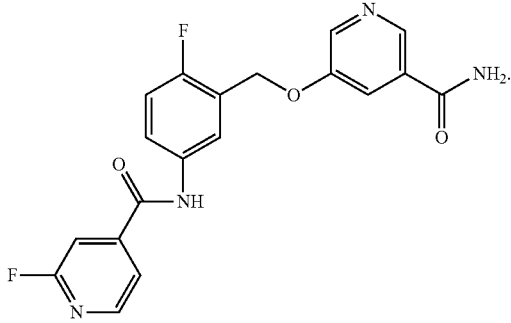 [SMILES: NC(=O)c1cncc(OCc2cc(NC(=O)c3ccnc(F)c3)ccc2F)c1]

5-((2-Fluoro-5-(2-fluoroisonicotinamido)benzyl)oxy)nicotinamide (F2-9)

Pale solid (40 mg, 68%). $^1$H NMR (DMSO-d$_6$, 600 MHz) δ 10.67 (s, 1H), 8.67 (s, 1H), 8.51 (d, J=3.0 Hz, 1H), 8.45 (d, J=5.4 Hz, 1H), 8.15 (s, 1H), 7.96 (dd, J=6.6, 2.4 Hz, 1H), 7.89 (s, 1H), 7.84-7.79 (m, 2H), 7.66 (s, 1H), 7.63 (s, 1H), 7.32 (dd, J=9.3, 9.3 Hz, 1H), 5.31 (s, 2H). HRMS (ESI$^+$) calcd for C$_{19}$H$_{15}$F$_2$N$_4$O$_3$ (M+H)$^+$ 385.1107, found 385.1113.

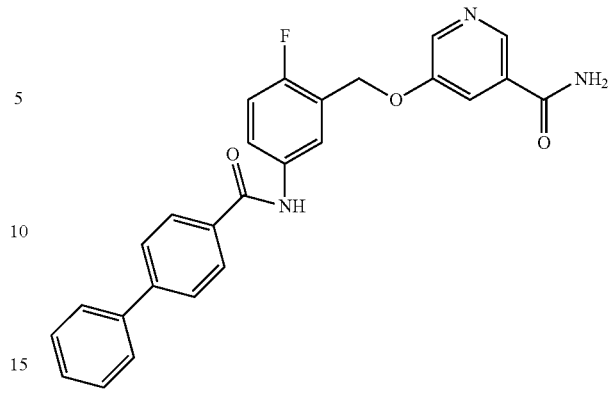

5-((5-([1,1'-Biphenyl]-4-ylcarboxamido)-2-fluorobenzyl)oxy)nicotinamide (F2-10)

White solid (13 mg, 20%). $^1$H NMR (DMSO-d$_6$, 600 MHz) δ 10.42 (s, 1H), 8.68 (s, 1H), 8.52 (d, J=3.0 Hz, 1H), 8.16 (s, 1H), 8.07 (d, J=8.4 Hz, 2H), 8.02 (d, J=4.2 Hz, 1H), 7.91 (s, 1H), 7.84 (d, J=8.4 Hz, 3H), 7.76 (d, J=7.2 Hz, 2H), 7.63 (s, 1H), 7.51 (dd, J=7.8, 7.8 Hz, 2H), 7.43 (dd, J=7.2, 7.2 Hz, 1H), 7.29 (dd, J=9.0 Hz, 1H), 5.30 (s, 2H). HRMS (ESI$^+$) calcd for C$_{26}$H$_{21}$FN$_3$O$_3$ (M+H)$^+$ 442.1561, found 442.1570.

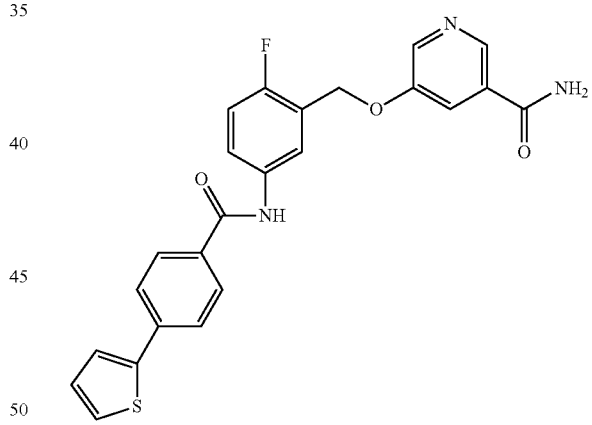

5-((2-Fluoro-5-(4-(thiophen-2-yl)benzamido)benzyl)oxy)nicotinamide (F2-11)

White solid (42 mg, 61%). $^1$H NMR (DMSO-d$_6$, 600 MHz) δ 10.38 (s, 1H), 8.68 (d, J=1.2 Hz, 1H), 8.51 (d, J=3.0 Hz, 1H), 8.16 (s, 1H), 8.02-7.97 (m, 3H), 7.90 (dd, J=1.8, 1.8 Hz, 1H), 7.84-7.80 (m, 3H), 7.68 (d, J=3.6 Hz, 1H), 7.65 (d, J=5.4 Hz, 1H), 7.63 (s, 1H), 7.29 (dd, J=9.3, 9.3 Hz, 1H), 7.20 (dd, J=5.1, 3.9 Hz, 1H), 5.30 (s, 2H). HRMS (ESI$^+$) calcd for C$_{24}$H$_{19}$FN$_3$O$_3$S (M+H)$^+$ 448.1126, found 448.1138.

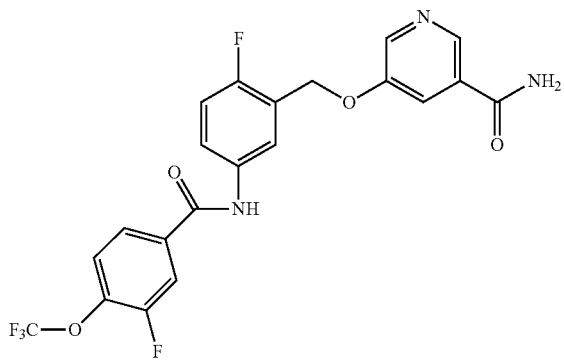 [SMILES: NC(=O)c1cncc(OCc2cc(NC(=O)c3ccc(OC(F)(F)F)c(F)c3)ccc2F)c1]

5-((2-Fluoro-5-(3-fluoro-4-(trifluoromethoxy)benzamido)benzyl)oxy)nicotinamide (F2-12)

White solid (32 mg, 45%). $^1$H NMR (DMSO-d$_6$, 600 MHz) δ 10.51 (s, 1H), 8.67 (d, J=1.2 Hz, 1H), 8.51 (d, J=2.4 Hz, 1H), 8.15 (s, 1H), 8.07 (dd, J=1.8, 10.5 Hz, 1H), 7.95 (dd, J=2.4, 6.6 Hz, 1H), 7.93-7.87 (m, 2H), 7.82-7.74 (m, 2H), 7.63 (s, 1H), 7.30 (d, J=9.0 Hz, 1H), 5.30 (s, 2H). HRMS (ESI$^+$) calcd for C$_{21}$H$_{15}$F$_5$N$_3$O$_4$ (M+H)$^+$ 468.0977, found 468.0986.

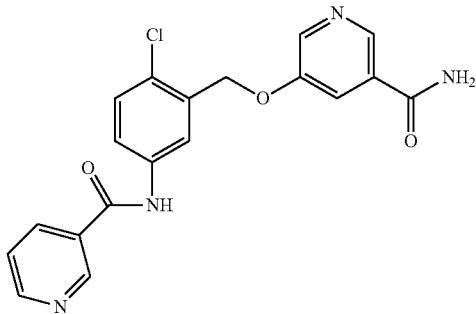 [SMILES: NC(=O)c1cncc(OCc2cc(NC(=O)c3cccnc3)ccc2Cl)c1]

N-(3-(((5-Carbamoylpyridin-3-yl)oxy)methyl)-4-chlorophenyl)nicotinamide (F3-1)

White solid (18 mg, 26%). $^1$H NMR (DMSO-d$_6$, 600 MHz) δ 10.62 (s, 1H), 9.10 (s, 1H), 8.77 (d, J=4.8 Hz, 1H), 8.69 (s, 1H), 8.52 (s, 1H), 8.29 (d, J=8.4 Hz, 1H), 8.17 (s, 1H), 8.04 (s, 1H), 7.89 (s, 1H), 7.86 (d, J=9.0 Hz, 1H), 7.64 (s, 1H), 7.57 (dd, J=5.7, 5.7 Hz, 1H), 7.54 (d, J=9.0 Hz, 1H), 5.31 (s, 2H). HRMS (ESI$^+$) calcd for C$_{19}$H$_{16}$ClN$_4$O$_3$ (M+H)$^+$ 383.0905, found 383.0913.

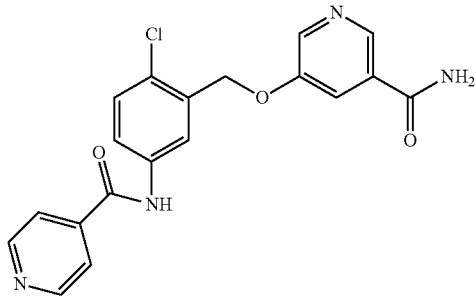 [SMILES: NC(=O)c1cncc(OCc2cc(NC(=O)c3ccncc3)ccc2Cl)c1]

5-((2-Chloro-5-(isonicotinamido)benzyl)oxy)nicotinamide (F3-2)

White solid (9.7 mg, 32%). $^1$H NMR (DMSO-d$_6$, 600 MHz) δ 10.68 (s, 1H), 8.79 (d, J=5.4 Hz, 2H), 8.69 (s, 1H), 8.52 (s, 1H), 8.17 (s, 1H), 8.03 (s, 1H), 7.91-7.83 (m, 4H), 7.64 (s, 1H), 7.55 (d, J=9.0 Hz, 1H), 5.31 (s, 2H). HRMS (ESI$^+$) calcd for C$_{19}$H$_{16}$ClN$_4$O$_3$ (M+H)$^+$ 383.0905, found 383.0904.

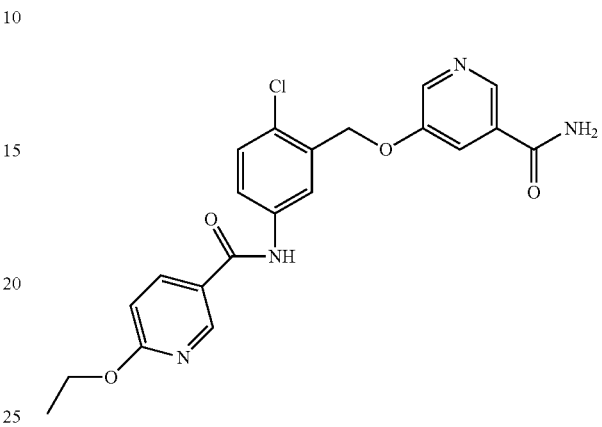

N-(3-(((5-Carbamoylpyridin-3-yl)oxy)methyl)-4-chlorophenyl)-6-ethoxynicotinamide (F3-3)

White solid (21 mg, 32%). $^1$H NMR (DMSO-d$_6$, 600 MHz) δ 10.41 (s, 1H), 8.76 (d, J=1.2 Hz, 1H), 8.68 (s, 1H), 8.51 (d, J=3.0 Hz, 1H), 8.21 (dd, J=2.7, 8.1 Hz, 1H), 8.17 (s, 1H), 8.02 (s, 1H), 7.88 (s, 1H), 7.83 (dd, J=2.4, 9.0 Hz, 1H), 7.63 (s, 1H), 7.52 (d, J=8.4 Hz, 1H), 6.92 (d, J=8.4 Hz, 1H), 5.30 (s, 2H), 4.39 (q, J=7.2 Hz, 2H), 1.34 (t, J=7.2 Hz, 3H). HRMS (ESI$^+$) calcd for C$_{21}$H$_{20}$ClN$_4$O$_4$ (M+H)$^+$ 427.1168, found 427.1175.

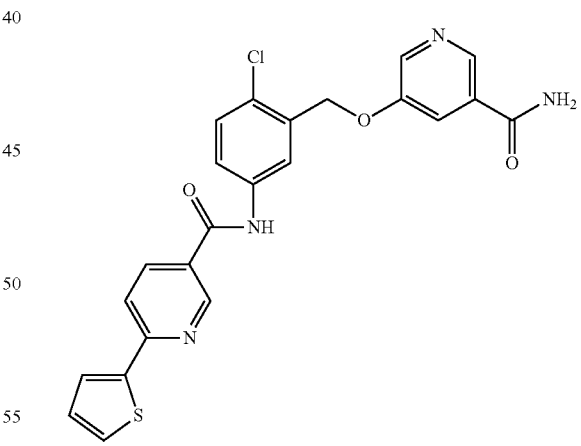

N-(3-(((5-Carbamoylpyridin-3-yl)oxy)methyl)-4-chlorophenyl)-6-(thiophen-2-yl)nicotinamide (F3-4)

White solid (57 mg, 42%). $^1$H NMR (DMSO-d$_6$, 600 MHz) δ 10.58 (s, 1H), 9.04 (d, J=2.4 Hz, 1H), 8.69 (s, 1H), 8.52 (d, J=2.4 Hz, 1H), 8.33 (dd, J=2.4, 8.4 Hz, 1H), 8.18 (s, 1H), 8.08 (d, J=8.4 Hz, 1H), 8.04 (d, J=2.4 Hz, 1H), 7.95 (d, J=3.6 Hz, 1H), 7.89 (s, 1H), 7.86 (dd, J=2.4, 8.4 Hz, 1H), 7.75 (d, J=5.4 Hz, 1H), 7.64 (s, 1H), 7.54 (d, J=8.4 Hz, 1H), 7.23 (dd, J=4.5, 4.5 Hz, 1H), 5.32 (s, 2H). HRMS (ESI+) calcd for C23H18ClN4O3S (M+H)+ 465.0783, found 465.0788.

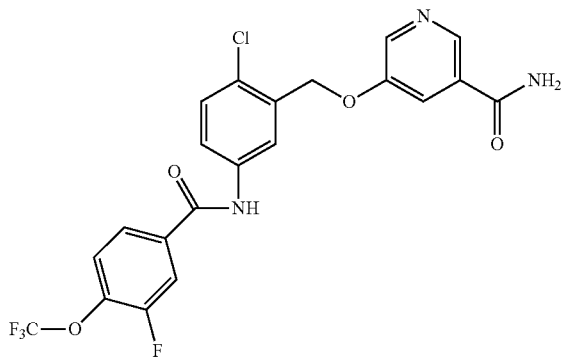 [SMILES: NC(=O)c1cncc(OCc2cc(NC(=O)c3ccc(OC(F)(F)F)c(F)c3)ccc2Cl)c1]

5-((2-Chloro-5-(3-fluoro-4-(trifluoromethoxy)benzamido)benzyl)oxy)nicotinamide (F3-5)

White solid (42 mg, 57%). $^1$H NMR (DMSO-d$_6$, 600 MHz) δ 10.57 (s, 1H), 8.67 (s, 1H), 8.51 (d, J=2.4 Hz, 1H), 8.17 (s, 1H), 8.07 (dd, J=1.8, 10.8 Hz, 1H), 8.01 (d, J=2.4 Hz, 1H), 7.92-7.87 (m, 2H), 7.84 (dd, J=2.4, 8.4 Hz, 1H), 7.77 (d, J=8.1, 8.1 Hz, 1H), 7.64 (s, 1H), 7.54 (d, J=9.0 Hz, 1H), 5.31 (s, 2H). HRMS (ESI+) calcd for C21H15ClF4N3O4 (M+H)+ 484.0682, found 484.0689.

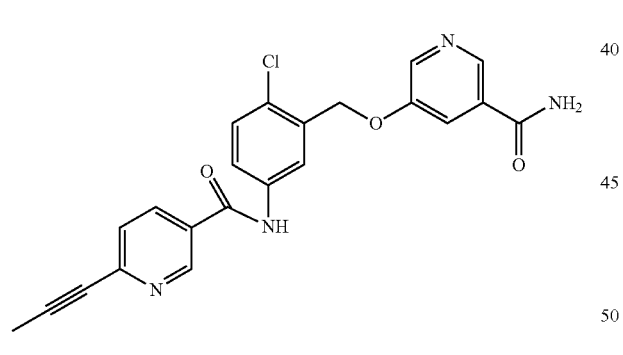

N-(3-(((5-Carbamoylpyridin-3-yl)oxy)methyl)-4-chlorophenyl)-6-(prop-1-yn-1-yl)nicotinamide (F3-6)

Pale solid (2 mg, 5%). $^1$H NMR (CD$_3$OD, 600 MHz) δ 8.98 (d, J=2.4 Hz, 1H), 8.66 (d, J=1.8 Hz, 1H), 8.49 (d, J=3.0 Hz, 1H), 8.27 (dd, J=2.4, 7.8 Hz, 1H), 8.00 (d, J=2.4 Hz, 1H), 7.95 (dd, J=1.8, 3.0 Hz, 1H), 7.76 (dd, J=2.4, 3.0 Hz, 1H), 7.58 (d, J=8.4 Hz, 1H), 7.47 (d, J=9.0 Hz, 1H), 5.34 (s, 2H), 2.12 (s, 3H). HRMS (ESI+) calcd for C22H18ClN4O3 (M+H)+ 421.1062, found 421.1062.

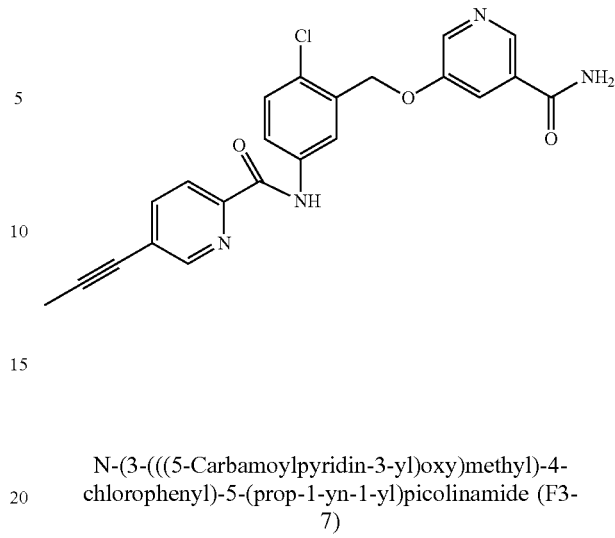

N-(3-(((5-Carbamoylpyridin-3-yl)oxy)methyl)-4-chlorophenyl)-5-(prop-1-yn-1-yl)picolinamide (F3-7)

White solid (23 mg, 55%). $^1$H NMR (DMSO-d$_6$, 600 MHz) δ 10.88 (s, 1H), 8.72 (d, J=1.8 Hz, 1H), 8.68 (d, J=1.8 Hz, 1H), 8.52 (d, J=3.0 Hz, 1H), 8.22 (d, J=2.4 Hz, 1H), 8.17 (s, 1H), 8.11 (d, J=7.8 Hz, 1H), 8.05 (dd, J=2.4, 8.4 Hz, 1H), 7.98 (dd, J=2.4, 8.4 Hz, 1H), 7.89 (dd, J=1.8, 1.8 Hz, 1H), 7.63 (s, 1H), 7.52 (d, J=9.0 Hz, 1H), 5.29 (s, 2H), 2.14 (s, 3H). HRMS (ESI+) calcd for C22H18ClN4O3 (M+H)+ 421.1062, found 421.1060.

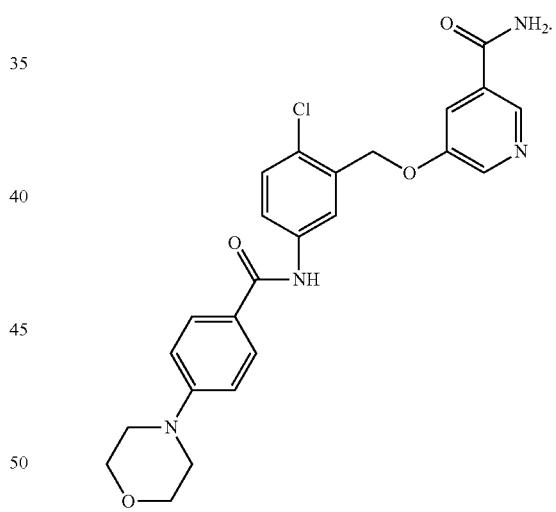

5-((2-Chloro-5-(4-morpholinobenzamido)benzyl)oxy)nicotinamide (F3-8)

White solid (6.3 mg, 13%). $^1$H NMR (DMSO-d$_6$, 600 MHz) δ 10.14 (s, 1H), 8.68 (s, 1H), 8.52 (d, J=2.4 Hz, 1H), 8.17 (s, 1H), 8.06-8.03 (m, 1H), 7.91-7.84 (m, 4H), 7.63 (s, 1H), 7.48 (d, J=8.4 Hz, 1H), 7.03 (d, J=8.4 Hz, 2H), 5.28 (s, 2H), 3.75 (t, J=4.8 Hz, 4H), 3.26 (t, J=4.8 Hz, 4H). HRMS (ESI+) calcd for C24H24ClN4O4 (M+H)+ 467.1481, found 467.1478.

181

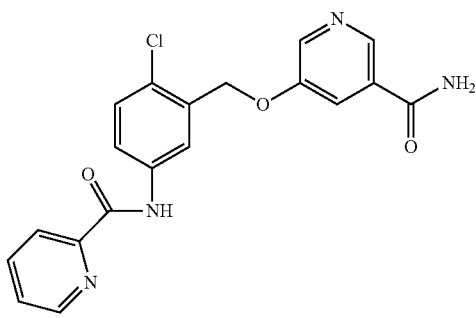 [SMILES: NC(=O)c1cncc(OCc2cc(NC(=O)c3ccccn3)ccc2Cl)c1]

N-(3-(((5-Carbamoylpyridin-3-yl)oxy)methyl)-4-chlorophenyl)picolinamide (F3-9)

White solid (14.0 mg, 51%). ¹H NMR (MeOH-d₄, 600 MHz) δ 8.71 (d, J=4.2 Hz, 1H), 8.66 (s, 1H), 8.52 (d, J=3.0 Hz, 1H), 8.21 (d, J=7.8 Hz, 1H), 8.13 (d, J=3.0 Hz, 1H), 8.02 (dd, J=7.8, 7.8 Hz, 1H), 7.98 (s, 1H), 8.84 (dd, J=8.4, 2.4 Hz, 1H), 7.62 (dd, J=7.8, 4.8 Hz, 1H), 7.49 (d, J=9.0 Hz, 1H), 5.35 (s, 2H). HRMS (ESI⁺) calcd for $C_{19}H_{15}ClN_4O_3$ (M+H)⁺ 383.0905, found 383.0909.

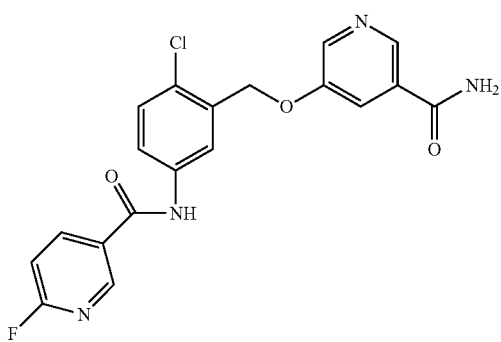 [SMILES: NC(=O)c1cncc(OCc2cc(NC(=O)c3ccc(F)nc3)ccc2Cl)c1]

N-(3-(((5-Carbamoylpyridin-3-yl)oxy)methyl)-4-chlorophenyl)-6-fluoronicotinamide (F3-10)

White solid (7.3 mg, 25%). ¹H NMR (MeOH-d₄, 600 MHz) δ 8.66 (d, J=1.8 Hz, 1H), 8.60 (d, J=3.0 Hz, 1H), 8.51 (d, J=3.0 Hz, 1H), 8.28 (dd, J=9.0, 4.8 Hz, 1H), 8.11 (d, J=2.4 Hz, 1H), 7.98 (dd, J=2.4, 2.4 Hz, 1H), 7.84-7.78 (m, 2H), 7.48 (d, J=9.0 Hz, 1H), 5.35 (s, 2H). HRMS (ESI⁺) calcd for $C_{19}H_{15}ClFN_4O_3$ (M+H)⁺ 401.0811, found 401.0813.

182

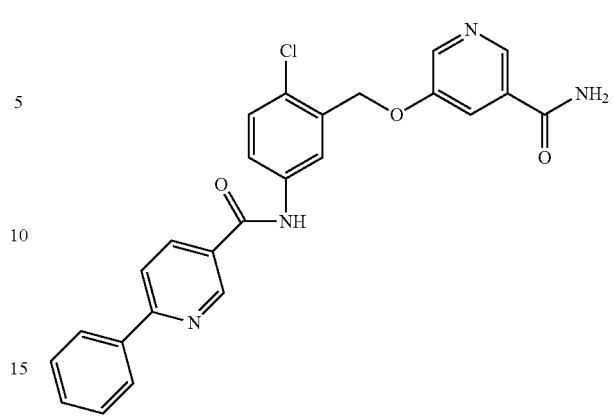

N-(3-(((5-Carbamoylpyridin-3-yl)oxy)methyl)-4-chlorophenyl)-6-phenylnicotinamide (F3-11)

White solid (16.0 mg, 49%). ¹H NMR (DMSO-d₆, 600 MHz) δ 10.65 (s, 1H), 9.19 (d, J=2.4 Hz, 1H), 8.69 (s, 1H), 8.53 (s, 1H), 8.40 (dd, J=7.8, 1.8 Hz, 1H), 8.20-8.14 (m, 4H), 8.07 (d, J=2.4 Hz, 1H), 7.91-7.87 (m, 2H), 7.64 (s, 1H), 7.57-7.52 (m 3H), 7.51 (d, J=7.2 Hz, 1H), 5.32 (s, 2H). HRMS (ESI⁺) calcd for $C_{25}H_{20}ClN_4O_3$ (M+H)⁺ 459.1218, found 459.1227.

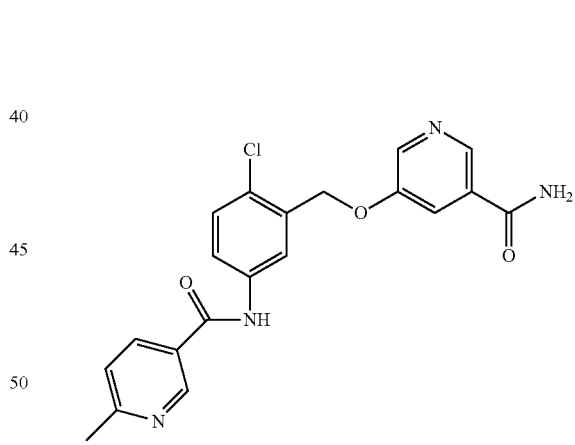

N-(3-(((5-Carbamoylpyridin-3-yl)oxy)methyl)-4-chlorophenyl)-6-methylnicotinamide (F3-12)

White solid (13.0 mg, 46%). ¹H NMR (MeOH-d₄, 600 MHz) δ 8.94 (d, J=1.8 Hz, 1H), 8.65 (s, 1H), 8.48 (s, 1H), 8.23 (dd, J=8.4, 2.4 Hz, 1H), 8.00 (d, J=1.8 Hz, 1H), 7.95 (s, 1H), 7.74 (dd, J=8.4, 2.4 Hz, 1H), 7.46-7.42 (m, 2H), 5.31 (s, 2H), 2.61 (s, 3H). HRMS (ESI⁺) calcd for $C_{20}H_{18}ClN_4O_3$ (M+H)⁺ 397.1062, found 397.1068.

183

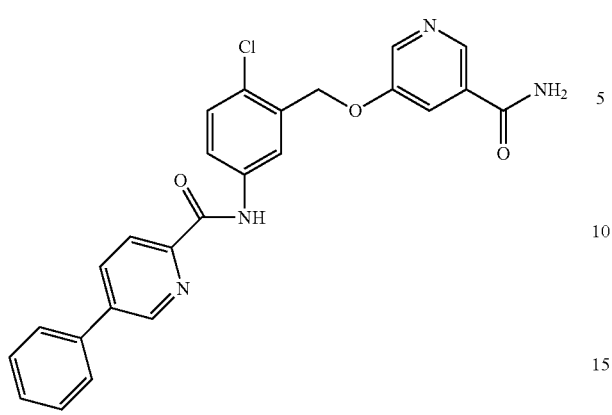

N-(3-(((5-Carbamoylpyridin-3-yl)oxy)methyl)-4-chlorophenyl)-5-phenylpicolinamide (F3-13)

White solid (7.0 mg, 21%). $^1$H NMR (DMSO-d$_6$, 600 MHz) δ 10.92 (s, 1H), 9.03 (s, 1H), 8.69 (s, 1H), 8.54 (d, J=1.8 Hz, 1H), 8.36 (dd, J=8.4, 1.8 Hz, 1H), 8.26 (s, 1H), 8.23 (d, J=8.4 Hz, 1H), 8.17 (s, 1H), 8.02 (dd, J=8.4, 3.0 Hz, 1H), 7.90 (s, 1H), 7.84 (d, J=7.8 Hz, 2H), 7.63 (s, 1H), 7.59-7.48 (m, 4H), 5.31 (s, 2H). HRMS (ESI$^+$) calcd for C$_{25}$H$_{20}$ClN$_4$O$_3$ (M+H)$^+$ 459.1218, found 459.1225.

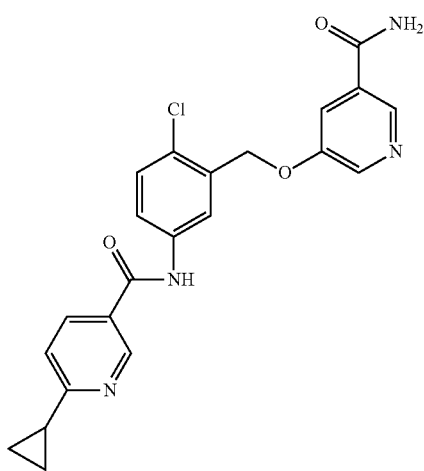 [SMILES: NC(=O)c1cncc(OCc2cc(NC(=O)c3ccc(C4CC4)nc3)ccc2Cl)c1]

N-(3-(((5-Carbamoylpyridin-3-yl)oxy)methyl)-4-chlorophenyl)-6-cyclopropylnicotinamide (F3-14)

Yellow solid (7.0 mg, 27%). $^1$H NMR (DMSO-d$_6$, 600 MHz) δ 10.48 (s, 1H), 8.92 (s, 1H), 8.69 (s, 1H), 8.52 (s, 1H), 8.20-8.12 (m, 2H), 8.02 (s, 1H), 7.88 (s, 1H), 7.84 (d, J=9.0 Hz, 1H), 7.64 (s, 1H), 7.52 (d, J=8.4 Hz, 1H), 7.45 (d, J=8.4 Hz, 1H), 5.30 (s, 2H), 2.23-2.17 (m, 1H), 1.08-0.97 (m, 4H). HRMS (ESI$^+$) calcd for C$_{22}$H$_{20}$ClN$_4$O$_3$ (M+H)$^+$ 423.1218, found 423.1222.

184

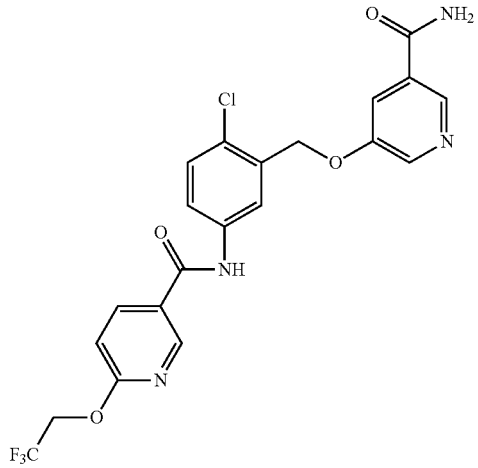 [SMILES: NC(=O)c1cncc(OCc2cc(NC(=O)c3ccc(OCC(F)(F)F)nc3)ccc2Cl)c1]

N-(3-(((5-carbamoylpyridin-3-yl)oxy)methyl)-4-chlorophenyl)-6-(2,2,2-trifluoroethoxy)nicotinamide (F3-15)

Yellow solid (7.0 mg, 27%). $^1$H NMR (DMSO-d$_6$, 600 MHz) δ 10.50 (s, 1H), 8.79 (s, 1H), 8.70 (s, 1H), 8.53 (s, 1H), 8.32 (d, J=8.4 Hz, 1H), 8.17 (s, 1H), 8.02 (s, 1H), 7.88 (s, 1H), 7.84 (d, J=9.0 Hz, 1H), 7.64 (s, 1H), 7.53 (d, J=8.4 Hz, 1H), 7.14 (d, J=8.4 Hz, 1H), 5.30 (s, 2H), 5.10 (q, J=9.0 Hz, 2H). HRMS (ESI$^+$) calcd for C$_{21}$H$_{17}$ClF$_3$N$_4$O$_4$ (M+H)$^+$ 481.0885, found 481.0888.

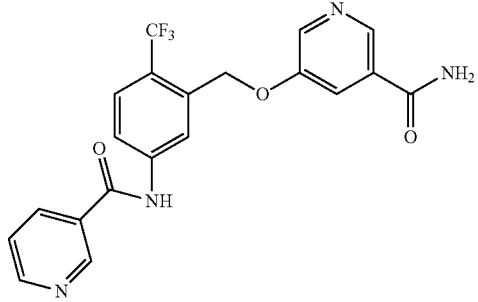

N-(3-(((5-Carbamoylpyridin-3-yl)oxy)methyl)-4-(trifluoromethyl)phenyl)nicotinamide (F4-1)

White solid (8 mg, 20%). $^1$H NMR (DMSO-d$_6$, 600 MHz) δ 10.83 (s, 1H), 9.12 (s, 1H), 8.78 (d, J=4.8 Hz, 1H), 8.69 (s, 1H), 8.50 (d, J=3.0 Hz, 1H), 8.31 (d, J=7.8 Hz, 1H), 8.18 (s, 2H), 8.05 (d, J=9.0 Hz, 1H), 7.87 (s, 1H), 7.84 (d, J=9.0 Hz, 1H), 7.64 (s, 1H), 7.59 (dd, J=7.8, 4.8 Hz, 1H), 5.37 (s, 2H). HRMS (ESI$^+$) calcd for C$_{20}$H$_{16}$F$_3$N$_4$O$_3$ (M+H)$^+$ 417.1169, found 417.1171.

185

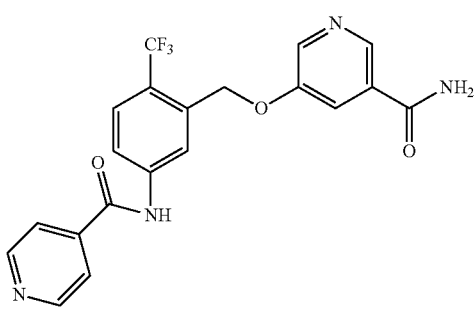 [SMILES: NC(=O)c1cncc(OCc2cc(NC(=O)c3ccncc3)ccc2C(F)(F)F)c1]

5-((5-(Isonicotinamido)-2-(trifluoromethyl)benzyl)oxy)nicotinamide (F4-2)

White solid (10 mg, 25%). $^1$H NMR (DMSO-d$_6$, 600 MHz)) δ 10.88 (s, 1H), 8.81 (d, J=6.0 Hz, 2H), 8.63 (d, J=1.2 Hz, 1H), 8.50 (d, J=2.4 Hz, 1H), 8.18 (s, 2H), 8.06 (d, J=9.0 Hz, 1H), 7.89-7.85 (m, 3H), 7.85 (d, J=8.4 Hz, 1H), 7.64 (s, 1H), 5.37 (s, 2H). HRMS (ESI$^+$) calcd for C$_{20}$H$_{16}$F$_3$N$_4$O$_3$ (M+H)$^+$ 417.1169, found 417.1176.

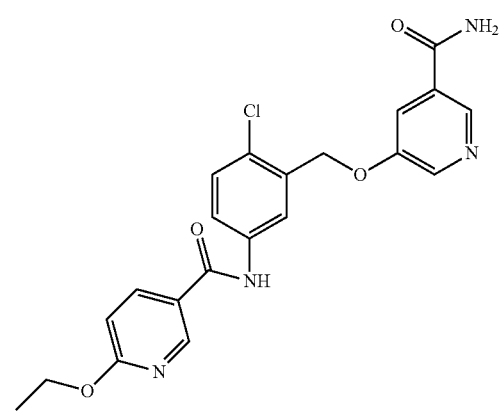 [SMILES: CCOc1ccc(C(=O)Nc2ccc(Cl)c(COc3cncc(C(N)=O)c3)c2)cn1]

N-(3-(((5-Carbamoylpyridin-3-yl)oxy)methyl)-4-(trifluoromethyl)phenyl)-6-ethoxynicotinamide (F4-3)

Pale solid (7 mg, 15%). $^1$H NMR (CD$_3$OD, 600 MHz) δ 8.75 (s, 1H), 8.67 (s, 1H), 8.48 (s, 1H), 8.20 (d, J=7.8 Hz, 1H), 8.16 (s, 1H), 7.98-7.92 (m, 2H), 7.76 (d, J=9.0 Hz, 1H), 7.87 (d, J=8.4 Hz, 1H), 5.41 (s, 2H), 4.43 (q, J=7.2 Hz, 2H), 1.40 (t, J=7.2 Hz, 3H). HRMS (ESI$^+$) calcd for C$_{22}$H$_{20}$F$_3$N$_4$O$_4$ (M+H)$^+$ 461.1431, found 461.1439.

186

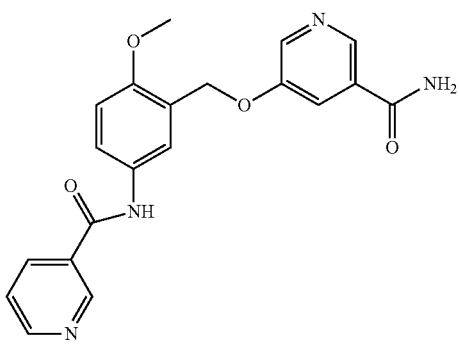 [SMILES: COc1ccc(NC(=O)c2cccnc2)cc1COc1cncc(C(N)=O)c1]

N-(3-(((5-Carbamoylpyridin-3-yl)oxy)methyl)-4-methoxyphenyl)nicotinamide (F5-1)

Light yellow solid (19 mg, 46%). $^1$H NMR (CD$_3$OD, 600 MHz) δ 9.07 (s, 1H), 8.71 (d, J=4.2 Hz, 1H), 8.62 (s, 1H), 8.44 (d, J=2.4 Hz, 1H), 8.34 (d, J=7.2 Hz, 1H), 7.94 (s, 1H), 7.78 (s, 1H), 7.69 (d, J=8.4 Hz, 1H), 7.58 (dd, J=8.1, 5.1 Hz, 1H), 7.06 (d, J=9.0, 1H), 5.27 (s, 2H), 3.91 (s, 3H). HRMS (ESI$^+$) calcd for C$_{20}$H$_{19}$N$_4$O$_4$ (M+H)$^+$ 379.1401, found 379.1407.

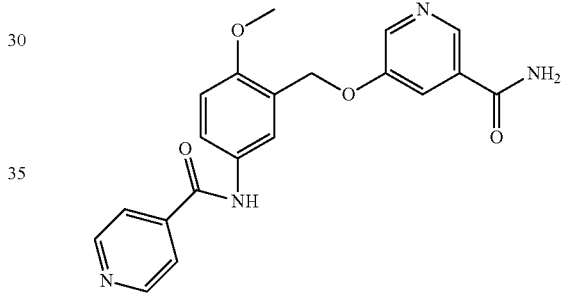

5-((5-(Isonicotinamido)-2-methoxybenzyl)oxy)nicotinamide (F5-2)

Light brown solid (14 mg, 34%) $^1$H NMR (DMSO-d$_6$, 600 MHz) δ 10.43 (s, 1H), 8.77 (d, J=4.2 Hz, 2H), 8.65 (s, 1H), 8.47 (d, J=1.8 Hz, 1H), 8.15 (s, 1H), 7.87-7.82 (m, 3H), 7.81 (s, 1H), 7.77 (d, J=9.0 Hz, 1H), 7.61 (s, 1H), 7.10 (d, J=8.4, 1H), 5.21 (s, 2H), 3.85 (s, 3H). HRMS (ESI$^+$) calcd for C$_{20}$H$_{19}$N$_4$O$_4$ (M+H)$^+$ 379.1401, found 379.1401.

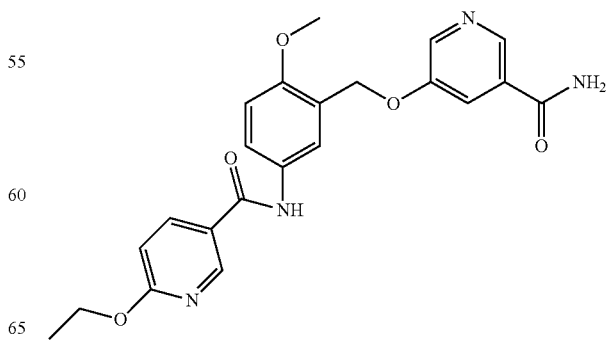

N-(3-(((5-Carbamoylpyridin-3-yl)oxy)methyl)-4-methoxyphenyl)-6-ethoxynicotinamide (F5-3)

White solid (22 mg, 47%). ¹H NMR (DMSO-d$_6$, 600 MHz) δ 10.15 (s, 1H), 8.75 (d, J=2.4 Hz, 1H), 8.65 (s, 1H), 8.47 (d, J=2.4 Hz, 1H), 8.21 (dd, J=9.0, 2.4 Hz, 1H), 8.15 (s, 1H), 7.85 (s, 1H), 7.78 (s, 1H), 7.74 (dd, J=8.7, 2.1 Hz, 1H), 7.61 (s, 1H), 7.08 (d, J=8.4 Hz, 1H), 7.90 (d, J=9.0 Hz, 1H), 5.20 (s, 2H), 4.38 (q, J=7.2 Hz, 2H), 3.32 (s, 3H), 1.34 (t, J=7.2 Hz, 3H). HRMS (ESI⁺) calcd for C$_{22}$H$_{23}$N$_4$O$_5$ (M+H)⁺ 423.1663, found 423.1667.

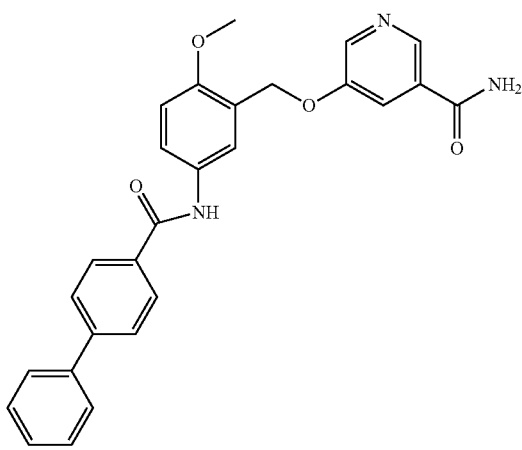 [SMILES: COc1ccc(NC(=O)c2ccc(-c3ccccc3)cc2)cc1COc1cncc(C(N)=O)c1]

5-((5-([1,1-Biphenyl]-4-ylcarboxamido)-2-methoxybenzyl)oxy)nicotinamide (F5-4)

White solid (70 mg, 95%). ¹H NMR (DMSO-d$_6$, 600 MHz) δ 10.27 (s, 1H), 8.66 (s, 1H), 8.47 (d, J=2.4 Hz, 1H), 8.20 (s, 1H), 8.07 (d, J=8.4 Hz, 2H), 7.87 (d, J=10.8 Hz, 2H), 7.84-7.78 (m, 3H), 7.76 (d, J=7.2 Hz, 2H), 7.61 (s, 1H), 7.51 (dd, J=7.8 Hz, 2H), 7.42 (dd, J=7.2 Hz, 1H), 7.08 (d, J=9.0 Hz, 1H), 5.21 (s, 2H), 3.85 (s, 3H). HRMS (ESI⁺) calcd for C$_{27}$H$_{24}$H$_3$O$_4$ (M+H)⁺ 454.1761, found 454.1767.

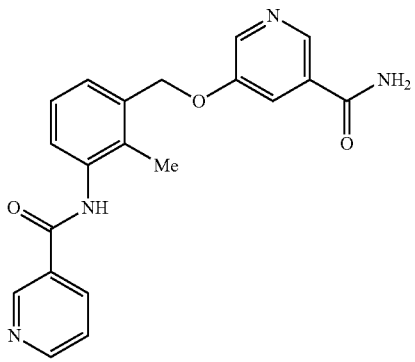 [SMILES: Cc1c(COc2cncc(C(N)=O)c2)cccc1NC(=O)c1cccnc1]

N-(3-(((5-Carbamoylpyridin-3-yl)oxy)methyl)-2-methylphenyl)nicotinamide (F6-1)

White solid (23 mg, 54%). ¹H NMR (DMSO-d$_6$, 600 MHz) δ 10.19 (s, 1H), 9.16 (s, 1H), 8.77 (d, J=4.5 Hz, 1H), 8.66 (s, 1H), 8.52 (d, J=2.4 Hz, 1H), 8.33 (d, J=7.6 Hz, 1H), 8.15 (br s, 1H), 7.91 (s, 1H), 7.63 (br s, 1H), 7.58 (dd, J$_1$=7.7 Hz, J$_2$=5.0 Hz, 1H), 7.42 (d, J=7.7 Hz, 1H), 7.36 (d, J=7.7 Hz, 1H), 7.28 (t, J=7.7 Hz, 1H), 5.29 (s, 2H), 2.24 (s, 3H). HRMS (ESI⁺) calcd for C$_{20}$H$_{19}$N$_4$O$_3$ (M+H)⁺ 363.1452, found 363.1445.

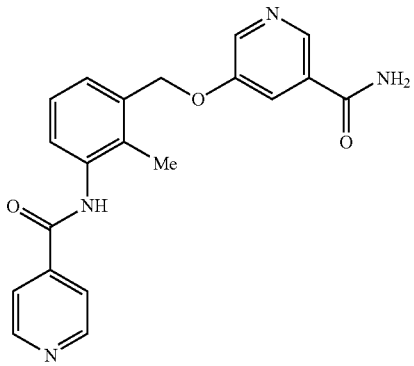 [SMILES: Cc1c(COc2cncc(C(N)=O)c2)cccc1NC(=O)c1ccncc1]

5-((3-(Isonicotinamido)-2-methylbenzyl)oxy)nicotinamide (F6-2)

White solid (17 mg, 40%).

¹H NMR (DMSO-d$_6$, 600 MHz) δ 10.27 (s, 1H), 8.80 (d, J=5.0 Hz, 2H), 8.66 (s, 1H), 8.52 (d, J=2.5 Hz, 1H), 8.15 (br s, 1H), 7.91-7.88 (m, 3H), 7.63 (br s, 1H), 7.43 (d, J=7.4 Hz, 1H), 7.36 (d, J=7.7 Hz, 1H), 7.28 (t, J=7.7 Hz, 1H), 5.29 (s, 2H), 2.23 (s, 3H). HRMS (ESI⁺) calcd for C$_{20}$H$_{19}$N$_4$O$_3$ (M+H)⁺ 363.1452, found 363.1459.

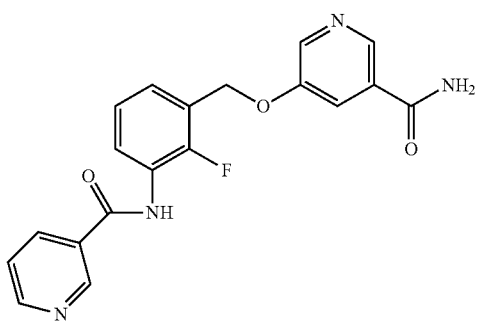 [SMILES: NC(=O)c1cncc(OCc2cccc(NC(=O)c3cccnc3)c2F)c1]

N-(3-(((5-Carbamoylpyridin-3-yl)oxy)methyl)-2-fluorophenyl)nicotinamide (F7-1)

White solid (10 mg, 19%). ¹H NMR (DMSO-d$_6$, 600 MHz) δ 10.42 (s, 1H), 9.13 (d, J=1.8 Hz, 1H), 8.78 (dd, J=1.8, 4.8 Hz, 1H), 8.67 (d, J=1.2 Hz, 1H), 8.51 (d, J=2.4 Hz, 1H), 8.32 (d, J=8.4 Hz, 1H), 8.15 (s, 1H), 7.91 (s, 1H), 7.68 (dd, J=7.8, 7.8 Hz, 1H), 7.63 (s, 1H), 7.58 (dd, J=4.8, 7.8 Hz, 1H), 7.48 (dd, J=6.6, 6.6 Hz, 1H), 7.29 (dd, J=7.8, 7.8 Hz, 1H), 5.32 (s, 2H). HRMS (ESI⁺) calcd for C$_{19}$H$_{16}$FN$_4$O$_3$ (M+H)⁺ 367.1201, found 367.1202.

189

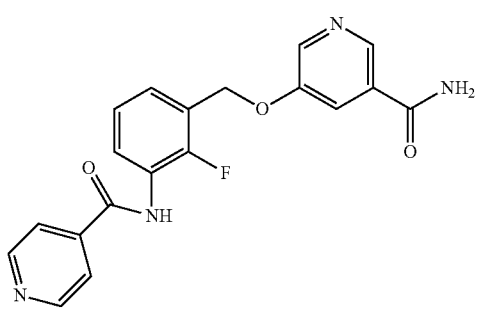 [SMILES: NC(=O)c1cncc(OCc2cccc(NC(=O)c3ccncc3)c2F)c1]

5-((2-Fluoro-3-(isonicotinamido)benzyl)oxy)nicotinamide (F7-2)

White solid (8 mg, 19%). $^1$H NMR (CD$_3$OD, 600 MHz) δ 7.76 (d, J=5.4 Hz, 2H), 8.65 (s, 1H), 8.48 (d, J=2.4 Hz, 1H), 7.96 (s, 1H), 7.92 (d, J=6.0 Hz, 2H), 7.80 (dd, J=7.8, 7.8 Hz, 1H), 7.47 (dd, J=6.6, 6.6 Hz, 1H), 7.28 (dd, J=7.8, 7.8 Hz, 1H), 5.35 (s, 2H). HRMS (ESI$^+$) calcd for C$_{19}$H$_{16}$FN$_4$O$_3$ (M+H)$^+$ 367.1201, found 367.1207.

190

5-((3-(Isonicotinamido)-4-methylbenzyl)oxy)nicotinamide (F8-2)

White solid (22 mg, 52%). $^1$H NMR (DMSO-d$_6$, 600 MHz) δ 10.22 (s, 1H), 8.79 (d, J=5.6 Hz, 2H), 8.64 (d, J=1.2 Hz, 1H), 8.48 (d, J=2.7 Hz, 1H), 8.13 (br s, 1H), 7.88 (d, J=5.3 Hz, 2H), 7.85 (t, J=1.8 Hz, 1H), 7.61 (br s, 1H), 7.48 (s, 1H), 7.34 (d, J=7.9 Hz, 1H), 7.31 (d, J=7.9 Hz, 1H), 5.23 (s, 2H), 2.25 (s, 3H). HRMS (ESI$^+$) calcd for C$_{20}$H$_{19}$N$_4$O$_3$ (M+H)$^+$ 363.1452, found 363.1445.

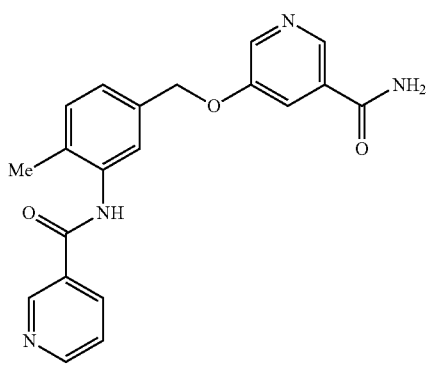 [SMILES: Cc1ccc(COc2cncc(C(N)=O)c2)cc1NC(=O)c1cccnc1]

N-(5-(((5-Carbamoylpyridin-3-yl)oxy)methyl)-2-methylphenyl)nicotinamide (F8-1)

White solid (17 mg, 39%). $^1$H NMR (DMSO-d$_6$, 600 MHz) δ 10.13 (s, 1H), 9.14 (s, 1H), 8.77 (d, J=4.5 Hz, 1H), 8.64 (s, 1H), 8.48 (d, J=2.4 Hz, 1H), 8.31 (d, J=7.6 Hz, 1H), 8.13 (br s, 1H), 7.85 (s, 1H), 7.61 (br s, 1H), 7.57 (dd, J$_1$=7.5 Hz, J$_2$=5.0 Hz, 1H), 7.50 (s, 1H), 7.33 (d, J=7.7 Hz, 1H), 7.30 (d, J=7.7 Hz, 1H), 5.23 (s, 2H), 2.26 (s, 3H). HRMS (ESI$^+$) calcd for C$_{20}$H$_{19}$N$_4$O$_3$ (M+H)$^+$ 363.1452, found 363.1451.

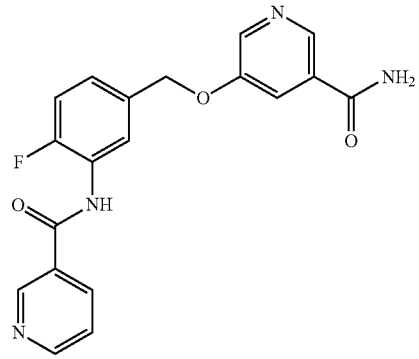 [SMILES: NC(=O)c1cncc(OCc2ccc(F)c(NC(=O)c3cccnc3)c2)c1]

N-(5-(((5-Carbamoylpyridin-3-yl)oxy)methyl)-2-fluorophenyl)nicotinamide (F9-1)

White solid (10 mg, 33%). $^1$H NMR (DMSO-d$_6$, 600 MHz) δ 10.41 (s, 1H), 9.12 (s, 1H), 8.78 (d, J=4.4 Hz, 1H), 8.66 (s, 1H), 8.49 (d, J=2.4 Hz, 1H), 8.31 (d, J=8.0 Hz, 1H), 8.14 (br s, 1H), 7.87 (s, 1H), 7.78 (d, J=6.8 Hz, 1H), 7.62 (br s, 1H), 7.58 (dt, J$_1$=7.9 Hz, J$_2$=4.8 Hz, 1H), 7.43-7.39 (m, 1H), 7.36 (t, J=9.2 Hz, 1H), 5.25 (s, 2H). HRMS (ESI$^+$) calcd for C$_{19}$H$_{16}$FN$_4$O$_3$ (M+H)$^+$ 367.1201, found 367.1202.

191

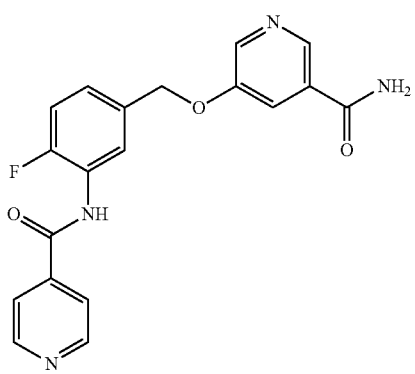 [SMILES: NC(=O)c1cncc(OCc2ccc(F)c(NC(=O)c3ccncc3)c2)c1]

5-((4-Fluoro-3-(isonicotinamido)benzyl)oxy)nicotinamide (F9-2)

White solid (12 mg, 40%). $^1$H NMR (DMSO-d$_6$, 600 MHz) δ 10.48 (s, 1H), 8.80 (d, J=5.9 Hz, 2H), 8.66 (d, J=1.2 Hz, 1H), 8.49 (d, J=2.9 Hz, 1H), 8.13 (s, 1H), 7.89-7.85 (m, 3H), 7.76 (d, J=7.2 Hz, 1H), 7.62 (s, 1H), 7.44-7.41 (m, 1H), 7.39-7.35 (m, 1H), 5.25 (s, 2H). HRMS (ESI$^+$) calcd for C$_{19}$H$_{16}$FN$_4$O$_3$ (M+H)$^+$ 367.1201, found 367.1208.

192

5-((3-(Isonicotinamido)-5-methylbenzyl)oxy)nicotinamide (F10-2)

White solid (33 mg, 78%). $^1$H NMR (DMSO-d$_6$, 600 MHz) δ 10.48 (s, 1H), 8.78 (d, J=5.5 Hz, 2H), 8.65 (s, 1H), 8.49 (d, J=2.8 Hz, 1H), 8.14 (br s, 1H), 7.86-7.84 (m, 3H), 7.70 (s, 1H), 7.61 (br s, 1H), 7.60 (s, 1H), 7.08 (s, 1H), 5.22 (s, 2H), 2.34 (s, 3H). HRMS (ESI$^+$) calcd for C$_{20}$H$_{19}$N$_4$O$_3$ (M+H)$^+$ 363.1452, found 363.1450.

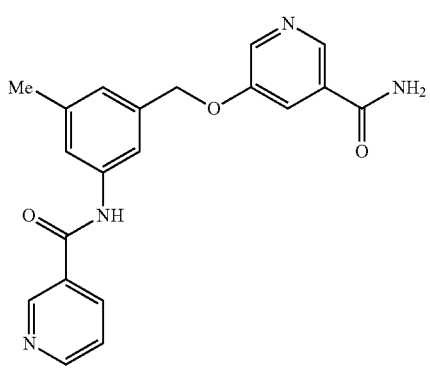 [SMILES: Cc1cc(COc2cncc(C(N)=O)c2)cc(NC(=O)c2cccnc2)c1]

N-(3-(((5-Carbamoylpyridin-3-yl)oxy)methyl)-5-methylphenyl)nicotinamide (F10-1)

White solid (32 mg, 76%). $^1$H NMR (DMSO-d$_6$, 600 MHz) δ 10.43 (s, 1H), 9.10 (d, J=2.2 Hz, 1H), 8.76 (dd, J$_1$=4.7 Hz, J$_2$=1.5 Hz, 1H), 8.65 (d, J=1.8 Hz, 1H), 8.49 (d, J=2.9 Hz, 1H), 8.29 (dt, J$_1$=8.0 Hz, J$_2$=2.0 Hz, 1H), 8.14 (br s, 1H), 7.86-7.85 (m, 1H), 7.71 (s, 1H), 7.61 (br s, 1H), 7.60 (s, 1H), 7.57 (dd, J$_1$=7.8 Hz, J$_2$=4.8 Hz, 1H), 7.07 (s, 1H), 5.21 (s, 2H), 2.34 (s, 3H). HRMS (ESI$^+$) calcd for C$_{24}$H$_{19}$N$_4$O$_3$ (M+H)$^+$ 363.1452, found 363.1448.

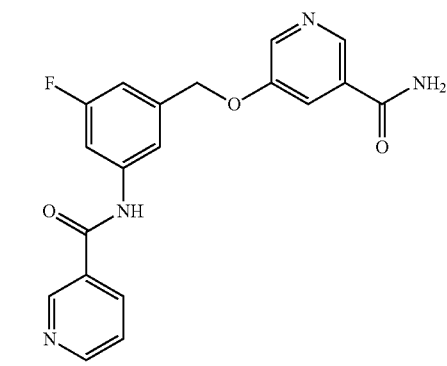 [SMILES: NC(=O)c1cncc(OCc2cc(F)cc(NC(=O)c3cccnc3)c2)c1]

N-(3-(((5-Carbamoylpyridin-3-yl)oxy)methyl)-5-fluorophenyl)nicotinamide (F11-1)

White solid (35 mg, 79%). $^1$H NMR (DMSO-d$_6$, 600 MHz) δ 10.68 (s, 1H), 9.10 (s, 1H), 8.78 (d, J=4.5 Hz, 1H), 8.67 (s, 1H), 8.51 (d, J=2.6 Hz, 1H), 8.29 (d, J=8.2 Hz, 1H), 8.14 (br s, 1H), 7.86 (s, 1H), 7.72 (d, J=11.3 Hz, 1H), 7.70 (s, 1H), 7.63 (br s, 1H), 7.58 (dd, J$_1$=7.7 Hz, J$_2$=4.8 Hz, 1H), 7.10 (d, J=9.0 Hz, 1H), 5.28 (s, 2H). HRMS (ESI$^+$) calcd for C$_{19}$H$_{16}$FN$_4$O$_3$ (M+H)$^+$ 367.1201, found 367.1195.

193

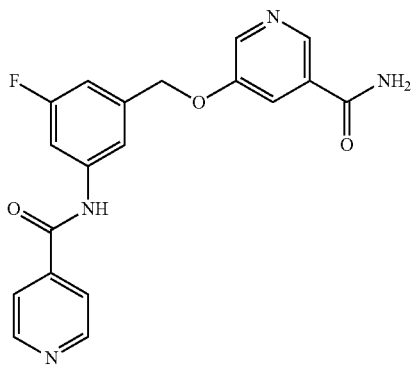 [SMILES: NC(=O)c1cncc(OCc2cc(F)cc(NC(=O)c3ccncc3)c2)c1]

5-((3-Fluoro-5-(isonicotinamido)benzyl)oxy)nicotinamide (F11-2)

White solid (39 mg, 87%). $^1$H NMR (DMSO-$d_6$, 600 MHz) δ 10.74 (s, 1H), 8.80 (d, J=5.9 Hz, 2H), 8.67 (s, 1H), 8.51 (d, J=2.6 Hz, 1H), 8.14 (br s, 1H), 7.87-7.85 (m, 3H), 7.74-7.69 (m, 2H), 7.63 (s, 1H), 7.11 (d, J=9.0 Hz, 1H), 5.28 (s, 2H). HRMS (ESI$^+$) calcd for $C_{19}H_{16}FN_4O_3$ (M+H)$^+$ 367.1201, found 367.1198.

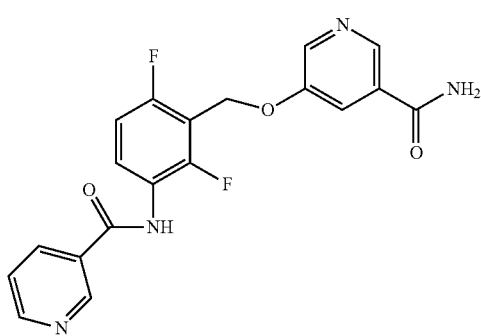 [SMILES: NC(=O)c1cncc(OCc2c(F)ccc(NC(=O)c3cccnc3)c2F)c1]

N-(3-(((5-Carbamoylpyridin-3-yl)oxy)methyl)-2,4-difluorophenyl)nicotinamide (F12-1)

White solid (7.8 mg, 13%). $^1$H NMR (DMSO-$d_6$, 600 MHz) δ 10.44 (s, 1H), 9.13 (s, 1H), 8.78 (d, J=4.2 Hz, 1H), 8.68 (s, 1H), 8.50 (d, J=2.4 Hz, 1H), 8.31 (d, J=8.4 Hz, 1H), 8.14 (s, 1H), 7.94 (s, 1H), 7.73 (d, J=9.0, 15.6 Hz, 1H), 7.64 (s, 1H), 7.59 (dd, J=7.2, 8.4 Hz, 1H), 7.27 (dd, J=9.0, 9.0 Hz, 1H), 5.31 (s, 2H). HRMS (ESI$^+$) calcd for $C_{19}H_{15}F_2N_4O_3$ (M+H)$^+$ 385.1107, found 385.1114.

194

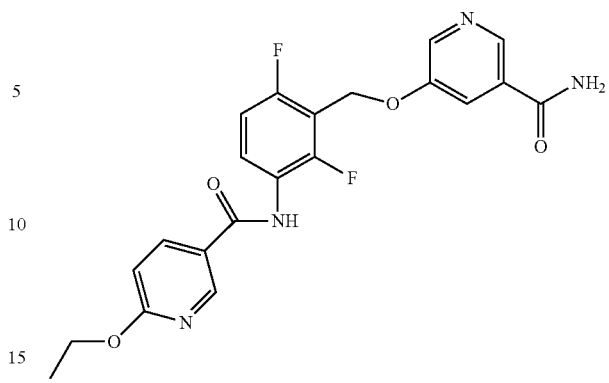

N-(3-(((5-Carbamoylpyridin-3-yl)oxy)methyl)-2,4-difluorophenyl)-6-ethoxynicotinamide (F12-2)

White solid (5.7 mg, 8.7%). $^1$H NMR (DMSO-$d_6$, 600 MHz) δ 10.21 (s, 1H), 8.72 (s, 1H), 8.68 (d, J=1.2 Hz, 1H), 8.50 (d, J=2.4 Hz, 1H), 8.22 (d, J=8.4 Hz, 1H), 8.14 (s, 1H), 7.93 (s, 1H), 7.69 (dd, J=7.8, 14.4 Hz, 1H), 7.63 (s, 1H), 7.25 (dd, J=9.0, 9.0 Hz, 1H), 6.93 (d, J=8.4 Hz, 1H), 5.30 (s, 2H), 4.39 (q, J=7.2 Hz, 2H), 1.35 (t, J=7.2 Hz, 3H). HRMS (ESI$^+$) calcd for $C_{21}H_{19}F_2N_4O_4$ (M+H)$^+$ 429.1369, found 429.1379.

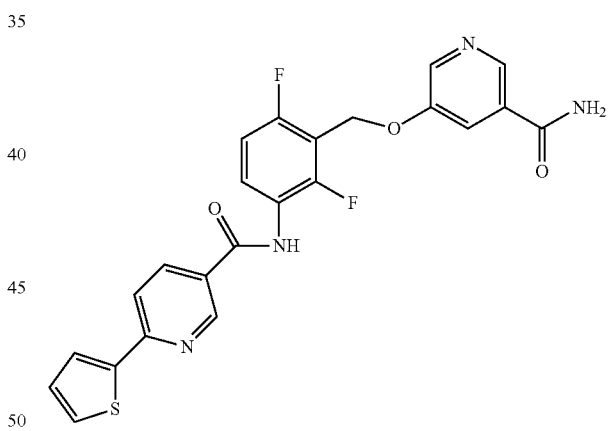

N-(3-(((5-Carbamoylpyridin-3-yl)oxy)methyl)-2,4-difluorophenyl)-6-(thiophen-2-yl)nicotinamide (F12-3)

White solid (18 mg, 25%). $^1$H NMR (DMSO-$d_6$, 600 MHz) δ 10.40 (s, 1H), 9.06 (s, 1H), 8.35 (d, J=9.0 Hz, 1H), 8.15 (s, 1H), 8.09 (d, J=8.4 Hz, 1H), 7.98-7.93 (m, 2H), 7.78-7.72 (m, 2H), 7.64 (s, 1H), 7.27 (dd, J=8.7, 8.7 Hz, 1H), 7.23 (dd, J=4.2, 4.2 Hz, 1H), 5.32 (s, 2H). HRMS (ESI$^+$) calcd for $C_{23}H_{17}F_2N_4O_3S$ (M+H)$^+$ 467.0984, found 467.0985.

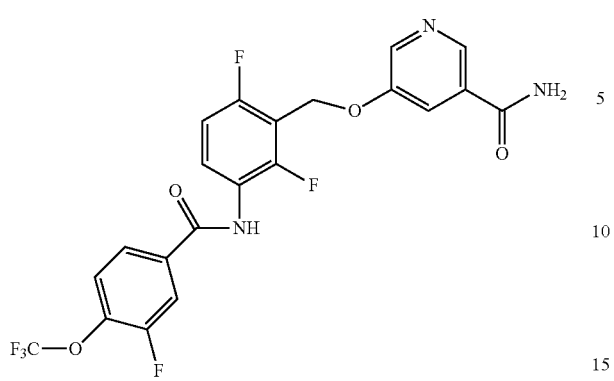

5-((2,6-Difluoro-3-(3-fluoro-4-(trifluoromethoxy)benzamido)benzyl)oxy)nicotinamide (F12-4)

White solid (16 mg, 21%). $^1$H NMR (DMSO-$d_6$, 600 MHz) δ 10.42 (s, 1H), 8.69 (s, 1H), 8.51 (s, 1H), 8.14 (s, 1H), 8.07 (d, J=10.8 Hz, 1H), 7.96-7.90 (m, 2H), 7.78 (dd, J=8.4, 8.4 Hz, 1H), 7.70 (dd, J=7.8, 14.4 Hz, 1H), 7.64 (s, 1H), 7.27 (dd, J=9.0 Hz, 1H), 5.31 (s, 2H). HRMS (ESI$^+$) calcd for $C_{21}H_{14}F_6N_3O_4$ (M+H)$^+$ 486.0883, found 486.0881.

Example 7

Representative compounds of formula (I) can be prepared as described below.

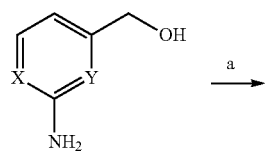

IG1a, X = N, Y = CH
IG1b, X = CH, Y = N

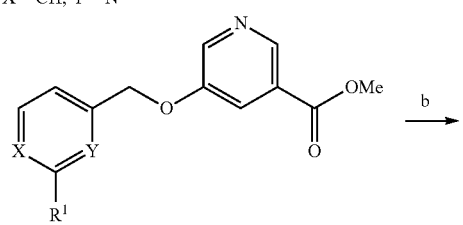

IG2a, X = N, Y = CH, R$^1$ = NH$_2$
IG2b, X = CH, Y = N, R$^1$ = N=P(Ph)$_3$

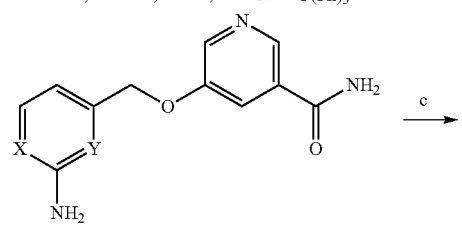

IG3a, X = N, Y = CH
IG3b, X = CH, Y = N

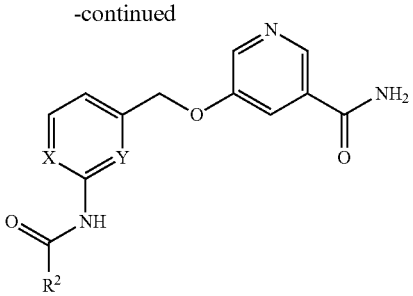

G1, X = N, Y = CH
G2, X = CH, Y = N

IG2a

In a manner similar to that described for the preparation of compound IF4f, a Mitsunobu reaction of IG1a (124 mg, 1.00 mmol) and methyl 5-hydroxy-3-pyridinecarboxylate (153 mg, 1.00 mmol) afforded IG2a as a yellow solid (49 mg, 19%). $^1$H NMR (CDCl$_3$, 600 MHz) δ 8.86 (d, J=1.8 Hz, 1H), 8.54 (d, J=2.9 Hz, 1H), 8.09 (d, J=5.3 Hz, 1H), 7.81-7.80 (m, 1H), 6.68 (d, J=5.3 Hz, 1H), 6.57 (s, 1H), 5.07 (s, 2H), 4.50 (br s, 2H), 3.96 (s, 3H). HRMS (ESI$^+$) calcd for $C_{13}H_{14}N_3O_3$ (M+H)$^+$ 260.1030, found 260.1038.

IG2b

In a manner similar to that described for the preparation of compound IF4f, a Mitsunobu reaction of IG1b (621 mg, 5.00 mmol) and methyl 5-hydroxy-3-pyridinecarboxylate (766 mg, 5.00 mmol) afforded IG2b as a brown solid (362 mg, 14%). $^1$H NMR (CDCl$_3$, 600 MHz) δ 8.78 (s, 1H), 8.27 (d, J=2.4 Hz, 1H), 7.83-7.75 (m, 6H), 7.65 (s, 1H), 7.51-7.47 (m, 3H), 7.43-7.33 (m, 7H), 6.86 (d, J=8.2 Hz, 1H), 6.59 (d, J=7.2 Hz, 1H), 4.71 (s, 2H), 3.94 (s, 3H). HRMS (ESI$^+$) calcd for $C_{31}H_{27}N_3O_3P$ (M+H)$^+$ 520.1785, found 520.1780.

IG3a

In a manner similar to that described for the preparation of compound IF6a, aminolysis of IG2a (46 mg, 0.18 mmol) afforded IG3a as a yellow solid (21 mg, 48%). $^1$H NMR (CD$_3$OD, 600 MHz) δ 8.63 (s, 1H), 8.45 (d, J=2.7 Hz, 1H), 7.89-7.87 (m, 2H), 6.67-6.65 (m, 2H), 5.15 (s, 2H). HRMS (ESI$^+$) calcd for $C_{12}H_{13}N_4O_2$ (M+H)$^+$ 245.1033, found 245.1028.

IG3b

In a manner similar to that described for the preparation of compound IF6a, aminolysis of IG2b (362 mg, 0.70 mmol) afforded IG3b as a white solid (120 mg, 70%). $^1$H NMR (CD$_3$OD, 600 MHz) S 8.62 (s, 1H), 8.44 (d, J=2.9 Hz, 1H), 7.90-7.88 (m, 1H), 7.46 (t, J=7.9 Hz, 1H), 6.75 (d, J=7.3 Hz, 1H), 6.52 (d, J=8.3 Hz, 1H), 5.07 (s, 2H). HRMS (ESI$^+$) calcd for $C_{12}H_{13}N_4O_2$ (M+H)$^+$ 245.1033, found 245.1035.

The following compounds were prepared through an amide formation reaction in a manner similar to that described for the preparation of compound F1-1.

197

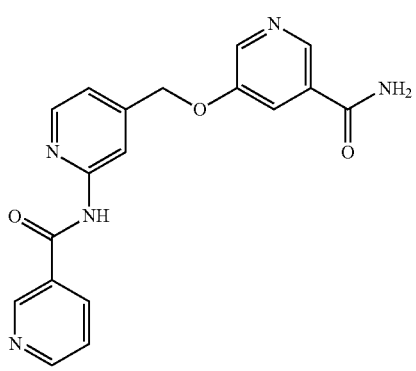 [SMILES: NC(=O)c1cncc(OCc2ccnc(NC(=O)c3cccnc3)c2)c1]

N-(4-(((5-Carbamoylpyridin-3-yl)oxy)methyl)pyridin-2-yl)nicotinamide (G1-1)

White solid (4 mg, 29%). ¹H NMR (DMSO-d₆, 600 MHz) δ 11.15 (s, 1H), 9.13 (s, 1H), 8.76 (d, J=4.1 Hz, 1H), 8.68 (s, 1H), 8.53 (d, J=2.7 Hz, 1H), 8.43 (d, J=5.0 Hz, 1H), 8.35 (d, J=7.9 Hz, 1H), 8.33 (s, 1H), 8.15 (br s, 1H), 7.87 (s, 1H), 7.63 (br s, 1H), 7.55 (dd, J₁=7.9 Hz, J₂=4.9 Hz, 1H), 7.27 (d, J=4.7 Hz, 1H), 5.38 (s, 2H). HRMS (ESI⁺) calcd for C₁₈H₁₆N₅O₃ (M+H)⁺ 350.1248, found 350.1254.

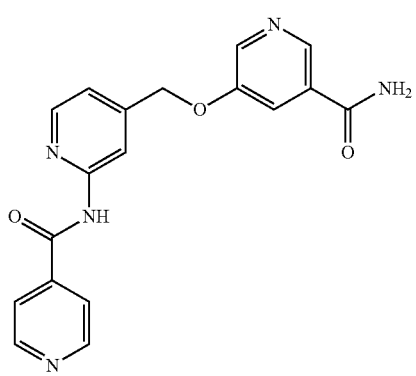 [SMILES: NC(=O)c1cncc(OCc2ccnc(NC(=O)c3ccncc3)c2)c1]

5-((2-(Isonicotinamido)pyridin-4-yl)methoxy)nicotinamide (GI-2)

White solid (5 mg, 41%). ¹H NMR (DMSO-d₆, 600 MHz) δ 11.19 (s, 1H), 8.77 (d, J=5.0 Hz, 2H), 8.68 (s, 1H), 8.53 (d, J=2.3 Hz, 1H), 8.43 (d, J=5.0 Hz, 1H), 8.32 (s, 1H), 8.15 (br s, 1H), 7.91 (d, J=5.0 Hz, 2H), 7.87 (s, 1H), 7.63 (br s, 1H), 7.29 (d, J=5.0 Hz, 1H), 5.39 (s, 2H). HRMS (ESI⁺) calcd for C₁₈H₁₆N₅O₃ (M+H)⁺ 350.1248, found 350.1256.

198

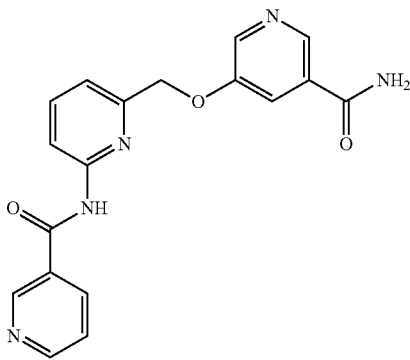 [SMILES: NC(=O)c1cncc(OCc2cccc(NC(=O)c3cccnc3)n2)c1]

N-(6-(((5-Carbamoylpyridin-3-yl)oxy)methyl)pyridin-2-yl)nicotinamide (G2-1)

White solid (10 mg, 26%). ¹H NMR (DMSO-d₆, 600 MHz) δ 11.20 (s, 1H), 9.14 (s, 1H), 8.75 (d, J=5.0 Hz, 1H), 8.67 (s, 1H), 8.53 (s, 1H), 8.35 (d, J=7.9 Hz, 1H), 8.17 (d, J=8.3 Hz, 1H), 8.14 (br s, 1H), 7.93 (t, J=7.8 Hz, 1H), 7.86 (s, 1H), 7.63 (br s, 1H), 7.56-7.53 (m, 1H), 7.35 (d, J=7.6 Hz, 1H), 5.28 (s, 2H). HRMS (ESI⁺) calcd for C₁₈H₁₆N₅O₃ (M+H)⁺ 350.1248, found 350.1246.

5-((6-(Isonicotinamido)pyridin-2-yl)methoxy)nicotinamide (G2-2)

White solid (12 mg, 30%). ¹H NMR (DMSO-d₆, 600 MHz) δ 11.23 (s, 1H), 8.77 (d, J=5.2 Hz, 2H), 8.67 (s, 1H), 8.53 (d, J=2.4 Hz, 1H), 8.17 (d, J=8.4 Hz, 1H), 8.14 (br s, 1H), 7.94 (t, J=7.9 Hz, 1H), 7.92 (d, J=5.2 Hz, 2H), 7.86 (s, 1H), 7.63 (br s, 1H), 7.37 (d, J=7.4 Hz, 1H), 5.28 (s, 2H). HRMS (ESI⁺) calcd for C₁₈H₁₆N₅O₃ (M+H)⁺ 350.1248, found 350.1254.

Example 8

Representative compounds of formula (I) can be prepared as described below.

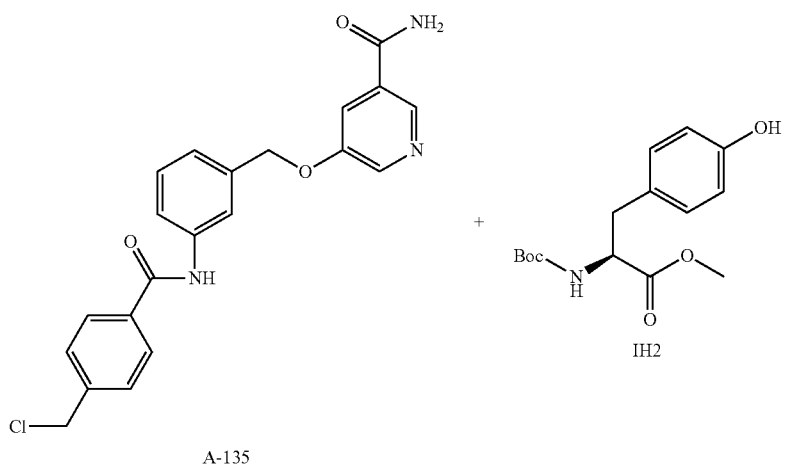

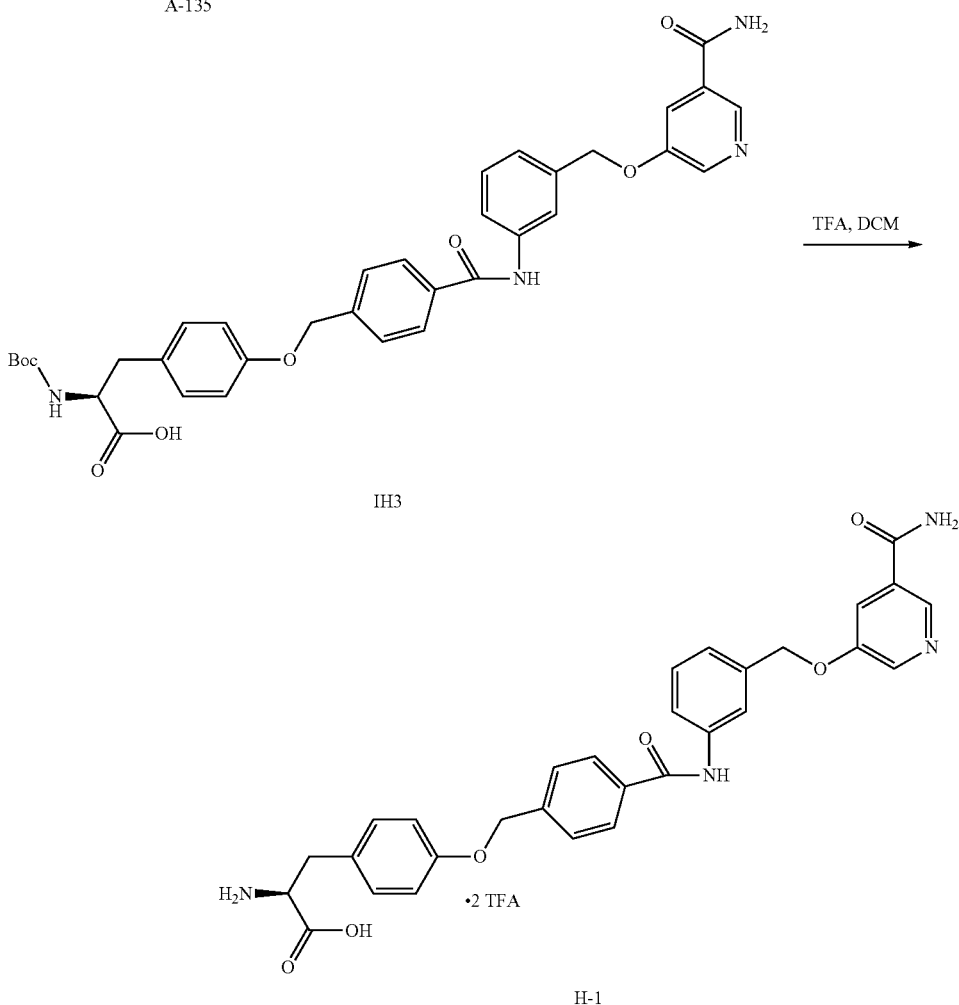

(S)-2-((tert-Butoxycarbonyl)amino)-3-(4-((4-((3-(((5-carbamoylpyridin-3-yl)oxy)methyl)phenyl)carbamoyl)benzyl)oxy)phenyl)propanoic acid (IH3)

To a solution of A-135 (6.0 mg, 0.015 mmol) in DMF (2 mL) was added $Cs_2CO_3$ (10.0 mg, 0.030 mmol) and Boc-Tyr-OMe (IH2, 5.0 mg, 0.017 mmol) and the reaction mixture was allowed to stir at rt for 12 h. The reaction mixture was diluted with saturated $NH_4Cl$ and extracted with EtOAc. The organic phase was washed with water, brine, dried over anhydrous $Na_2SO_4$, and concentrated in vacuo. The residue was then dissolved in MeOH (5 mL) and 1 N NaOH (2 mL). The reaction mixture was allowed to stir at rt for 12 h. Upon removal of MeOH, aqueous phase was acidified with 1 N HCl to pH=5. Aqueous solution was extracted with EtOAc, The organic phase was washed with water, brine, dried over anhydrous $Na_2SO_4$, and concentrated in vacuo. The residue was purified by flash column chromatography (0-30% MeOH/CH$_2$Cl$_2$) to afford acid IH3 as a white solid (8.0 mg, 83% over two steps). $^1$H NMR (MeOH-d$_4$, 600 MHz) δ 8.65 (bs, 1H), 8.49 (bs, 1H), 7.99-7.90 (m, 3H), 7.88 (s, 1H), 7.67 (d, J=7.8 Hz, 1H), 7.58 (d, J=7.8 Hz, 2H), 7.40 (dd, J=8.4 Hz, 1H), 7.27 (d, J=7.2 Hz, 1H), 7.15 (d, J=7.8 Hz, 2H), 6.92 (d, J=7.8 Hz, 2H), 5.25 (s, 2H), 5.15 (s, 2H), 4.31-4.25 (m, 1H), 3.12-3.05 (m, 1H), 2.88-2.80 (m, 1H), 1.38 (s, 9H). HRMS (ESI$^+$) calcd for C$_{35}$H$_{37}$N$_4$O$_8$ (M+H)$^+$ 641.2606, found 641.2606.

(S)-2-Amino-3-(4-((4-((3-(((5-carbamoylpyridin-3-yl)oxy)methyl)phenyl)carbamoyl)-benzyl)oxy)phenyl)propanoic acid (H-1)

To a solution of IH3 (8.0 mg, 0.015 mmol) in DCM (2 mL) was added TFA (0.5 mL) and the reaction mixture was allowed to stir at rt for 2 h. The reaction mixture was concentrated in vacuo to afford acid H-1 as a white solid (7.2 mg, 78%). $^1$H NMR (MeOH-d$_4$, 600 MHz) δ 8.70 (bs, 1H), 8.55 (bs, 1H), 8.07 (s, 1H), 7.96 (d, J=8.4 Hz, 2H), 7.90 (s, 1H), 7.67 (d, J=7.8 Hz, 1H), 7.59 (d, J=8.4 Hz, 2H), 7.41 (dd, J=8.4 Hz, 1H), 7.28 (d, J=7.2 Hz, 1H), 7.22 (d, J=8.4 Hz, 2H), 7.02 (d, J=9.0 Hz, 2H), 5.29 (s, 2H), 5.19 (s, 2H), 4.20 (dd, J=7.2, 5.4 Hz, 1H), 3.28-3.21 (m, 1H), 3.12-3.05 (m, 1H). HRMS (ESI$^+$) calcd for C$_{30}$H$_{29}$N$_4$O$_6$ (M+H)$^+$ 541.2082, found 541.2077.

Example 9

Biological Assays and Data

SIRT1-3 Biochemical Assays (I)

Full length human SIRT1 (GenBank Accession No. NM_012238, MW=82 kDa), full length human SIRT2 (GenBank Accession No. NM_012237, MW=43 kDa), and catalytically active human SIRT3 (GenBank Accession No. NM_012239, amino acids 102-399, MW=32.7 kDa) were expressed in E. coli and purified. The peptide substrate for SIRT1-3 was a fluorogenic 7-amino-4-methylcoumarin (AMC)-labeled peptide Ac-Arg-His-Lys-Lys(Ac)-AMC. The assays were performed in a buffer of 50 mM Tris-HCl (pH 8.0), 137 mM NaCl, 2.7 mM KCl, 1 mM MgCl$_2$ and 1 mg/ml BSA, which was added before use. The testing involved a two-step reaction. First, 50 μM AMC-labeled substrate with an acetylated lysine side chain was incubated with 91 nM SIRT1 (6 μL reaction volume) for 2 hours at 30° C. to produce the deacetylated substrate. The concentrations of SIRT2 and SIRT3 were 233 and 917 nM, respectively. Second, the deacetylated substrate was digested by a mixture of developer (6 μL) to release AMC that was detected at 360/460 Ex/Em. Each compound was dissolved in DMSO (1% or less final concentration, which does not significantly affect the enzymatic assay), sequentially diluted, and used for testing. Background fluorescence produced by compounds if detected was subtracted. The percentages of enzyme activity (relative to DMSO controls) were calculated. To determine the IC$_{50}$ values, compounds were tested in a 10-dose mode with a 3-fold serial dilution starting at 200 μM (200 μM-10.2 nM) in singlet. The IC$_{50}$ values were calculated from the resulting sigmoidal dose-response curves using GraphPad Prism. Suramin was used as a reference compound for SIRT1 as well as SIRT2, and nicotinamide for SIRT3.

SIRT1-3 Biochemical Assays (II)

The full length human SIRT2 gene (Accession No. NM_012237) was cloned into the expression vector pReceiver-B01 (GeneCopoeia). The recombinant human SIRT2 contains a his$_6$-affinity purification tag at the N terminal of the protein. The plasmid was transformed into E. coli BL21 (DE3) cells, and cultured to an OD600 of 0.6. The E. coli was induced with 0.4 mM isopropyl β-D-thiogalactoside (IPTG) and cultured for 16 h at 18° C. The cultures were harvested by centrifugation and the cell pellets were stored at −80° C. The cell pellets were resuspended in 40 ml binding buffer (50 mM HEPES pH 8.0, 300 mM NaCl, 10 mM imidazole). Cells were sonicated 4 times on ice using a Branson Sonifier 250 (power 8, 30% duty cycle, 2 min) and centrifuged at 45,000 g for 10 min at 4° C. The protein was recovered from the cleared lysate by the addition of 0.5 mL His60 resin (Clontech) followed by incubation at 4° C. for 1 hr with constant rotation. The resin was recovered by pouring the lysate into a gravity column. The column was washed using 15 mL wash buffer (50 mM HEPES pH 8.0, 300 mM NaCl, 20 mM imidazole) to remove all of the unbound proteins. Then the bound protein was eluted with 2.5 mL elution buffer (50 mM HEPES pH 8.0, 300 mM NaCl, 500 mM imidazole). The SIRT2 protein was desalted into storage buffer (25 mM Tris-HCl, pH 7.5, 100 mM NaCl, and 10% glycerol) using PD-10 columns (GE Healthcare) and stored at −80° C. The yield of the protein was approximately 5.7 mg/L. Plasmids for the expression of SIRT1 (SIRT1.1, plasmid 13735) and SIRT3 (SIRT3L-12, plasmid 13736) were obtained from Addgene and transformed into E. coli BL21 (DE3). Expression and purification were performed as for SIRT2 and yielded 3.6 and 8.1 mg/L of culture for SIRT1 and SIRT3, respectively.

Compounds were aliquoted (0.5 μL) in duplicate into black 384 well non-binding surface plates (Corning). A master mix containing assay buffer (50 mM Tris pH 8.0, 137 mM NaCl, 2.7 mM KCl, 1 mM MgCl$_2$), NAD, 1 mM DTT, and 1 mg/mL BSA, was added to 2 wells to serve as a negative control. Enzyme was added to the remaining master mix, which was then aliquoted into all remaining wells. The plate was mixed for 30 s at 15000 RPM on a MixMate (Eppendorf) and left at 25° C. for 10 min. The reactions were initiated by the addition of peptide (to a final volume of 50 μL) followed by mixing of the plate as described above. The reaction was allowed to proceed at 37° C. for the desired time and then quenched by the addition of 10 pt developing buffer (12 mM nicotinamide, 30000 U/mL trypsin). The plates were once again mixed and then developed for 20 min at 37° C. before analyzing the plate by exciting at 355 nm and reading the emission at 460 nm.

| Enzyme specific conditions for assays (II) | | | |
|---|---|---|---|
| Enzyme | SIRT1 | SIRT2 | SIRT3 |
| NAD, mM | 0.26 | 0.2 | 0.344 |
| Peptide, mM | 0.453 | 0.297 | 0.255 |
| Enzyme, μM | 0.25 | 0.1 (titrated) | 1.5 |
| Reaction time, min | 20 | 20 | 60 |

TABLE 1

Activities against SIRT1-3.

| | | IC$_{50}$ or K$_i^{app}$ (μM) | | |
|---|---|---|---|---|
| Compound | Assays | SIRT1 | SIRT2 | SIRT3 |
| A-1 | I | 7.14 | 0.107 | 6.39 |
| A-2 | I | >200 | 15.1 | 22.3 |

TABLE 1-continued

Activities against SIRT1-3.

| Compound | Assays | IC$_{50}$ or K$_i^{app}$ (μM) SIRT1 | SIRT2 | SIRT3 |
|---|---|---|---|---|
| A-3 | I | 42.4 | 2.05 | 28.4 |
| A-4 | I | >200 | 0.505 | >200 |
| A-5 | I | 21.8 | 0.546 | 17.9 |
| A-6 | I | 12.5 | 0.252 | 11.5 |
| A-7 | I | 9.50 | 0.235 | 7.86 |
| A-8 | I | 50.8 | 4.80 | 6.03 |
| A-9 | I | 44.6 | 1.37 | 4.08 |
| A-10 | I | 19.7 | 0.156 | 18.5 |
| A-11 | I | 192 | 0.572 | 1.08 |
| A-12 | I | 52.1 | 0.0234 | 1.59 |
| A-13 | I | 1.62 | 0.0331 | 3.29 |
| A-14 | I | 9.93 | 0.0647 | 2.37 |
| A-15 | I | 7.33 | 0.0714 | 1.77 |
| A-16 | I | 65.2 | 0.437 | 36.2 |
| A-17 | I | 8.09 | 0.313 | 2.71 |
| A-18 | I | 1.81 | 0.0831 | 1.56 |
| A-19 | I | 2.23 | 0.0354 | 1.39 |
| A-20 | I | 0.483 | 0.0157 | 1.22 |
| A-21 | I | 192 | 4.15 | 19.5 |
| A-22 | I | 30.4 | 0.580 | 9.06 |
| A-23 | I | 8.54 | 0.111 | 5.84 |
| A-24 | I | 53.2 | 3.49 | 8.55 |
| A-25 | I | 29.5 | 0.841 | 9.93 |
| A-26 | I | 13.0 | 0.173 | 7.12 |
| A-27 | I | 53.2 | 3.82 | 11.6 |
| A-28 | I | 10.5 | 0.293 | 20.9 |
| A-29 | I | 2.96 | 0.113 | 8.05 |
| A-30 | I | 97.8 | 6.01 | 17.9 |
| A-31 | I | 26.3 | 0.273 | 8.04 |
| A-32 | I | 8.37 | 0.174 | 7.27 |
| A-33 | I | 194 | 7.04 | 12.6 |
| A-34 | I | 15.2 | 0.280 | 11.8 |
| A-35 | I | 1.64 | 0.0916 | 4.60 |
| A-36 | I | 30.2 | 0.288 | 2.94 |
| A-37 | I | 10.1 | 0.0754 | 3.39 |
| A-38 | I | 4.19 | 0.0368 | 2.57 |
| A-39 | I | 31.4 | 0.277 | 15.5 |
| A-40 | I | 7.97 | 0.0418 | 1.56 |
| A-41 | I | 16.5 | 0.474 | 5.79 |
| A-42 | I | 16.3 | 0.0954 | 13.0 |
| A-43 | I | 16.6 | 0.384 | 4.32 |
| A-44 | I | 19.9 | 0.0353 | 15.1 |
| A-45 | I | 71.8 | 0.109 | 1.33 |
| A-46 | I | 9.26 | 0.0217 | 1.60 |
| A-47 | I | 21.0 | 0.151 | 8.24 |
| A-48 | I | 13.5 | 0.0947 | 2.50 |
| A-49 | I | 15.3 | 0.113 | 4.89 |
| A-50 | I | 71.5 | 0.133 | 3.50 |
| A-51 | I | 15.6 | 0.0135 | >200 |
| A-52 | I | 106 | 0.0263 | 66.4 |
| A-53 | I | 13.4 | 0.0460 | 8.15 |
| A-54 | I | 14.7 | 0.476 | 6.50 |
| A-55 | I | 3.51 | 0.0447 | 4.18 |
| A-56 | I | 0.237 | 0.251 | 0.827 |
| A-57 | I | 0.367 | 0.0190 | 0.843 |
| A-58 | I | 2.55 | 0.0227 | 0.503 |
| A-59 | I | 1.55 | 0.0281 | 0.829 |
| A-60 | I | 0.974 | 0.0229 | 0.697 |
| A-61 | I | 3.01 | 0.0415 | 3.20 |
| A-62 | I | 8.02 | 0.102 | 8.90 |
| A-63 | I | 142 | 2.58 | 106 |
| A-64 | I | 1.88 | 0.0478 | 7.35 |
| A-65 | I | 1.39 | 0.0281 | 2.64 |
| A-66 | I | 6.27 | 0.519 | 5.58 |
| A-67 | I | 0.672 | 0.0486 | 1.88 |
| A-68 | I | 24.1 | 0.465 | 17.7 |
| A-69 | I | >200 | 0.196 | 85.8 |
| A-70 | I | >200 | 0.138 | >200 |
| A-71 | I | 2.82 | 0.216 | 5.62 |
| A-72 | I | 3.03 | 0.104 | 5.59 |
| A-73 | I | 10.5 | 0.0267 | 7.51 |
| A-74 | I | 11.5 | 0.366 | 8.19 |
| A-75 | I | 5.66 | 0.0982 | 0.910 |
| A-76 | I | 6.32 | 0.251 | 3.33 |
| A-77 | I | 6.56 | 0.0167 | 1.87 |
| A-78 | I | 2.08 | 0.112 | 0.580 |
| A-79 | I | 9.02 | 0.282 | 16.6 |
| A-80 | I | 5.54 | 0.268 | 5.40 |
| A-81 | I | 13.0 | 0.775 | 14.2 |
| A-82 | I | 10.7 | 0.865 | 11.5 |
| A-83 | I | 8.34 | 0.242 | 5.16 |
| A-84 | I | 3.89 | 0.711 | 6.01 |
| A-85 | I | 8.04 | 0.0914 | 9.02 |
| A-86 | I | 40.3 | 0.751 | 38.3 |
| A-87 | I | 2.95 | 0.186 | 6.78 |
| A-88 | I | 5.23 | 0.194 | 11.8 |
| A-89 | I | 5.78 | 0.159 | 9.51 |
| A-90 | I | 2.19 | 0.0422 | 5.06 |
| A-91 | I | 20.3 | 1.54 | 4.79 |
| A-92 | I | 18.7 | 0.193 | 13.4 |
| A-93 | I | 2.46 | 0.0341 | 2.40 |
| A-94 | I | 15.5 | 0.500 | 9.66 |
| A-95 | I | 7.92 | 0.171 | 6.86 |
| A-96 | I | 33.3 | 1.95 | 9.04 |
| A-97 | I | 90.9 | 4.46 | 7.32 |
| A-98 | I | 48.5 | 0.450 | 1.81 |
| A-99 | I | 11.3 | 0.157 | 2.70 |
| A-100 | I | 3.47 | 0.0436 | 0.723 |
| A-101 | I | 18.8 | 0.0468 | 5.85 |
| A-102 | I | 145 | 0.0419 | >200 |
| A-103 | I | 14.9 | 0.0289 | 7.12 |
| A-104 | I | 1.23 | 0.0224 | 1.62 |
| A-105 | I | 11.3 | 0.0333 | 4.11 |
| A-106 | I | 115 | 0.0293 | 11.4 |
| A-107 | I | 2.27 | 0.0297 | 0.776 |
| A-108 | I | 2.23 | 0.0460 | 5.02 |
| A-109 | I | 1.45 | 0.0552 | 0.940 |
| A-110 | I | 146 | 0.0776 | 15.9 |
| A-111 | I | 2.87 | 0.0473 | 12.6 |
| A-112 | I | 13.1 | 0.206 | 14.6 |
| A-113 | I | 256 | 0.0764 | 164 |
| A-114 | I | 241 | 0.0342 | 6.87 |
| A-115 | I | 8.77 | 0.411 | 5.08 |
| A-116 | I | 9.96 | 0.161 | 7.55 |
| A-117 | I | 44.8 | 0.444 | 7.59 |
| A-118 | I | 10.5 | 0.0747 | 4.51 |
| A-119 | I | 24.6 | 0.136 | 12.5 |
| A-120 | I | 20.6 | 0.124 | 10.3 |
| A-121 | I | 17.3 | 0.0683 | 14.9 |
| A-122 | I | 132 | 0.464 | 7.41 |
| A-123 | I | 11.4 | 0.0639 | 11.0 |
| A-124 | I | 42.0 | 0.353 | 16.0 |
| A-125 | I | 2.07 | 0.0687 | 7.23 |
| A-126 | II | >100 | 4.39 | >100 |
| A-127 | II | >100 | 2.49 | 47.2 |
| A-128 | II | 2.1 | 0.513 | 6.7 |
| A-129 | II | 3.8 | 0.925 | 10.2 |
| A-130 | II | 4.8 | 0.864 | 11.2 |
| A-131 | II | 18.1 | 0.902 | 5.7 |
| A-132 | II | 47.8 | 8.19 | 45.1 |
| A-133 | II | 26 | 1.30 | 2.9 |
| B1-1 | I | 64.0 | 9.36 | 2.56 |
| B1-2 | I | 43.2 | 3.36 | 0.760 |
| B1-3 | I | 20.7 | 2.59 | 0.535 |
| B1-4 | I | 94.9 | 3.28 | 3.01 |
| B1-5 | I | 104 | 3.28 | 1.45 |
| B1-6 | I | 85.6 | 6.14 | 7.53 |
| B1-7 | I | 52.1 | 3.84 | 3.09 |
| B1-8 | I | 37.3 | 5.04 | 2.77 |
| B1-9 | I | 46.6 | 4.96 | 2.63 |
| B1-10 | I | 86.9 | 5.99 | 14.7 |
| B1-11 | I | 13.9 | 0.666 | 1.23 |
| B1-12 | I | 41.0 | 3.12 | 1.80 |
| B1-13 | I | 124 | 1.17 | 8.45 |
| B2-1 | I | 15.7 | 0.763 | 1.57 |
| B3-1 | I | 9.71 | 0.488 | 16.9 |
| B3-2 | I | 43.4 | 0.193 | 6.77 |
| B4-1 | I | 41.4 | 0.436 | 9.77 |

TABLE 1-continued

Activities against SIRT1-3.

| Compound | Assays | IC$_{50}$ or K$_i^{app}$ (μM) SIRT1 | SIRT2 | SIRT3 |
|---|---|---|---|---|
| B4-2 | I | 15.0 | 0.572 | 2.15 |
| C1-1 | I | 25.6 | 0.281 | 4.36 |
| C1-2 | I | 8.51 | 0.163 | 5.28 |
| C1-3 | I | 14.4 | 0.144 | 4.34 |
| C1-4 | I | 15.3 | 0.0480 | 2.73 |
| C1-5 | I | 19.8 | 0.120 | 3.40 |
| C1-6 | I | 9.99 | 0.0503 | 0.856 |
| C4-1 | I | 23.6 | 0.540 | 16.0 |
| C4-2 | I | 69.8 | 0.166 | 19.5 |
| C4-3 | I | 41.5 | 0.212 | 10.7 |
| C4-4 | I | 29.9 | 0.0710 | 5.43 |
| C4-5 | I | 50.2 | 0.216 | 12.8 |
| C4-6 | I | 36.6 | 0.109 | 11.6 |
| C2-1 | I | 10.6 | 0.0343 | 1.46 |
| C2-2 | I | 1.18 | 0.0576 | 0.495 |
| C2-3 | I | 101 | 0.0634 | 6.00 |
| C3-1 | I | 25.1 | 0.105 | 0.709 |
| C3-2 | I | 18.3 | 0.0957 | 5.13 |
| C3-3 | I | 76.3 | 0.0286 | 13.9 |
| C5-1 | I | 73.2 | 0.269 | 18.6 |
| C5-2 | I | 113 | 0.152 | 5.79 |
| C5-3 | I | 78.2 | 0.0540 | 51.4 |
| C6-1 | I | 37.2 | 0.163 | 53.1 |
| C6-2 | I | 66.7 | 0.178 | 9.84 |
| C6-3 | I | 79.7 | 0.197 | 31.1 |
| C7-1 | I | 23.9 | 3.28 | 15.0 |
| C7-2 | I | 34.8 | 1.33 | 22.8 |
| C7-3 | I | 38.5 | 1.49 | 24.8 |
| C7-4 | I | 52.3 | 1.43 | 29.5 |
| C8-1 | I | 266 | 3.00 | 32.8 |
| C8-2 | I | 194 | 1.44 | 20.8 |
| C8-3 | I | 252 | 1.98 | 37.6 |
| C8-4 | I | 225 | 1.28 | 11.8 |
| C8-5 | I | 227 | 2.81 | 37.4 |
| D1-1 | I | 591 | 0.736 | 18.7 |
| D2-1 | I | 3.52 | 0.282 | 2.48 |
| D3-1 | I | 9.84 | 0.535 | 13.7 |
| D4-1 | I | 0.305 | 0.0477 | 1.85 |
| D4-2 | I | 1.41 | 0.0290 | 1.04 |
| D5-1 | I | 6.70 | 0.935 | 17.1 |
| D6-1 | I | 221 | 1.14 | 13.6 |
| D7-1 | I | 14.4 | 0.369 | 20.7 |
| D8-1 | I | 16.6 | 0.863 | 14.1 |
| D9-1 | I | 61.2 | 0.0704 | 1.14 |
| D10-1 | I | 32.3 | 1.78 | 24.9 |
| D11-1 | I | 17.3 | 0.397 | 14.2 |
| D11-2 | I | 3.34 | 0.191 | 5.81 |
| D11-4 | I | 9.89 | 0.581 | 11.9 |
| D11-5 | I | 5.35 | 0.158 | 13.1 |
| D11-6 | I | 8.54 | 0.381 | 10.7 |
| D11-7 | I | 4.72 | 0.359 | 5.88 |
| D11-8 | I | 7.67 | 0.751 | 11.4 |
| D11-9 | I | 8.34 | 0.277 | 12.0 |
| D11-10 | I | 3.71 | 0.136 | 8.22 |
| D11-11 | I | 3.01 | 0.152 | 8.72 |
| D11-12 | I | 3.60 | 0.152 | 12.1 |
| D11-13 | I | 6.76 | 0.341 | 13.1 |
| E1-1 | I | 2.27 | 0.0905 | 11.6 |
| E2-1 | I | 14.7 | 0.110 | 13.4 |
| E3-1 | II | >100 | 0.738 | >100 |
| E3-2 | II | >100 | 7.31 | >100 |
| F1-1 | II | 22.0 | 0.0440 | 20.5 |
| F1-2 | II | 9.8 | 0.0752 | 17.2 |
| F1-3 | II | >100 | 0.141 | >100 |
| F1-4 | II | 77.4 | 0.131 | 36.7 |
| F1-5 | II | 30.6 | 0.0962 | 25.6 |
| F1-6 | II | >100 | 0.0996 | >100 |
| F1-7 | II | >100 | 0.0198 | >100 |
| F1-8 | II | >100 | 0.0404 | >100 |
| F1-9 | II | 29 | 0.180 | 27 |
| F1-10 | II | >100 | 0.0394 | >100 |
| F1-11 | II | >100 | 0.0416 | >100 |
| F1-12 | II | >100 | 0.300 | >100 |
| F1-13 | II | 22.9 | 0.0432 | 11.6 |
| F1-14 | II | 51.6 | 0.0950 | 26.7 |
| F1-15 | II | 24 | 0.0110 | 9.6 |
| F1-16 | II | 59.9 | 0.0630 | 24.3 |
| F1-17 | II | >100 | 0.0169 | 7.2 |
| F1-18 | II | >100 | 0.0338 | >100 |
| F1-19 | II | 28.5 | 0.166 | 30.4 |
| F1-20 | II | 43.3 | 0.150 | 26.6 |
| F1-21 | II | >100 | 0.221 | 53.6 |
| F1-22 | II | >100 | 0.879 | >100 |
| F1-23 | II | >100 | 0.790 | >100 |
| F1-24 | II | 21.4 | 0.130 | 11.5 |
| F1-25 | II | 59.6 | 0.201 | 46.3 |
| F2-1 | II | 8.21 | 0.0530 | 1.92 |
| F2-2 | II | 1.51 | 0.0653 | 7 |
| F2-3 | II | 41.9 | 0.183 | 12.1 |
| F2-4 | II | 10 | 0.113 | 12.4 |
| F2-5 | II | 7.8 | 0.0849 | 9.9 |
| F2-6 | II | 20.7 | 0.111 | 8.3 |
| F2-7 | II | >100 | 0.0242 | >100 |
| F2-8 | II | >100 | 0.0455 | >100 |
| F2-9 | II | 4 | 0.124 | 7.6 |
| F2-10 | II | >100 | 0.0396 | >100 |
| F2-11 | II | >100 | 0.0532 | >100 |
| F2-12 | II | 99.2 | 0.218 | 21.4 |
| F3-1 | II | 23.0 | 0.0290 | 4.79 |
| F3-2 | II | 3.4 | 0.0687 | 5.9 |
| F3-3 | II | >100 | 0.0813 | >100 |
| F3-4 | II | >100 | 0.0455 | >100 |
| F3-5 | II | >100 | 0.214 | >100 |
| F3-6 | II | 90 | 0.031 | 5.2 |
| F3-7 | II | >100 | 0.450 | >100 |
| F3-8 | II | 9.0 | 0.0641 | 6.6 |
| F3-9 | II | >100 | 1.48 | 14.8 |
| F3-10 | II | >100 | 0.870 | 28.5 |
| F3-11 | II | >100 | 0.0489 | >100 |
| F3-12 | II | 20 | 0.126 | 7.8 |
| F3-13 | II | >100 | 0.475 | >100 |
| F3-14 | II | 49.8 | 0.139 | 18 |
| F4-1 | II | 93 | 0.163 | 19.3 |
| F4-2 | II | 23.5 | 0.0683 | 13.1 |
| F4-3 | II | >100 | 0.523 | 28.2 |
| F5-1 | II | 53.2 | 0.186 | 29.1 |
| F5-2 | II | 8.0 | 0.0643 | 17.2 |
| F5-3 | II | >100 | 0.0952 | 51.6 |
| F5-4 | II | >100 | 0.0724 | >100 |
| F6-1 | II | >100 | 2.557 | >100 |
| F6-2 | II | >100 | 1.634 | >100 |
| F7-1 | II | >100 | 1.242 | >100 |
| F7-2 | II | 19.9 | 0.532 | 33.3 |
| F8-1 | II | 47 | 0.352 | 27.2 |
| F8-2 | II | 10.3 | 0.147 | 17.5 |
| F9-1 | II | 25.1 | 0.268 | 46.7 |
| F9-2 | II | 4.8 | 0.121 | 23.1 |
| F10-1 | II | 47.8 | 0.342 | 22.7 |
| F10-2 | II | 14.7 | 0.122 | 10.9 |
| F11-1 | II | 23.5 | 0.484 | 18.5 |
| F11-2 | II | 4.7 | 0.153 | 13.6 |
| F12-1 | II | 3.68 | 0.0770 | 7.39 |
| F12-2 | II | >100 | 0.361 | 20.4 |
| F12-3 | II | >100 | 0.148 | >100 |
| F12-4 | II | >100 | 0.730 | 91.4 |
| G1-1 | II | >100 | 21.3 | >100 |
| G1-2 | II | >100 | 6.29 | >100 |
| G2-1 | II | >100 | 22.7 | >100 |
| G2-2 | II | >100 | 8.03 | >100 |

Note:
For the inhibitory activity against SIRT2, K$_i^{app}$ was usually determined when the assays (II) were used.

Example 10

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |

| (vi) Aerosol | mg/can |
|---|---|
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

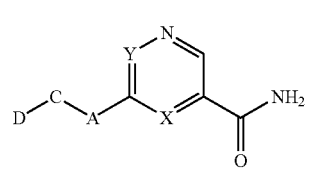

wherein:
X is CH;
Y is CH;
A is -A'-B'—
A' is

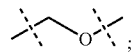

B' is phenyl, wherein A' and C are attached to B' in a meta-orientation, and the phenyl, is optionally substituted with one or more groups independently selected from F, Cl, deuterium, methyl, trifluoromethyl, methoxy, and trifluoromethoxy;

C is selected from the group consisting of:

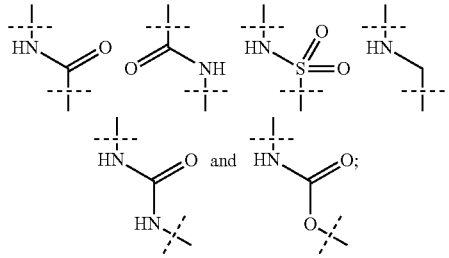

D is selected from the group consisting of naphthyl, phenyl, pyridyl, and pyrimidinyl, wherein D is optionally substituted with one or more groups $R^z$ independently selected from halo, deuterium, nitro, hydroxy, cyano, carboxy, —$NR^aR^b$, —$C(\!=\!O)NR^aR^b$ ($C_1$-$C_4$) alkyl, ($C_2$-$C_4$)alkenyl, ($C_2$-$C_4$)alkynyl, ($C_1$-$C_4$)alkoxy, ($C_1$-$C_4$)alkanoyl, ($C_1$-$C_4$)alkoxycarbonyl, ($C_1$-$C_4$)alkanoyloxy, and ($C_3$-$C_{15}$)carbocycle, wherein any ($C_1$-$C_4$)alkyl, ($C_2$-$C_4$)alkenyl, ($C_2$-$C_4$)alkynyl, ($C_1$-$C_4$) alkoxy, ($C_1$-$C_4$)alkanoyl, ($C_1$-$C_4$)alkoxycarbonyl, ($C_3$-

$C_{15}$)carbocycle, and ($C_1$-$C_4$)alkanoyloxy of $R^z$ is optionally substituted with one or more groups independently selected from the group consisting of halo, hydroxy, deuterium, —$NR^aR^b$, ($C_1$-$C_4$)alkoxy, ($C_1$-$C_4$)alkoxycarbonyl, and ($C_1$-$C_4$)alkanoyloxy each $R^a$ and $R^b$ is independently selected from the group consisting of H, ($C_1$-$C_4$)alkyl, ($C_3$-$C_8$)cycloalkyl, ($C_2$-$C_4$)alkenyl, ($C_2$-$C_4$)alkynyl, ($C_1$-$C_4$)alkoxy, ($C_1$-$C_4$)alkanoyl, ($C_1$-$C_4$)alkoxycarbonyl, and ($C_1$-$C_4$)alkanoyloxy and each $R^x$ is ($C_1$-$C_4$)alkyl that is substituted with one or more (e.g. 1, 2, 3, or 4) groups independently selected from oxo, carboxy, ($C_1$-$C_4$)alkoxycarbonyl, and amino; or a salt thereof.

2. The compound of claim 1 which is a compound of formula (Ia):

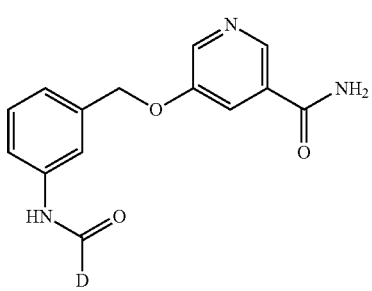

(Ia)

or a salt thereof.

3. The compound of claim 1 which is a compound of formula (Ib):

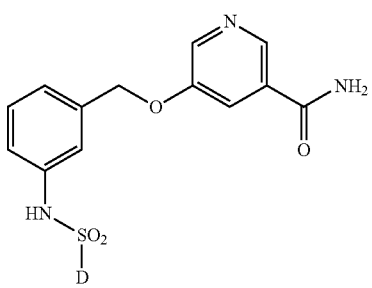

(Ib)

or a salt thereof.

4. The compound of claim 1 which is a compound of formula (Id):

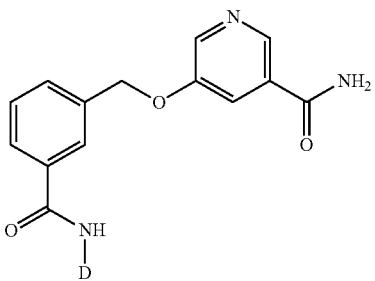

(Id)

or a salt thereof.

5. The compound of claim 1 which is a compound of formula (Ig):

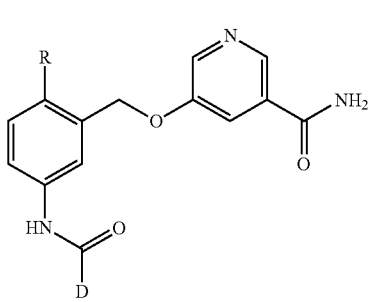

(Ig)

wherein:
R is selected from F, Cl, deuterium, methyl, trifluoromethyl, methoxy, and trifluoromethoxy;
or a salt thereof.

6. The compound of claim 1 which is a compound of formula (Ih):

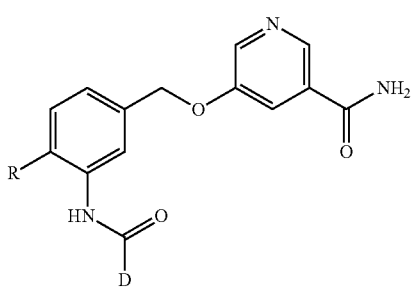

(Ih)

wherein:
R is selected from F, Cl, deuterium, methyl, trifluoromethyl, methoxy, and trifluoromethoxy;
or a salt thereof.

7. The compound of claim 1 which is a compound of formula (Ii):

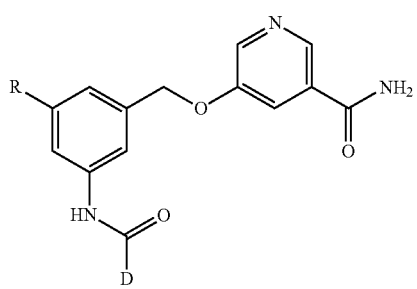

(Ii)

wherein:
R is selected from F, Cl, deuterium, methyl, trifluoromethyl, methoxy, and trifluoromethoxy;
or a salt thereof.

8. The compound of claim 1 wherein D is substituted with —$NR^aR^b$; or a salt thereof.

9. A pharmaceutical composition comprising a compound as described in claim 1, or a pharmaceutically acceptable salt thereof, and a pharmaceutically acceptable diluent or carrier.

10. A compound selected from the group consisting of:
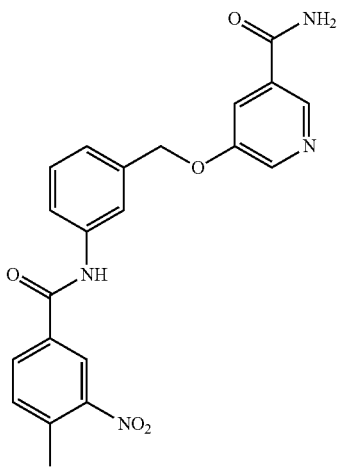
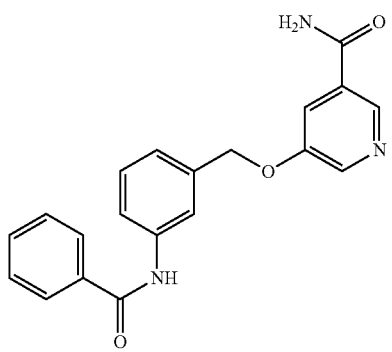
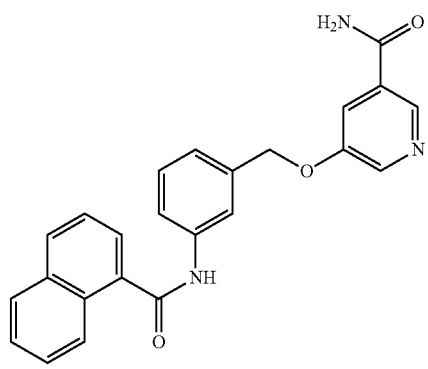
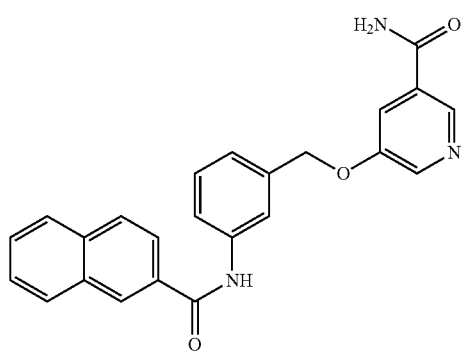
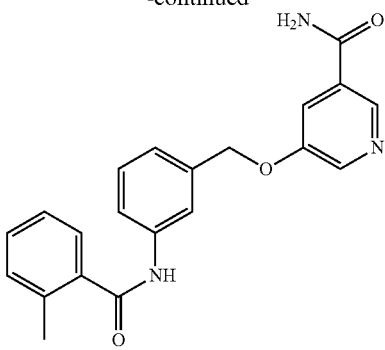
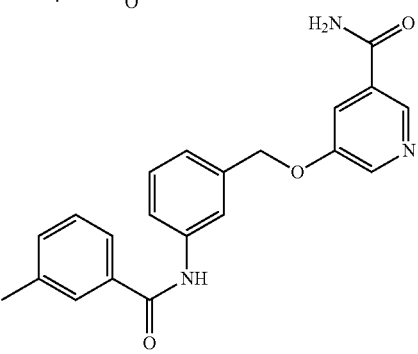
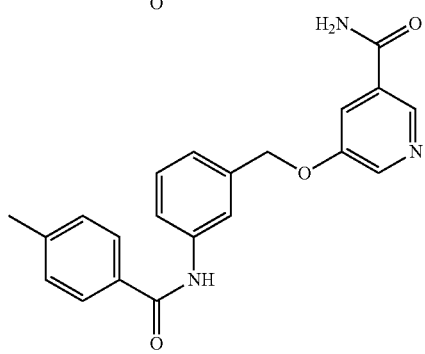
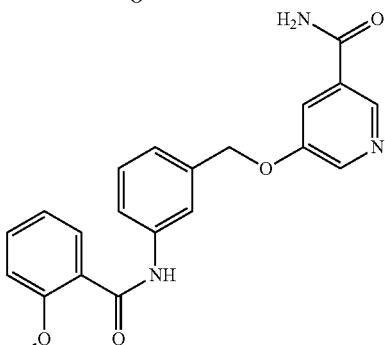
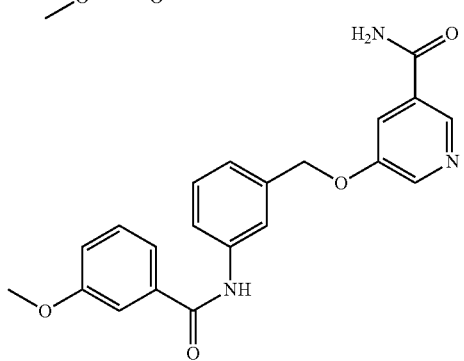

213
-continued
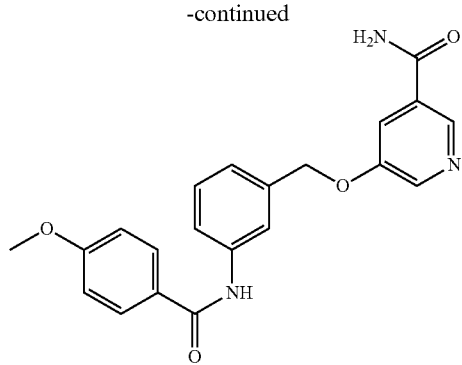
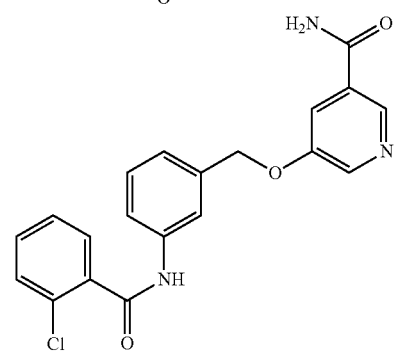
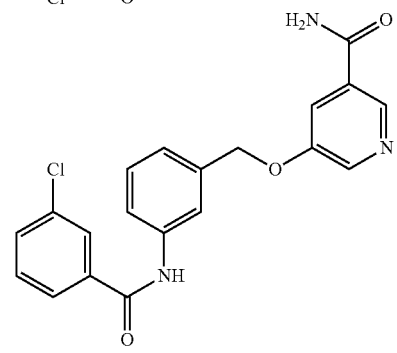
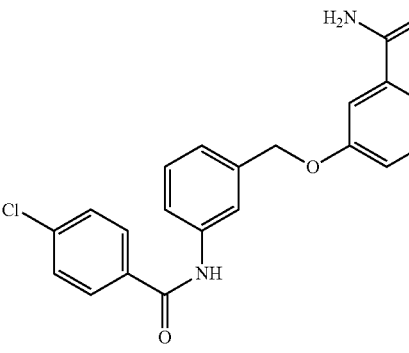
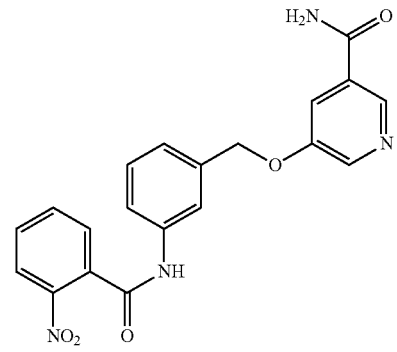
214
-continued
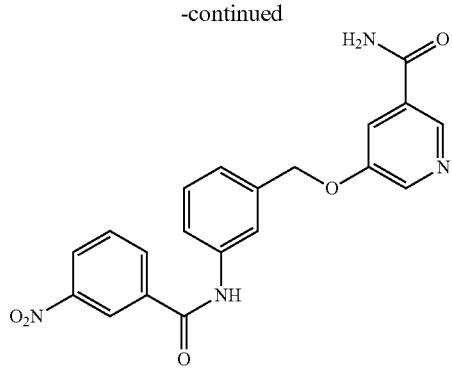
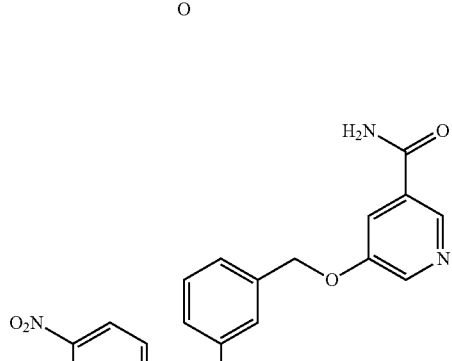
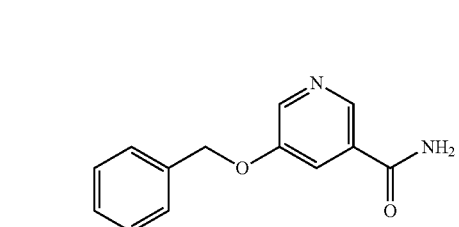

215
-continued
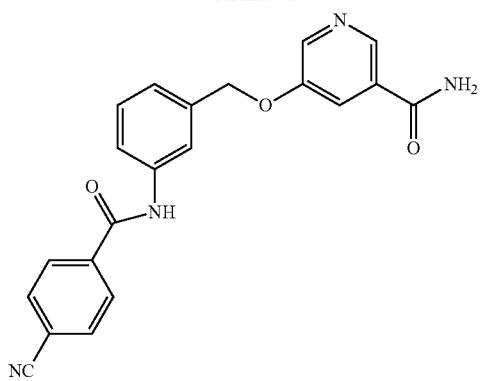
216
-continued
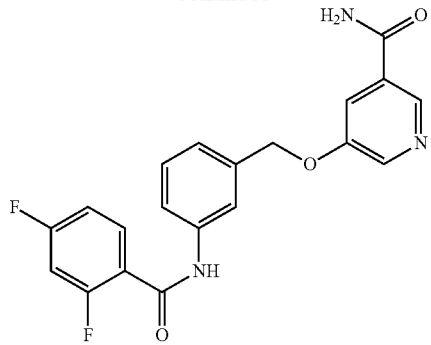
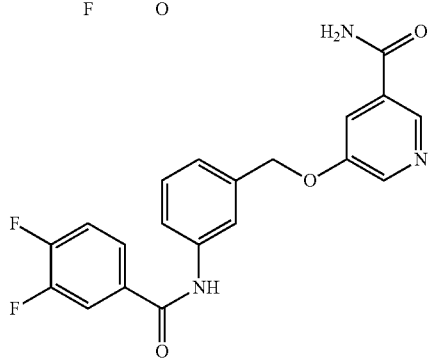
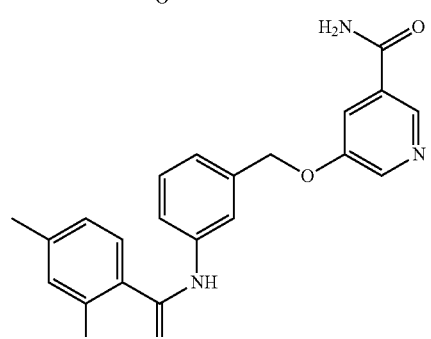
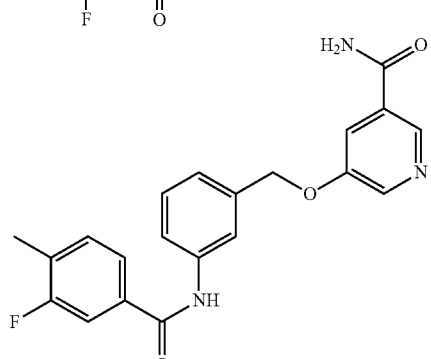
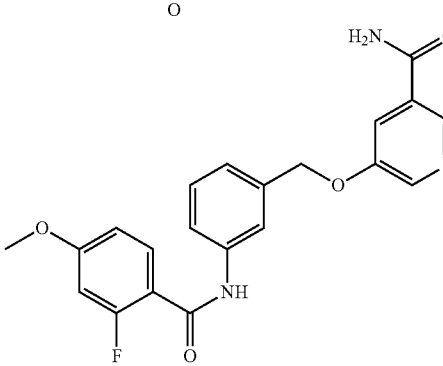

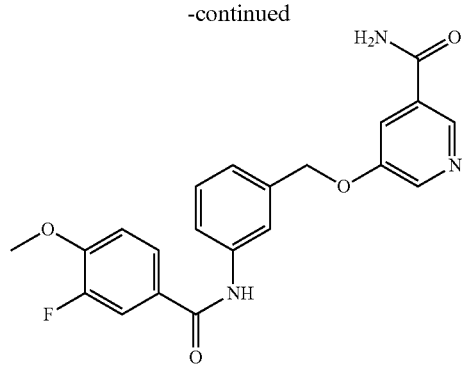
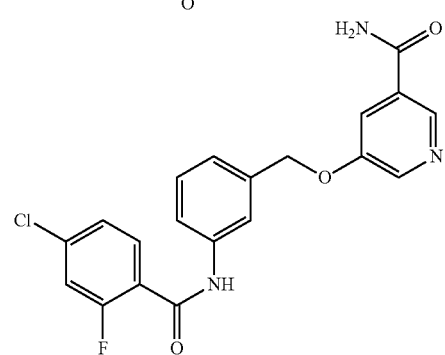
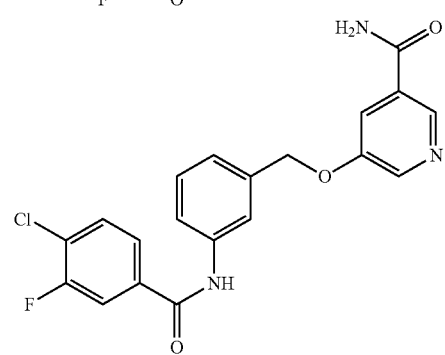
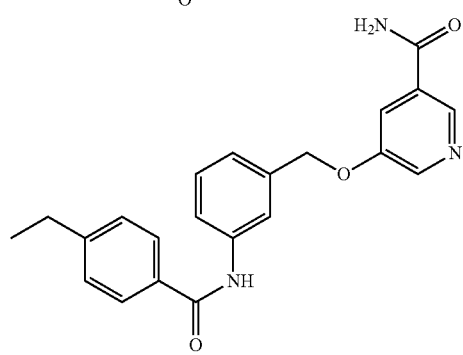
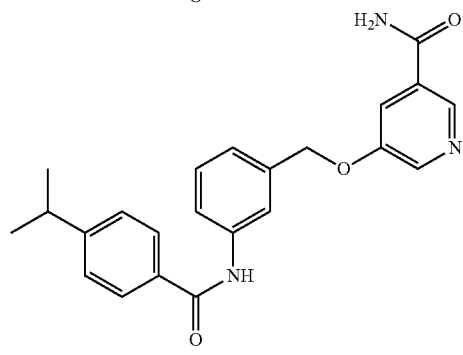
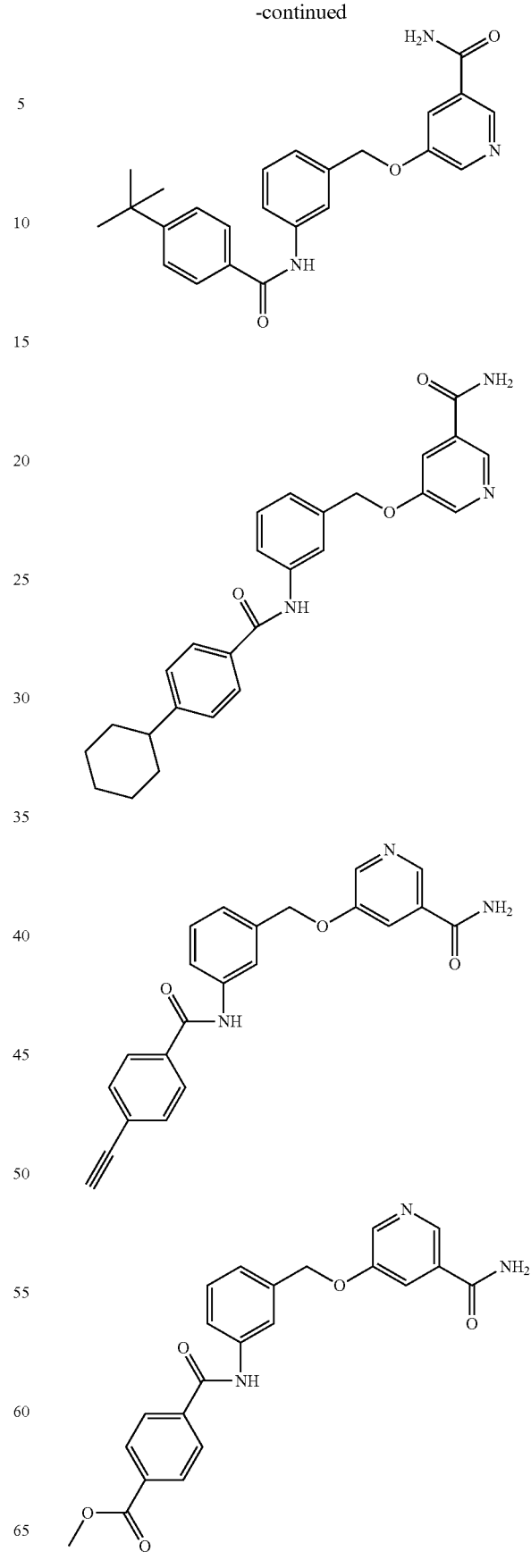

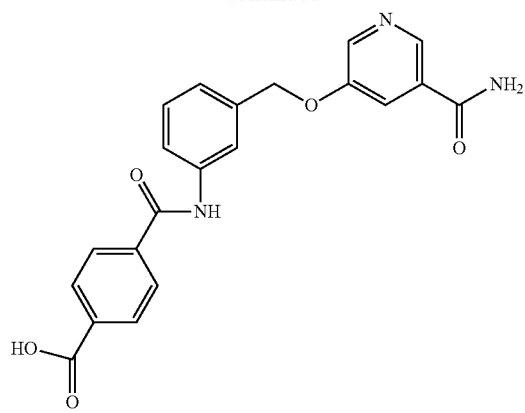
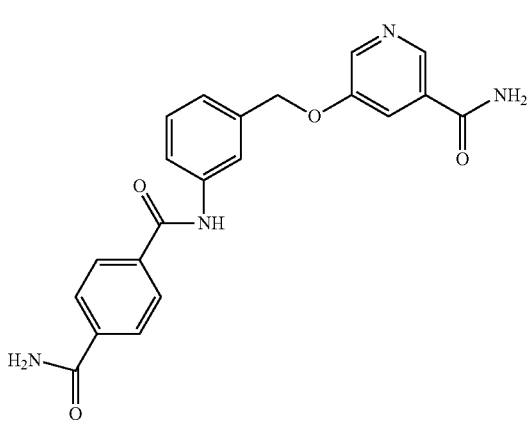
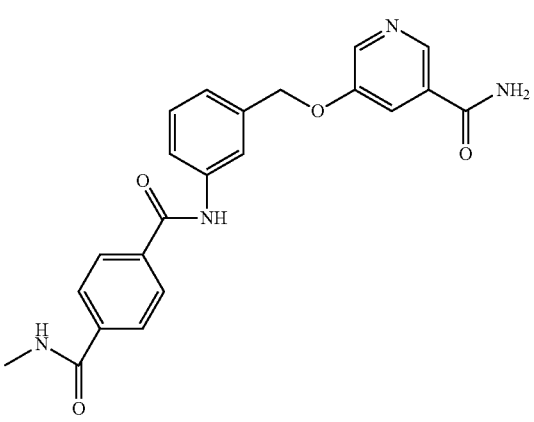
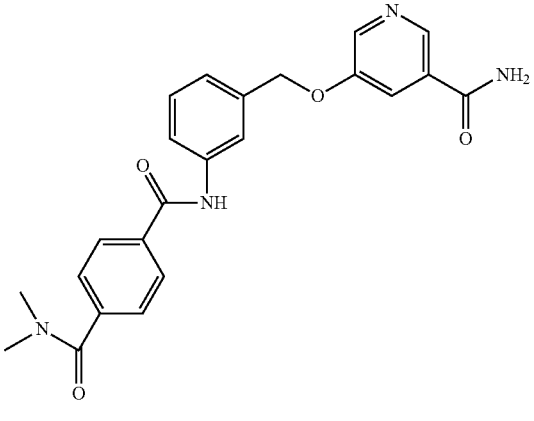
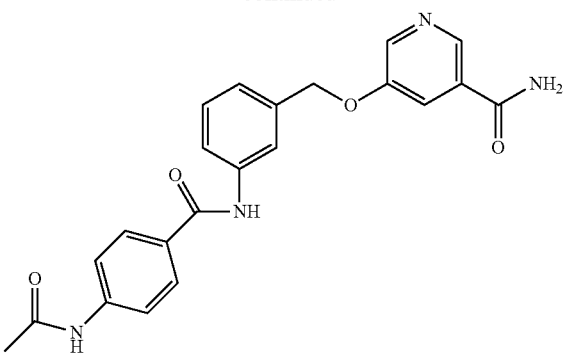
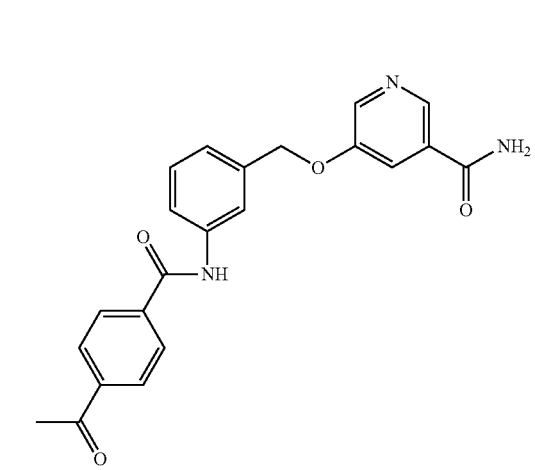
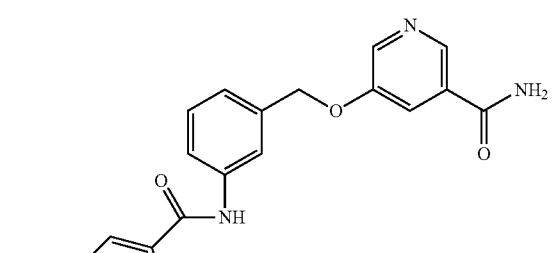
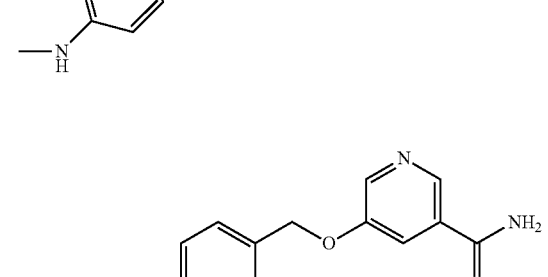

221
-continued
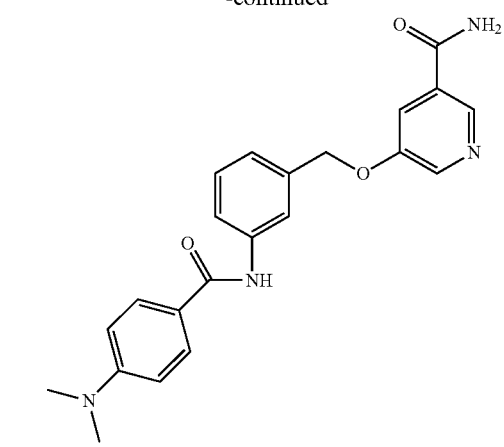
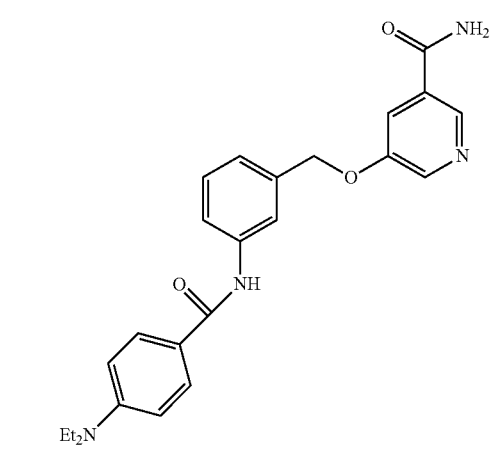
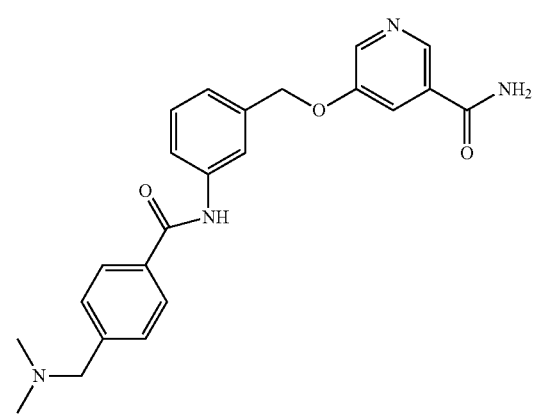
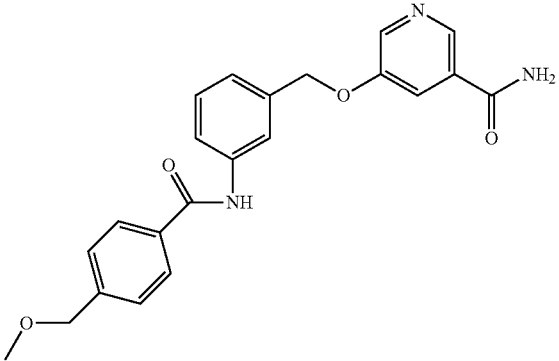
222
-continued
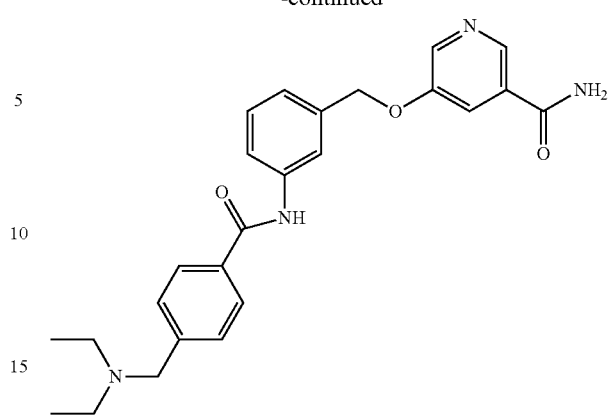
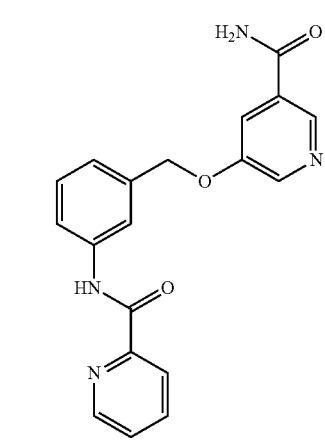
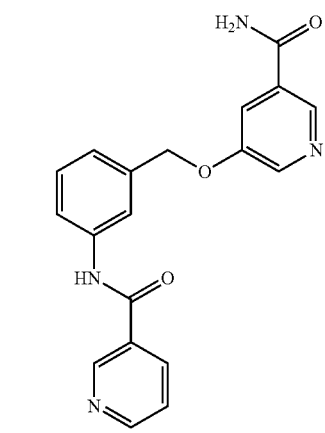
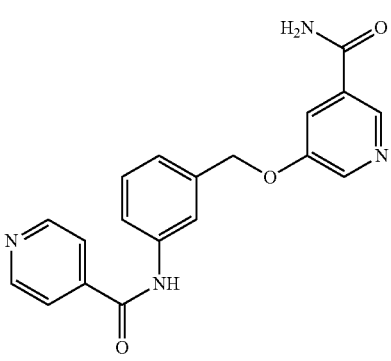

223
-continued
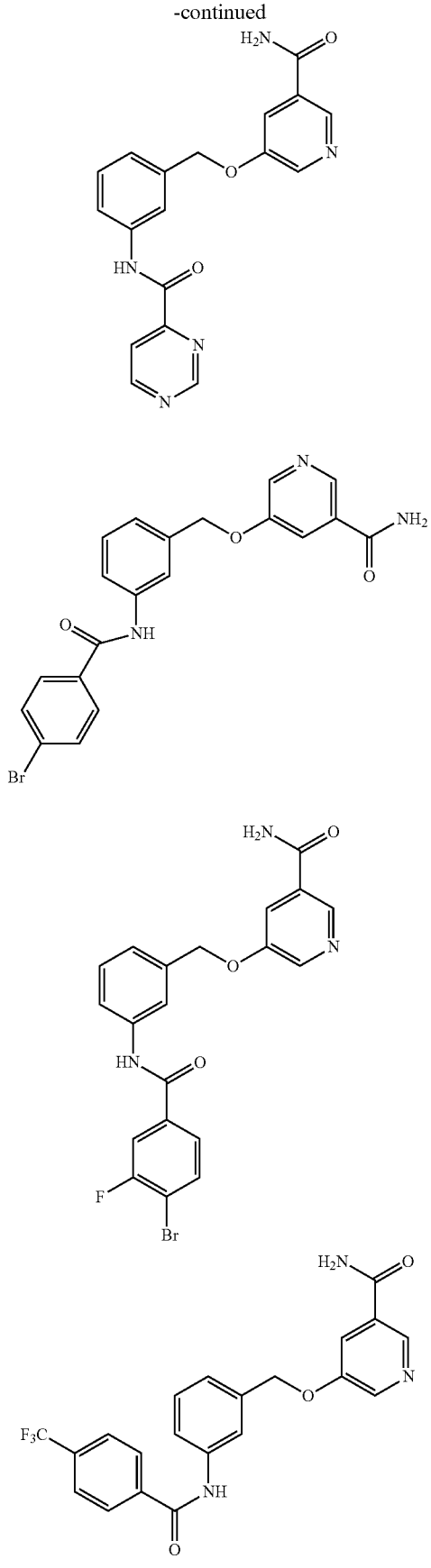
224
-continued
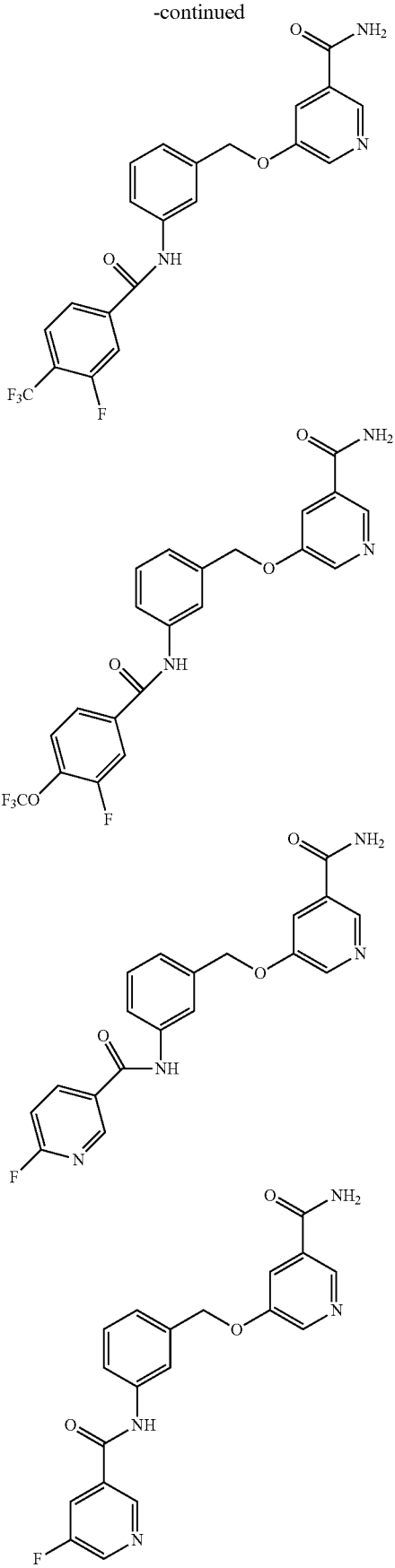

225
-continued
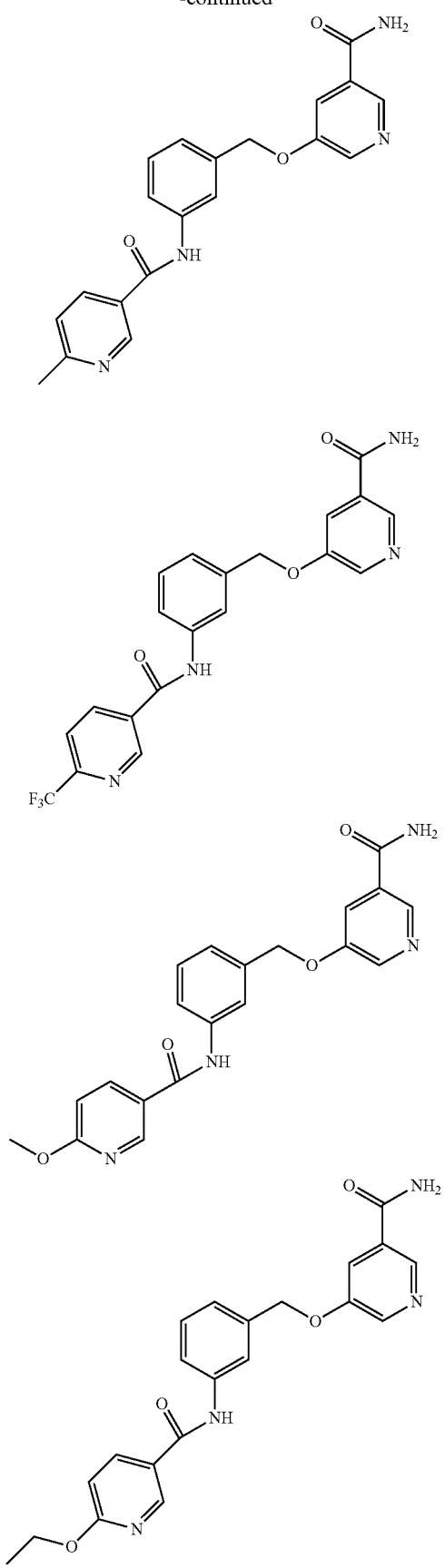
226
-continued
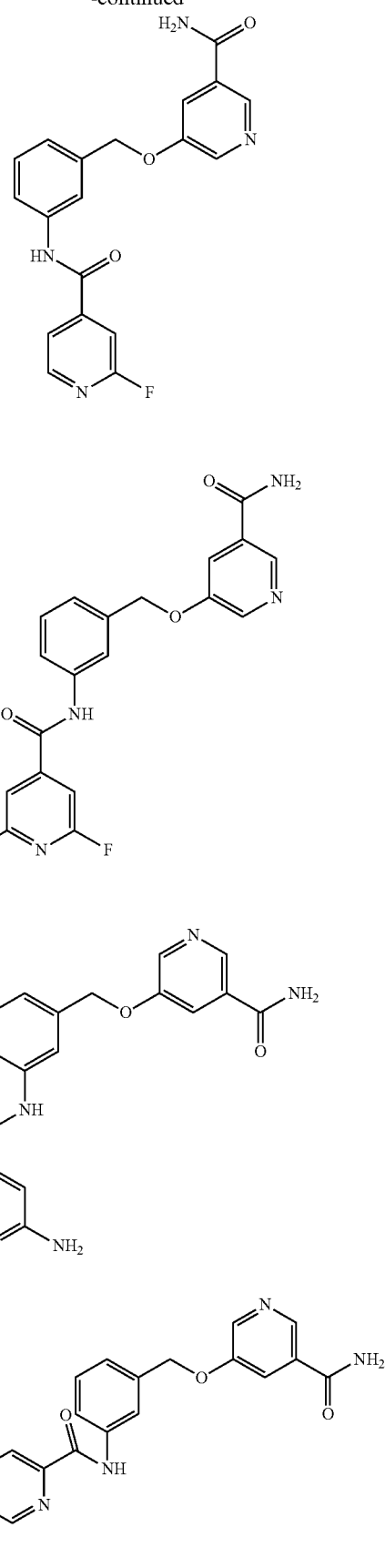

-continued
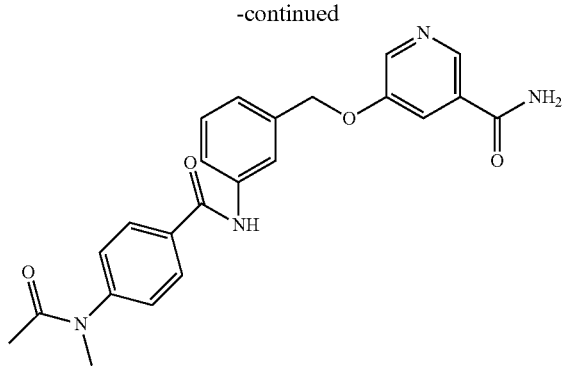
11. A compound selected from the group consisting of:
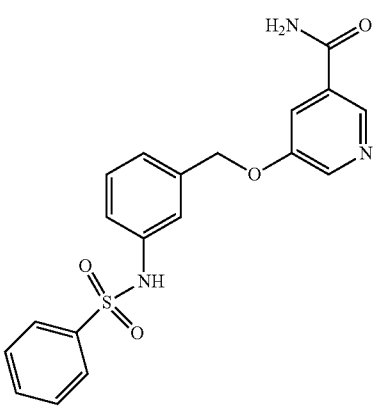
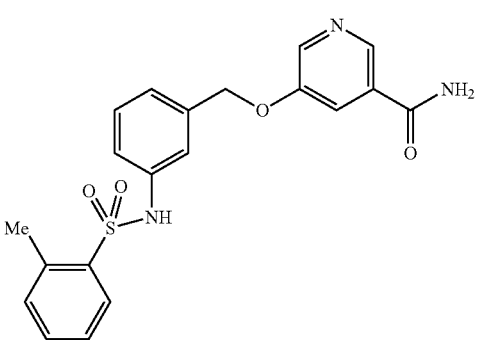
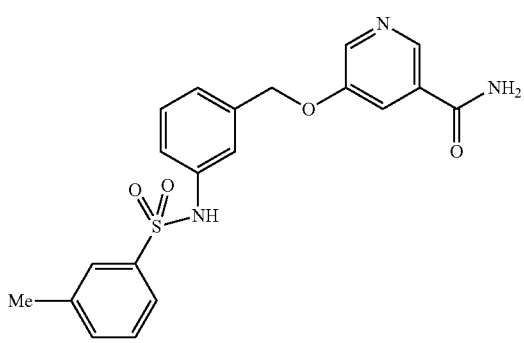
and
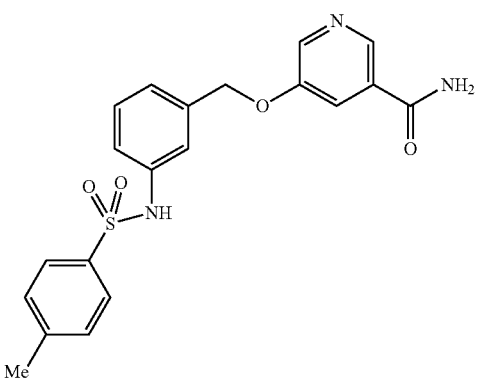

229
-continued
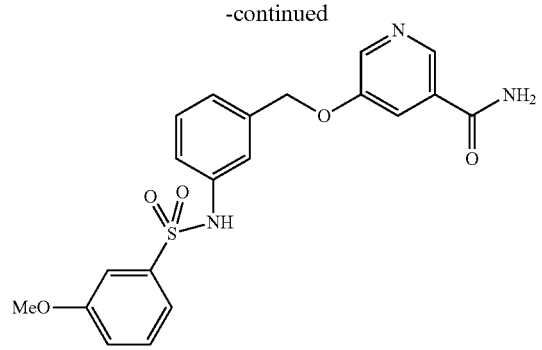
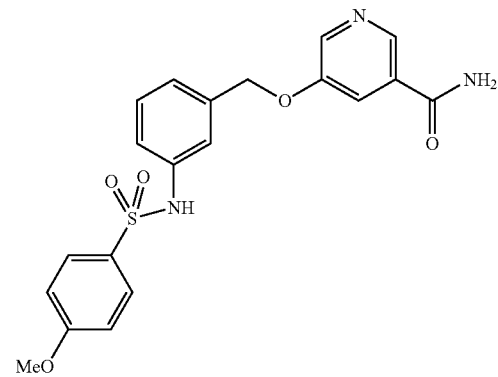
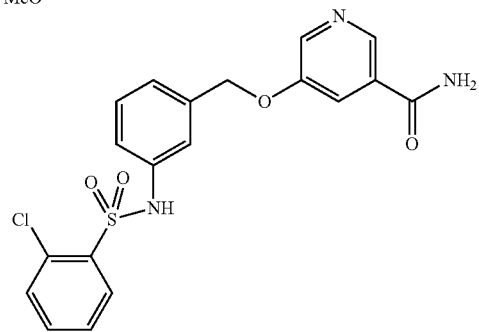
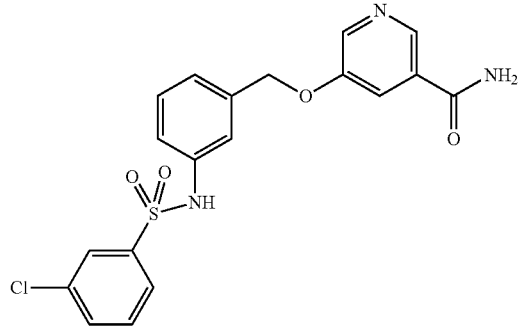
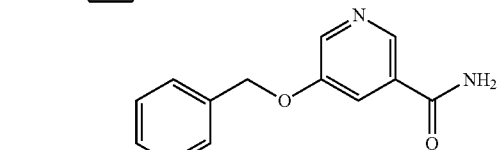
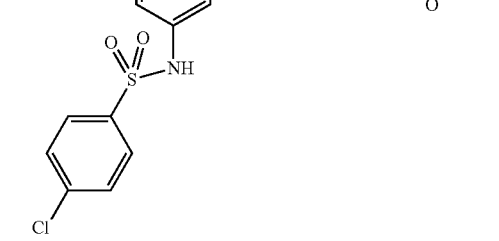
230
-continued
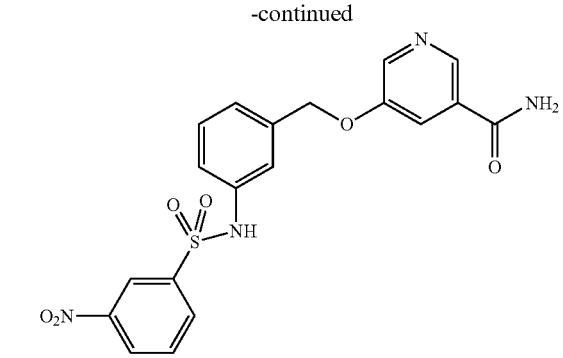
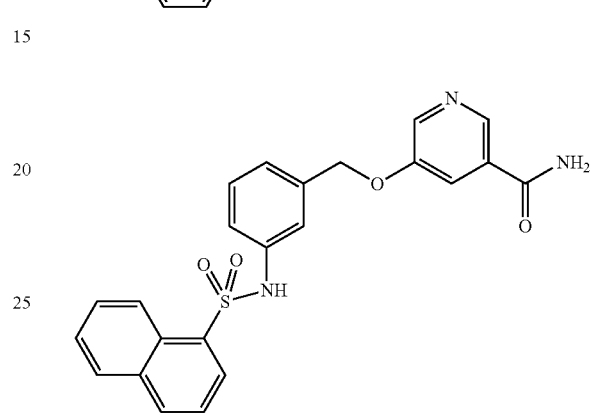
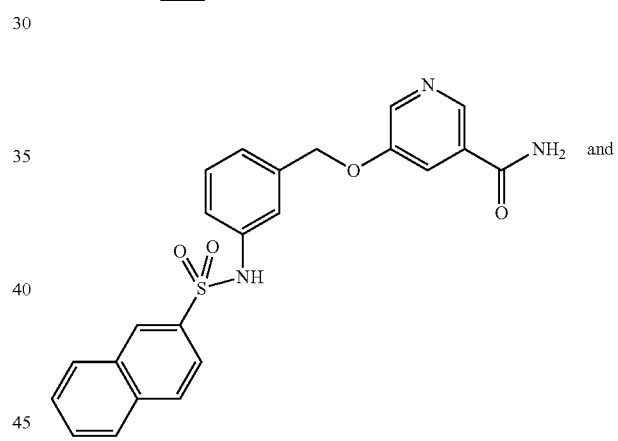 and
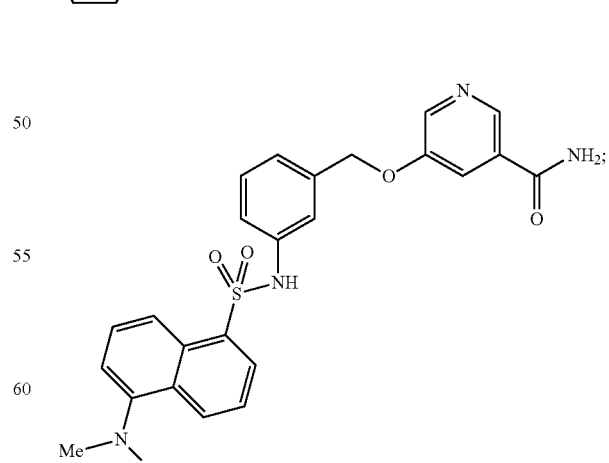
or a salt thereof.

12. A compound selected from the group consisting of:
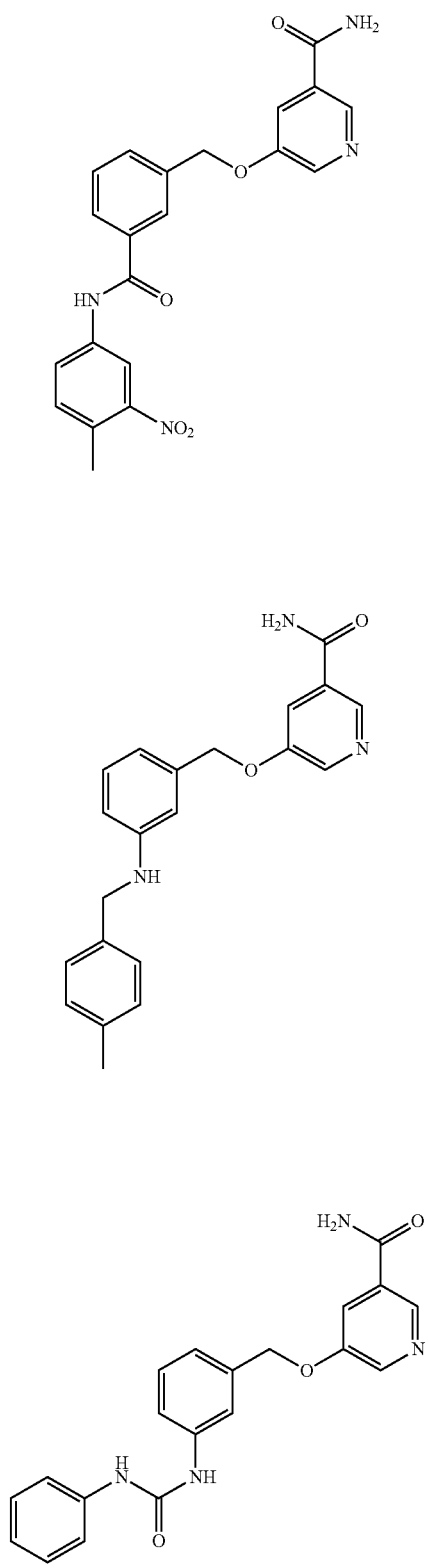
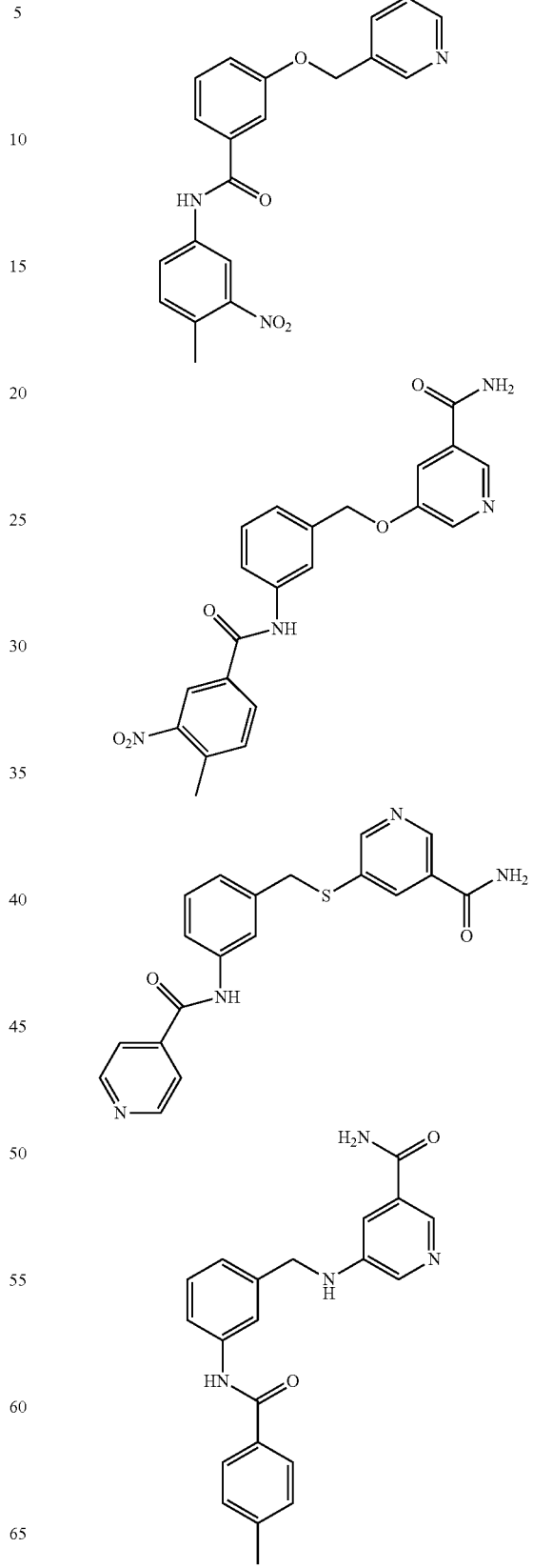

-continued
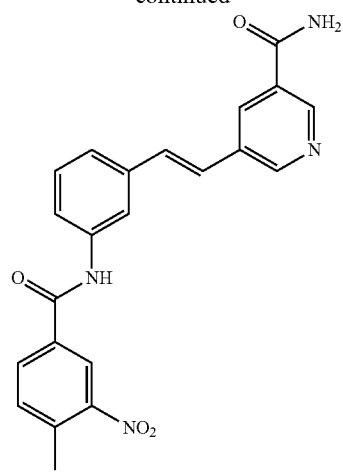
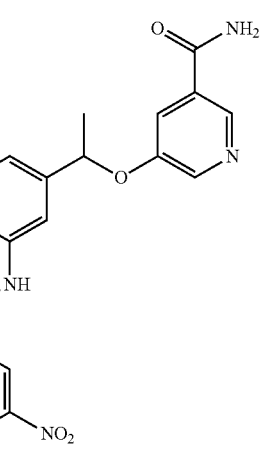
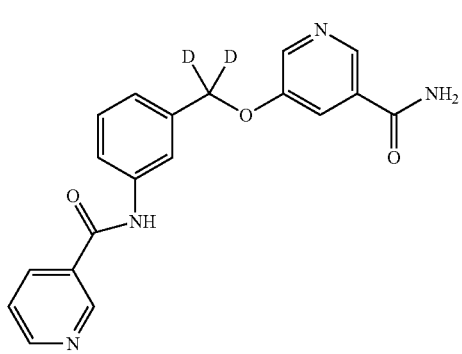
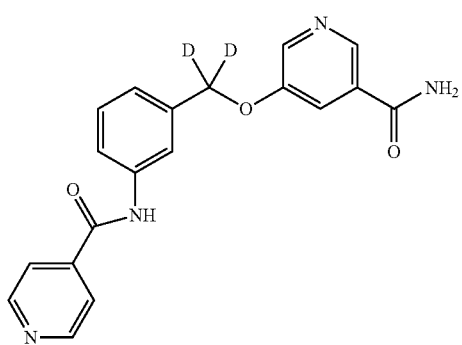
-continued
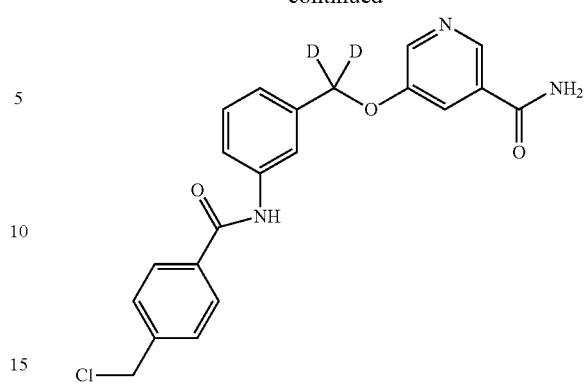
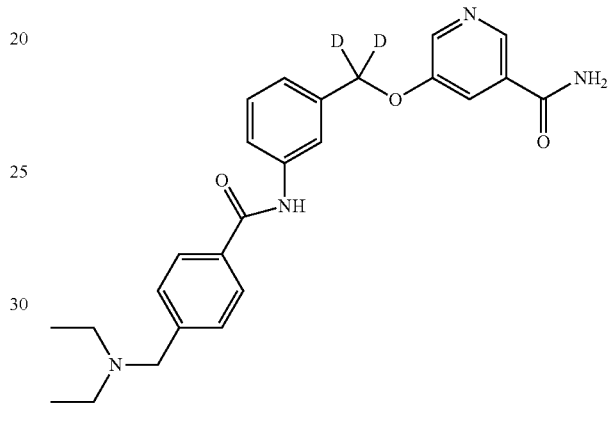
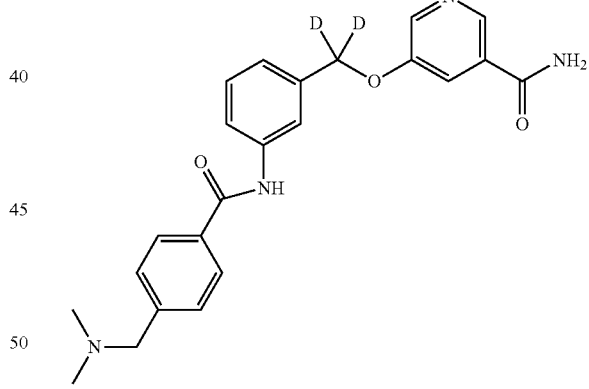
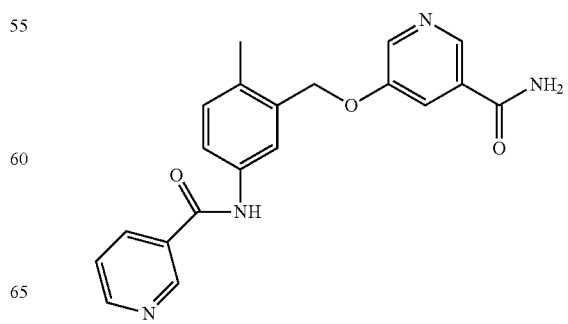

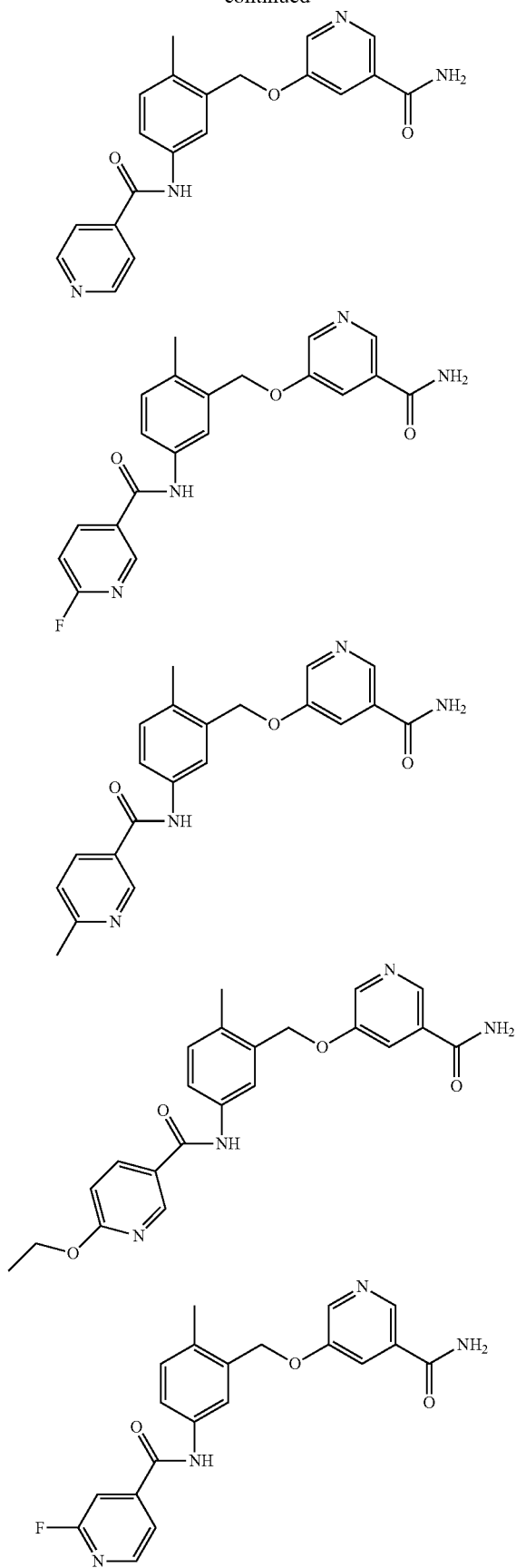

237
-continued
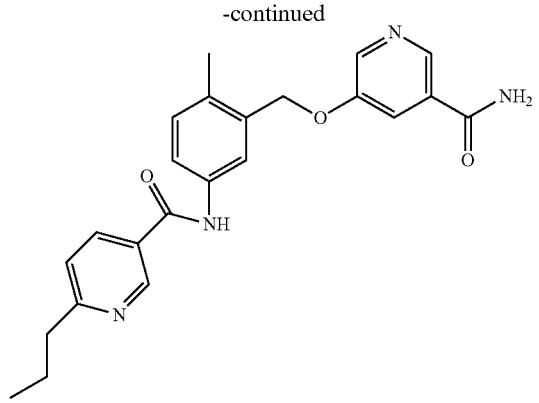
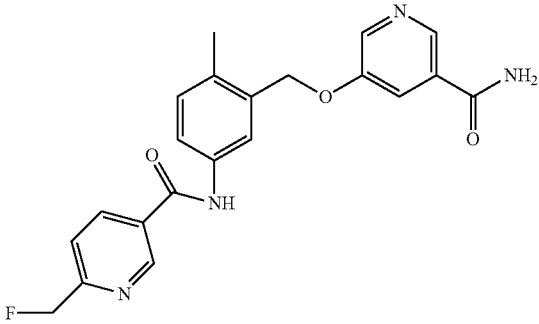
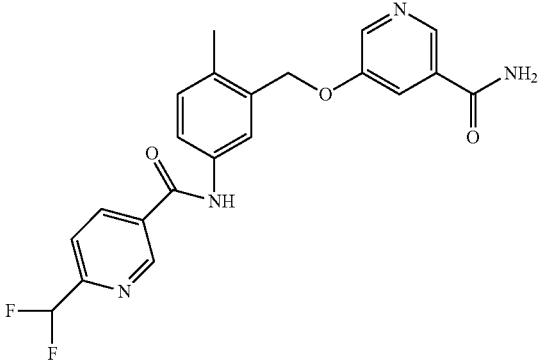
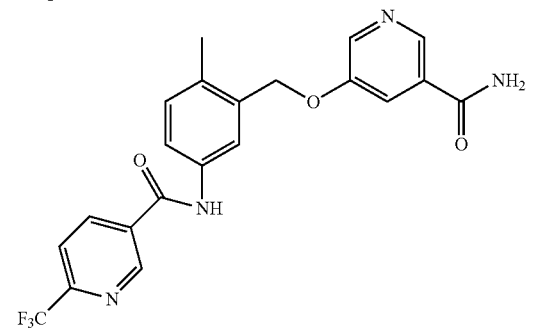
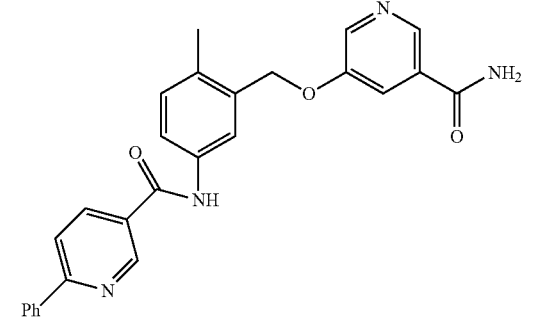
238
-continued
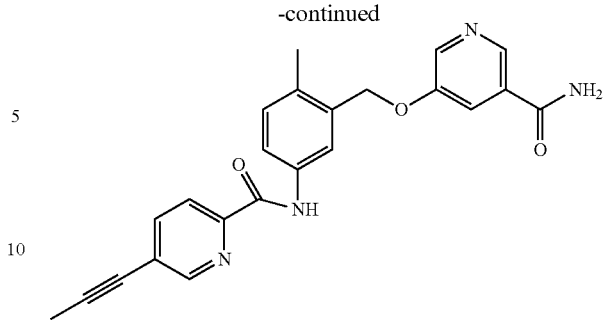
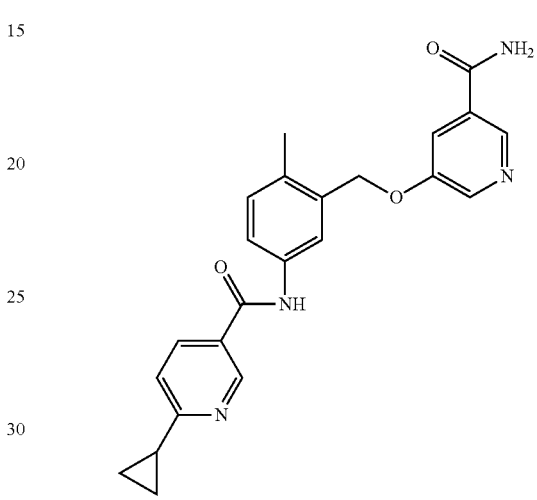
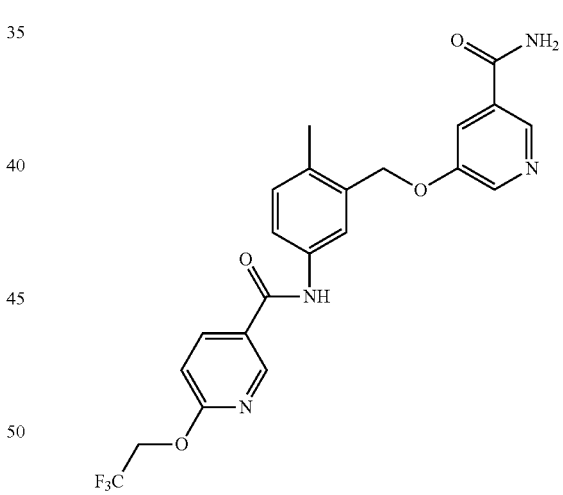
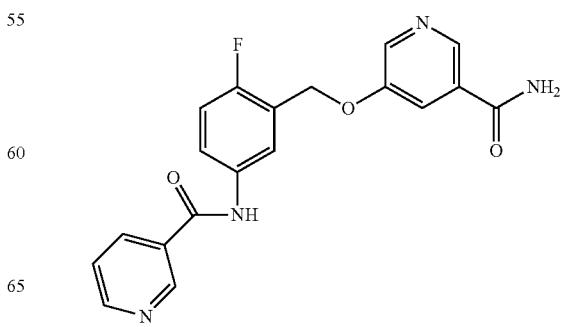

239
-continued
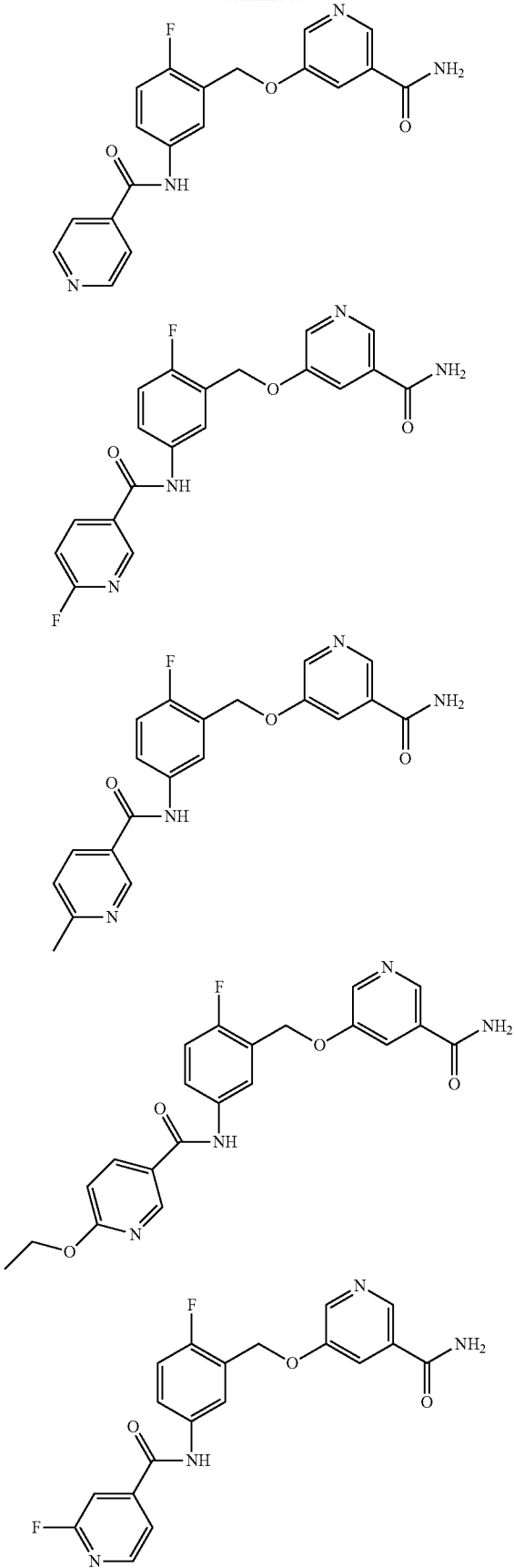
240
-continued
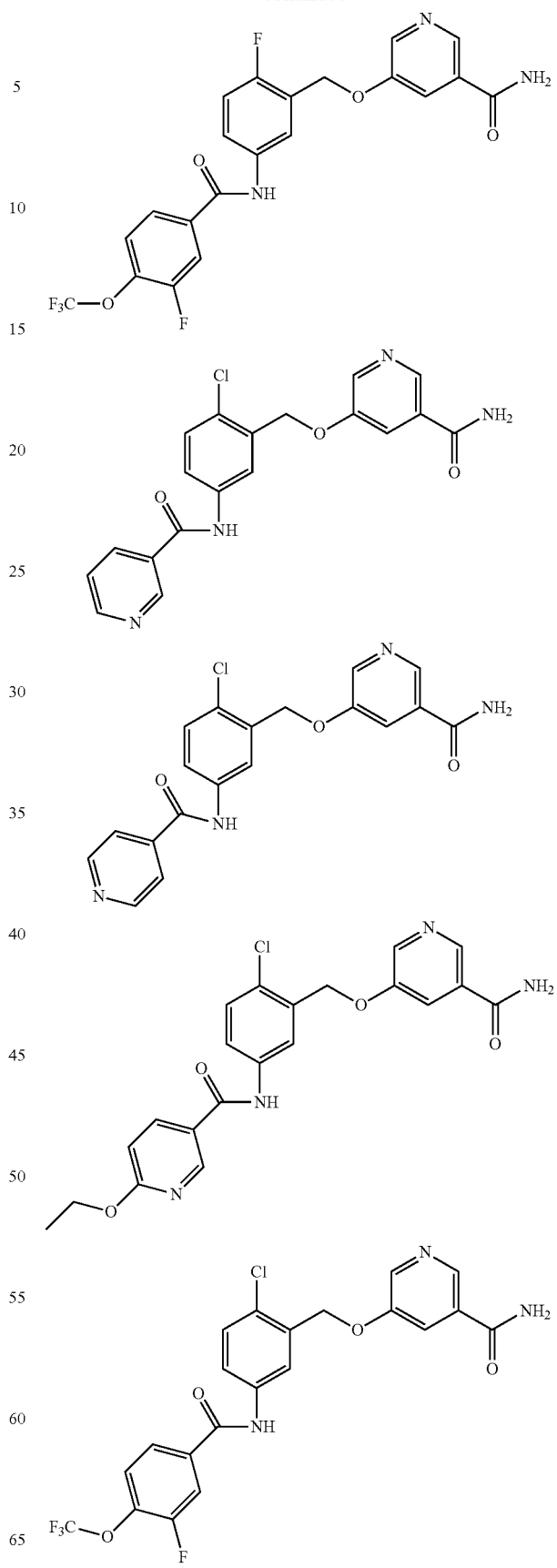

-continued
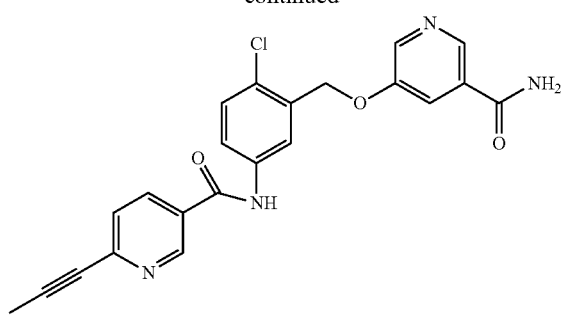
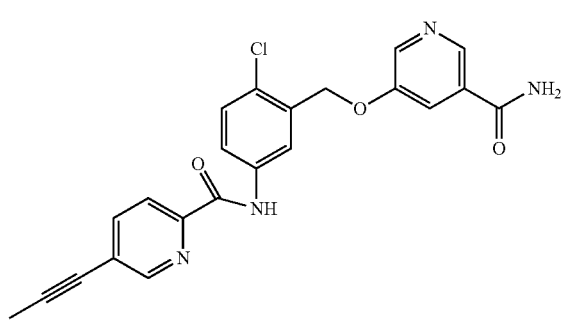
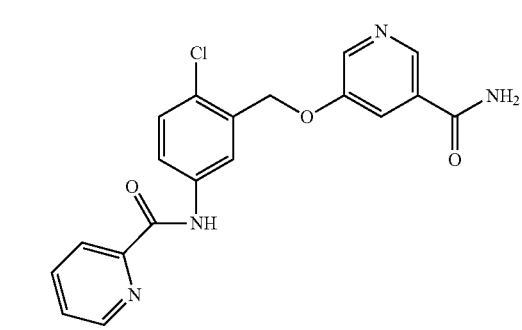
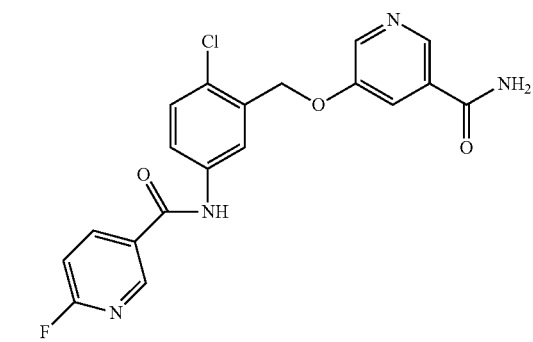
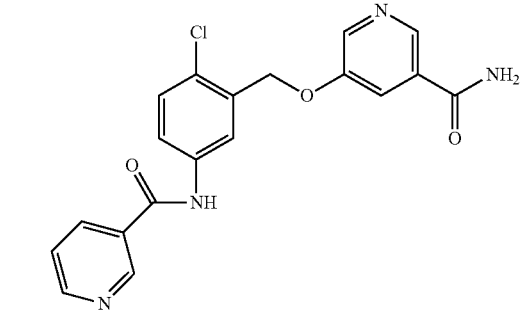
-continued
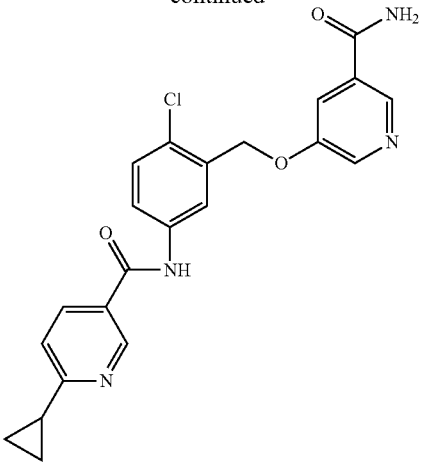
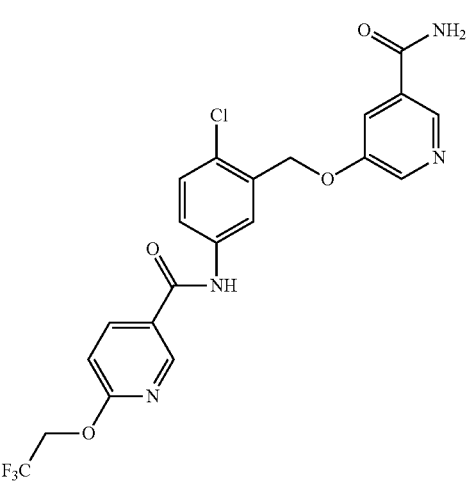
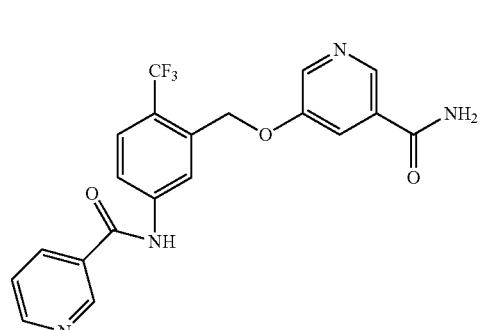
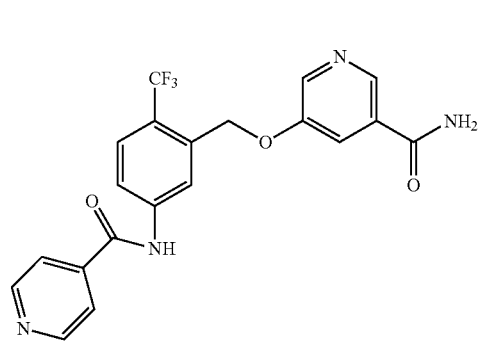

243
-continued
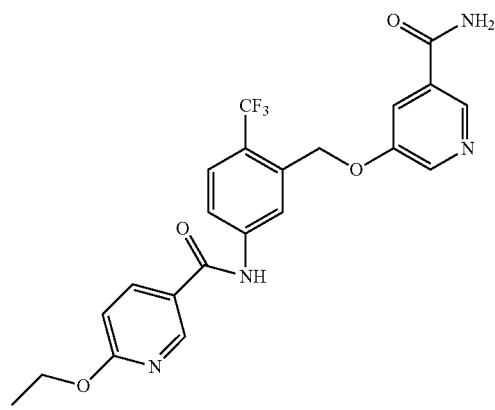
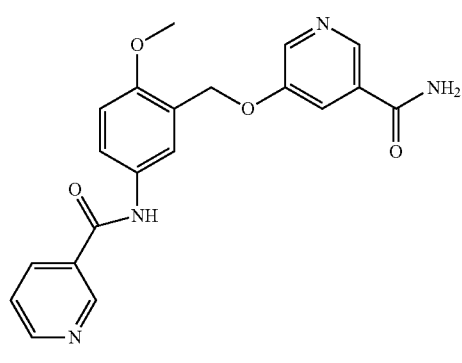
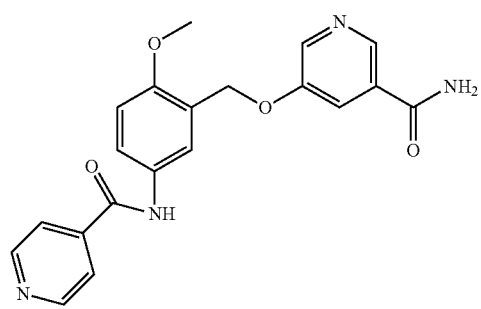
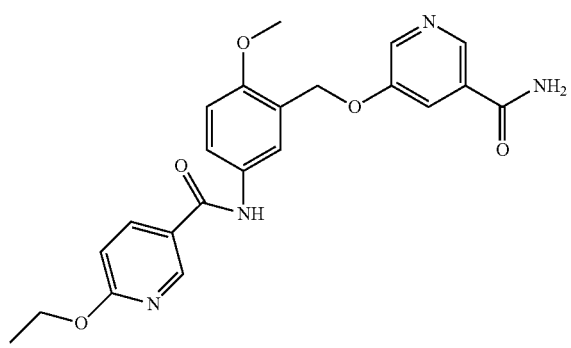
244
-continued
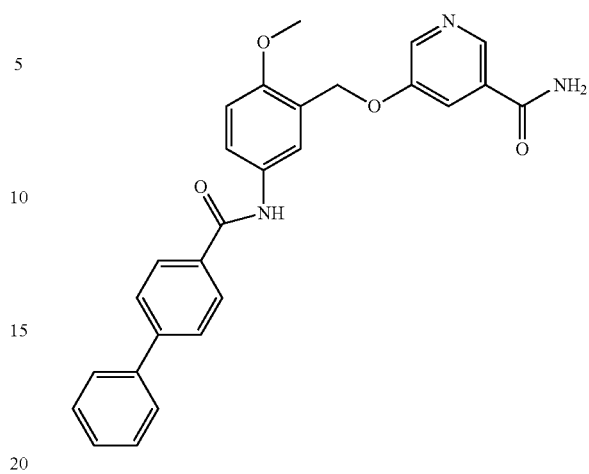
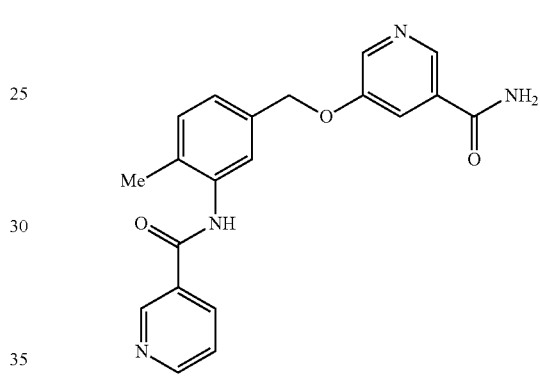
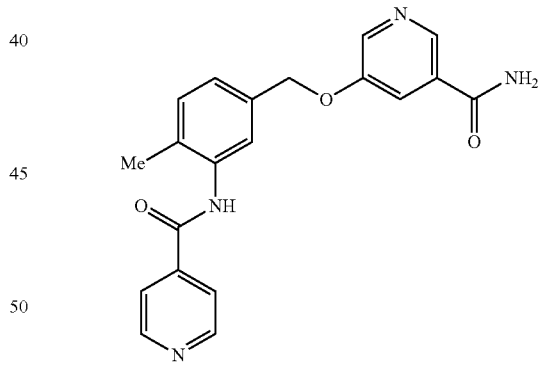
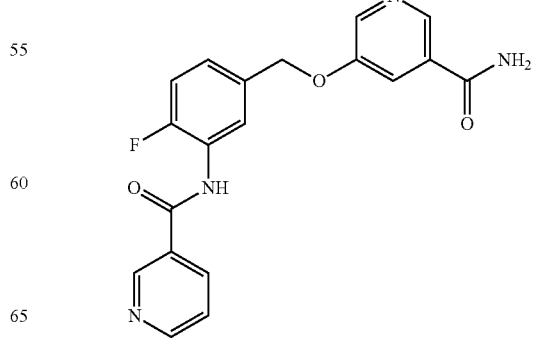

-continued
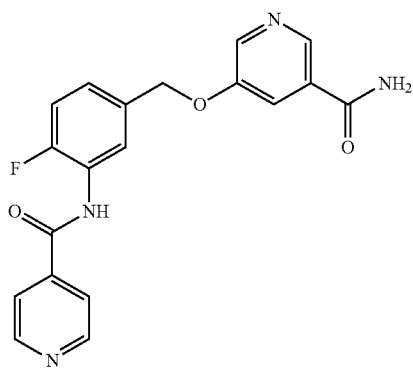
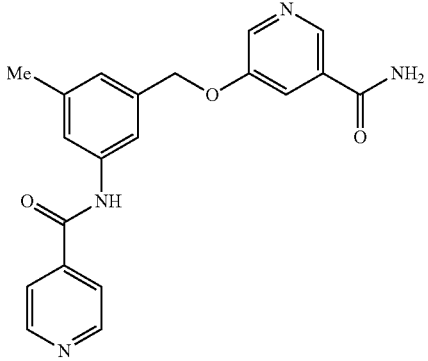
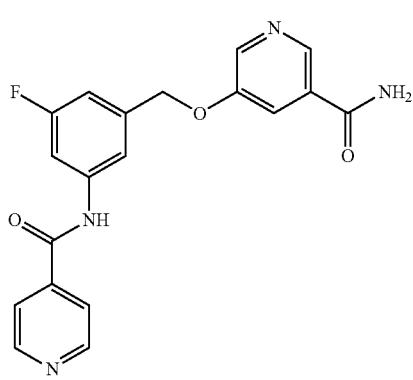
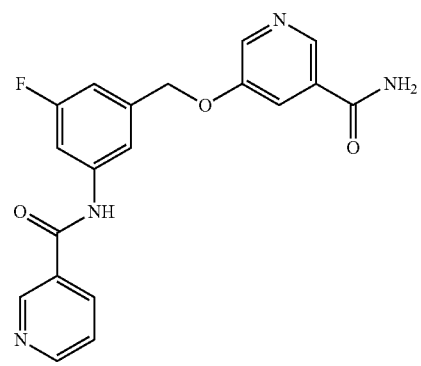
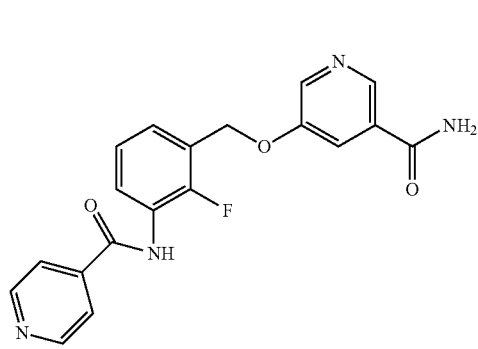
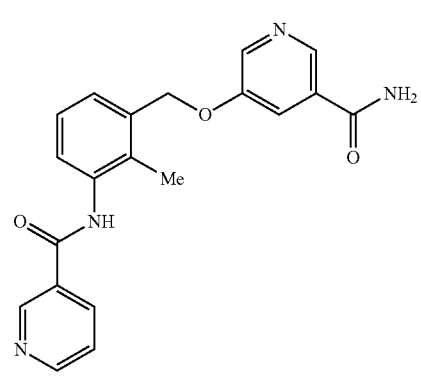
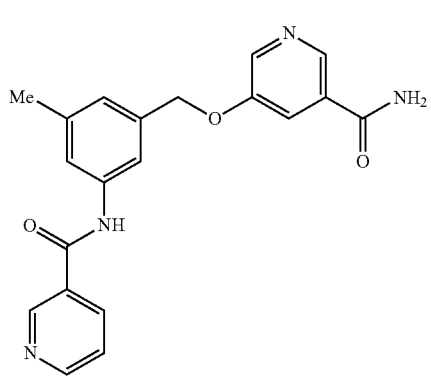
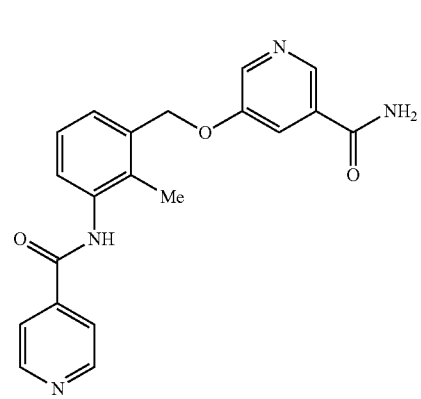

247
-continued
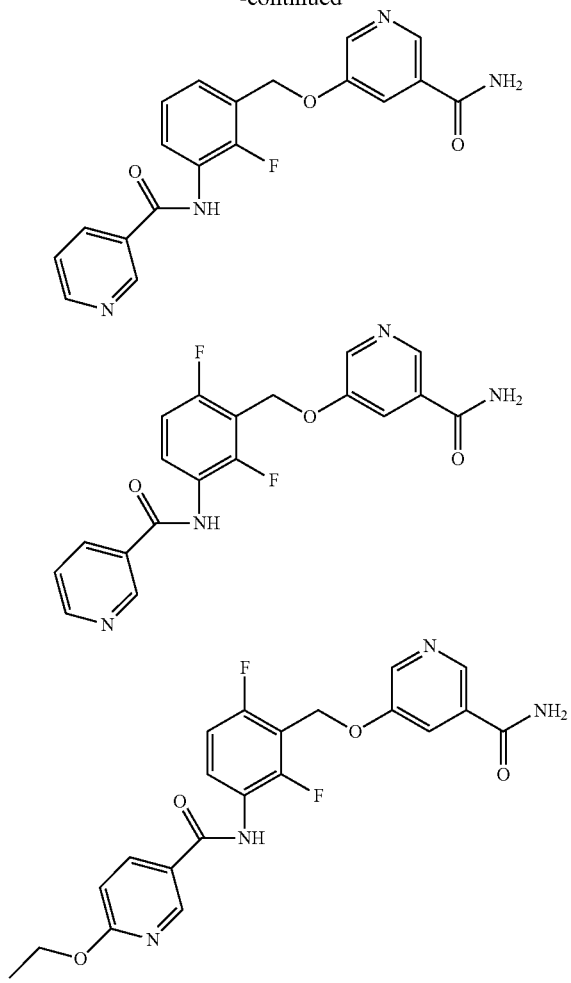
248
-continued
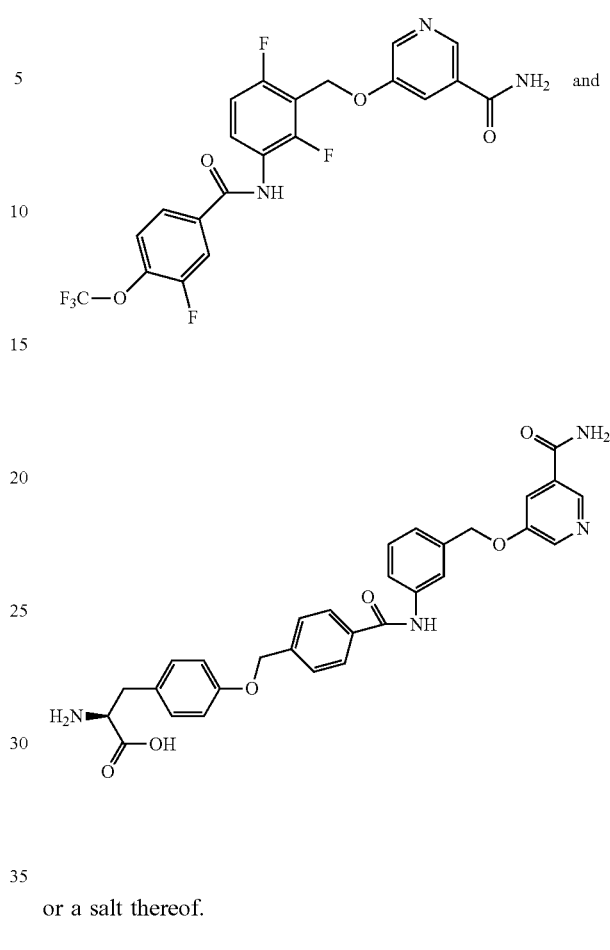
or a salt thereof.
* * * * *

UNITED STATES PATENT AND TRADEMARK OFFICE
CERTIFICATE OF CORRECTION

PATENT NO. : 9,951,019 B2
APPLICATION NO. : 15/192728
DATED : April 24, 2018
INVENTOR(S) : Liqiang Chen, Teng Ai and Swati More It is certified that error appears in the above-identified patent and that said Letters Patent is hereby corrected as shown below:

In the Claims

Column 227, Line 65, Claim 10, please insert the following after last compound -- or a salt thereof. --;

Column 231, Lines 30-47, Claim 12, please delete the following compound:

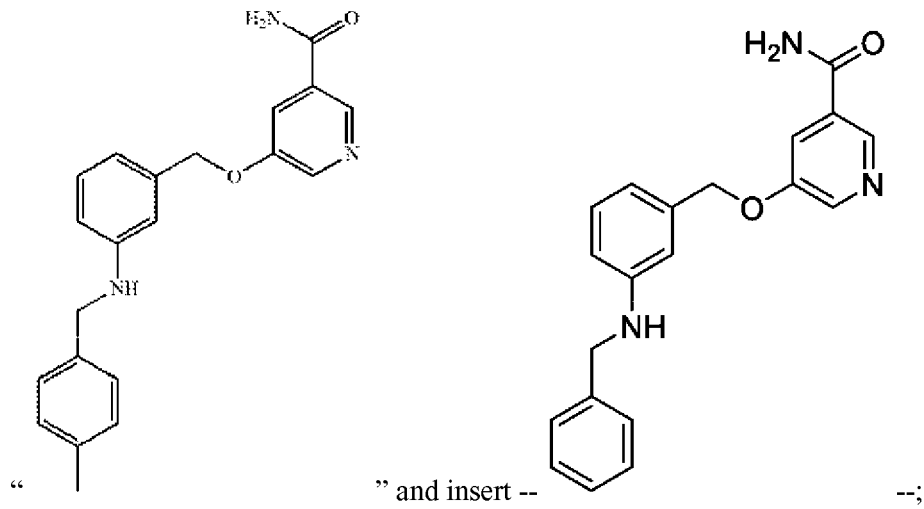

" and insert --                    --;

Column 237, Lines 55-65, Claim 12, please delete the following compound:

Signed and Sealed this
Twenty-sixth Day of June, 2018

Andrei Iancu
*Director of the United States Patent and Trademark Office*

CERTIFICATE OF CORRECTION (continued)
U.S. Pat. No. 9,951,019 B2

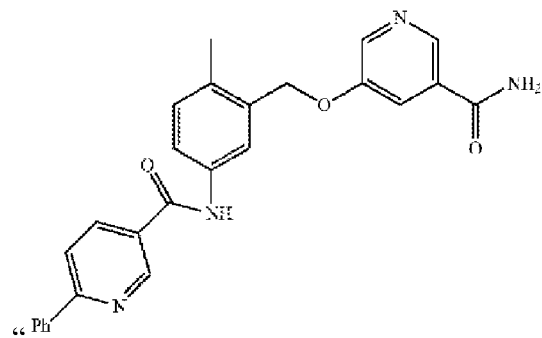 " and insert -- 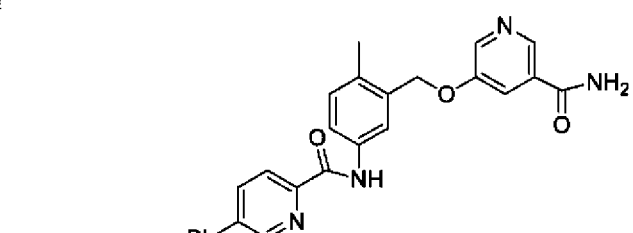 --;

Column 241, Lines 54-65, Claim 12, please delete the following compound:

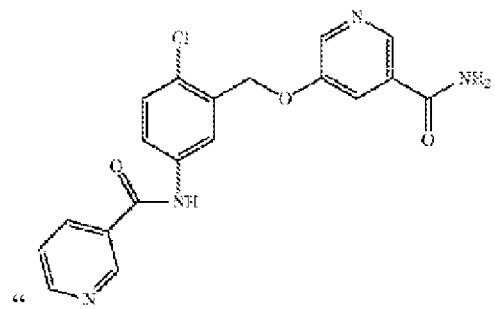 " and insert -- 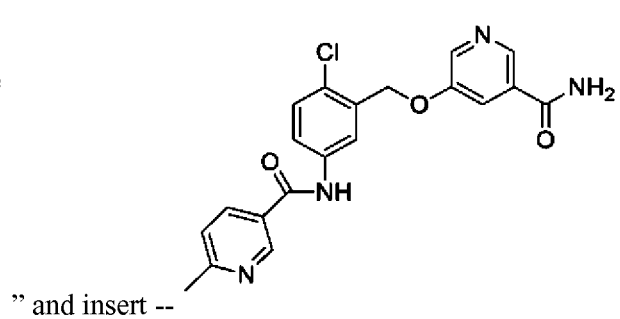 -- therefor.